United States Patent [19]
Pruitt et al.

[11] Patent Number: 6,060,491
[45] Date of Patent: May 9, 2000

[54] 6-MEMBERED AROMATICS AS FACTOR XA INHIBITORS

[75] Inventors: James Russell Pruitt, Landenberg, Pa.;
Donald Joseph Phillip Pinto; Mimi Lifen Quan, both of Newark, Del.;
Ruth Richmond Wexler, Wilmington, Del.

[73] Assignee: Dupont Pharmaceuticals, Wilmington, Del.

[21] Appl. No.: 09/099,663

[22] Filed: Jun. 18, 1998

Related U.S. Application Data
[60] Provisional application No. 60/050,214, Jun. 19, 1997.

[51] Int. Cl.$^7$ ............................ A61K 31/44; C07D 211/82
[52] U.S. Cl. ............................ 514/355; 546/314; 546/315; 564/86; 514/354; 514/631
[58] Field of Search ...................................... 546/314, 316; 514/354, 355, 631; 564/86

[56] References Cited

FOREIGN PATENT DOCUMENTS
9616940 6/1996 WIPO .

OTHER PUBLICATIONS

Kunitada et al., "Factor Xa Inhibitors", *Current Pharmaceutical Design*, 1996, vol. 2, pp. 531–542.

Shi–Shan Mao, "Factor Xa Inhibitors", *Perspectives in Drug Discovery and Design*, vol. 1 (1993), pp. 423–430.

Edmunds et al., "Cardiovascular and Pulmonary Diseases", *Annual Reports in Medicinal Chemistry*, (1996) vol. 31, pp. 51–60.

Tidwell et al., "Strategies for Anticoagulation with Synthetic Protease Inhibitors. Xa Inhibitors Versus Thrombin Inhibitors", *Thrombosis Research*, (1980) vol. 19, pp. 339–349.

Sturzebecher et al., "Synthetic Inhibitors of Serine Proteinases XXIII. Inhibition of Factor Xa by Diamidines", *Thrombosis Research*, (1980) vol. 17, pp. 545–548.

*Primary Examiner*—Zinna Northington Davis

[57] ABSTRACT

The present application describes 6-membered aromatics of formula I:

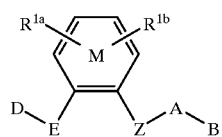

or pharmaceutically acceptable salt forms thereof, wherein D may be $CH_2NH_2$ or $C(=NH)NH_2$, which are useful as inhibitors of factor Xa.

15 Claims, No Drawings

6-MEMBERED AROMATICS AS FACTOR Xa INHIBITORS

This application claims the benefit of U.S. Provisional Application No. 60/050,214, filed Jun. 19, 1997.

FIELD OF THE INVENTION

This invention relates generally to novel 6-membered aromatics which are inhibitors of trypsin-like serine protease enzymes, especially factor Xa, pharmaceutical compositions containing the same, and methods of using the same as anticoagulant agents for treatment and prevention of thromboembolic disorders.

BACKGROUND OF THE INVENTION

WO 96/28427 describes benzamidine anticoagulants of the formula:

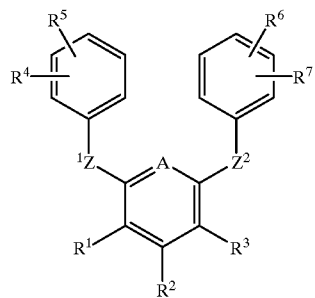

wherein $Z^1$ and $Z^2$ are O, N(R), S or $OCH_2$ and the central ring may be phenyl or a variety of heterocycles. The presently claimed compounds do not contain the $Z^1$ linker or the substitution pattern of the above compounds.

WO 95/18111 addresses fibrinogen receptor antagonists, containing basic and acidic termini, of the formula:

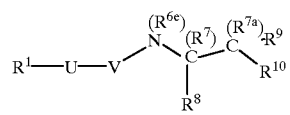

wherein $R^1$ represents the basic termini, U is an alkylene or heteroatom linker, V may be a heterocycle, and the right hand portion of the molecule represents the acidic termini. The presently claimed compounds do not contain the acidic termini of WO 95/18111.

Activated factor Xa, whose major practical role is the generation of thrombin by the limited proteolysis of prothrombina holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, $Ca^{2+}$ and phospholipid). Since it is calculated that one molecule of factor Xa can generate 138 molecules of thrombin (Elodi, S., Varadis K.: *Optimization of conditions for the catalytic effect of the factor IXa-factor VIII Complex: Probable role of the complex in the amplification of blood coagulation. Thromb. Res.* 1979, 15, 617–629), inhibition of factor Xa may be more efficient than inactivation of throibin in interrupting th e blood coagulation system.

Therefore, efficacious and specific inhibitors of factor Xa are needed as potentially valuable therapeutic agents for the treatment of thromboembolic disorders. It is thus desirable to discover new factor Xa inhibitors.

SUMMARY OF THE INVENTION

Accordingly, one object of the present invention is to provide novel 6-membered aromatics which are useful as factor Xa inhibitors or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating thromboembolic disorders comprising administering to a host in need of such treatment a therapeutically effective amount of at least one of the compounds of the present invention or a pharmaceutically acceptable salt or prodrug form thereof.

These and other objects, which will become apparent during the following detailed description, have been achieved by the inventors' discovery that compounds of formula (I):

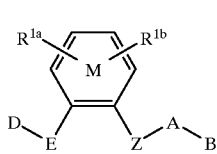

or pharmaceutically acceptable salt or prodrug forms thereof, wherein A, B, D, E, M, $R^{1a}$, $R^{1b}$, and Z are defined below, are effective factor Xa inhibitors.

DETAILED DESCRIPTION OF PREFERRED EMBODIMENTS

[1] Thus, in a first embodiment, the present invention provides novel compounds of formula I:

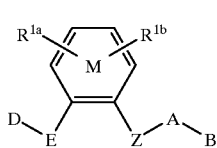

or a stereoisomer or pharmaceutically acceptable salt form thereof, wherein;

ring M contains from 0–4 N atoms;

D is selected from CN, C(=$NR^7$)$NR^8R^9$, NHC(=$NR^7$) $NR^8R^9$, $NR^8$CH(=$NR^7$), C(O)$NR^8R^9$, and ($CR^8R^9$)$_r$ $NR^8R^9$;

E is selected from phenyl, 2-pyridyl, 4-pyridyl, pyrimidyl, and piperidinyl substituted with 1 R;

R is selected from H, F, Cl, Br, I, $OR^3$, $SR^3$, $CO_2R^3$, $NO_2$, and $CH_2OR^3$, and ($CR^8R^9$)$_r$$NR^8R^9$;

alternatively, E and R combine to form methylenedioxy or ethylenedioxy;

Z is selected from a bond, $C_{1-4}$ alkylene, $(CH_2)_rO(CH_2)_r$, $(CH_2)_rNR^3(CH_2)_r$, $(CH_2)_rC(O)(CH_2)_r$, $(CH_2)_rC(O)O$ $(CH_2)_r$, $(CH_2)_rOC(O)$ $(CH_2)_r$, $(CH_2)_rC(O)NR^3(CH_2)_r$, $(CH_2)_rNR^3C(O)(CH_2)_r$, $(CH_2)_rOC(O)O(CH_2)_r$, $(CH_2)$ $_r$OC(O)NR$^3$(CH$_2$)$_r$, (CH$_2$)$_r$NR$^3$C(O)O(CH$_2$)$_r$, (CH$_2$)$_r$NR$^3$C(O)NR$^3$(CH$_2$)$_r$, (CH$_2$)$_r$S(O)p(CH$_2$)$_r$, (CH$_2$)$_r$SO$_2$NR$^3$(CH$_2$)$_r$, (CH$_2$)$_r$NR$^3$SO$_2$(CH$_2$)$_r$, and (CH$_2$)$_r$NR$^3$SO$_2$NR$^3$(CH$_2$)$_r$, provided that Z does not form a N—N, N—O, N—S, NCH$_2$N, NCH$_2$O, or NCH$_2$S bond with ring M or group A;

R$^{1a}$ and R$^{1b}$ are independently absent or selected from —(CH$_2$)$_r$—R$^{1'}$, —CH=CH—R$^{1'}$, NCH$_2$R$^{1''}$, OCH$_2$R$^{1''}$, SCH$_2$R$^{1''}$, NH(CH$_2$)$_2$(CH$_2$)$_r$R$^{1'}$, O(CH$_2$)$_2$(CH$_2$)$_R^{1'}$, and S(CH$_2$)$_2$(CH$_2$)$_R^{1'}$;

alternatively, R$^{1a}$ and R$^{1b}$, when attached to adjacent carbon atoms, together with the atoms to which they are attached form a 5–8 membered saturated, partially saturated or unsaturated ring substituted with 0–2 R$^4$ and which contains from 0–2 heteroatoms selected from the group consisting of N, O, and S;

alternatively, when Z is C(O)NH and R$^{1a}$ is attached to a ring carbon adjacent to Z, then R$^{1a}$ is a C(O) which replaces the amide hydrogen of Z to form a cyclic imide;

R$^{1'}$ is selected from H, C$_{1-3}$ alkyl, F, Cl, Br, I, —CN, —CHO, (CF$_2$)$_r$CF$_3$, (CH$_2$)$_r$OR$^2$, NR$^2$R$^{2a}$, C(O)R$^{2c}$, OC(O)R$^2$, (CF$_2$)$_r$CO$_2$R$^{2c}$, S(O)$_p$R$^{2b}$, NR$^2$(CH$_2$)$_r$OR$^2$, CH(=NR$^{2c}$)NR$^2$R$^{2a}$, NR$^2$C(O)R$^{2b}$, NR$^2$C(O)NHR$^{2b}$, NR$^2$C(O)$_2$R$^{2a}$, OC(O)NR$^{2a}$R$^{2b}$, C(O)NR$^2$R$^{2a}$, C(O)NR$^2$(CH$_2$)$_r$OR$^2$, SO$_2$NR$^2$R$^{2a}$, NR$^2$SO$_2$R$^{2b}$, C$_{3-6}$ carbocyclic residue substituted with 0–2 R$^4$, and 5–10 membered heterocyclic system containing from 1–4 heteroatoms selected from the group consisting of N, O, and S substituted with 0–2 R$^4$;

R$^{1''}$ is selected from H, CH(CH$_2$OR$^2$)$_2$, C(O)R$^{2c}$, C(O)NR$^2$R$^{2a}$, S(O)R$^{2b}$, S(O)$_2$R$^{2b}$, and SO$_2$NR$^2$R$^{2a}$;

R$^2$, at each occurrence, is selected from H, CF$_3$, C$_{1-6}$ alkyl, benzyl, C$_{3-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

R$^{2a}$, at each occurrence, is selected from H, CF$_3$, C$_{1-6}$ alkyl, benzyl, phenethyl, C$_{3-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

R$^{2b}$, at each occurrence, is selected from CF$_3$, C$_{1-4}$ alkoxy, C$_{1-6}$ alkyl, benzyl, C$_{3-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

R$^{2c}$, at each occurrence, is selected from CF$_3$, OH, C$_{1-4}$ alkoxy, C$_{1-6}$ alkyl, benzyl, C$_{3-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

alternatively, R$^2$ and R$^{2a}$, together with the atom to which they are attached, combine to form a 5 or 6 membered saturated, partially saturated or unsaturated ring substituted with 0–2 R$^{4b}$ and containing from 0–1 additional heteroatoms selected from the group consisting of N, O, and S;

R$^3$, at each occurrence, is selected from H, C$_{1-4}$ alkyl, and phenyl;

R$^{3a}$, at each occurrence, is selected from H, C$_{1-4}$ alkyl, and phenyl;

R$^{3b}$, at each occurrence, is selected from H, C$_{1-4}$ alkyl, and phenyl;

R$^{3c}$, at each occurrence, is selected from C$_{1-4}$ alkyl, and phenyl;

A is selected from:
C$_{3-10}$ carbocyclic residue substituted with 0–2 R$^4$, and
5–10 membered heterocyclic system containing from 1–4 heteroatoms selected from the group consisting of N, O, and S substituted with 0–2 R$^4$;

B is selected from: H, Y, and X—Y;

X is selected from C$_{1-4}$ alkylene, —CR$^2$ (CR$^2$R$^{2b}$) (CH$_2$)$_r$—, —C(O)—, —C(=NR$^1$)—, —CR$^2$(NR$^{1''}$R$^2$)—, —CR$^2$(OR$^2$)—, —CR$^2$(SR$^2$)—, —C(O)CR$^2$R$^{2a}$—, —CR$^2$R$^{2a}$C(O), —S(O)$_p$—, —S(O)$_p$CR$^2$R$^{2a}$—, —CR$^2$R$^{2a}$S(O)$_p$—, S(O)$_2$NR$^2$—, —NR$^2$S(O)$_2$—, —NR$^2$S(O)$_2$CR$^2$R$^{2a}$—, CR$^2$R$^{2a}$S(O)$_2$NR$^2$—, —NR$^2$S(O)$_2$NR$^2$—, —C(O)NR$^2$—, —NR$^2$C(O)—, —C(O)NR$^{2c}$R$^2$R$^{2a}$—, ,NR$^2$C(O)CR$^2$R$^{2a}$—, —CR$^2$R$^{2a}$C(O)NR$^2$—, —CR$^2$R$^{2a}$NR$^2$C(O)—, —NR$^2$C(O)O—, —OC(O)NR$^2$—, —NR$^2$C(O)NR$^2$—, —NR$^2$—, —NR$^2$CR$^2$R$^{2a}$—, —CR$^2$R$^{2a}$NR$^2$—, O, —CR$^2$R$^{2a}$O—, and —OCR$^2$R$^{2a}$—;

Y is selected from:
(CH$_2$)$_r$NR$^2$R$^{2a}$, provided that X—Y do not form a N—N, O—N, or S—N bond,
C$_{3-10}$ carbocyclic residue substituted with 0–2 R$^{4a}$, and
5–10 membered heterocyclic system containing from 1–4 heteroatoms selected from the group consisting of N, O, and S substituted with 0–2 R$^{4a}$;

R$^4$, at each occurrence, is selected from H, =O, (CH$_2$)$_r$OR$^2$, F, Cl, Br, I, C$_{1-4}$ alkyl, —CN, NO$_2$, (CH$_2$)$_r$NR$^2$R$^{2a}$, (CH$_2$)$_r$C(O)R$^{2c}$, NR$^2$C(O)R$^{2b}$, C(O)NR$^2$R$^{2a}$, NR$^2$C(O)NR$^2$R$^{2a}$, CH(=NR$^2$)NR$^2$R$^{2a}$, CH(=NS(O)$_2$R$^5$)NR$^2$R$^{2a}$, NHC(=NR$^2$)NR$^2$R$^{2a}$, C(O)NHC(=NR$^2$)NR$^2$R$^{2a}$, SO$_2$NR$^2$R$^{2a}$, NR$^2$SO$_2$NR$^2$R$^{2a}$, NR$^2$SO$_2$-C$_{1-4}$ alkyl, NR$^2$SO$_2$R$^5$, S(O)$_p$R$^5$, (CF$_2$)$_r$CF$_3$, NCH$_2$R$^{1''}$, OCH$_2$R$^{1''}$, SCH$_2$R$^{1''}$, N(CH$_2$)$_2$(CH$_2$)$_r$R$^{1'}$, O(CH$_2$)$_2$(CH$_2$)$_r$R$^{1'}$, and S(CH$_2$)$_2$(CH$_2$)$_r$R$^{1'}$;

alternatively, one R$^4$ is a 5–6 membered aromatic heterocycle containing from 1–4 heteroatoms selected from the group consisting of N, O, and S;

R$^{4a}$, at each occurrence, is selected from H, =O, (CH$_2$)$_r$OR$^2$, (CH$_2$)$_r$—F, (CH$_2$)$_r$—Br, (CH$_2$)$_r$—Cl, I, C$_{1-4}$ alkyl, —CN, NO$_2$, (CH$_2$)$_r$NR$^2$R$^{2a}$, (CH$_2$)$_r$NR$^2$R$^{2b}$, (CH$_2$)$_r$C(O)R$^{2c}$, NR$^2$C(O)R$^{2b}$, C(O) NR$^2$R$^{2a}$, C(O) NH(CH$_2$)$_2$NR$^2$R$^{2a}$, NR$^2$C(O)NR$^2$R$^{2a}$, CH(=NR$^2$) NR$^2$R$^{2a}$, NHC(=NR$^2$)NR$^2$R$^{2a}$, SO$_2$NR$^2$R$^{2a}$, NR$^2$SO$_2$NR$^2$NR$^{2a}$, NR$^2$SO$_2$-C$_{1-4}$ alkyl, C(O)NHSO$_2$-C$_{1-4}$ alkyl, NR$^2$SO$_2$R$^5$, S(O)$_p$R$^5$, and (CF$_2$)$_r$CF$_3$;

alternatively, one R$^{4a}$ is a 5–6 membered aromatic heterocycle containing from 1–4 heteroatoms selected from the group consisting of N, O, and S and substituted with 0–1 R$^5$;

R$^{4b}$, at each occurrence, is selected from H, =O, (CH$_2$)$_r$OR$^3$, F, Cl, Br, I, C$_{1-4}$ alkyl, —CN, NO$_2$, (CH$_2$)$_r$NR$^3$R$^{3a}$, (CH$_2$)$_r$C(O)R$^3$, (CH$_2$)$_r$C(O)OR$^{3c}$, NR$^3$C(O)R$^{3a}$, C(O)NR$^3$R$^{3a}$, NR$^3$C(O) NR$^3$R$^{3a}$, CH(=NR$^3$)NR$^3$R$^{3a}$, NH$_3$C(=NR$^3$)NR$^3$R$^{3a}$, SO$_2$NR$^3$R$^{3a}$, NR$^3$SO$_2$NR$^3$R$^{3a}$, NR$^3$SO$_2$-C$_{1-4}$ alkyl, NR$^3$SO$_2$CF$_3$, NR$^3$SO$_2$-phenyl, S(O)$_p$CF$_3$, S(O)$_p$-C$_{1-4}$ alkyl, S(O)$_p$-phenyl, and (CF$_2$)$_r$CF$_3$;

R$^5$, at each occurrence, is selected from CF$_3$, C$_{1-6}$ alkyl, phenyl substituted with 0–2 R$^6$, and benzyl substituted with 0–2 R$^6$;

R$^6$, at each occurrence, is selected from H, OH, (CH$_2$)$_r$OR$^2$, F, Cl, Br, I, C$_{1-4}$ alkyl, CN, NO$_2$, (CH$_2$)$_r$NR$^2$R$^{2a}$, $(CH_2)_rC(O)R^{2b}$, $NR^2C(O)R^{2b}$, $NR^2C(O)NR^2R^{2a}$, $CH(=NH)NH_2$, $NHC(=NH)NH_2$, $SO_2NR^2R^{2a}$, $NR^2SO_2NR^2R^{2a}$, and $NR^2SO_2C_{1-4}$ alkyl;

$R^7$, at each occurrence, is selected from H, OH, $C_{1-6}$ alkyl, $C_{1-6}$ alkylcarbonyl, $C_{1-6}$ alkoxy, $C_{1-4}$ alkoxycarbonyl, $(CH_2)_n$-phenyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl-$C_{1-4}$ alkoxycarbonyl;

$R^8$, at each occurrence, is selected from H, $C_{1-6}$ alkyl and $(CH_2)_n$-phenyl;

alternatively, $R^7$ and $R^8$ combine to form a 5 or 6 membered saturated, ring which contains from 0–1 additional heteroatoms selected from the group consisting of N, O, and S;

$R^9$, at each occurrence, is selected from H, $C_{1-6}$ alkyl and $(CH_2)_n$-phenyl;

n is selected from 0, 1, 2, and 3;

m is selected from 0, 1, and 2;

p is selected from 0, 1, and 2;

r is selected from 0, 1, 2, and 3;

s is selected from 0, 1, and 2; and, t is selected from 0 and 1.

[2] In a preferred embodiment, the present invention provides novel compounds of formulae Ia–Io:

a

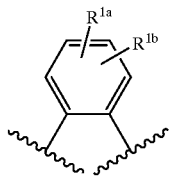

b

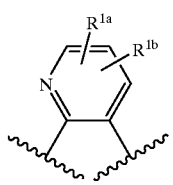

c

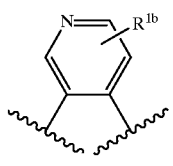

d

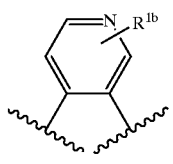

-continued e

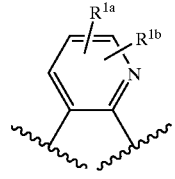

f

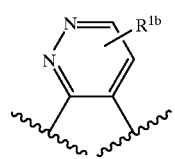

g

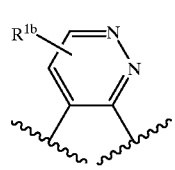

h

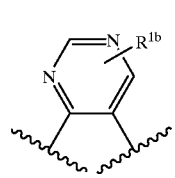

i

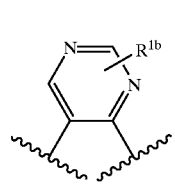

j

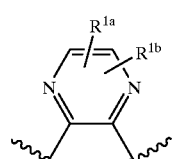

k

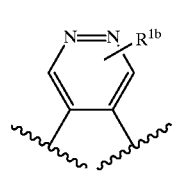

l

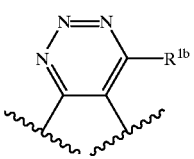

m

-continued

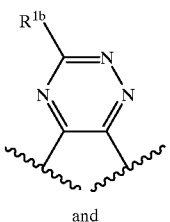

n and

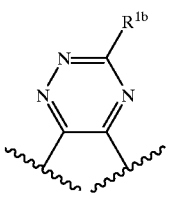

o

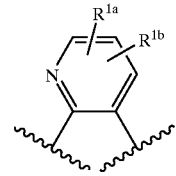

b

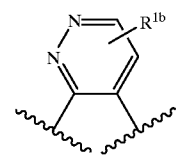

f

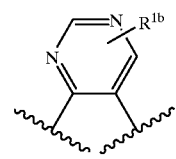

h

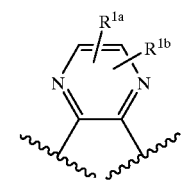

j

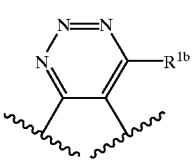

l

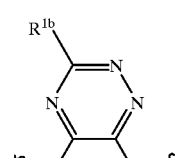

n and o wherein:
Z is selected from a bond, CH$_2$O, OCH$_2$, CH$_2$NH, NHCH$_2$, CH$_2$C(O), C(O)CH$_2$, C(O)NH, C(O)NH, CH$_2$S(O)$_2$, S(O)$_2$(CH$_2$), SO$_2$NH, and SO$_2$NH;

B is selected from: Y, X—Y, and NR$^2$R$^{2a}$;

Y is selected from one of the following carbocyclic and heterocyclic systems which are substituted with 0–2 R$^{4a}$;
  phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, 1,3,4-triazole, benzofuran, benzothiofuran, indole, benzimidazole, benzoxazole, benzthiazole, indazole, benzisoxazole, benzisothiazole, and isoindazole;

Y may also be selected from the following bicyclic heteroaryl ring systems:

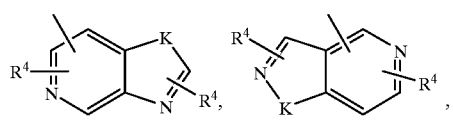

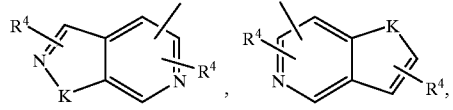

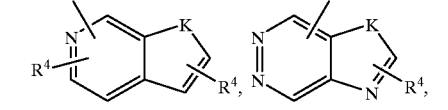

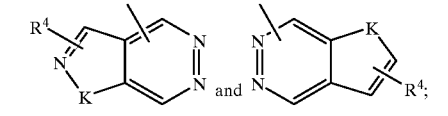

K is selected from O, S, NH, and N.

[3] In a more preferred embodiment, the present invention provides novel compounds of formulae:

wherein
D is selected from C(=NR$^7$)NR$^8$R$^9$ and; (CR$^8$R$^9$)$_t$NR$^8$R$^9$;

R is selected from H, F, Cl, OR$^3$, CH$_2$OR$^3$, CH$_2$NH$_2$;

A is selected from:
  piperidinyl,
  piperazinyl,
  C$_{5-6}$ carbocyclic residue substituted with 0–2 R$^4$, and 5–6 membered heteroaryl containing from 1–4 heteroatoms selected from the group consisting of N, O, and S substituted with 0–2 $R^4$;

Y is selected from one of the following carbocyclic and heterocyclic systems which are substituted with 0–2 $R^{4a}$;

phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, benzimidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, and 1,3,4-triazole.

[4] In an even more preferred embodiment, the present invention provides novel compounds wherein:

E is phenyl;

D is selected from $C(=NH)NH_2$ and $CH_2NH_2$;

R is selected from H, F, Cl, and Br;

A is selected from:
$C_{5-6}$ carbocyclic residue substituted with 0–2 $R^4$, and
5–6 membered heteroaryl containing from 1–3 heteroatoms selected from the group consisting of N, O, and S substituted with 0–2 $R^4$;

Y is selected from one of the following carbocyclic and heterocyclic systems which are substituted with 0–2 $R^{4a}$;

phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, benzimidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, and 1,3,4-triazole;

$R^2$, at each occurrence, is selected from H, $CF_3$, $C_{1-6}$ alkyl, benzyl, $C_{5-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^{2a}$, at each occurrence, is selected from H, $CF_3$, $C_{1-6}$ alkyl, benzyl, phenethyl, $C_{5-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^{2b}$, at each occurrence, is selected from $CF_3$, $C_{1-4}$ alkoxy, $C_{1-6}$ alkyl, benzyl, $C_{5-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^{2c}$, at each occurrence, is selected from $CF_3$, OH, $C_{1-4}$ alkoxy, $C_{1-6}$ alkyl, benzyl, $C_{5-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

alternatively, $R^2$ and $R^{2a}$, together with the atom to which they are attached, combine to form a ring selected from imidazolyl, morpholino, piperazinyl, pyridyl, and pyrrolidinyl, substituted with 0–2 $R^{4b}$;

$R^4$, at each occurrence, is selected from H, =O, $OR^2$, $CH_2OR^2$, F, Cl, $C_{1-4}$ alkyl, $NR^2R^{2a}$, $CH_2NR^2R^{2a}$, $C(O)$ $R^{2c}$, $CH_2C(O)R^{2c}$, $C(O)NR^2R^{2a}$, $CH(=NR^2)NR^2R^{2a}$, $CH(=NS(O)_2R^5)NR^2R^{2a}$, $SO_2NR^2R^{2a}$, $NR^2SO_2-C_{1-4}$ alkyl, $S(O)_2R^5$, and $CF_3$ provided that if B is H, then $R^4$ is other than tetrazole, C(O)-alkoxy, and $C(O)NR^2R^{2a}$;

$R^{4a}$, at each occurrence, is selected from H, =O, $(CH_2)_r$ $OR^2$, F, Cl, $C_{1-4}$ alkyl, $NR^2R^{2a}$, $CH_2NR^2R^{2a}$, $NR^2R^{2b}$, $CH_2NR^2R^{2b}$, $(CH_2)_rC(O)R^{2c}$, $NR^2C(O)R^{2b}$, $C(O)$ $NR^2R^{2a}$, $C(O)NH(CH_2)_2NR^2R^{2a}$, $NR^2C(O)NR^2R^{2a}$, $SO_2NR^2R^{2a}$, $S(O)_2R^5$, and $CF_3$; and, $R^{4b}$, at each occurrence, is selected from H, =O, $(CH_2)_r$ $OR^3$, F, Cl, $C_{1-4}$ alkyl, $NR^3R^{3a}$, $CH_2NR^3R^{3a}$, $C(O)R^3$, $CH_2C(O)R^3$, $C(O)OR^{3c}$, $C(O)NR^3R^{3a}$, $CH(=NR^3)$ $NR^3R^{3a}$, $SO_2NR^3R^{3a}$, $NR^3SO_2-C_{1-4}$ alkyl, $NR^3SO_2CF_3$, $NR^3SO_2$-phenyl, $S(O)_2CF_3$, $S(O)_2-C_{1-4}$ alkyl, $S(O)_2$-phenyl, and $CF_3$.

[5] In a further preferred embodiment, the present invention provides novel compounds selected from:

N-(2'-Aminosulfonyl-[1,1']biphen-4-yl)-2-(3'-amidinophenyl)nicotinamide;

N-[5-(2-aminosulfonyl)phenylpyrid-2-yl]-2-(3'-amidinophenyl)nicotinamide;

N-[5-(2-t-butylaminosulfonyl)phenylpyrid-2-yl]-2-(3'-amidinophenyl)nicotinamide; and, N-[5-(2-aminosulfonyl)phenylpyrid-2-yl]-2-(3'-carboxamidophenyl)nicotinamide;

or a pharmaceutically acceptable salt thereof.

In a second embodiment, the present invention provides novel pharmaceutical compositions, comprising: a pharmaceutically acceptable carrier and a therapeutically effective amount of a compound of formula (I) or a pharmaceutically acceptable salt form thereof.

In a third embodiment, the present invention provides a novel method for treating or preventing a thromboembolic disorder, comprising: administering to a patient in need thereof a therapeutically effective amount of a compound of formula (I) or a pharmaceutically acceptable salt form thereof.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced. Keto substituents are not present on aromatic moieties.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. Alkenyl" is intended to include hydrocarbon chains of either a straight or branched configuration and one or more unsaturated carbon-carbon bonds which may occur in any stable point along the chain, such as ethenyl, propenyl and the like. "Alkynyl" is intended to include hydrocarbon chains of either a straight or branched configuration and one or more triple carbon-carbon bonds which may occur in any stable point along the chain, such as ethynyl, propynyl and the like.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "carbocycle" or "carbocyclic residue" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, or tetrahydronaphthyl.

As used herein, the term "heterocycle" or "heterocyclic system" is intended to mean a stable 5- to 7-membered monocyclic or bicyclic or 7- to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S. It is preferred that the total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2, 3-triazolyl, 1,2,4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrrolidinyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and Spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like. Preferred prodrugs are amidine prodrugs wherein D is C(=NR$^7$)NH$_2$, and R$^7$ is selected from OH, C$_{1-4}$ alkoxy, C$_{6-10}$ aryloxy, C$_{1-4}$ alkoxycarbonyl, C$_{6-10}$ aryloxycarbonyl, C$_{6-10}$ arylmethylcarbonyl, C$_{1-4}$ alkylcarbonyloxy C$_{1-4}$ alkoxycarbonyl, and C$_{6-10}$ arylcarbonyloxy C$_{1-4}$ alkoxycarbonyl. More preferred prodrugs are where R$^7$ is OH, methoxy, ethoxy, benzyloxycarbonyl, methoxycarbonyl, and methylcarbonyloxymethoxycarbonyl.

"Stable compound" and "stable structure" are meant to indicate a compound that is sufficiently robust to survive isolation to a useful degree of purity from a reaction mixture, and formulation into an efficacious therapeutic agent.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

"Therapeutically effective amount" is intended to include an amount of a compound of the present invention or an amount of the combination of compounds claimed effective to inhibit HIV infection or treat the symptoms of HIV infection in a host. The combination of compounds is preferably a synergistic combination. Synergy, as described for example by Chou and Talalay, Adv. Enzyme Regul. 22:27–55 (1984), occurs when the effect (in this case, inhibition of HIV replication) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

SYNTHESIS

The compounds of the present invention can be prepared in a number of ways known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. The reactions are performed in a solvent appropriate to the reagents and materials employed and suitable for the transformations being effected. It will sometimes require a judgment to modify the order of synthetic steps or to select one particular process scheme over another in order to obtain a desired compound of the invention. It will also be recognized that another major consideration in the planning of any synthetic route in this field is the judicious choice of the protecting group used for the protection of the reactive functional groups present in the compounds described in this invention. An authoritative account describing the many alternatives to the trained practitioner is Greene and Wuts (*Protective Groups in Organic Chemistry*, Wiley and Sons, 1991). All references cited herein are hereby incorporated in their entirety herein by reference. Compounds of this invention where B is either a carbocyclic or heterocyclic residue as defined in Formula 1 are coupled to A as shown generically and by specific example in Schemes 1 and 2, respectively. Either or both of A and B may be substituted with 0–2 R$^4$. W is defined as a suitable protected nitrogen, such as NO$_2$ or NHBOC; a protected sulfur, such as S-tBu or SMOM; or a methyl ester. Halogen-metal exchange of the bromine in bromo-B with n-butyl lithium, quenching with triisopropyl borate and acidic hydrolysis gives the required boronic acid, B—B(OH)$_2$. The W—A—Br subunit may be already linked to ring M before the Suzuki coupling reaction. Deprotection provides the complete subunit.

Scheme 1

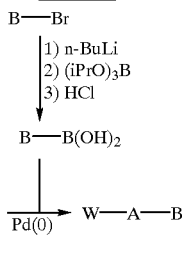

Scheme 1

-continued

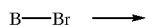

B—Br ⟶ 

Scheme 2 describes a typical example of how the A-B subunit is prepared for attachment to ring M. 4-Bromoaniline is protected as Boc-derivative and the coupled to 2-(t-butylamino)sulfonylphenylboronic acid under Suzuki conditions. 2-(t-Butylamino) sulfonylphenylboronic acid is prepared by the method described by Rivero (*Bioorg. Med. Chem. Lett.* 1994, 189). Deprotection with TFA can provide the aminobiphenyl compound. The aminobiphenyl is then coupled to the core ring structures as described below.

Scheme 2

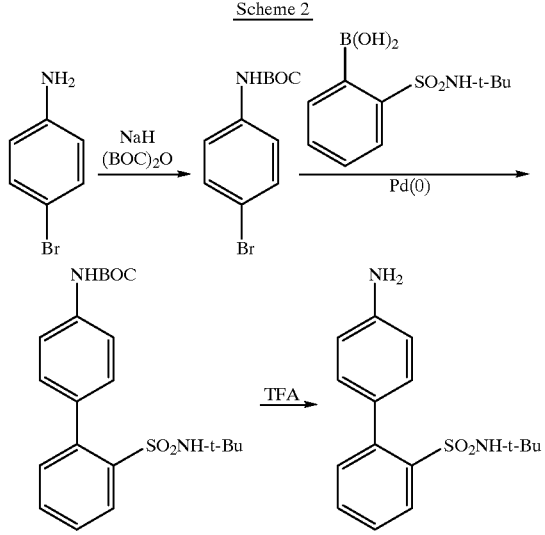

When B is defined as X—Y, the following description applies. Groups A and B are available either through commercial sources, known in the literature or readily synthesized by the adaptation of standard procedures known to practitioners skilled in the art of organic synthesis. the required reactive functional groups appended to analogs of A and B are also available either through commercial sources, known in the literature or readily synthesized by the adaptation of standard procedures known to practitioners skilled in the art of synthesis. In the tables that follow the chemistry required to effect the coupling of A to B is outlined.

TABLE A

Preparation of Amide Ester, Urea, Sulfonamide and Sulfamide Linkages Between A and B.

| If A contains: | then the reactive substituent of Y is: | to give the following product A—X—Y: |
|---|---|---|
| A—NHR$^2$ as a substituent | ClC(O)—Y | A—NR$^2$—C(O)—Y |
| a secondary NH as part of a ring or chain | ClC(O)—Y | A—C(O)—Y |
| A—OH as a substituent | ClC(O)—Y | A—O—C(O)—Y |
| A—NHR$^2$ as a substituent | ClC(O)—CR$^2$R$^{2a}$—Y | A—NR$^2$—C(O)—CR$^2$R$^{2a}$—Y |
| a secondary NH as part of a ring or chain | ClC(O)—CR$^2$R$^{2a}$—Y | A—C(O)—CR$^2$R$^{2a}$—Y |
| A—OH as a substituent | ClC(O)—CR$^2$R$^{2a}$—Y | A—O—C(O)—CR$^2$R$^{2a}$—Y |
| A—NHR$^2$ as a substituent | ClC(O)—CNR$^2$—Y | A—NR$^2$—C(O)—CNR$^2$—Y |
| a secondary NH as part of a ring or chain | ClC(O)—CNR$^2$—Y | A—C(O)—CNR$^2$—Y |
| A—OH as a substituent | ClC(O)—CNR$^2$—Y | A—O—C(O)—CNR$^2$—Y |
| A—NHR$^2$ as a substituent | ClSO$_2$—Y | A—NR$^2$—SO$_2$—Y |
| a secondary NH as part of a ring or chain | ClSO$_2$—Y | A—SO$_2$—Y |
| A—NHR$^2$ as a substituent | ClSO$_2$—CR$^2$R$^{2a}$—Y | A—NR$^2$—SO$_2$—CR$^2$R$^{2a}$—Y |
| a secondary NH as part of a ring or chain | ClSO$_2$—CR$^2$R$^{2a}$—Y | A—SO$_2$—CR$^2$R$^{2a}$—Y |
| A—NHR$^2$ as a substituent | ClSO$_2$—NR$^2$—Y | A—NR$^2$—SO$_2$—NR$^2$—Y |
| a secondary NH as part of a ring or chain | ClSO$_2$—NR$^2$—Y | A—SO$_2$—NR$^2$—Y |
| A—C(O)Cl | HO—Y as a substituent | A—C(O)—O—Y |
| A—C(O)Cl | NHR$^2$—Y as a substituent | A—C(O)—NR$^2$—Y |
| A—C(O)Cl | a secondary NH as part of a ring or chain | A—C(O)—Y |
| A—CR$^2$R$^{2a}$C(O)Cl | HO—Y as a substituent | A—CR$^2$R$^{2a}$C(O)—O—Y |
| A—CR$^2$R$^{2a}$C(O)Cl | NHR$^2$—Y as a substituent | A—CR$^2$R$^{2a}$C(O)—NR$^2$—Y |
| A—CR$^2$R$^{2a}$C(O)Cl | a secondary NH as part of a ring or chain | A—CR$^2$R$^{2a}$C(O)—Y |
| A—SO$_2$Cl | NHR$^2$—Y as a substituent | A—SO$_2$—NR$^2$—Y |
| A—SO$_2$Cl | a secondary NH as part of a ring or chain | A—SO$_2$—Y |
| A—CR$^2$R$^{2a}$SO$_2$Cl | NHR$^2$—Y as a substituent | A—CR$^2$R$^{2a}$SO$_2$—NR$^2$—Y |
| A—CR$^2$R$^{2a}$SO$_2$Cl | a secondary NH as part of a ring or chain | A—CR$^2$R$^{2a}$SO$_2$—Y |

The chemistry of Table A can be carried out in aprotic solvents such as a chlorocarbon, pyridine, benzene or toluene, at temperatures ranging from −20° C. to the reflux point of the solvent and with or without a trialkylamine base.

TABLE B

Preparation of Ketone Linkages between A and B.

| If A contains: | then the reactive substituent of Y is: | to give the following product A—X—Y: |
|---|---|---|
| A—C(O)Cl | BrMg—Y | A—C(O)—Y |
| A—$CR^2R^{2a}$C(O)Cl | BrMg—Y | A—$CR^2R^{2a}$C(O)—Y |
| A—C(O)Cl | BrMg$CR^2R^{2a}$—Y | A—C(O)$CR^2R^{2a}$—Y |
| A—$CR^2R^{2a}$C(O)Cl | BrMg$CR^2R^{2a}$—Y | A—$CR^2R^{2a}$C(O)$CR^2R^{2a}$—Y |

The coupling chemistry of table B can be carried out by a variety of methods. The Grignard reagent required for Y is prepared from a halogen analog of Y in dry ether, dimethoxyethane or tetrahydrofuran at 0° C. to the reflux point of the solvent. This Grignard reagent can reacted directly under very controlled conditions, that is low temperature (−20° C. or lower) and with a large excess of acid chloride or with catalytic or stoichiometric copper bromide•dimethyl sulfide complex in dimethyl sulfide as a solvent or with a variant thereof. Other methods available include transforming the Grignard reagent to the cadmium reagent and coupling according to the procedure of Carson and Prout (Org. Syn. Col. Vol. 3 (1955) 601) or a coupling mediated by Fe(acac)3 according to Fiandanese et al. (*Tetr. Lett.* 1984, 4805), or a coupling mediated by manganese (II) catalysis (Cahiez and Laboue, *Tetr. Lett.* 1992, 33(31), 4437).

TABLE C

Preparation of Ether and Thioether linkages between A and B.

| If A contains: | then the reactive substituent of Y is: | to give the following product A—X—Y: |
|---|---|---|
| A—OH | Br—Y | A—O—Y |
| A—$CR^2R^{2a}$—OH | Br—Y | A—$CR^2R^{2a}$O—Y |
| A—OH | Br—$CR^2R^{2a}$—Y | A—O$CR^2R^{2a}$—Y |
| A—SH | Br—Y | A—S—Y |
| A—$CR^2R^{2a}$—SH | Br—Y | A—$CR^2R^{2a}$S—Y |
| A—SH | Br—$CR^2R^{2a}$—Y | A—S$CR^2R^{2a}$—Y |

The ether and thioether linkages of Table C can be prepared by reacting the two components in a polar aprotic solvent such as acetone, dimethylformamide or dimethylsulfoxide in the presence of a base such as potassium carbonate, sodium hydride or potassium t-butoxide at a temperature ranging from ambient to the reflux point of the solvent used.

TABLE D

Preparation of —SO— and —$SO_2$— linkages from thioether of Table C.

| If the starting material is: | then it is oxidized with wet Alumina/Oxone to give: | then it is oxidized with m-chloroperbenzoic acid to give: |
|---|---|---|
| A—S—Y | A—S(O)—Y | A—$SO_2$—Y |
| A—$CR^2R^{2a}$S—Y | A—$CR^2R^{2a}$S(O)—Y | A—$CR^2R^{2a}SO_2$—Y |
| A—S$CR^2R^{2a}$—Y | A—S(O)$CR^2R^{2a}$—Y | A—$SO_2CR^2R^{2a}$—Y |

The thioethers of Table C serve as a convenient starting material for the preparation of the sulfoxide and sulfone analogs of Table D. A combination of wet alumina and Oxone can provide a reliable reagents for the oxidation of the thioether to the sulfoxide as shown by Greenhalgh (*Syn. Lett.* 1992, 235). The sulfone can be prepared according to the method of Satoh (*Chem. Lett.* 1992, 381) using m-chloroperbenzoic acid.

Scheme 3 describes the synthesis of compounds wherein M is a benzene ring and Q is a protected precursor of group D of Formula I and V is a nitro, protected sulfonamide or ester group and precursor of group Z of Formula I. The V group is placed on an appropriately substituted phenol either via nitration as shown by Poirier et al. (*Tetrahedron* 1989, 45(5), 1415), sulfonylation as shown by Kuznetsov (*Akad. Nauk SSSR Ser. Khim* 1990, 8, 1888) or carboxylation by Sartori et al. (*Synthesis* 1988, 10, 763). Bromination with triphenylphosphine and bromine (*J. Am. Chem. Soc.* 1964, 86, 964) gives the desired bromide. Suzuki coupling with the appropriate boronic acid provides the desired substituted pyridine.

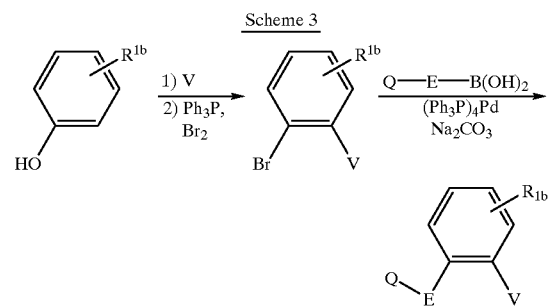

Schemes 4, 5, 6, and 7 describe the synthesis of compounds wherein M is pyridine and Q is a protected precursor of group D of Formula I. Each scheme represents a different substitution pattern for the pyridine ring. In Scheme 4, a suitably protected aldehyde is subjected to base-catalyzed condensation with an activated ester to give after deprotection the desired aldehyde. Refluxing with ammonium chloride as shown by Dornow and Ische (*Chem. Ber.* 1956, 89, 876) provides the pyridinol which is brominated with $POBr_3$ (Tjeenk et al. *Rec. Trav. Chim.* 1948, 67, 380) to give the desired 2-bromopyridine. Suzuki coupling with the appropriate boronic acid provides the desired substituted pyridine.

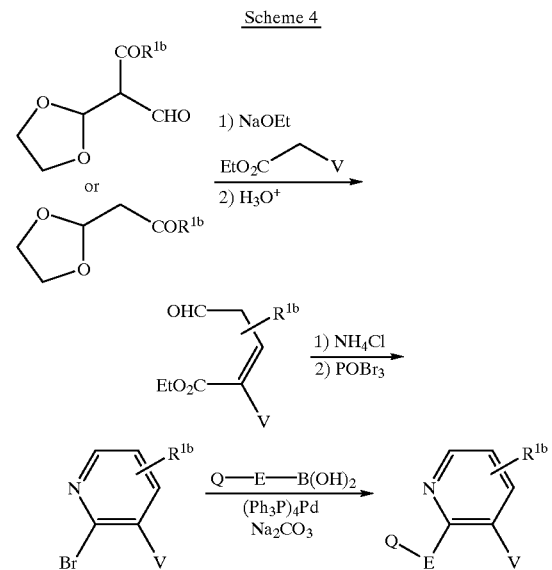

Treatment of an appropriately substituted 5-ethoxyoxazole with an alkene as shown by Kondrat'eva et al. *Dokl. Akad. Nauk SSSR* 1965, 164, 816) provides a pyridine with the V substituent at the para position. Bromination at the 3-position as shown by van der Does and Hertog (*Rec. Trav. Khim. Pays-Bas* 1965, 84, 951) followed by palladium-catalyzed boronic acid coupling provides the desired substituted pyridine.

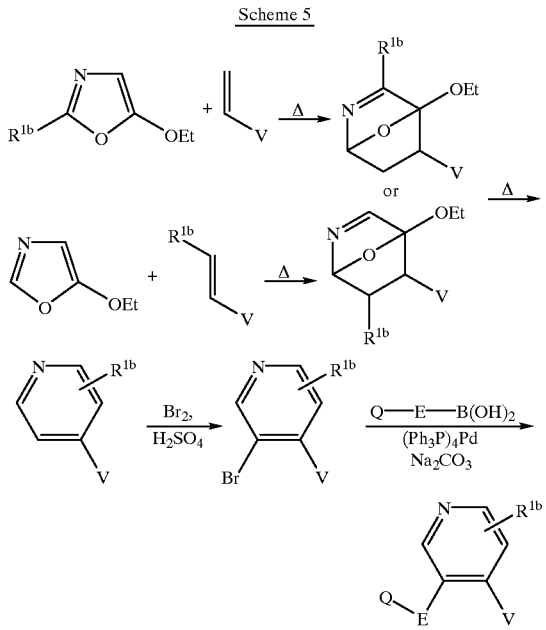

Scheme 6 describes a synthesis of a third substitution pattern on a pyridine ring. The appropriate tricarbonyl compound which can be prepared by methods described in Scheme 4 is treated with ammonium chloride to form the pyridinol which is subsequently brominated. Palladium-catalyzed coupling provides the desired substituted pyridine.

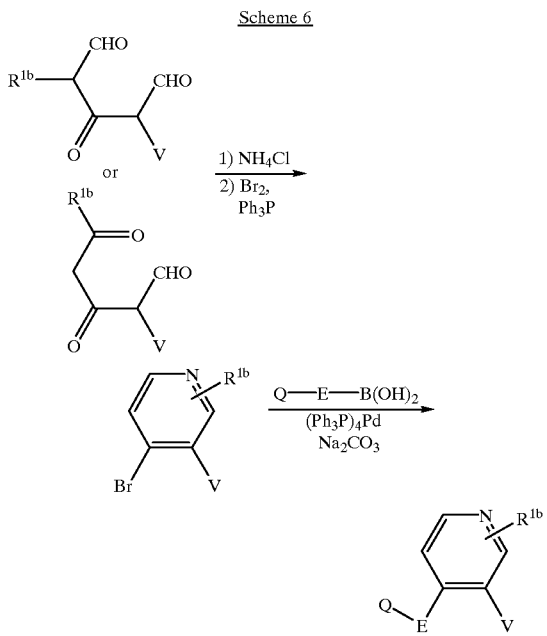

Scheme 7 takes a suitably substituted dicarbonyl compound and by chemistry illustrated in Schemes 4 and 6, reacts it with ammonium chloride. Bromination gives the 3-bromopyridine which upon palladium-catalyzed coupling provides the desired substituted pyridine.

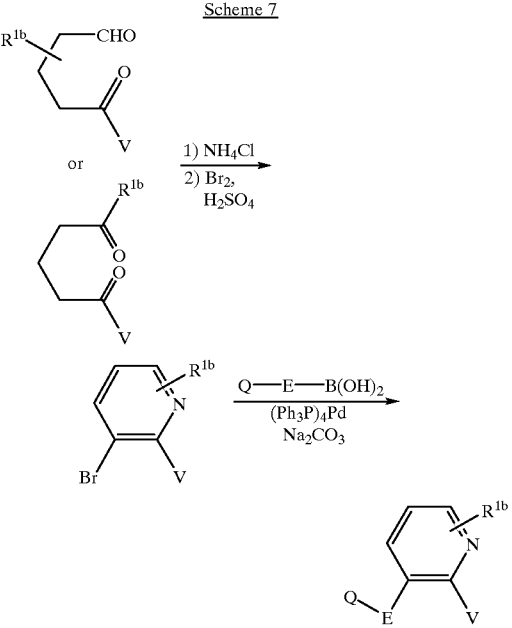

Schemes 8, 9, and 10 describe the synthesis of compounds wherein M is pyridazine and Q is a protected precursor of group D of Formula I. Each scheme represents a different substitution pattern for the pyridine ring. In Scheme 8 an activated ester is reacted with an appropriately substituted α-keto aldehyde and hydrazine as shown by Schmidt and Druey (*Helv. Chim. Acta* 1954, 37, 134 and 1467). Conversion of the pyridazinone to the bromide using $POBr_3$ and palladium-catalyzed coupling provides the desired substituted pyridazine.

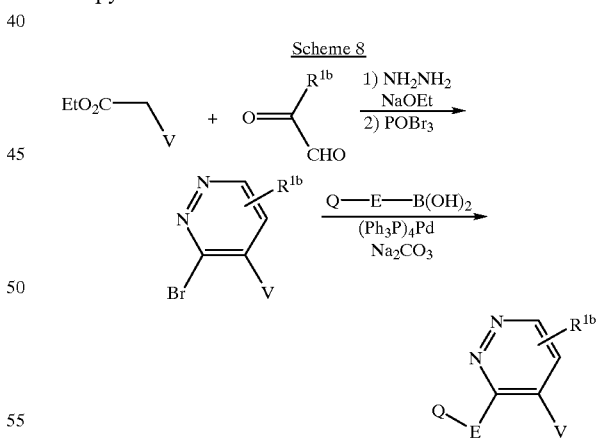

In Scheme 9, glyoxal can react under basic conditions with an activated ketone and subsequently brominated/dehydro-brominated to give the desired ketoaldehyde. Alternatively, a protected ketone can react with an activated aldehyde, undergo bromination/dehydrobromination, be deprotected and oxidized to give the regioisomeric ketoaldehyde. Cyclization as shown by Sprio and Madonia (*Ann. Chim.* 1958, 48, 1316) with hydrazine followed by palladium-catalyzed coupling provides the desired substituted pyridazine.

Scheme 9

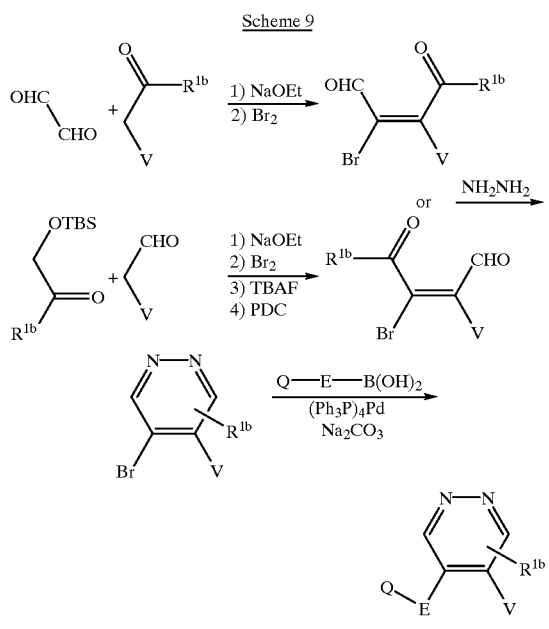

By analogy to Scheme 9, in Scheme 10 a aldehyde can be reacted with an activated ketone, brominated, dehydrobrominated and deprotected to give the desired diketone. Alternatively, a regioisomeric ketone can be placed through the same reaction sequence to produce an isomeric keto aldehyde. Reaction with hydrazine followed by palladium-catalyzed coupling provides the desired substituted pyridazine.

Scheme 10

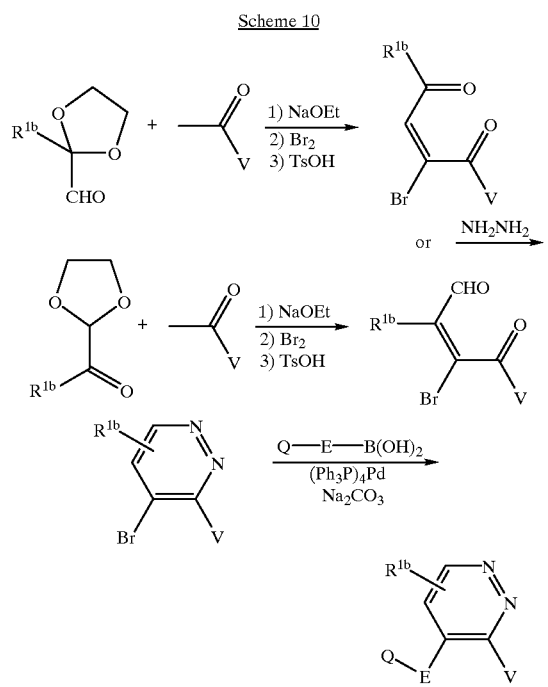

Schemes 11, and 12 describe the synthesis of compounds wherein M is pyrimidine and Q is a protected precursor of group D of Formula I. Each scheme represents a different substitution pattern for the pyrimidine ring. In Scheme 11, a condensation with an appropriately substituted acid chloride and an activated ester followed by conjugate reduction by tin hydride (Moriya et al. *J. Org. Chem.* 1986, 51, 4708) gives the desired 1,4 dicarbonyl compound. Cyclization with formamidine or a substituted amidine followed by bromination gives the desired regioisomeric pyrimidine. Palladium-catalyzed coupling provides the desired substituted pyrimidine.

Scheme 11

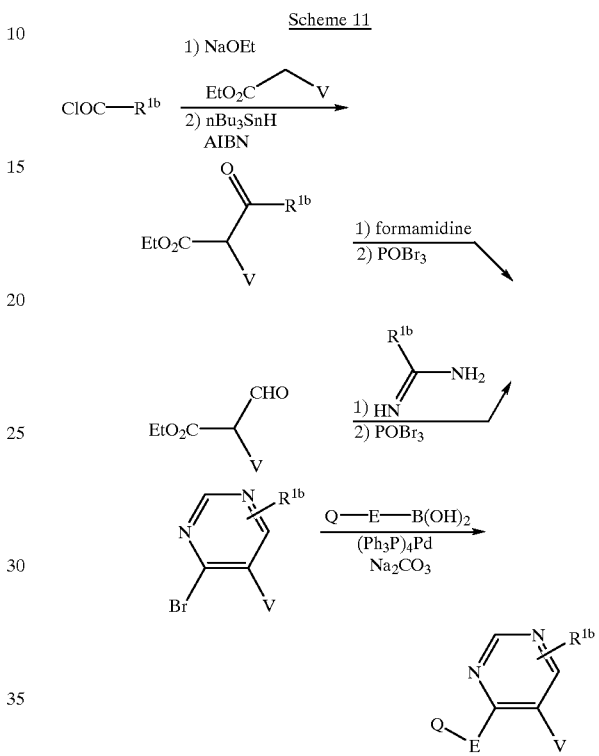

Using similar chemistry, Scheme 12 shows how an amidine can be condensed with a 1,3-dicarbonyl compound and subsequently brominated in the 5-position (*J. Het. Chem.* 1973, 10, 153) to give a specific regioisomeric bromopyrimidine. Palladium-catalyzed coupling provides the desired substituted pyrimidine.

Scheme 12

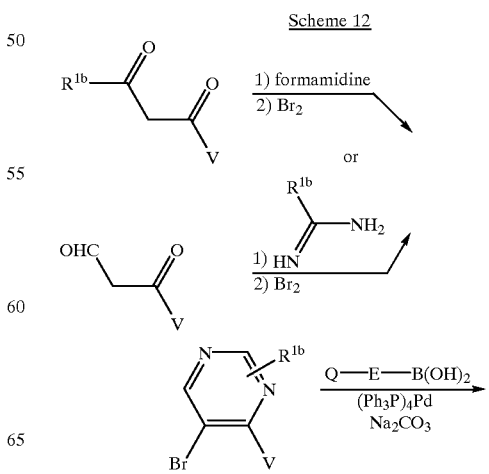

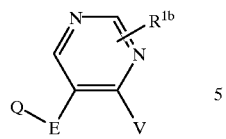

Using the same ketoaldehyde from Scheme 12, cyclization with an appropriately substituted 1,2-diamine (*Chimia* 1967, 21, 510) followed by aromatization (*Helv. Chim. Acta* 1967, 50, 1754) provides a regioisomeric mixture of pyrazines as illustrated in Scheme 13. Bromination of the hydrobromide salt (U.S. Pat. No. 2,403,710) yields the intermediate for the palladium-catalyzed coupling step which occurs as shown above.

Scheme 13

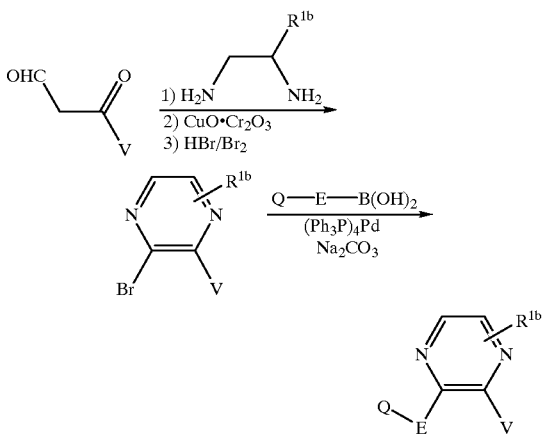

Schemes 14 and 15 describe the synthesis of compounds wherein M is a 1,2,3-triazine and Q is a protected precursor of group D of Formula I. In Scheme 14, a vinyl bromide is palladium coupled to a molecule containing the substituent R$^{1b}$. Allylic bromination followed by azide displacement provide the cyclization precursor. Triphenylphosphine-mediated cyclization (*J. Org. Chem.* 1990, 55, 4724) give the 1-aminopyrazole which is subsequently brominated with N-bromosuccimide. Lead tetraacetate mediated rearrangement as shown by Neunhoeffer et al. (*Ann.* 1985, 1732) provides the desired regioisomeric 1,2,3-triazine. Palladium-catalyzed coupling provides the substituted triazine.

Scheme 14

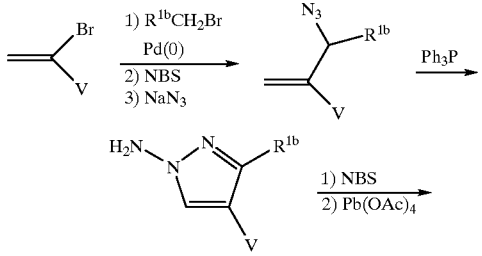

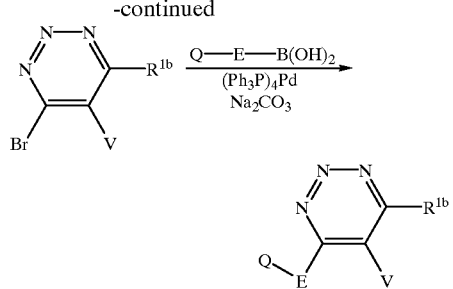

In Scheme 15, an alkene is allylically brominated and the bromide is displaced to give a regioisomer of the azide in Scheme 14. Following the same reaction sequence as shown above, cyclization provides the 1-aminopyrazole. Bromination followed by lead tetraacetate mediated rearrangement give the 1,2,3-triazine. Palladium-catalyzed coupling provides the other desired triazine.

Scheme 15

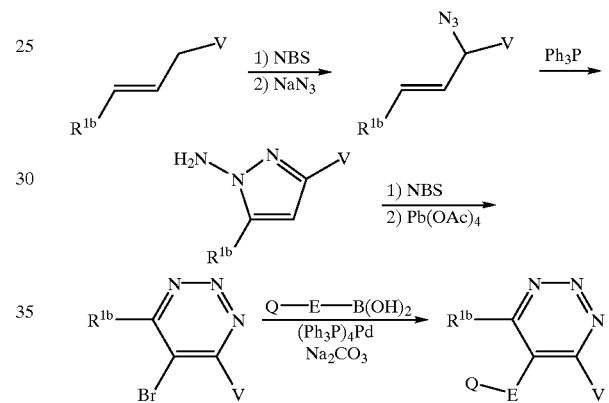

Schemes 16 and 17 describe the synthesis of compounds wherein M is a 1,2,4-triazine and Q is a protected precursor of group D of Formula I. In Scheme 16, a nitrile is converted using hydrazine to give the amidrazone which is condensed with a α-ketoester to give the triazinone as shown by Paudler and Lee (*J. Org. Chem.* 1971, 36, 3921). Bromination as shown by Rykowski and van der Plas (*J. Org. Chem.* 1987, 52, 71) followed by palladium-catalyzed coupling provides the desired 1,2,4-triazine.

Scheme 16

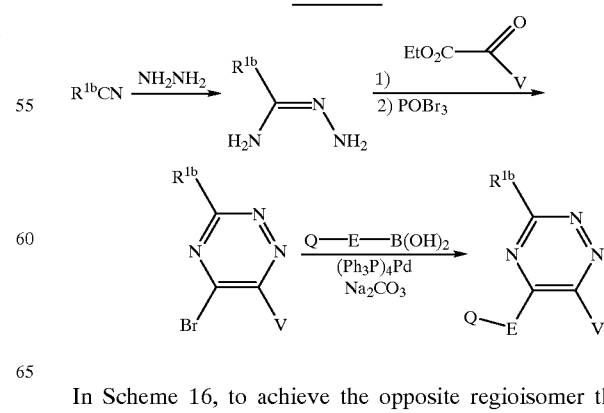

In Scheme 16, to achieve the opposite regioisomer the reaction scheme shown above is modify by the substituting a protect α-ketoester. This allows the most nucleophilic nitrogen to attack the ester functionality setting up the opposite regiochemistry. Deprotection and thermal cyclization gives the triazinone which is brominated as shown above. Palladium-catalyzed coupling provides the other desired 1,2,4-triazine.

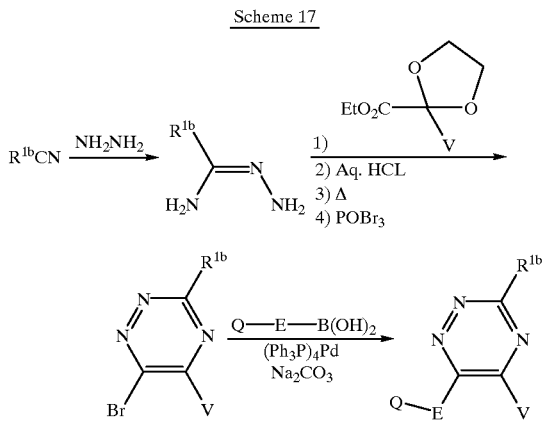

Scheme 17

Scheme 18 describes the synthesis of compounds wherein M is a 1,2,3,4-tetrazine and Q is a protected precursor of group D of Formula I. Lithiation of a vinyl bromide, transmetallation with tin, palladium catalyzed carbonylation and hydrazone formation provides a diene for a subsequent Diels-Alder reaction as shown by Carboni and Lindsey (*J. Am. Chem. Soc.* 1959, 81, 4342). Reaction with dibenzyl azodicarboxylate followed by catalytic hydrogenation to debenzylate and decarboxylate should give after bromination the desired 1,2,3,4-tetrazine. Palladium-catalyzed coupling provides the desired substitution.

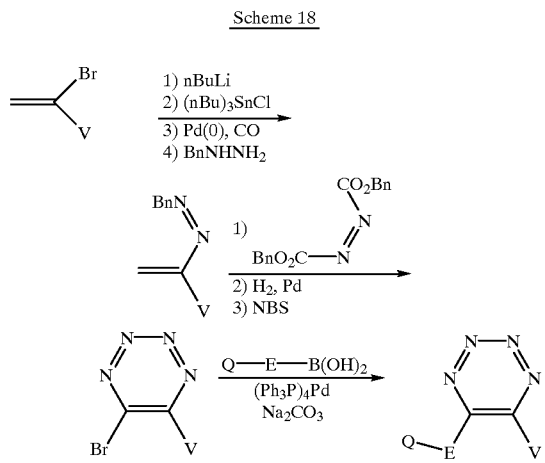

Scheme 18

Other features of the invention will become apparent in the course of the following descriptions of exemplary embodiments which are given for illustration for the invention and are not intended to be limiting thereof.

EXAMPLES

Example 1

N-(2'-Aminosulfonyl-[1,1']biphen-4-yl)-2-(3'-amidinophenyl)nicotinamide, trifluoroacetic Acid Salt Part A. Preparation of 2-bromonicotinic Acid.

Potassium permanganate (18.4 g, 116 mmol) was dissolved in water (400 mL) and added to 2-bromo-3-methylpyridine (10.0 g, 58 mmol) and refluxed for 16 hours. After cooling to room temperature, the slurry was filtered through a celite plug and rinsed with water and chloroform. The entire filtrate was transferred to a separatory funnel and the layers were separated. The aqueous layer was extracted again with $CHCl_3$ and acidified with 6N HCl to pH 1. A white solid was obtained on standing (2.08 g of product). The pH of the remaining aqueous was adjusted to pH 4 with 2M NaOH and 2M HCl, then concentrated to <100 mL. A white precipitate was filtered. The pH was adjusted to 4 and the mixture filtered again, combining the isolated solids for a total of 3.88 g of product. The filtrate was concentrated again to <100 mL and adjusted to pH 1.5 and an additional quanitity of white solid was obtained (1.80 g), for a combined yield of 3 crops, (8.76 g, 66%). $^1$H NMR (DMSO-d6): δ 13.76 (bs, 1H), 8.46 (m, 1H), 8.09 (dd, 1H, J=7.7, J'=2.2), 7.51 (m, 1H).

Part B. Preparation of methyl 2-bromonicotinate.

2-Bromonicotinic acid (7.33 g, 36 mmol) was suspended in dry $Et_2O$ (40 mL), and MeOH (2.3 mL) and diethyl azodicarboxylate (5.8 mL, 37 mmol) were added. Triphenylphosphine (9.61 g in 40 mL $Et_2O$, 37 mmol) was added dropwise over 2.5 hours. After stirring an additional two hours, the reaction was filtered and evaporated. The resulting clear liquid was chromatographed on silica gel (10–40% EtOAc/hexanes) to yield a clear oil (8.63 g, 100%). $^1$H NMR ($CDCl_3$): δ 8.49 (dd, 1H, J=4.8, J'=2.2), 8.09 (dd, 1H, J=7.7, J'=1.8), 7.36 (m, 1H), 3.97 (s, 3H).

Part C. Preparation of 3-cyanophenylboronic Acid.

3-Bromobenzonitrile (10.0 g, 55 mmol) was dissolved in dry THF (100 mL) and cooled to $-100°$ C. ($Et_2O/N_2$). n-Butyllithium (24.2 mL, 2.5 M in hexane) was added over 30 minutes, maintaining the internal temp under $-90°$. After 20 minutes, triisopropylborate (18.0 mL) was added over 15 minutes, again maintaining the internal temperature. After the addition was complete, the reaction was allowed to warm slowly to room temperature over 1.5 hours. The reaction was stirred at room temp for 16 hours, then cooled to 15° C., after which 6 M HCl (25 mL) was added. After stirring vigorously for 3.5 hours, the reaction was partitioned between water and EtOAc. After extracting a second time with EtOAc, the combined organics were washed with 2 M NaOH. The aqueous extract was neutralized with 6 M HCl. The white precipitate was filtered, yielding the desired product (4.80 g, 60%). $^1$H NMR (DMSO-$d_6$): δ 8.37 (s, 2H), 8.10 (s, 1H), 8.03 (dt, 1H, J=7.3, J'=1.1), 7.83 (dt, 1H, J=7.6, J'=1.4), 7.53 (t, 1H, J=7.7).

Part D. Preparation of methyl 2-(3'-cyanophenyl)nicotinate.

Methyl 2-bromonicotinate (2.0 g, 9.3 mmol) and 3-cyanophenylboronic acid (2.7 g, 18.4 mmol) were combined in 190 mL benzene. Sodium carbonate (19 mL of a 2 M aqueous solution), tetrabutylammonium bromide (152 mg, 0.5 mmol), and bis(triphenylphosphine)palladium(II) chloride (325 mg, 0.5 mmol) were added. The entire mixture was evacuated to remove dissolved gasses, then placed under argon. The reaction was refluxed for 14 hours, diluted with water and EtOAc, separated, dried over $Na_2SO_4$, filtered, and evaporated. The resulting yellow solid was chromatographed on silica gel (30% EtOAc/hexanes) to yield a light yellow solid (1.70 g, 77%). $^1$H NMR (CDCl$_3$): δ 8.81 (dd, 1H, J=4.8, J'=1.8), 8.23 (dd, 1H, J=8.0, J'=1.9), 7.85 (s, 1H), 7.73 (m, 2H), 7.55 (t, 1H, J=7.7), 7.43 (m, 1H), 3.76 (s, 3H).

Part E. Preparation of 2-(t-butylaminosulfonyl) phenylboronic Acid.

To a solution of 206.5 g (0.968 mol) of benzene-(N-t-butyl)sulfonamide in 2500 mL of THF under N$_2$ was added 790 mL (1.98 mol) of 2.5M n-butyllithium in hexane over 35 minutes, keeping the temperature between 0–5° C. The reaction mixture was allowed to warm to 10° C., at which time a thick precipitate formed. Triisopropylborate (305 mL, 1.32 mol) was added keeping the temperature below 35° C. After 1 hour, the reaction mixture was cooled, 1N HCl (1570 mL) was added, and the mixture was stirred overnight. The mixture was extracted with 400 mL of ether three times, and the combined organic extracts were extracted with 500 mL of 1N NaOH three times. The aqueous extracts were acidified to pH 1 with 6N HCl, and then extracted with 500 mL ether three times. The combined ether extracts were dried over MgSO$_4$, and the solvents evaporated in vacuo until the volume was 700 mL. Hexane (150 mL) was added and overnight, a white precipitate formed. The solid was collected and washed with 10% ether/hexane (250 mL), then dried in vacuo to give 216.3 g (87%) of the desired compound as white crystals. m.p. 118–119° C.; $^1$H NMR (CDCl$_3$): δ 8.00 (d, 1H); 7.82 (d, 1H); 7.53 (m, 2H); 6.29 (br s, 2H); 5.13 (s, 1H); 1.18 (s, 9H).

Part F. Preparation of 4-amino-21-t-butylaminosulfonyl-[1, 1']biphenyl.

A mixture of 3.44 g (20 mmol) of 4-bromoaniline and 5.14 g (20 mmol) of 2-(t-butylaminosulfonyl)phenylboronic acid, 1.16 g of tetrakis(triphenylphosphine) palladium(O) (1 mmol), 0.32 g of tetrabutylammonium bromide (1 mmol) and 20 mL of 2M aqueous sodium carbonate were refluxed with 180 mL of benzene under N$_2$ for 5.5 hours. After cooling, the mixture was diluted with methylene chloride and water. The two phases were separated and the organic phase was washed with water, dried with MgSO$_4$ and concentrated in vacuo. The resulting thick oil was chromatographed on silica with 30% EtOAc/hexane to afford 2.52 g (41%) of the aniline. $^1$H NMR (CDCl$_3$): δ 8.14 (d, 1H); 7.53 (t, 1H); 7.43 (t, 1H); 7.33 (d, 2H); 7.27 (d, 1H); 6.76 (d, 2H); 3.7 (br s, 1H); 0.99 (s, 9H).

Part G. Preparation of N-(2'-t-butylaminosulfonyl-[1,1'] biphen-4-yl) -2-(3'-cyanophenyl)nicotinamide.

Methyl 2-(3'-cyanophenyl)nicotinate (300 mg, 1.3 mmol) was combined with of 4-amino-2'-t-butylaminosulfonyl-[1, 1']biphenyl (383 mg, 1.3 mmol) in 12 mL dry CH$_2$Cl$_2$. A solution of trimethylaluminum (3.8 mL, 2.0 M in heptane) was added, and an exothermic reaction immediately occurred and the mixture darkened. The resulting solution was stirred at room temperature under argon for 3 days and then quenched carefully with a few drops of 1 M HCl. An emulsion was obtained on dilution with EtOAc and water. The layers were separated, and the organic was extracted again with water and brine, dried over Na$_2$SO$_4$, filtered, and evaporated. A small amount of additional material was obtained from the aqueous extract by adjusting the pH to 8 with sat. NaHCO$_3$ and extracting with EtOAc. This material was dried over Na$_2$SO$_4$, filtered, evaporated, and combined with the previous extract for chromatography on silica gel (50–60% EtOAc/hexanes) to yield the desired product (190 mg, 30%). $^1$H NMR (CDCl$_3$): δ 8.86 (dd, 1H, J=4.7, J'=1.9), 8.14 (m, 3H), 8.00 (d, 1H, J=7.7), 7.73 (d, 1H, J=8.1), 7.50 (m, 9H), 7.29 (dd, 1H, J=7.4, J'=1.1), 3.60 (s, 1H), 1.02 (s, 9H).

Part H. Preparation of N-(2'-aminosulfonyl-[1,1']biphen-4-yl)-2-(3'-amidinophenyl)nicotinamide, trifluoroacetic acid Salt.

N-(2'-t-butylaminosulfonyl-[1,1']biphen-4-yl)-2-(3'-cyanophenyl)nicotinamide (190 mg, 0.37 mmol) was dissolved in dry MeOH (10 mL) and cooled to 0° C. HCl(g) was generated by the addition of concentrated H$_2$SO$_4$ (60 mL) to NaCl (240 g) over 40 minutes and was bubbled into the reaction mixture. The gas was permitted to continue bubbling through the reaction for 3 hours after the H$_2$SO$_4$ addition was complete. At this point, the HCl generator and ice bath were removed, and the reaction stirred under argon for 19 hours. This solution was then evaporated, placed under high vacuum, and redissolved in dry MeOH (10 mL). Ammonium carbonate (200 mg) was added, stirred for 24 hours under argon, and evaporated. The product was purified by preparative HPLC on a C-18 reverse phase column (10–70% MeCN/H$_2$O/0.05% TFA), yielding a white powder (140 mg, 54%). $^1$H NMR (DMSO-d$_6$): δ 10.65 (s, 1H), 9.38 (s, 2H), 8.92 (s, 2H), 8.81 (dd, 1H, J=4.4, J'=1.4), 8.10 (m, 2H), 7.97 (m, 2H), 7.76 (m, 1H), 7.67 (t, 1H, J=8.0), 7.57 (m, 5H), 7.29 (m, 5H). HRMS calc. for C$_{25}$H$_{22}$N$_5$O$_3$S: m/z 472.1443; found, 472.1457.

Examples 2, 3 and 4

N-[5-(2-aminosulfonyl)phenylpyrid-2-yl]-2-(3'-amidinophenyl)nicotinamide, trifluoroacetic acid salt (Example 2), N-[5-(2-t-butylaminosulfonyl) phenylpyrid-2-yl]-2-(3'-amidinophenyl) nicotinamide, trifluoroacetic acid salt (Example 3), and N-[5-(2-aminosulfonyl)phenylpyrid-2-yl]-2-(3'-carboxamidophenyl)nicotinanside, trifluoroacetic acid salt Example 4

Part A. Preparation of 2-(3'-cyanophenyl)nicotinic acid.

Methyl 2-(3'-cyanophenyl)nicotinate (1.21 g, 5.1 mmol) was partially dissolved in MeOH (40 mL), and lithium hydroxide monohydrate (234 mg dissolved in 6 mL H$_2$O, 5.6 mmol) was added. After 20 hours, the resulting solution was diluted with water and extracted with CHCl$_3$. The aqueous was acidified to pH 4 with 1 M HCl and extracted several times with CHCl$_3$. Solid sodium chloride was added to the aqueous solution and the solution was extracted with 5–10% MeOH/CHCl$_3$. The organic extracts were combined, dried over Na$_2$SO$_4$, filtered, and evaporated to yield a white solid (1.06 g, 93%).

$^1$H NMR (CDCl$_3$): δ 8.85 (dd, 1H, J=5.1, J'=1.5), 8.35 (dd, 1H, J=7.6, J'=1.4), 7.84 (s, 1H), 7.75 (m, 2H), 7.55 (t, 1H, J=7.7), 7.47 (m, 1H).

Part B. Preparation of 2-amino-5-(2-t-butylaminosulfonyl) phenylpyridine.

A mixture of 1.55 g (9.0 mmol) of 2-amino-5-bromopyridine and 2.3 g (9.0 mmol) of 2-(t-butylaminosulfonyl)phenylboronic acid, 0.52 g of tetrakis (triphenylphosphine) palladium(O) (0.45 mmol), 0.15 g of tetrabutylammonium bromide (0.45 mmol) and 9 mL of 2M aqueous sodium carbonate were refluxed with 80 mL of benzene under Ar for 5 hours. After cooling, the mixture was diluted with 25 mL of methylene chloride and 25 mL of water. The two phases were separated and the organic phase was washed with water, dried with MgSO$_4$ and concentrated in vacuo. The resulting thick oil was chromatographed on silica with 50% EtOAc/hexane to afford 1.34 g (49%) of the aniline.

$^1$H NMR (CDCl$_3$): δ 8.18 (d, 1H); 8.07 (m, 1H); 7.70 (dd, 1H); 7.58 (dt, 1H); 7.48 (dt, 1H); 7.28 (d, 1H); 6.56 (d, 1H); 4.62 (br s, 2H); 3.88 (br s, 1H); 1.06 (s, 9H).

Part C. Preparation of N-[5-(2-t-butylaminosulfonyl) phenylpyrid-2-yl]-2-(3'-cyanophenyl)nicotinamide.

2-(3'-cyanophenyl)nicotinic acid (300 mg, 1.3 mmol) was suspended in 5 mL dry $CH_2Cl_2$, and oxalyl chloride (175 μl, 2.0 mmol) was added, followed by 2 drops of dry DES. The reaction stirred at room temperature under argon for 2 hours and then evaporated. This solid was redissolved in 8 mL dry $CH_2Cl_2$, and dimethylaminopyridine (490 mg, 4.0 mmol) was added, followed by 2-amino-5-(2-t-butylaminosulfonyl) phenylpyridine (410 mg, 1.3 mmol). The reaction was stirred 3 days at room temperature, diluted with $CH_2Cl_2$, extracted with saturated $NaHCO_3$, dried over $Na_2SO_4$, filtered, and evaporated. The resulting material was chromatographed on silica gel (50–75% EtOAc/hexanes) to yield the desired product (423 mg, 62%).

$^1$H NMR ($CDCl_3$): δ 8.83 (dd, 1H, J=4.8, J'=1.5), 8.40 (bs, 1H), 8.29 (bd, 1H, J=8.4), 8.17 (dd, 1H), J=8.0, J'=1.1), 8.09 (m, 3H), 7.97 (d, 1H, J=7.7), 7.79 (d, 1H, J=8.4), 7.69 (d, 1H, J=7.7), 7.54 (m, 4H), 7.25 (m, 1H), 4.19 (bs, 1H), 1.08 (s, 9H).

Part D. Preparation of N-[5-(2-aminosulfonyl)phenylpyrid-2-yl]-2-(3'-amidinophenyl)nicotinamide, trifluoroacetic acid salt (Example 2), N-[5-(2-t-butylaminosulfonyl) phenylpyrid-2-yl]-2-(3'-amidinophenyl)nicotinamide, trifluoroacetic acid salt (Example 3), and N-[5-(2-aminosulfonyl)phenylpyrid-2-yl]-2-(3'-carboxamidophenyl)nicotinamide, trifluoroacetic acid salt (Example 4).

N-[5-(2-t-butylaminosulfonyl)phenylpyrid-2-yl]-2-(3'-cyanophenyl)nicotinamide (410 mg, 1.03) was dissolved in a mixture of dry MeOH (5 mL) and dry $CHCl_3$ (15 mL) and cooled to 0° C. HCl(g) was generated by the addition of concentrated $H_2SO_4$ (45 mL) to NaCl (220 g) over 55 min and was bubbled into the reaction mixture. The HCl generator and ice bath were removed, and the reaction was stirred under argon for 16 hours and evaporated. The resulting solid was redissolved in dry MeOH (15 mL), and ammonium carbonate (385 mg) was added. The reaction was stirred 19 hours at room temperature under argon and evaporated. The resulting solid was purified by preparative HPLC on a C-18 reverse phase column (5–70% MeCN/$H_2O$/0.05% TFA) to yield N-[5-(2-aminosulfonyl) phenylpyrid-2-yl]-2-(3'-amidinophenyl)nicotinamide, trifluoroacetic acid salt (Example 2), (250 mg, 45%). $^1$H NMR (DMSO-$d_6$): δ 11.27 (s, 1H), 9.43 (s, 2H), 8.98 (s, 2H), 8.83 (dd, 1H, J=4.8, J'=1.9), 8.32 (s, 1H), 8.13 (m, 2H), 8.05 (m, 2H), 7.96 (d, 1H, J=7.3), 7.81 (d, 2H, J=8.4), 7.65 (m, 4H), 7.47 (s, 2H), 7.37 (m, 1H). HRMS calc. for $C_{24}H_{21}N_6O_3S$: m/z 473.1396; found, 473.1397. A second product, N-[5-(2-t-butylaminosulfonyl)-phenylpyrid-2-yl]-2-(3'-amidinophenyl)nicotinamide, trifluoroacetic acid salt (Example 3), was also obtained (58 mg, 10%). $^1$H NMR (DMSO-$d_6$): δ 9.7 (s, 1H), 9.41 (s, 2H), 8.95 (s, 2H), 8.82 (m, 1H), 8.28 (s, 1H), 8.09 (m, 4H), 7.95 (d, 1H, J=7.7), 7.79 (m, 2H), 7.63 (m, 4H), 7.34 (d, 1H, J=7.7), 7.18 (s, 1H), 1.04 (s, 9H). HRMS calc. for $C_{28}H_{29}N_6O_3S$: 529.2022; found, 529.2050. A third product, N-[5-(2-aminosulfonyl) phenylpyrid-2-yl]-2-(3'-carboxamidophenyl)nicotinamide, trifluoroacetic acid salt (Example 4) was isolated and chromatographed on silica gel (10–20% MeOH/$CHCl_3$) to yield a white solid (77 mg, 20%). $^1$H NMR (DMSO-$d_6$): δ 11.13 (s, 1H), 8.75 (dd, 1H, J=4.8, J'=1.9), 8.26 (m, 2H), 8.02 (m, 4H), 7.84 (d, 1H, J=7.7), 7.74 (m, 2H), 7.59 (m, 2H), 7.47 (m, 2H), 7.36 (m, 4H).

TABLE 1

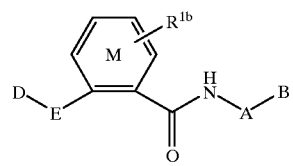

| Ex | D | $R_2$ | A' | MS $(M + H)^+$ |
|---|---|---|---|---|
| 1 | C(=NH)$NH_2$ | $SO_2NH_2$ | CH | 472.1 |
| 2 | C(=NH)$NH_2$ | $SO_2NH_2$ | N | 473.1 |
| 3 | C(=NH)$NH_2$ | $SO_2$NHtBu | N | 529.2 |
| 4 | C(O)$NH_2$ | $SO_2NH_2$ | N | 474.1 |

The following table contains representative examples of the present invention. Each entry in the table is intended to be paired with each formulae at the start of the table. For example, example 1 in Table 2 is intended to be paired with each of formulae $a_1$-$ss_4$.

TABLE 2

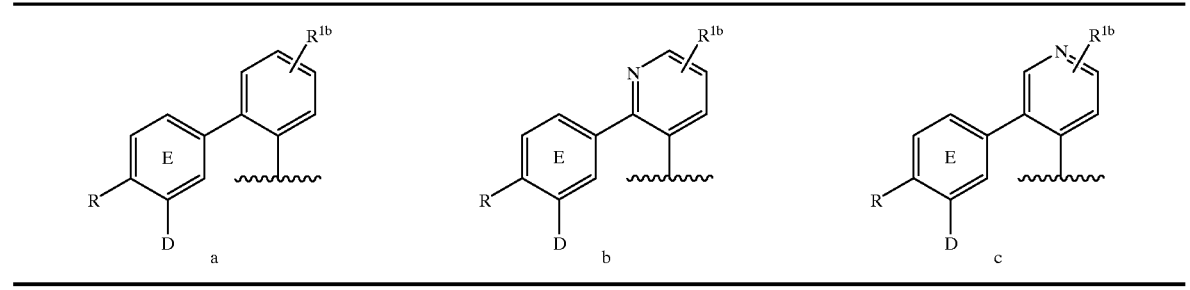

TABLE 2-continued

[Structure: benzamide core with substituents R¹ᵇ on ring M, D-E group, and C(=O)-NH-A-B amide]

| | | | | | |
|---|---|---|---|---|---|
| $a_1$ | R = F, D = NH$_2$ | $b_1$ | R = F, D = NH$_2$ | $c_1$ | R = F, D = NH$_2$ |
| $a_2$ | R = H, D = NH$_2$ | $b_2$ | R = H, D = NH$_2$ | $c_2$ | R = H, D = NH$_2$ |
| $a_3$ | R = F, D = CH$_2$NH$_2$ | $b_3$ | R = F, D = CH$_2$NH$_2$ | $c_3$ | R = F, D = CH$_2$NH$_2$ |
| $a_4$ | R = H, D = CH$_2$NH$_2$ | $b_4$ | R = H, D = CH$_2$NH$_2$ | $c_4$ | R = H, D = CH$_2$NH$_2$ |
| $a_5$ | R = F, D = C(=NH)NH$_2$ | $b_5$ | R = F, D = C(=NH)NH$_2$ | $c_5$ | R = F, D = C(=NH)NH$_2$ |
| $a_6$ | R = H, D = C(=NH)NH$_2$ | $b_6$ | R = H, D = C(=NH)NH$_2$ | $c_6$ | R = H, D = C(=NH)NH$_2$ |
| $a_7$ | R = F, D = C(O)NH$_2$ | $b_7$ | R = F, D = C(O)NH$_2$ | $c_7$ | R = F, D = C(O)NH$_2$ |
| $a_8$ | R = H, D = C(O)NH$_2$ | $b_8$ | R = H, D = C(O)NH$_2$ | $c_8$ | R = H, D = C(O)NH$_2$ |

[Structures d, e, f: phenyl-pyridine/pyridazine variants with R¹ᵇ]

| | | | | | |
|---|---|---|---|---|---|
| $d_1$ | R = F, D = NH$_2$ | $e_1$ | R = F, D = NH$_2$ | $f_1$ | R = F, D = NH$_2$ |
| $d_2$ | R = H, D = NH$_2$ | $e_2$ | R = H, D = NH$_2$ | $f_2$ | R = H, D = NH$_2$ |
| $d_3$ | R = F, D = CH$_2$NH$_2$ | $e_3$ | R = F, D = CH$_2$NH$_2$ | $f_3$ | R = F, D = CH$_2$NH$_2$ |
| $d_4$ | R = H, D = CH$_2$NH$_2$ | $e_4$ | R = H, D = CH$_2$NH$_2$ | $f_4$ | R = H, D = CH$_2$NH$_2$ |
| $d_5$ | R = F, D = C(=NH)NH$_2$ | $e_5$ | R = F, D = C(=NH)NH$_2$ | $f_5$ | R = F, D = C(=NH)NH$_2$ |
| $d_6$ | R = H, D = C(=NH)NH$_2$ | $e_6$ | R = H, D = C(=NH)NH$_2$ | $f_6$ | R = H, D = C(=NH)NH$_2$ |
| $d_7$ | R = F, D = C(O)NH$_2$ | $e_7$ | R = F, D = C(O)NH$_2$ | $f_7$ | R = F, D = C(O)NH$_2$ |
| $d_8$ | R = H, D = C(O)NH$_2$ | $e_8$ | R = H, D = C(O)NH$_2$ | $f_8$ | R = H, D = C(O)NH$_2$ |

[Structures g, h, i: phenyl-pyrimidine/pyrazine variants with R¹ᵇ]

| | | | | | |
|---|---|---|---|---|---|
| $g_1$ | R = F, D = NH$_2$ | $h_1$ | R = F, D = NH$_2$ | $i_1$ | R = F, D = NH$_2$ |
| $g_2$ | R = H, D = NH$_2$ | $h_2$ | R = H, D = NH$_2$ | $i_2$ | R = H, D = NH$_2$ |
| $g_3$ | R = F, D = CH$_2$NH$_2$ | $h_3$ | R = F, D = CH$_2$NH$_2$ | $i_3$ | R = F, D = CH$_2$NH$_2$ |
| $g_4$ | R = H, D = CH$_2$NH$_2$ | $h_4$ | R = H, D = CH$_2$NH$_2$ | $i_4$ | R = H, D = CH$_2$NH$_2$ |
| $g_5$ | R = F, D = C(=NH)NH$_2$ | $h_5$ | R = F, D = C(=NH)NH$_2$ | $i_5$ | R = F, D = C(=NH)NH$_2$ |
| $g_6$ | R = H, D = C(=NH)NH$_2$ | $h_6$ | R = H, D = C(=NH)NH$_2$ | $i_6$ | R = H, D = C(=NH)NH$_2$ |
| $g_7$ | R = F, D = C(O)NH$_2$ | $h_7$ | R = F, D = C(O)NH$_2$ | $i_7$ | R = F, D = C(O)NH$_2$ |
| $g_8$ | R = H, D = C(O)NH$_2$ | $h_8$ | R = H, D = C(O)NH$_2$ | $i_8$ | R = H, D = C(O)NH$_2$ |

[Structures j, k, l: phenyl-pyrimidine/pyridazine/triazine variants with R¹ᵇ]

| | | | | | |
|---|---|---|---|---|---|
| $j_1$ | R = F, D = NH$_2$ | $k_1$ | R = F, D = NH$_2$ | $l_1$ | R = F, D = NH$_2$ |
| $j_2$ | R = H, D = NH$_2$ | $k_2$ | R = H, D = NH$_2$ | $l_2$ | R = H, D = NH$_2$ |
| $j_3$ | R = F, D = CH$_2$NH$_2$ | $k_3$ | R = F, D = CH$_2$NH$_2$ | $l_3$ | R = F, D = CH$_2$NH$_2$ |

TABLE 2-continued

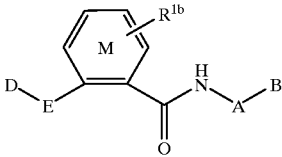

| | | | | | |
|---|---|---|---|---|---|
| j₄ | R = H, D = CH₂NH₂ | k₄ | R = H, D = CH₂NH₂ | l₄ | R = H, D = CH₂NH₂ |
| j₅ | R = F, D = C(=NH)NH₂ | k₅ | R = F, D = C(=NH)NH₂ | l₅ | R = F, D = C(=NH)NH₂ |
| j₆ | R = H, D = C(=NH)NH₂ | k₆ | R = H, D = C(=NH)NH₂ | l₆ | R = H, D = C(=NH)NH₂ |
| j₇ | R = F, D = C(O)NH₂ | k₇ | R = F, D = C(O)NH₂ | l₇ | R = F, D = C(O)NH₂ |
| j₈ | R = H, D = C(O)NH₂ | k₈ | R = H, D = C(O)NH₂ | l₈ | R = H, D = C(O)NH₂ |

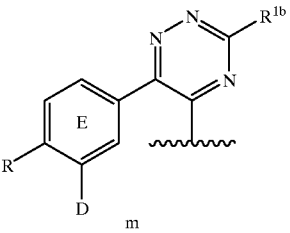 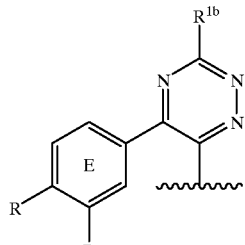 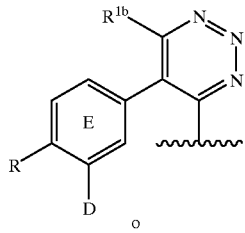

m  n  o

| | | | | | |
|---|---|---|---|---|---|
| m₁ | R = F, D = NH₂ | n₁ | R = F, D = NH₂ | o₁ | R = F, D = NH₂ |
| m₂ | R = H, D = NH₂ | n₂ | R = H, D = NH₂ | o₂ | R = H, D = NH₂ |
| m₃ | R = F, D = CH₂NH₂ | n₃ | R = F, D = CH₂NH₂ | o₃ | R = F, D = CH₂NH₂ |
| m₄ | R = H, D = CH₂NH₂ | n₄ | R = H, D = CH₂NH₂ | o₄ | R = H, D = CH₂NH₂ |
| m₅ | R = F, D = C(=NH)NH₂ | n₅ | R = F, D = C(=NH)NH₂ | o₅ | R = F, D = C(=NH)NH₂ |
| m₆ | R = H, D = C(=NH)NH₂ | n₆ | R = H, D = C(=NH)NH₂ | o₆ | R = H, D = C(=NH)NH₂ |
| m₇ | R = F, D = C(O)NH₂ | n₇ | R = F, D = C(O)NH₂ | o₇ | R = F, D = C(O)NH₂ |
| m₈ | R = H, D = C(O)NH₂ | n₈ | R = H, D = C(O)NH₂ | o₈ | R = H, D = C(O)NH₂ |

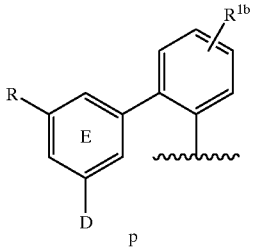 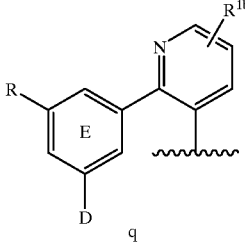 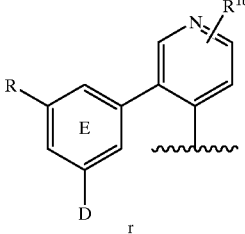

p  q  r

| | | | | | |
|---|---|---|---|---|---|
| p₁ | R = F, D = NH₂ | q₁ | R = F, D = NH₂ | r₁ | R = F, D = NH₂ |
| p₂ | R = Cl, D = NH₂ | q₂ | R = Cl, D = NH₂ | r₂ | R = Cl, D = NH₂ |
| p₃ | R = OMe, D = NH₂ | q₃ | R = OMe, D = NH₂ | r₃ | R = OMe, D = NH₂ |
| p₄ | R = F, D = CH₂NH₂ | q₄ | R = F, D = CH₂NH₂ | r₄ | R = F, D = CH₂NH₂ |
| p₅ | R = Cl, D = CH₂NH₂ | q₅ | R = Cl, D = CH₂NH₂ | r₅ | R = Cl, D = CH₂NH₂ |
| p₆ | R = OMe, D = CH₂NH₂ | q₆ | R = OMe, D = CH₂NH₂ | r₆ | R = OMe, D = CH₂NH₂ |
| p₇ | R = F, D = C(=NH)NH₂ | q₇ | R = F, D = C(=NH)NH₂ | r₇ | R = F, D = C(=NH)NH₂ |
| p₈ | R = Cl, D = C(=NH)NH₂ | q₈ | R = Cl, D = C(=NH)NH₂ | r₈ | R = Cl, D = C(=NH)NH₂ |
| p₉ | R = OMe, D = C(=NH)NH₂ | q₉ | R = OMe, D = C(=NH)NH₂ | r₉ | R = OMe, D = C(=NH)NH₂ |
| p₁₀ | R = F, D = C(O)NH₂ | q₁₀ | R = F, D = C(O)NH₂ | r₁₀ | R = F, D = C(O)NH₂ |
| p₁₁ | R = Cl, D = C(O)NH₂ | q₁₁ | R = Cl, D = C(O)NH₂ | r₁₁ | R = Cl, D = C(O)NH₂ |
| p₁₂ | R = OMe, D = C(O)NH₂ | q₁₂ | R = OMe, D = C(O)NH₂ | r₁₂ | R = OMe, D = C(O)NH₂ |

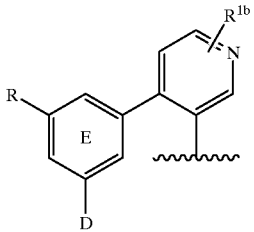 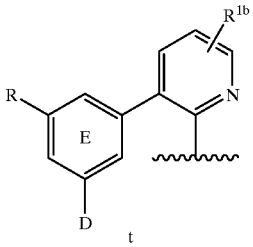 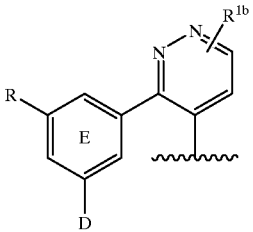

s  t  u

| | | | | | |
|---|---|---|---|---|---|
| s₁ | R = F, D = NH₂ | t₁ | R = F, D = NH₂ | u₁ | R = F, D = NH₂ |

TABLE 2-continued

[Structure: benzamide with M ring bearing R^1b, D-E substituent, and N-H-A-B amide]

| | | | | | |
|---|---|---|---|---|---|
| s₂ | R = Cl, D = NH₂ | t₂ | R = Cl, D = NH₂ | u₂ | R = Cl, D = NH₂ |
| s₃ | R = OMe, D = NH₂ | t₃ | R = OMe, D = NH₂ | u₃ | R = OMe, D = NH₂ |
| s₄ | R = F, D = CH₂NH₂ | t₄ | R = F, D = CH₂NH₂ | u₄ | R = F, D = CH₂NH₂ |
| s₅ | R = Cl, D = CH₂NH₂ | t₅ | R = Cl, D = CH₂NH₂ | u₅ | R = Cl, D = CH₂NH₂ |
| s₆ | R = OMe, D = CH₂NH₂ | t₆ | R = OMe, D = CH₂NH₂ | u₆ | R = OMe, D = CH₂NH₂ |
| s₇ | R = F, D = C(=NH)NH₂ | t₇ | R = F, D = C(=NH)NH₂ | u₇ | R = F, D = C(=NH)NH₂ |
| s₈ | R = Cl, D = C(=NH)NH₂ | t₈ | R = Cl, D = C(=NH)NH₂ | u₈ | R = Cl, D = C(=NH)NH₂ |
| s₉ | R = OMe, D = C(=NH)NH₂ | t₉ | R = OMe, D = C(=NH)NH₂ | u₉ | R = OMe, D = C(=NH)NH₂ |
| s₁₀ | R = F, D = C(O)NH₂ | t₁₀ | R = F, D = C(O)NH₂ | u₁₀ | R = F, D = C(O)NH₂ |
| s₁₁ | R = Cl, D = C(O)NH₂ | t₁₁ | R = Cl, D = C(O)NH₂ | u₁₁ | R = Cl, D = C(O)NH₂ |
| s₁₂ | R = OMe, D = C(O)NH₂ | t₁₂ | R = OMe, D = C(O)NH₂ | u₁₂ | R = OMe, D = C(O)NH₂ |

[Structures v, w, x: phenyl-pyrimidine/pyrazine/pyridazine variants with R, D substituents and R^1b]

v, w, x

| | | | | | |
|---|---|---|---|---|---|
| v₁ | R = F, D = NH₂ | w₁ | R = F, D = NH₂ | x₁ | R = F, D = NH₂ |
| v₂ | R = Cl, D = NH₂ | w₂ | R = Cl, D = NH₂ | x₂ | R = Cl, D = NH₂ |
| v₃ | R = OMe, D = NH₂ | w₃ | R = OMe, D = NH₂ | x₃ | R = OMe, D = NH₂ |
| v₄ | R = F, D = CH₂NH₂ | w₄ | R = F, D = CH₂NH₂ | x₄ | R = F, D = CH₂NH₂ |
| v₅ | R = Cl, D = CH₂NH₂ | w₅ | R = Cl, D = CH₂NH₂ | x₅ | R = Cl, D = CH₂NH₂ |
| v₆ | R = OMe, D = CH₂NH₂ | w₆ | R = OMe, D = CH₂NH₂ | x₆ | R = OMe, D = CH₂NH₂ |
| v₇ | R = F, D = C(=NH)NH₂ | w₇ | R = F, D = C(=NH)NH₂ | x₇ | R = F, D = C(=NH)NH₂ |
| v₈ | R = Cl, D = C(=NH)NH₂ | w₈ | R = Cl, D = C(=NH)NH₂ | x₈ | R = Cl, D = C(=NH)NH₂ |
| v₉ | R = OMe, D = C(=NH)NH₂ | w₉ | R = OMe, D = C(=NH)NH₂ | x₉ | R = OMe, D = C(=NH)NH₂ |
| v₁₀ | R = F, D = C(O)NH₂ | w₁₀ | R = F, D = C(O)NH₂ | x₁₀ | R = F, D = C(O)NH₂ |
| v₁₁ | R = Cl, D = C(O)NH₂ | w₁₁ | R = Cl, D = C(O)NH₂ | x₁₁ | R = Cl, D = C(O)NH₂ |
| v₁₂ | R = OMe, D = C(O)NH₂ | w₁₂ | R = OMe, D = C(O)NH₂ | x₁₂ | R = OMe, D = C(O)NH₂ |

[Structures y, z, aa: phenyl-pyrimidine/pyridazine/triazine variants with R, D substituents and R^1b]

y, z, aa

| | | | | | |
|---|---|---|---|---|---|
| y₁ | R = F, D = NH₂ | z₁ | R = F, D = NH₂ | aa₁ | R = F, D = NH₂ |
| y₂ | R = Cl, D = NH₂ | z₂ | R = Cl, D = NH₂ | aa₂ | R = Cl, D = NH₂ |
| y₃ | R = OMe, D = NH₂ | z₃ | R = OMe, D = NH₂ | aa₃ | R = OMe, D = NH₂ |
| y₄ | R = F, D = CH₂NH₂ | z₄ | R = F, D = CH₂NH₂ | aa₄ | R = F, D = CH₂NH₂ |
| y₅ | R = Cl, D = CH₂NH₂ | z₅ | R = Cl, D = CH₂NH₂ | aa₅ | R = Cl, D = CH₂NH₂ |
| y₆ | R = OMe, D = CH₂NH₂ | z₆ | R = OMe, D = CH₂NH₂ | aa₆ | R = OMe, D = CH₂NH₂ |
| y₇ | R = F, D = C(=NH)NH₂ | z₇ | R = F, D = C(=NH)NH₂ | aa₇ | R = F, D = C(=NH)NH₂ |
| y₈ | R = Cl, D = C(=NH)NH₂ | z₈ | R = Cl, D = C(=NH)NH₂ | aa₈ | R = Cl, D = C(=NH)NH₂ |
| y₉ | R = OMe, D = C(=NH)NH₂ | z₉ | R = OMe, D = C(=NH)NH₂ | aa₉ | R = OMe, D = C(=NH)NH₂ |
| y₁₀ | R = F, D = C(O)NH₂ | z₁₀ | R = F, D = C(O)NH₂ | aa₁₀ | R = F, D = C(O)NH₂ |
| y₁₁ | R = Cl, D = C(O)NH₂ | z₁₁ | R = Cl, D = C(O)NH₂ | aa₁₁ | R = Cl, D = C(O)NH₂ |
| y₁₂ | R = OMe, D = C(O)NH₂ | z₁₂ | R = OMe, D = C(O)NH₂ | aa₁₂ | R = OMe, D = C(O)NH₂ |

TABLE 2-continued

[Structure: M ring with R^1b, D-E substituent, C(=O)NH-A-B]

| bb | cc | dd |
|---|---|---|
| bb₁ R = F, D = NH₂ | cc₁ R = F, D = NH₂ | dd₁ R = F, D = NH₂ |
| bb₂ R = Cl, D = NH₂ | cc₂ R = Cl, D = NH₂ | dd₂ R = Cl, D = NH₂ |
| bb₃ R = OMe, D = NH₂ | cc₃ R = OMe, D = NH₂ | dd₃ R = OMe, D = NH₂ |
| bb₄ R = F, D = CH₂NH₂ | cc₄ R = F, D = CH₂NH₂ | dd₄ R = F, D = CH₂NH₂ |
| bb₅ R = Cl, D = CH₂NH₂ | cc₅ R = Cl, D = CH₂NH₂ | dd₅ R = Cl, D = CH₂NH₂ |
| bb₆ R = OMe, D = CH₂NH₂ | cc₆ R = OMe, D = CH₂NH₂ | dd₆ R = OMe, D = CH₂NH₂ |
| bb₇ R = F, D = C(=NH)NH₂ | cc₇ R = F, D = C(=NH)NH₂ | dd₇ R = F, D = C(=NH)NH₂ |
| bb₈ R = Cl, D = C(=NH)NH₂ | cc₈ R = Cl, D = C(=NH)NH₂ | dd₈ R = Cl, D = C(=NH)NH₂ |
| bb₉ R = OMe, D = C(=NH)NH₂ | cc₉ R = OMe, D = C(=NH)NH₂ | dd₉ R = OMe, D = C(=NH)NH₂ |
| bb₁₀ R = F, D = C(O)NH₂ | cc₁₀ R = F, D = C(O)NH₂ | dd₁₀ R = F, D = C(O)NH₂ |
| bb₁₁ R = Cl, D = C(O)NH₂ | cc₁₁ R = Cl, D = C(O)NH₂ | dd₁₁ R = Cl, D = C(O)NH₂ |
| bb₁₂ R = OMe, D = C(O)NH₂ | cc₁₂ R = OMe, D = C(O)NH₂ | dd₁₂ R = OMe, D = C(O)NH₂ |

| ee | ff | gg |
|---|---|---|
| ee₁ R = F, D = CH₂NH₂ | ff₁ R = F, D = CH₂NH₂ | gg₁ R = F, D = CH₂NH₂ |
| ee₂ R = Cl, D = CH₂NH₂ | ff₂ R = Cl, D = CH₂NH₂ | gg₂ R = Cl, D = CH₂NH₂ |
| ee₃ R = OMe, D = CH₂NH₂ | ff₃ R = OMe, D = CH₂NH₂ | gg₃ R = OMe, D = CH₂NH₂ |
| ee₄ R = CH₂NH₂, D = CH₂NH₂ | ff₄ R = CH₂NH₂, D = CH₂NH₂ | gg₄ R = CH₂NH₂, D = CH₂NH₂ |

| hh | ii | jj |
|---|---|---|
| hh₁ R = F, D = CH₂NH₂ | ii₁ R = F, D = CH₂NH₂ | jj₁ R = F, D = CH₂NH₂ |
| hh₂ R = Cl, D = CH₂NH₂ | ii₂ R = Cl, D = CH₂NH₂ | jj₂ R = Cl, D = CH₂NH₂ |
| hh₃ R = OMe, D = CH₂NH₂ | ii₃ R = OMe, D = CH₂NH₂ | jj₃ R = OMe, D = CH₂NH₂ |
| hh₄ R = CH₂NH₂, D = CH₂NH₂ | ii₄ R = CH₂NH₂, D = CH₂NH₂ | jj₄ R = CH₂NH₂, D = CH₂NH₂ |

TABLE 2-continued

| | kk | | ll | | mm |
|---|---|---|---|---|---|
| kk₁ | R = F, D = CH₂NH₂ | ll₁ | R = F, D = CH₂NH₂ | mm₁ | R = F, D = CH₂NH₂ |
| kk₂ | R = Cl, D = CH₂NH₂ | ll₂ | R = Cl, D = CH₂NH₂ | mm₂ | R = Cl, D = CH₂NH₂ |
| kk₃ | R = OMe, D = CH₂NH₂ | ll₃ | R = OMe, D = CH₂NH₂ | mm₃ | R = OMe, D = CH₂NH₂ |
| kk₄ | R = CH₂NH₂, D = CH₂NH₂ | ll₄ | R = CH₂NH₂, D = CH₂NH₂ | mm₄ | R = CH₂NH₂, D = CH₂NH₂ |

| | nn | | oo | | pp |
|---|---|---|---|---|---|
| nn₁ | R = F, D = CH₂NH₂ | oo₁ | R = F, D = CH₂NH₂ | pp₁ | R = F, D = CH₂NH₂ |
| nn₂ | R = Cl, D = CH₂NH₂ | oo₂ | R = Cl, D = CH₂NH₂ | pp₂ | R = Cl, D = CH₂NH₂ |
| nn₃ | R = OMe, D = CH₂NH₂ | oo₃ | R = OMe, D = CH₂NH₂ | pp₃ | R = OMe, D = CH₂NH₂ |
| nn₄ | R = CH₂NH₂, D = CH₂NH₂ | oo₄ | R = CH₂NH₂, D = CH₂NH₂ | pp₄ | R = CH₂NH₂, D = CH₂NH₂ |

| | qq | | rr | | ss |
|---|---|---|---|---|---|
| qq₁ | R = F, D = CH₂NH₂ | rr₁ | R = F, D = CH₂NH₂ | ss₁ | R = F, D = CH₂NH₂ |
| qq₂ | R = Cl, D = CH₂NH₂ | rr₂ | R = Cl, D = CH₂NH₂ | ss₂ | R = Cl, D = CH₂NH₂ |
| qq₃ | R = OMe, D = CH₂NH₂ | rr₃ | R = OMe, D = CH₂NH₂ | ss₃ | R = OMe, D = CH₂NH₂ |
| qq₄ | R = CH₂NH₂, D = CH₂NH₂ | rr₄ | R = CH₂NH₂, D = CH₂NH₂ | ss₄ | R = CH₂NH₂, D = CH₂NH₂ |

| Ex # | $R^{1b}$ | A | B | Ex # | $R^{1b}$ | A | B |
|---|---|---|---|---|---|---|---|
| 1 | H | phenyl | 2-(aminosulfonyl)phenyl | 5 | H | phenyl | 4-morpholino |
| 2 | H | phenyl | 2-(methylaminosulfonyl)phenyl | 6 | H | phenyl | 2-(1'-CF₃-tetrazol-2-yl)phenyl |
| 3 | H | phenyl | 1-pyrrolidinocarbonyl | 7 | H | phenyl | 4-morpholinocarbonyl |
| 4 | H | phenyl | 2-(methylsulfonyl)phenyl | 8 | H | 2-pyridyl | 2-(aminosulfonyl)phenyl |

-continued

| Ex # | R$^{1b}$ | A | B |
|---|---|---|---|
| 9 | H | 2-pyridyl | 2-(methylaminosulfonyl)phenyl |
| 10 | H | 2-pyridyl | 1-pyrrolidinocarbonyl |
| 11 | H | 2-pyridyl | 2-(methylsulfonyl)phenyl |
| 12 | H | 2-pyridyl | 4-morpholino |
| 13 | H | 2-pyridyl | 2-(1'-CF$_3$-tetrazol-2-yl)phenyl |
| 14 | H | 2-pyridyl | 4-morpholinocarbonyl |
| 15 | H | 3-pyridyl | 2-(aminosulfonyl)phenyl |
| 16 | H | 3-pyridyl | 2-(methylaminosulfonyl)phenyl |
| 17 | H | 3-pyridyl | 1-pyrrolidinocarbonyl |
| 18 | H | 3-pyridyl | 2-(methylsulfonyl)phenyl |
| 19 | H | 3-pyridyl | 4-morpholino |
| 20 | H | 3-pyridyl | 2-(1'-CF$_3$-tetrazol-2-yl)phenyl |
| 21 | H | 3-pyridyl | 4-morpholinocarbonyl |
| 22 | H | 2-pyrimidyl | 2-(aminosulfonyl)phenyl |
| 23 | H | 2-pyrimidyl | 2-(methylaminosulfonyl)phenyl |
| 24 | H | 2-pyrimidyl | 1-pyrrolidinocarbonyl |
| 25 | H | 2-pyrimidyl | 2-(methylsulfonyl)phenyl |
| 26 | H | 2-pyrimidyl | 4-morpholino |
| 27 | H | 2-pyrimidyl | 2-(1'-CF$_3$-tetrazol-2-yl)phenyl |
| 28 | H | 2-pyrimidyl | 4-morpholinocarbonyl |
| 29 | H | 5-pyrimidyl | 2-(aminosulfonyl)phenyl |
| 30 | H | 5-pyrimidyl | 2-(methylaminosulfonyl)phenyl |
| 31 | H | 5-pyrimidyl | 1-pyrrolidinocarbonyl |
| 32 | H | 5-pyrimidyl | 2-(methylsulfonyl)phenyl |
| 33 | H | 5-pyrimidyl | 4-morpholino |
| 34 | H | 5-pyrimidyl | 2-(1'-CF$_3$-tetrazol-2-yl)phenyl |
| 35 | H | 5-pyrimidyl | 4-morpholinocarbonyl |
| 36 | H | 2-Cl-phenyl | 2-(aminosulfonyl)phenyl |
| 37 | H | 2-Cl-phenyl | 2-(methylaminosulfonyl)phenyl |
| 38 | H | 2-Cl-phenyl | 1-pyrrolidinocarbonyl |
| 39 | H | 2-Cl-phenyl | 2-(methylsulfonyl)phenyl |
| 40 | H | 2-Cl-phenyl | 4-morpholino |
| 41 | H | 2-Cl-phenyl | 2-(1'-CF$_3$-tetrazol-2-yl)phenyl |
| 42 | H | 2-Cl-phenyl | 4-morpholinocarbonyl |
| 43 | H | 2-F-phenyl | 2-(aminosulfonyl)phenyl |
| 44 | H | 2-F-phenyl | 2-(methylaminosulfonyl)phenyl |
| 45 | H | 2-F-phenyl | 1-pyrrolidinocarbonyl |
| 46 | H | 2-F-phenyl | 2-(methylsulfonyl)phenyl |
| 47 | H | 2-F-phenyl | 4-morpholino |
| 48 | H | 2-F-phenyl | 2-(1'-CF$_3$-tetrazol-2-yl)phenyl |
| 49 | H | 2-F-phenyl | 4-morpholinocarbonyl |
| 50 | H | 2,5-diF-phenyl | 2-(aminosulfonyl)phenyl |
| 51 | H | 2,5-diF-phenyl | 2-(methylaminosulfonyl)phenyl |
| 52 | H | 2,5-diF-phenyl | 1-pyrrolidinocarbonyl |
| 53 | H | 2,5-diF-phenyl | 2-(methylsulfonyl)phenyl |
| 54 | H | 2,5-diF-phenyl | 4-morpholino |
| 55 | H | 2,5-diF-phenyl | 2-(1'-CF$_3$-tetrazol-2-yl)phenyl |
| 56 | H | 2,5-diF-phenyl | 4-morpholinocarbonyl |
| 57 | H | phenyl | 2-(N-pyrrolidinyl-methyl)phenyl |
| 58 | H | phenyl | 2-(N-piperidinyl-methyl)phenyl |
| 59 | H | phenyl | 2-(N-morpholino-methyl)phenyl |
| 60 | H | phenyl | 2-(N,N'-methylmorpholinium-methyl)phenyl |
| 61 | H | phenyl | 2-(N-pyridinium-methyl)phenyl |
| 62 | H | phenyl | 2-(N-4-(N,N'-dimethylamino)-pyridinium-methyl)phenyl |
| 63 | H | phenyl | 2-(N-azatanyl-methyl)phenyl |
| 64 | H | phenyl | 2-(N-azetidinyl-methyl)phenyl |
| 65 | H | phenyl | 2-(N-piperazinyl-methyl)phenyl |
| 66 | H | phenyl | 2-(N,N'-BOC-piperazinyl-methyl)phenyl |
| 67 | H | phenyl | 2-(N-imidazolyl-methyl)phenyl |
| 68 | H | phenyl | 2-(N-methoxy-N-methylamino-methyl)phenyl |
| 69 | H | phenyl | 2-(N-pyridonyl-methyl)phenyl |
| 70 | H | phenyl | 2-(N-(N',N'-dimethylhydrazinyl-methyl)phenyl |
| 71 | H | phenyl | 2-(amidinyl)phenyl |
| 72 | H | phenyl | 2-(N-guanidinyl)phenyl |
| 73 | H | phenyl | 2-(imidazolyl)phenyl |
| 74 | H | phenyl | 2-(imidazolidinyl)phenyl |
| 75 | H | phenyl | 2-(2-imidazolidinyl-sulfonyl)phenyl |
| 76 | H | phenyl | 2-(2-pyrrolidinyl)phenyl |
| 77 | H | phenyl | 2-(2-piperidinyl)phenyl |
| 78 | H | phenyl | 2-(amidinyl-methyl)phenyl |
| 79 | H | phenyl | 2-(2-imidazolidinyl-methyl)phenyl |
| 80 | H | phenyl | 2-(N-(2-aminoimidazolyl)-methyl)phenyl |
| 81 | H | phenyl | 2-dimethylaminoimidazol-1-yl |
| 82 | H | phenyl | 2-(3-aminophenyl) |
| 83 | H | phenyl | 2-(3-pyrrolidinylcarbonyl) |
| 84 | H | phenyl | 2-glycinoyl |
| 85 | H | phenyl | 2-(imidazol-1-ylacetyl) |
| 86 | H | 2-pyridyl | 2-(N-pyrrolidinyl-methyl)phenyl |
| 87 | H | 2-pyridyl | 2-(N-piperidinyl-methyl)phenyl |
| 88 | H | 2-pyridyl | 2-(N-morpholino-methyl)phenyl |
| 89 | H | 2-pyridyl | 2-(N,N'-methylmorpholinium-methyl)phenyl |
| 90 | H | 2-pyridyl | 2-(N-pyridinium-methyl)phenyl |
| 91 | H | 2-pyridyl | 2-(N-4-(N,N'-dimethylamino)-pyridinium-methyl)phenyl |
| 92 | H | 2-pyridyl | 2-(N-azatanyl-methyl)phenyl |
| 93 | H | 2-pyridyl | 2-(N-azetidinyl-methyl)phenyl |
| 94 | H | 2-pyridyl | 2-(N-piperazinyl-methyl)phenyl |
| 95 | H | 2-pyridyl | 2-(N,N'-BOC-piperazinyl-methyl)phenyl |
| 96 | H | 2-pyridyl | 2-(N-imidazolyl-methyl)phenyl |
| 97 | H | 2-pyridyl | 2-(N-methoxy-N-methylamino-methyl)phenyl |
| 98 | H | 2-pyridyl | 2-(N-pyridonyl-methyl)phenyl |
| 99 | H | 2-pyridyl | 2-(N-(N',N'-dimethylhydrazinyl-methyl)phenyl |
| 100 | H | 2-pyridyl | 2-(amidinyl)phenyl |
| 101 | H | 2-pyridyl | 2-(N-guanidinyl)phenyl |
| 102 | H | 2-pyridyl | 2-(imidazolyl)phenyl |
| 103 | H | 2-pyridyl | 2-(imidazolidinyl)phenyl |
| 104 | H | 2-pyridyl | 2-(2-imidazolidinyl-sulfonyl)phenyl |
| 105 | H | 2-pyridyl | 2-(2-pyrrolidinyl)phenyl |
| 106 | H | 2-pyridyl | 2-(2-piperidinyl)phenyl |
| 107 | H | 2-pyridyl | 2-(amidinyl-methyl)phenyl |
| 108 | H | 2-pyridyl | 2-(2-imidazolidinyl-methyl)phenyl |
| 109 | H | 2-pyridyl | 2-(N-(2-aminoimidazolyl)-methyl)phenyl |
| 110 | H | 2-pyridyl | 2-dimethylaminoimidazol-1-yl |
| 111 | H | 2-pyridyl | 2-(3-aminophenyl) |
| 112 | H | 2-pyridyl | 2-(3-pyrrolidinylcarbonyl) |
| 113 | H | 2-pyridyl | 2-glycinoyl |
| 114 | H | 2-pyridyl | 2-(imidazol-1-ylacetyl) |
| 115 | H | 3-pyridyl | 2-(N-pyrrolidinyl-methyl)phenyl |
| 116 | H | 3-pyridyl | 2-(N-piperidinyl-methyl)phenyl |
| 117 | H | 3-pyridyl | 2-(N-morpholino-methyl)phenyl |
| 118 | H | 3-pyridyl | 2-(N,N'-methylmorpholinium-methyl)phenyl |
| 119 | H | 3-pyridyl | 2-(N-pyridiniuin-methyl)phenyl |
| 120 | H | 3-pyridyl | 2-(N-4-(N,N'-dimethylamino)-pyridinium-methyl)phenyl |
| 121 | H | 3-pyridyl | 2-(N-azatanyl-methyl)phenyl |
| 122 | H | 3-pyridyl | 2-(N-azetidinyl-methyl)phenyl |
| 123 | H | 3-pyridyl | 2-(N-piperazinyl-methyl)phenyl |
| 124 | H | 3-pyridyl | 2-(N,N'-BOC-piperazinyl-methyl)phenyl |
| 125 | H | 3-pyridyl | 2-(N-imidazolyl-methyl)phenyl |
| 126 | H | 3-pyridyl | 2-(N-methoxy-N-methylamino-methyl)phenyl |
| 127 | H | 3-pyridyl | 2-(N-pyridonyl-methyl)phenyl |
| 128 | H | 3-pyridyl | 2-(N-(N',N'-dimethylhydrazinyl-methyl)phenyl |
| 129 | H | 3-pyridyl | 2-(amidinyl)phenyl |
| 130 | H | 3-pyridyl | 2-(N-guanidinyl)phenyl |
| 131 | H | 3-pyridyl | 2-(imidazolyl)phenyl |
| 132 | H | 3-pyridyl | 2-(imidazolidinyl)phenyl |
| 133 | H | 3-pyridyl | 2-(2-imidazolidinyl-sulfonyl)phenyl |
| 134 | H | 3-pyridyl | 2-(2-pyrrolidinyl)phenyl |
| 135 | H | 3-pyridyl | 2-(2-piperidinyl)phenyl |
| 136 | H | 3-pyridyl | 2-(amidinyl-methyl)phenyl |
| 137 | H | 3-pyridyl | 2-(2-imidazolidinyl-methyl)phenyl |
| 138 | H | 3-pyridyl | 2-(N-(2-aminoimidazolyl)-methyl)phenyl |

-continued

| Ex # | R¹ᵇ | A | B |
|---|---|---|---|
| 139 | H | 3-pyridyl | 2-dimethylaminoimidazol-1-yl |
| 140 | H | 3-pyridyl | 2-(3-aminophenyl) |
| 141 | H | 3-pyridyl | 2-(3-pyrrolidinylcarbonyl) |
| 142 | H | 3-pyridyl | 2-glycinoyl |
| 143 | H | 3-pyridyl | 2-(imidazol-1-ylacetyl) |
| 144 | H | 2-pyrimidyl | 2-(N-pyrrolidinyl-methyl)phenyl |
| 145 | H | 2-pyrimidyl | 2-(N-piperidinyl-methyl)phenyl |
| 146 | H | 2-pyrimidyl | 2-(N-morpholino-methyl)phenyl |
| 147 | H | 2-pyrimidyl | 2-(N,N'-methylmorpholinium-methyl)phenyl |
| 148 | H | 2-pyrimidyl | 2-(N-pyridinium-methyl)phenyl |
| 149 | H | 2-pyrimidyl | 2-(N-4-(N,N'-dimethylamino)-pyridinium-methyl)phenyl |
| 150 | H | 2-pyrimidyl | 2-(N-azatanyl-methyl)phenyl |
| 151 | H | 2-pyrimidyl | 2-(N-azetidinyl-methyl)phenyl |
| 152 | H | 2-pyrimidyl | 2-(N-piperazinyl-methyl)phenyl |
| 153 | H | 2-pyrimidyl | 2-(N,N'-BOC-piperazinyl-methyl)phenyl |
| 154 | H | 2-pyrimidyl | 2-(N-imidazolyl-methyl)phenyl |
| 155 | H | 2-pyrimidyl | 2-(N-methoxy-N-methylamino-methyl)phenyl |
| 156 | H | 2-pyrimidyl | 2-(N-pyridonyl-methyl)phenyl |
| 157 | H | 2-pyrimidyl | 2-(N-(N',N'-dimethylhydrazinyl-methyl)phenyl |
| 158 | H | 2-pyrimidyl | 2-(amidinyl)phenyl |
| 159 | H | 2-pyrimidyl | 2-(N-guanidinyl)phenyl |
| 160 | H | 2-pyrimidyl | 2-(imidazolyl)phenyl |
| 161 | H | 2-pyrimidyl | 2-(imidazolidinyl)phenyl |
| 162 | H | 2-pyrimidyl | 2-(2-imidazolidinyl-sulfonyl)phenyl |
| 163 | H | 2-pyrimidyl | 2-(2-pyrrolidinyl)phenyl |
| 164 | H | 2-pyrimidyl | 2-(2-piperidinyl)phenyl |
| 165 | H | 2-pyrimidyl | 2-(amidinyl-methyl)phenyl |
| 166 | H | 2-pyrimidyl | 2-(2-imidazolidinyl-methyl)phenyl |
| 167 | H | 2-pyrimidyl | 2-(N-(2-aminoimidazolyl)-methyl)phenyl |
| 168 | H | 2-pyrimidyl | dimethylaminoimidazol-1-yl |
| 169 | H | 2-pyrimidyl | 2-(3-aminophenyl) |
| 170 | H | 2-pyrimidyl | 2-(3-pyrrolidinylcarbonyl) |
| 171 | H | 2-pyrimidyl | 2-glycinoyl |
| 172 | H | 2-pyrimidyl | 2-(imidazol-1-ylacetyl) |
| 173 | H | 2-Cl-phenyl | 2-(N-pyrrolidinyl-methyl)phenyl |
| 174 | H | 2-Cl-phenyl | 2-(N-piperidinyl-methyl)phenyl |
| 175 | H | 2-Cl-phenyl | 2-(N-morpholino-methyl)phenyl |
| 176 | H | 2-Cl-phenyl | 2-(N,N'-methylmorpholinium-methyl)phenyl |
| 177 | H | 2-Cl-phenyl | 2-(N-pyridinium-methyl)phenyl |
| 178 | H | 2-Cl-phenyl | 2-(N-4-(N,N'-dimethylamino)-pyridinium-methyl)phenyl |
| 179 | H | 2-Cl-phenyl | 2-(N-azatanyl-methyl)phenyl |
| 180 | H | 2-Cl-phenyl | 2-(N-azetidinyl-methyl)phenyl |
| 181 | H | 2-Cl-phenyl | 2-(N-piperazinyl-methyl)phenyl |
| 182 | H | 2-Cl-phenyl | 2-(N,N'-BOC-piperazinyl-methyl)phenyl |
| 183 | H | 2-Cl-phenyl | 2-(N-imidazolyl-methyl)phenyl |
| 184 | H | 2-Cl-phenyl | 2-(N-methoxy-N-methylamino-methyl)phenyl |
| 185 | H | 2-Cl-phenyl | 2-(N-pyridonyl-methyl)phenyl |
| 186 | H | 2-Cl-phenyl | 2-(N-(N',N'-dimethylhydrazinyl-methyl)phenyl |
| 187 | H | 2-Cl-phenyl | 2-(amidinyl)phenyl |
| 188 | H | 2-Cl-phenyl | 2-(N-guanidinyl)phenyl |
| 189 | H | 2-Cl-phenyl | 2-(imidazolyl)phenyl |
| 190 | H | 2-Cl-phenyl | 2-(imidazolidinyl)phenyl |
| 191 | H | 2-Cl-phenyl | 2-(2-imidazolidinyl-sulfonyl)phenyl |
| 192 | H | 2-Cl-phenyl | 2-(2-pyrrolidinyl)phenyl |
| 193 | H | 2-Cl-phenyl | 2-(2-piperidinyl)phenyl |
| 194 | H | 2-Cl-phenyl | 2-(amidinyl-methyl)phenyl |
| 195 | H | 2-Cl-phenyl | 2-(2-imidazolidinyl-methyl)phenyl |
| 196 | H | 2-Cl-phenyl | 2-(N-(2-aminoimidazolyl)-methyl)phenyl |
| 197 | H | 2-Cl-phenyl | 2-dimethylaminoimidazol-1-yl |
| 198 | H | 2-Cl-phenyl | 2-(3-aminophenyl) |
| 199 | H | 2-Cl-phenyl | 2-(3-pyrrolidinylcarbonyl) |
| 200 | H | 2-Cl-phenyl | 2-glycinoyl |
| 201 | H | 2-Cl-phenyl | 2-(imidazol-1-ylacetyl) |
| 202 | H | 2-F-phenyl | 2-(N-pyrrolidinyl-methyl)phenyl |
| 203 | H | 2-F-phenyl | 2-(N-piperidinyl-methyl)phenyl |
| 204 | H | 2-F-phenyl | 2-(N-morpholino-methyl)phenyl |
| 205 | H | 2-F-phenyl | 2-(N,N'-methylmorpholinium-methyl)phenyl |
| 206 | H | 2-F-phenyl | 2-(N-pyridinium-methyl)phenyl |
| 207 | H | 2-F-phenyl | 2-(N-4-(N,N'-dimethylamino)-pyridinium-methyl)phenyl |
| 208 | H | 2-F-phenyl | 2-(N-azatanyl-methyl)phenyl |
| 209 | H | 2-F-phenyl | 2-(N-azetidinyl-methyl)phenyl |
| 210 | H | 2-F-phenyl | 2-(N-piperazinyl-methyl)phenyl |
| 211 | H | 2-F-phenyl | 2-(N,N'-BOC-piperazinyl-methyl)phenyl |
| 212 | H | 2-F-phenyl | 2-(N-imidazolyl-methyl)phenyl |
| 213 | H | 2-F-phenyl | 2-(N-methoxy-N-methylamino-methyl)phenyl |
| 214 | H | 2-F-phenyl | 2-(N-pyridonyl-methyl)phenyl |
| 215 | H | 2-F-phenyl | 2-(N-(N',N'-dimethylhydrazinyl-methyl)phenyl |
| 216 | H | 2-F-phenyl | 2-(amidinyl)phenyl |
| 217 | H | 2-F-phenyl | 2-(N-guanidinyl)phenyl |
| 218 | H | 2-F-phenyl | 2-(imidazolyl)phenyl |
| 219 | H | 2-F-phenyl | 2-(imidazolidinyl)phenyl |
| 220 | H | 2-F-phenyl | 2-(2-imidazolidinyl-sulfonyl)phenyl |
| 221 | H | 2-F-phenyl | 2-(2-pyrrolidinyl)phenyl |
| 222 | H | 2-F-phenyl | 2-(2-piperidinyl)phenyl |
| 223 | H | 2-F-phenyl | 2-(amidinyl-methyl)phenyl |
| 224 | H | 2-F-phenyl | 2-(2-imidazolidinyl-methyl)phenyl |
| 225 | H | 2-F-phenyl | 2-(N-(2-aminoimidazolyl)-methyl)phenyl |
| 226 | H | 2-F-phenyl | 2-dimethylaminoimidazol-1-yl |
| 227 | H | 2-F-phenyl | 2-(3-aminophenyl) |
| 228 | H | 2-F-phenyl | 2-(3-pyrrolidinylcarbonyl) |
| 229 | H | 2-F-phenyl | 2-glycinoyl |
| 230 | H | 2-F-phenyl | 2-(imidazol-1-ylacetyl) |
| 231 | H | 2,5-diF-phenyl | 2-(N-pyrrolidinyl-methyl)phenyl |
| 232 | H | 2,5-diF-phenyl | 2-(N-piperidinyl-methyl)phenyl |
| 233 | H | 2,5-diF-phenyl | 2-(N-morpholino-methyl)phenyl |
| 234 | H | 2,5-diF-phenyl | 2-(N,N'-methylmorpholinium-methyl)phenyl |
| 235 | H | 2,5-diF-phenyl | 2-(N-pyridinium-methyl)phenyl |
| 236 | H | 2,5-diF-phenyl | 2-(N-4-(N,N'-dimethylamino)-pyridinium-methyl)phenyl |
| 237 | H | 2,5-diF-phenyl | 2-(N-azatanyl-methyl)phenyl |
| 238 | H | 2,5-diF-phenyl | 2-(N-azetidinyl-methyl)phenyl |
| 239 | H | 2,5-diF-phenyl | 2-(N-piperazinyl-methyl)phenyl |
| 240 | H | 2,5-diF-phenyl | 2-(N,N'-BOC-piperazinyl-methyl)phenyl |
| 241 | H | 2,5-diF-phenyl | 2-(N-imidazolyl-methyl)phenyl |
| 242 | H | 2,5-diF-phenyl | 2-(N-methoxy-N-methylamino-methyl)phenyl |
| 243 | H | 2,5-diF-phenyl | 2-(N-pyridonyl-methyl)phenyl |
| 244 | H | 2,5-diF-phenyl | 2-(N-(N',N'-dimethylhydrazinyl-methyl)phenyl |
| 245 | H | 2,5-diF-phenyl | 2-(amidinyl)phenyl |
| 246 | H | 2,5-diF-phenyl | 2-(N-guanidinyl)phenyl |
| 247 | H | 2,5-diF-phenyl | 2-(imidazolyl)phenyl |
| 248 | H | 2,5-diF-phenyl | 2-(imidazolidinyl)phenyl |
| 249 | H | 2,5-diF-phenyl | 2-(2-imidazolidinyl-sulfonyl)phenyl |
| 250 | H | 2,5-diF-phenyl | 2-(2-pyrrolidinyl)phenyl |
| 251 | H | 2,5-diF-phenyl | 2-(2-piperidinyl)phenyl |
| 252 | H | 2,5-diF-phenyl | 2-(amidinyl-methyl)phenyl |
| 253 | H | 2,5-diF-phenyl | 2-(2-imidazolidinyl-methyl)phenyl |
| 254 | H | 2,5-diF-phenyl | 2-(N-(2-aminoimidazolyl)-methyl)phenyl |
| 255 | H | 2,5-diF-phenyl | 2-dimethylaminoimidazol-1-yl |
| 256 | H | 2,5-diF-phenyl | 2-(3-aminophenyl) |
| 257 | H | 2,5-diF-phenyl | 2-(3-pyrrolidinylcarbonyl) |
| 258 | H | 2,5-diF-phenyl | 2-glycinoyl |
| 259 | H | 2,5-diF-phenyl | 2-(imidazol-1-ylacetyl) |
| 260 | —CN | phenyl | 2-(aminosulfonyl)phenyl |

| Ex # | R¹ᵇ | A | B |
|---|---|---|---|
| 261 | —CN | phenyl | 2-(methylaminosulfonyl)phenyl |
| 262 | —CN | phenyl | 1-pyrrolidinocarbonyl |
| 263 | —CN | phenyl | 2-(methylsulfonyl)phenyl |
| 264 | —CN | phenyl | 4-morpholino |
| 265 | —CN | phenyl | 2-(1'-CF$_3$-tetrazol-2-yl)phenyl |
| 266 | —CN | phenyl | 4-morpholinocarbonyl |
| 267 | —CN | 2-pyridyl | 2-(aminosulfonyl)phenyl |
| 268 | —CN | 2-pyridyl | 2-(methylaminosulfonyl)phenyl |
| 269 | —CN | 2-pyridyl | 1-pyrrolidinocarbonyl |
| 270 | —CN | 2-pyridyl | 2-(methylsulfonyl)phenyl |
| 271 | —CN | 2-pyridyl | 4-morpholino |
| 272 | —CN | 2-pyridyl | 2-(1'-CF$_3$-tetrazol-2-yl)phenyl |
| 273 | —CN | 2-pyridyl | 4-morpholinocarbonyl |
| 274 | —CN | 3-pyridyl | 2-(aminosulfonyl)phenyl |
| 275 | —CN | 3-pyridyl | 2-(methylaminosulfonyl)phenyl |
| 276 | —CN | 3-pyridyl | 1-pyrrolidinocarbonyl |
| 277 | —CN | 3-pyridyl | 2-(methylsulfonyl)phenyl |
| 278 | —CN | 3-pyridyl | 4-morpholino |
| 279 | —CN | 3-pyridyl | 2-(1'-CF$_3$-tetrazol-2-yl)phenyl |
| 280 | —CN | 3-pyridyl | 4-morpholinocarbonyl |
| 281 | —CN | 2-pyrimidyl | 2-(aminosulfonyl)phenyl |
| 282 | —CN | 2-pyrimidyl | 2-(methylaminosulfonyl)phenyl |
| 283 | —CN | 2-pyrimidyl | 1-pyrrolidinocarbonyl |
| 284 | —CN | 2-pyrimidyl | 2-(methylsulfonyl)phenyl |
| 285 | —CN | 2-pyrimidyl | 4-morpholino |
| 286 | —CN | 2-pyrimidyl | 2-(1'-CF$_3$-tetrazol-2-yl)phenyl |
| 287 | —CN | 2-pyrimidyl | 4-morpholinocarbonyl |
| 288 | —CN | 5-pyrimidyl | 2-(aminosulfonyl)phenyl |
| 289 | —CN | 5-pyrimidyl | 2-(methylaminosulfonyl)phenyl |
| 290 | —CN | 5-pyrimidyl | 1-pyrrolidinocarbonyl |
| 291 | —CN | 5-pyrimidyl | 2-(methylsulfonyl)phenyl |
| 292 | —CN | 5-pyrimidyl | 4-morpholino |
| 293 | —CN | 5-pyrimidyl | 2-(1'-CF$_3$-tetrazol-2-yl)phenyl |
| 294 | —CN | 5-pyrimidyl | 4-morpholinocarbonyl |
| 295 | —CN | 2-Cl-phenyl | 2-(aminosulfonyl)phenyl |
| 296 | —CN | 2-Cl-phenyl | 2-(methylaminosulfonyl)phenyl |
| 297 | —CN | 2-Cl-phenyl | 1-pyrrolidinocarbonyl |
| 298 | —CN | 2-Cl-phenyl | 2-(methylsulfonyl)phenyl |
| 299 | —CN | 2-Cl-phenyl | 4-morpholino |
| 300 | —CN | 2-Cl-phenyl | 2-(1'-CF$_3$-tetrazol-2-yl)phenyl |
| 301 | —CN | 2-Cl-phenyl | 4-morpholinocarbonyl |
| 302 | —CN | 2-F-phenyl | 2-(aminosulfonyl)phenyl |
| 303 | —CN | 2-F-phenyl | 2-(methylaminosulfonyl)phenyl |
| 304 | —CN | 2-F-phenyl | 1-pyrrolidinocarbonyl |
| 305 | —CN | 2-F-phenyl | 2-(methylsulfonyl)phenyl |
| 306 | —CN | 2-F-phenyl | 4-morpholino |
| 307 | —CN | 2-F-phenyl | 2-(1'-CF$_3$-tetrazol-2-yl)phenyl |
| 308 | —CN | 2-F-phenyl | 4-morpholinocarbonyl |
| 309 | —CN | 2,5-diF-phenyl | 2-(aminosulfonyl)phenyl |
| 310 | —CN | 2,5-diF-phenyl | 2-(methylaminosulfonyl)phenyl |
| 311 | —CN | 2,5-diF-phenyl | 1-pyrrolidinocarbonyl |
| 312 | —CN | 2,5-diF-phenyl | 2-(methylsulfonyl)phenyl |
| 313 | —CN | 2,5-diF-phenyl | 4-morpholino |
| 314 | —CN | 2,5-diF-phenyl | 2-(1'-CF$_3$-tetrazol-2-yl)phenyl |
| 315 | —CN | 2,5-diF-phenyl | 4-morpholinocarbonyl |
| 316 | —CN | phenyl | 2-(N-pyrrolidinyl-methyl)phenyl |
| 317 | —CN | phenyl | 2-(N-piperidinyl-methyl)phenyl |
| 318 | —CN | phenyl | 2-(N-morpholino-methyl)phenyl |
| 319 | —CN | phenyl | 2-(N,N'-methylmorpholinium-methyl)phenyl |
| 320 | —CN | phenyl | 2-(N-pyridinium-methyl)phenyl |
| 321 | —CN | phenyl | 2-(N-4-(N,N'-dimethylamino)-pyridinium-methyl)phenyl |
| 322 | —CN | phenyl | 2-(N-azatanyl-methyl)phenyl |
| 323 | —CN | phenyl | 2-(N-azetidinyl-methyl)phenyl |
| 324 | —CN | phenyl | 2-(N-piperazinyl-methyl)phenyl |
| 325 | —CN | phenyl | 2-(N,N'-BOC-piperazinyl-methyl)phenyl |
| 326 | —CN | phenyl | 2-(N-imidazolyl-methyl)phenyl |
| 327 | —CN | phenyl | 2-(N-methoxy-N-methylamino-methyl)phenyl |
| 328 | —CN | phenyl | 2-(N-pyridonyl-methyl)phenyl |
| 329 | —CN | phenyl | 2-(N-(N',N'-dimethylhydrazinyl-methyl)phenyl |
| 330 | —CN | phenyl | 2-(amidinyl)phenyl |
| 331 | —CN | phenyl | 2-(N-guanidinyl)phenyl |
| 332 | —CN | phenyl | 2-(imidazolyl)phenyl |
| 333 | —CN | phenyl | 2-(imidazolidinyl)phenyl |
| 334 | —CN | phenyl | 2-(2-imidazolidinyl-sulfonyl)phenyl |
| 335 | —CN | phenyl | 2-(2-pyrrolidinyl)phenyl |
| 336 | —CN | phenyl | 2-(2-piperidinyl)phenyl |
| 337 | —CN | phenyl | 2-(amidinyl-methyl)phenyl |
| 338 | —CN | phenyl | 2-(2-imidazolidinyl-methyl)phenyl |
| 339 | —CN | phenyl | 2-(N-(2-aminoimidazolyl)-methyl)phenyl |
| 340 | —CN | phenyl | 2-dimethylaminoimidazol-1-yl |
| 341 | —CN | phenyl | 2-(3-aminophenyl) |
| 342 | —CN | phenyl | 2-(3-pyrrolidinylcarbonyl) |
| 343 | —CN | phenyl | 2-glycinoyl |
| 344 | —CN | phenyl | 2-(imidazol-1-ylacetyl) |
| 345 | —CN | 2-pyridyl | 2-(N-pyrrolidinyl-methyl)phenyl |
| 346 | —CN | 2-pyridyl | 2-(N-piperidinyl-methyl)phenyl |
| 347 | —CN | 2-pyridyl | 2-(N-morpholino-methyl)phenyl |
| 348 | —CN | 2-pyridyl | 2-(N,N'-methylmorpholinium-methyl)phenyl |
| 349 | —CN | 2-pyridyl | 2-(N-pyridinium-methyl)phenyl |
| 350 | —CN | 2-pyridyl | 2-(N-4-(N,N'-dimethylamino)-pyridinium-methyl)phenyl |
| 351 | —CN | 2-pyridyl | 2-(N-azatanyl-methyl)phenyl |
| 352 | —CN | 2-pyridyl | 2-(N-azetidinyl-methyl)phenyl |
| 353 | —CN | 2-pyridyl | 2-(N-piperazinyl-methyl)phenyl |
| 354 | —CN | 2-pyridyl | 2-(N,N'-BOC-piperazinyl-methyl)phenyl |
| 355 | —CN | 2-pyridyl | 2-(N-imidazolyl-methyl)phenyl |
| 356 | —CN | 2-pyridyl | 2-(N-methoxy-N-methylamino-methyl)phenyl |
| 357 | —CN | 2-pyridyl | 2-(N-pyridonyl-methyl)phenyl |
| 358 | —CN | 2-pyridyl | 2-(N-(N',N'-dimethylhydrazinyl-methyl)phenyl |
| 359 | —CN | 2-pyridyl | 2-(amidinyl)phenyl |
| 360 | —CN | 2-pyridyl | 2-(N-guanidinyl)phenyl |
| 361 | —CN | 2-pyridyl | 2-(imidazolyl)phenyl |
| 362 | —CN | 2-pyridyl | 2-(imidazolidinyl)phenyl |
| 363 | —CN | 2-pyridyl | 2-(2-imidazolidinyl-sulfonyl)phenyl |
| 364 | —CN | 2-pyridyl | 2-(2-pyrrolidinyl)phenyl |
| 365 | —CN | 2-pyridyl | 2-(2-piperidinyl)phenyl |
| 366 | —CN | 2-pyridyl | 2-(amidinyl-methyl)phenyl |
| 367 | —CN | 2-pyridyl | 2-(2-imidazolidinyl-methyl)phenyl |
| 368 | —CN | 2-pyridyl | 2-(N-(2-aminoimidazolyl)-methyl)phenyl |
| 369 | —CN | 2-pyridyl | 2-dimethylaminoimidazol-1-yl |
| 370 | —CN | 2-pyridyl | 2-(3-aminophenyl) |
| 371 | —CN | 2-pyridyl | 2-(3-pyrrolidinylcarbonyl) |
| 372 | —CN | 2-pyridyl | 2-glycinoyl |
| 373 | —CN | 2-pyridyl | 2-(imidazol-1-ylacetyl) |
| 374 | —CN | 3-pyridyl | 2-(N-pyrrolidinyl-methyl)phenyl |
| 375 | —CN | 3-pyridyl | 2-(N-piperidinyl-methyl)phenyl |
| 376 | —CN | 3-pyridyl | 2-(N-morpholino-methyl)phenyl |
| 377 | —CN | 3-pyridyl | 2-(N,N'-methylmorpholinium-methyl)phenyl |
| 378 | —CN | 3-pyridyl | 2-(N-pyridinium-methyl)phenyl |
| 379 | —CN | 3-pyridyl | 2-(N-4-(N,N'-dimethylamino)-pyridinium-methyl)phenyl |
| 380 | —CN | 3-pyridyl | 2-(N-azatanyl-methyl)phenyl |
| 381 | —CN | 3-pyridyl | 2-(N-azetidinyl-methyl)phenyl |
| 382 | —CN | 3-pyridyl | 2-(N-piperazinyl-methyl)phenyl |
| 383 | —CN | 3-pyridyl | 2-(N,N'-BOC-piperazinyl-methyl)phenyl |
| 384 | —CN | 3-pyridyl | 2-(N-imidazolyl-methyl)phenyl |
| 385 | —CN | 3-pyridyl | 2-(N-methoxy-N-methylamino-methyl)phenyl |
| 386 | —CN | 3-pyridyl | 2-(N-pyridonyl-methyl)phenyl |
| 387 | —CN | 3-pyridyl | 2-(N-(N',N'-dimethylhydrazinyl-methyl)phenyl |
| 388 | —CN | 3-pyridyl | 2-(amidinyl)phenyl |
| 389 | —CN | 3-pyridyl | 2-(N-guanidinyl)phenyl |
| 390 | —CN | 3-pyridyl | 2-(imidazolyl)phenyl |
| 391 | —CN | 3-pyridyl | 2-(imidazolidinyl)phenyl |
| 392 | —CN | 3-pyridyl | 2-(2-imidazolidinyl-sulfonyl)phenyl |

| Ex # | R$^{1b}$ | A | B |
|---|---|---|---|
| 393 | —CN | 3-pyridyl | 2-(2-pyrrolidinyl)phenyl |
| 394 | —CN | 3-pyridyl | 2-(2-piperidinyl)phenyl |
| 395 | —CN | 3-pyridyl | 2-(amidinyl-methyl)phenyl |
| 396 | —CN | 3-pyridyl | 2-(2-imidazolidinyl-methyl)phenyl |
| 397 | —CN | 3-pyridyl | 2-(N-(2-aminoimidazolyl)-methyl)phenyl |
| 398 | —CN | 3-pyridyl | 2-dimethylaminoimidazol-1-yl |
| 399 | —CN | 3-pyridyl | 2-(3-aminophenyl) |
| 400 | —CN | 3-pyridyl | 2-(3-pyrrolidinylcarbonyl) |
| 401 | —CN | 3-pyridyl | 2-glycinoyl |
| 402 | —CN | 3-pyridyl | 2-(imidazol-1-ylacetyl) |
| 403 | —CN | 2-pyrimidyl | 2-(N-pyrrolidinyl-methyl)phenyl |
| 404 | —CN | 2-pyrimidyl | 2-(N-piperidinyl-methyl)phenyl |
| 405 | —CN | 2-pyrimidyl | 2-(N-morpholino-methyl)phenyl |
| 406 | —CN | 2-pyrimidyl | 2-(N,N'-methylmorpholinium-methyl)phenyl |
| 407 | —CN | 2-pyrimidyl | 2-(N-pyridinium-methyl)phenyl |
| 408 | —CN | 2-pyrimidyl | 2-(N-4-(N,N'-dimethylamino)-pyridinium-methyl)phenyl |
| 409 | —CN | 2-pyrimidyl | 2-(N-azatanyl-methyl)phenyl |
| 410 | —CN | 2-pyrimidyl | 2-(N-azetidinyl-methyl)phenyl |
| 411 | —CN | 2-pyrimidyl | 2-(N-piperazinyl-methyl)phenyl |
| 412 | —CN | 2-pyrimidyl | 2-(N,N'-BOC-piperazinyl-methyl)phenyl |
| 413 | —CN | 2-pyrimidyl | 2-(N-imidazolyl-methyl)phenyl |
| 414 | —CN | 2-pyrimidyl | 2-(N-methoxy-N-methylamino-methyl)phenyl |
| 415 | —CN | 2-pyrimidyl | 2-(N-pyridonyl-methyl)phenyl |
| 416 | —CN | 2-pyrimidyl | 2-(N-(N',N'-dimethylhydrazinyl-methyl)phenyl |
| 417 | —CN | 2-pyrimidyl | 2-(amidinyl)phenyl |
| 418 | —CN | 2-pyrimidyl | 2-(N-guanidinyl)phenyl |
| 419 | —CN | 2-pyrimidyl | 2-(imidazolyl)phenyl |
| 420 | —CN | 2-pyrimidyl | 2-(imidazolidinyl)phenyl |
| 421 | —CN | 2-pyrimidyl | 2-(2-imidazolidinyl-sulfonyl)phenyl |
| 422 | —CN | 2-pyrimidyl | 2-(2-pyrrolidinyl)phenyl |
| 423 | —CN | 2-pyrimidyl | 2-(2-piperidinyl)phenyl |
| 424 | —CN | 2-pyrimidyl | 2-(amidinyl-methyl)phenyl |
| 425 | —CN | 2-pyrimidyl | 2-(2-imidazolidinyl-methyl)phenyl |
| 426 | —CN | 2-pyrimidyl | 2-(N-(2-aminoimidazolyl)-methyl)phenyl |
| 427 | —CN | 2-pyrimidyl | 2-dimethylaminoimidazol-1-yl |
| 428 | —CN | 2-pyrimidyl | 2-(3-aminophenyl) |
| 429 | —CN | 2-pyrimidyl | 2-(3-pyrrolidinylcarbonyl) |
| 430 | —CN | 2-pyrimidyl | 2-glycinoyl |
| 431 | —CN | 2-pyrimidyl | 2-(imidazol-1-ylacetyl) |
| 432 | —CN | 2-Cl-phenyl | 2-(N-pyrrolidinyl-methyl)phenyl |
| 433 | —CN | 2-Cl-phenyl | 2-(N-piperidinyl-methyl)phenyl |
| 434 | —CN | 2-Cl-phenyl | 2-(N-morpholino-methyl)phenyl |
| 435 | —CN | 2-Cl-phenyl | 2-(N,N'-methylmorpholinium-methyl)phenyl |
| 436 | —CN | 2-Cl-phenyl | 2-(N-pyridinium-methyl)phenyl |
| 437 | —CN | 2-Cl-phenyl | 2-(N-4-(N,N'-dimethylamino)-pyridinium-methyl)phenyl |
| 438 | —CN | 2-Cl-phenyl | 2-(N-azatanyl-methyl)phenyl |
| 439 | —CN | 2-Cl-phenyl | 2-(N-azetidinyl-methyl)phenyl |
| 440 | —CN | 2-Cl-phenyl | 2-(N-piperazinyl-methyl)phenyl |
| 441 | —CN | 2-Cl-phenyl | 2-(N,N'-BOC-piperazinyl-methyl)phenyl |
| 442 | —CN | 2-Cl-phenyl | 2-(N-imidazolyl-methyl)phenyl |
| 443 | —CN | 2-Cl-phenyl | 2-(N-methoxy-N-methylamino-methyl)phenyl |
| 444 | —CN | 2-Cl-phenyl | 2-(N-pyridonyl-methyl)phenyl |
| 445 | —CN | 2-Cl-phenyl | 2-(N-(N',N'-dimethylhydrazinyl-methyl)phenyl |
| 446 | —CN | 2-Cl-phenyl | 2-(amidinyl)phenyl |
| 447 | —CN | 2-Cl-phenyl | 2-(N-guanidinyl)phenyl |
| 448 | —CN | 2-Cl-phenyl | 2-(imidazolyl)phenyl |
| 449 | —CN | 2-Cl-phenyl | 2-(imidazolidinyl)phenyl |
| 450 | —CN | 2-Cl-phenyl | 2-(2-imidazolidinyl-sulfonyl)phenyl |
| 451 | —CN | 2-Cl-phenyl | 2-(2-pyrrolidinyl)phenyl |
| 452 | —CN | 2-Cl-phenyl | 2-(2-piperidinyl)phenyl |
| 453 | —CN | 2-Cl-phenyl | 2-(amidinyl-methyl)phenyl |
| 454 | —CN | 2-Cl-phenyl | 2-(2-imidazolidinyl-methyl)phenyl |
| 455 | —CN | 2-Cl-phenyl | 2-(N-(2-aminoimidazolyl)-methyl)phenyl |
| 456 | —CN | 2-Cl-phenyl | 2-dimethylaminoimidazol-1-yl |
| 457 | —CN | 2-Cl-phenyl | 2-(3-aminophenyl) |
| 458 | —CN | 2-Cl-phenyl | 2-(3-pyrrolidinylcarbonyl) |
| 459 | —CN | 2-Cl-phenyl | 2-glycinoyl |
| 460 | —CN | 2-Cl-phenyl | 2-(imidazol-1-ylacetyl) |
| 461 | —CN | 2-F-phenyl | 2-(N-pyrrolidinyl-methyl)phenyl |
| 462 | —CN | 2-F-phenyl | 2-(N-piperidinyl-methyl)phenyl |
| 463 | —CN | 2-F-phenyl | 2-(N-morpholino-methyl)phenyl |
| 464 | —CN | 2-F-phenyl | 2-(N,N'-methylmorpholinium-methyl)phenyl |
| 465 | —CN | 2-F-phenyl | 2-(N-pyridinium-methyl)phenyl |
| 466 | —CN | 2-F-phenyl | 2-(N-4-(N,N'-dimethylamino)-pyridinium-methyl)phenyl |
| 467 | —CN | 2-F-phenyl | 2-(N-azatanyl-methyl)phenyl |
| 468 | —CN | 2-F-phenyl | 2-(N-azetidinyl-methyl)phenyl |
| 469 | —CN | 2-F-phenyl | 2-(N-piperazinyl-methyl)phenyl |
| 470 | —CN | 2-F-phenyl | 2-(N,N'-BOC-piperazinyl-methyl)phenyl |
| 471 | —CN | 2-F-phenyl | 2-(N-imidazolyl-methyl)phenyl |
| 472 | —CN | 2-F-phenyl | 2-(N-methoxy-N-methylamino-methyl)phenyl |
| 473 | —CN | 2-F-phenyl | 2-(N-pyridonyl-methyl)phenyl |
| 474 | —CN | 2-F-phenyl | 2-(N-(N',N'-dimethylhydrazinyl-methyl)phenyl |
| 475 | —CN | 2-F-phenyl | 2-(amidinyl)phenyl |
| 476 | —CN | 2-F-phenyl | 2-(N-guanidinyl)phenyl |
| 477 | —CN | 2-F-phenyl | 2-(imidazolyl)phenyl |
| 478 | —CN | 2-F-phenyl | 2-(imidazolidinyl)phenyl |
| 479 | —CN | 2-F-phenyl | 2-(2-imidazolidinyl-sulfonyl)phenyl |
| 480 | —CN | 2-F-phenyl | 2-(2-pyrrolidinyl)phenyl |
| 481 | —CN | 2-F-phenyl | 2-(2-piperidinyl)phenyl |
| 482 | —CN | 2-F-phenyl | 2-(amidinyl-methyl)phenyl |
| 483 | —CN | 2-F-phenyl | 2-(2-imidazolidinyl-methyl)phenyl |
| 484 | —CN | 2-F-phenyl | 2-(N-(2-aminoimidazolyl)-methyl)phenyl |
| 485 | —CN | 2-F-phenyl | 2-dimethylaminoimidazol-1-yl |
| 486 | —CN | 2-F-phenyl | 2-(3-aminophenyl) |
| 487 | —CN | 2-F-phenyl | 2-(3-pyrrolidinylcarbonyl) |
| 488 | —CN | 2-F-phenyl | 2-glycinoyl |
| 489 | —CN | 2-F-phenyl | 2-(imidazol-1-ylacetyl) |
| 490 | —CN | 2,5-diF-phenyl | 2-(N-pyrrolidinyl-methyl)phenyl |
| 491 | —CN | 2,5-diF-phenyl | 2-(N-piperidinyl-methyl)phenyl |
| 492 | —CN | 2,5-diF-phenyl | 2-(N-morpholino-methyl)phenyl |
| 493 | —CN | 2,5-diF-phenyl | 2-(N,N'-methylmorpholinium-methyl)phenyl |
| 494 | —CN | 2,5-diF-phenyl | 2-(N-pyridinium-methyl)phenyl |
| 495 | —CN | 2,5-diF-phenyl | 2-(N-4-(N,N'-dimethylamino)-pyridinium-methyl)phenyl |
| 496 | —CN | 2,5-diF-phenyl | 2-(N-azatanyl-methyl)phenyl |
| 497 | —CN | 2,5-diF-phenyl | 2-(N-azetidinyl-methyl)phenyl |
| 498 | —CN | 2,5-diF-phenyl | 2-(N-piperazinyl-methyl)phenyl |
| 499 | —CN | 2,5-diF-phenyl | 2-(N,N'-BOC-piperazinyl-methyl)phenyl |
| 500 | —CN | 2,5-diF-phenyl | 2-(N-imidazolyl-methyl)phenyl |
| 501 | —CN | 2,5-diF-phenyl | 2-(N-methoxy-N-methylamino-methyl)phenyl |
| 502 | —CN | 2,5-diF-phenyl | 2-(N-pyridonyl-methyl)phenyl |
| 503 | —CN | 2,5-diF-phenyl | 2-(N-(N',N'-dimethylhydrazinyl-methyl)phenyl |
| 504 | —CN | 2,5-diF-phenyl | 2-(amidinyl)phenyl |
| 505 | —CN | 2,5-diF-phenyl | 2-(N-guanidinyl)phenyl |
| 506 | —CN | 2,5-diF-phenyl | 2-(imidazolyl)phenyl |
| 507 | —CN | 2,5-diF-phenyl | 2-(imidazolidinyl)phenyl |
| 508 | —CN | 2,5-diF-phenyl | 2-(2-imidazolidinyl-sulfonyl)phenyl |
| 509 | —CN | 2,5-diF-phenyl | 2-(2-pyrrolidinyl)phenyl |
| 510 | —CN | 2,5-diF-phenyl | 2-(2-piperidinyl)phenyl |
| 511 | —CN | 2,5-diF-phenyl | 2-(amidinyl-methyl)phenyl |
| 512 | —CN | 2,5-diF-phenyl | 2-(2-imidazolidinyl-methyl)phenyl |
| 513 | —CN | 2,5-diF-phenyl | 2-(N-(2-aminoimidazolyl)- |

-continued

| Ex # | R¹ᵇ | A | B |
|---|---|---|---|
| 514 | —CN | 2,5-diF-phenyl | 2-dimethylaminoimidazol-1-yl |
| 515 | —CN | 2,5-diF-phenyl | 2-(3-aminophenyl) |
| 516 | —CN | 2,5-diF-phenyl | 2-(3-pyrrolidinylcarbonyl) |
| 517 | —CN | 2,5-diF-phenyl | 2-glycinoyl |
| 518 | —CN | 2,5-diF-phenyl | 2-(imidazol-1-ylacetyl) |
| 519 | CF₃ | phenyl | 2-(aminosulfonyl)phenyl |
| 520 | CF₃ | phenyl | 2-(methylaminosulfonyl)phenyl |
| 521 | CF₃ | phenyl | 1-pyrrolidinocarbonyl |
| 522 | CF₃ | phenyl | 2-(methylsulfonyl)phenyl |
| 523 | CF₃ | phenyl | 4-morpholino |
| 524 | CF₃ | phenyl | 2-(1'-CF₃-tetrazol-2-yl)phenyl |
| 525 | CF₃ | phenyl | 4-morpholinocarbonyl |
| 526 | CF₃ | 2-pyridyl | 2-(aminosulfonyl)phenyl |
| 527 | CF₃ | 2-pyridyl | 2-(methylaminosulfonyl)phenyl |
| 528 | CF₃ | 2-pyridyl | 1-pyrrolidinocarbonyl |
| 529 | CF₃ | 2-pyridyl | 2-(methylsulfonyl)phenyl |
| 530 | CF₃ | 2-pyridyl | 4-morpholino |
| 531 | CF₃ | 2-pyridyl | 2-(1'-CF₃-tetrazol-2-yl)phenyl |
| 532 | CF₃ | 2-pyridyl | 4-morpholinocarbonyl |
| 533 | CF₃ | 3-pyridyl | 2-(aminosulfonyl)phenyl |
| 534 | CF₃ | 3-pyridyl | 2-(methylaminosulfonyl)phenyl |
| 535 | CF₃ | 3-pyridyl | 1-pyrrolidinocarbonyl |
| 536 | CF₃ | 3-pyridyl | 2-(methylsulfonyl)phenyl |
| 537 | CF₃ | 3-pyridyl | 4-morpholino |
| 538 | CF₃ | 3-pyridyl | 2-(1'-CF₃-tetrazol-2-yl)phenyl |
| 539 | CF₃ | 3-pyridyl | 4-morpholinocarbonyl |
| 540 | CF₃ | 2-pyrimidyl | 2-(aminosulfonyl)phenyl |
| 541 | CF₃ | 2-pyrimidyl | 2-(methylaminosulfonyl)phenyl |
| 542 | CF₃ | 2-pyrimidyl | 1-pyrrolidinocarbonyl |
| 543 | CF₃ | 2-pyrimidyl | 2-(methylsulfonyl)phenyl |
| 544 | CF₃ | 2-pyrimidyl | 4-morpholino |
| 545 | CF₃ | 2-pyrimidyl | 2-(1'-CF₃-tetrazol-2-yl)phenyl |
| 546 | CF₃ | 2-pyrimidyl | 4-morpholinocarbonyl |
| 547 | CF₃ | 5-pyrimidyl | 2-(aminosulfonyl)phenyl |
| 548 | CF₃ | 5-pyrimidyl | 2-(methylaminosulfonyl)phenyl |
| 549 | CF₃ | 5-pyrimidyl | 1-pyrrolidinocarbonyl |
| 550 | CF₃ | 5-pyrimidyl | 2-(methylsulfonyl)phenyl |
| 551 | CF₃ | 5-pyrimidyl | 4-morpholino |
| 552 | CF₃ | 5-pyrimidyl | 2-(1'-CF₃-tetrazol-2-yl)phenyl |
| 553 | CF₃ | 5-pyrimidyl | 4-morpholinocarbonyl |
| 554 | CF₃ | 2-Cl-phenyl | 2-(aminosulfonyl)phenyl |
| 555 | CF₃ | 2-Cl-phenyl | 2-(methylaminosulfonyl)phenyl |
| 556 | CF₃ | 2-Cl-phenyl | 1-pyrrolidinocarbonyl |
| 557 | CF₃ | 2-Cl-phenyl | 2-(methylsulfonyl)phenyl |
| 558 | CF₃ | 2-Cl-phenyl | 4-morpholino |
| 559 | CF₃ | 2-Cl-phenyl | 2-(1'-CF₃-tetrazol-2-yl)phenyl |
| 560 | CF₃ | 2-Cl-phenyl | 4-morpholinocarbonyl |
| 561 | CF₃ | 2-F-phenyl | 2-(aminosulfonyl)phenyl |
| 562 | CF₃ | 2-F-phenyl | 2-(methylaminosulfonyl)phenyl |
| 563 | CF₃ | 2-F-phenyl | 1-pyrrolidinocarbonyl |
| 564 | CF₃ | 2-F-phenyl | 2-(methylsulfonyl)phenyl |
| 565 | CF₃ | 2-F-phenyl | 4-morpholino |
| 566 | CF₃ | 2-F-phenyl | 2-(1'-CF₃-tetrazol-2-yl)phenyl |
| 567 | CF₃ | 2-F-phenyl | 4-morpholinocarbonyl |
| 568 | CF₃ | 2,5-diF-phenyl | 2-(aminosulfonyl)phenyl |
| 569 | CF₃ | 2,5-diF-phenyl | 2-(methylaminosulfonyl)phenyl |
| 570 | CF₃ | 2,5-diF-phenyl | 1-pyrrolidinocarbonyl |
| 571 | CF₃ | 2,5-diF-phenyl | 2-(methylsulfonyl)phenyl |
| 572 | CF₃ | 2,5-diF-phenyl | 4-morpholino |
| 573 | CF₃ | 2,5-diF-phenyl | 2-(1'-CF₃-tetrazol-2-yl)phenyl |
| 574 | CF₃ | 2,5-diF-phenyl | 4-morpholinocarbonyl |
| 575 | CF₃ | phenyl | 2-(N-pyrrolidinyl-methyl)phenyl |
| 576 | CF₃ | phenyl | 2-(N-piperidinyl-methyl)phenyl |
| 577 | CF₃ | phenyl | 2-(N-morpholino-methyl)phenyl |
| 578 | CF₃ | phenyl | 2-(N,N'-methylmorpholinium-methyl)phenyl |
| 579 | CF₃ | phenyl | 2-(N-pyridinium-methyl)phenyl |
| 580 | CF₃ | phenyl | 2-(N-4-(N,N'-dimethylamino)-pyridinium-methyl)phenyl |
| 581 | CF₃ | phenyl | 2-(N-azatanyl-methyl)phenyl |
| 582 | CF₃ | phenyl | 2-(N-azetidinyl-methyl)phenyl |
| 583 | CF₃ | phenyl | 2-(N-piperazinyl-methyl)phenyl |
| 584 | CF₃ | phenyl | 2-(N,N'-BOC-piperazinyl-methyl)phenyl |
| 585 | CF₃ | phenyl | 2-(N-imidazolyl-methyl)phenyl |
| 586 | CF₃ | phenyl | 2-(N-methoxy-N-methylamino-methyl)phenyl |
| 587 | CF₃ | phenyl | 2-(N-pyridonyl-methyl)phenyl |
| 588 | CF₃ | phenyl | 2-(N-(N',N'-dimethylhydrazinyl-methyl)phenyl |
| 589 | CF₃ | phenyl | 2-(amidinyl)phenyl |
| 590 | CF₃ | phenyl | 2-(N-guanidinyl)phenyl |
| 591 | CF₃ | phenyl | 2-(imidazolyl)phenyl |
| 592 | CF₃ | phenyl | 2-(imidazolidinyl)phenyl |
| 593 | CF₃ | phenyl | 2-(2-imidazolinyl-sulfonyl)phenyl |
| 594 | CF₃ | phenyl | 2-(2-pyrrolidinyl)phenyl |
| 595 | CF₃ | phenyl | 2-(2-piperidinyl)phenyl |
| 596 | CF₃ | phenyl | 2-(amidinyl-methyl)phenyl |
| 597 | CF₃ | phenyl | 2-(2-imidazolidinyl-methyl)phenyl |
| 598 | CF₃ | phenyl | 2-(N-(2-aminoimidazolyl)-methyl)phenyl |
| 599 | CF₃ | phenyl | 2-dimethylaminoimidazol-1-yl |
| 600 | CF₃ | phenyl | 2-(3-aminophenyl) |
| 601 | CF₃ | phenyl | 2-(3-pyrrolidinylcarbonyl) |
| 602 | CF₃ | phenyl | 2-glycinoyl |
| 603 | CF₃ | phenyl | 2-(imidazol-1-ylacetyl) |
| 604 | CF₃ | 2-pyridyl | 2-(N-pyrrolidinyl-methyl)phenyl |
| 605 | CF₃ | 2-pyridyl | 2-(N-piperidinyl-methyl)phenyl |
| 606 | CF₃ | 2-pyridyl | 2-(N-morpholino-methyl)phenyl |
| 607 | CF₃ | 2-pyridyl | 2-(N,N'-methylmorpholinium-methyl)phenyl |
| 608 | CF₃ | 2-pyridyl | 2-(N-pyridinium-methyl)phenyl |
| 609 | CF₃ | 2-pyridyl | 2-(N-4-(N,N'-dimethylamino)-pyridinium-methyl)phenyl |
| 610 | CF₃ | 2-pyridyl | 2-(N-azatanyl-methyl)phenyl |
| 611 | CF₃ | 2-pyridyl | 2-(N-azetidinyl-methyl)phenyl |
| 612 | CF₃ | 2-pyridyl | 2-(N-piperazinyl-methyl)phenyl |
| 613 | CF₃ | 2-pyridyl | 2-(N,N'-BOC-piperazinyl-methyl)phenyl |
| 614 | CF₃ | 2-pyridyl | 2-(N-imidazolyl-methyl)phenyl |
| 615 | CF₃ | 2-pyridyl | 2-(N-methoxy-N-methylamino-methyl)phenyl |
| 616 | CF₃ | 2-pyridyl | 2-(N-pyridonyl-methyl)phenyl |
| 617 | CF₃ | 2-pyridyl | 2-(N-(N',N'-dimethylhydrazinyl-methyl)phenyl |
| 618 | CF₃ | 2-pyridyl | 2-(amidinyl)phenyl |
| 619 | CF₃ | 2-pyridyl | 2-(N-guanidinyl)phenyl |
| 620 | CF₃ | 2-pyridyl | 2-(imidazolyl)phenyl |
| 621 | CF₃ | 2-pyridyl | 2-(imidazolidinyl)phenyl |
| 622 | CF₃ | 2-pyridyl | 2-(2-imidazolidinyl-sulfonyl)phenyl |
| 623 | CF₃ | 2-pyridyl | 2-(2-pyrrolidinyl)phenyl |
| 624 | CF₃ | 2-pyridyl | 2-(2-piperidinyl)phenyl |
| 625 | CF₃ | 2-pyridyl | 2-(amidinyl-methyl)phenyl |
| 626 | CF₃ | 2-pyridyl | 2-(2-imidazolidinyl-methyl)phenyl |
| 627 | CF₃ | 2-pyridyl | 2-(N-(2-aminoimidazolyl)-methyl)phenyl |
| 628 | CF₃ | 2-pyridyl | 2-dimethylaminoimidazol-1-yl |
| 629 | CF₃ | 2-pyridyl | 2-(3-aminophenyl) |
| 630 | CF₃ | 2-pyridyl | 2-(3-pyrrolidinylcarbonyl) |
| 631 | CF₃ | 2-pyridyl | 2-glycinoyl |
| 632 | CF₃ | 2-pyridyl | 2-(imidazol-1-ylacetyl) |
| 633 | CF₃ | 3-pyridyl | 2-(N-pyrrolidinyl-methyl)phenyl |
| 634 | CF₃ | 3-pyridyl | 2-(N-piperidinyl-methyl)phenyl |
| 635 | CF₃ | 3-pyridyl | 2-(N-morpholino-methyl)phenyl |
| 636 | CF₃ | 3-pyridyl | 2-(N,N'-methylmorpholinium-methyl)phenyl |
| 637 | CF₃ | 3-pyridyl | 2-(N-pyridinium-methyl)phenyl |
| 638 | CF₃ | 3-pyridyl | 2-(N-4-(N,N'-dimethylamino)-pyridinium-methyl)phenyl |
| 639 | CF₃ | 3-pyridyl | 2-(N-azatanyl-methyl)phenyl |
| 640 | CF₃ | 3-pyridyl | 2-(N-azetidinyl-methyl)phenyl |
| 641 | CF₃ | 3-pyridyl | 2-(N-piperazinyl-methyl)phenyl |
| 642 | CF₃ | 3-pyridyl | 2-(N,N'-BOC-piperazinyl-methyl)phenyl |
| 643 | CF₃ | 3-pyridyl | 2-(N-imidazolyl-methyl)phenyl |
| 644 | CF₃ | 3-pyridyl | 2-(N-methoxy-N-methylamino-methyl)phenyl |
| 645 | CF₃ | 3-pyridyl | 2-(N-pyridonyl-methyl)phenyl |
| 646 | CF₃ | 3-pyridyl | 2-(N-(N',N'-dimethylhydrazinyl- |

-continued

| Ex # | R<sup>1b</sup> | A | B |
|---|---|---|---|
| 647 | CF<sub>3</sub> | 3-pyridyl | 2-(amidinyl)phenyl |
| 648 | CF<sub>3</sub> | 3-pyridyl | 2-(N-guanidinyl)phenyl |
| 649 | CF<sub>3</sub> | 3-pyridyl | 2-(imidazolyl)phenyl |
| 650 | CF<sub>3</sub> | 3-pyridyl | 2-(imidazolidinyl)phenyl |
| 651 | CF<sub>3</sub> | 3-pyridyl | 2-(2-imidazolidinyl-sulfonyl)phenyl |
| 652 | CF<sub>3</sub> | 3-pyridyl | 2-(2-pyrrolidinyl)phenyl |
| 653 | CF<sub>3</sub> | 3-pyridyl | 2-(2-piperidinyl)phenyl |
| 654 | CF<sub>3</sub> | 3-pyridyl | 2-(amidinyl-methyl)phenyl |
| 655 | CF<sub>3</sub> | 3-pyridyl | 2-(2-imidazolidinyl-methyl)phenyl |
| 656 | CF<sub>3</sub> | 3-pyridyl | 2-(N-(2-aminoimidazolyl)-methyl)phenyl |
| 657 | CF<sub>3</sub> | 3-pyridyl | 2-dimethylaminoimidazol-1-yl |
| 658 | CF<sub>3</sub> | 3-pyridyl | 2-(3-aminophenyl) |
| 659 | CF<sub>3</sub> | 3-pyridyl | 2-(3-pyrrolidinylcarbonyl) |
| 660 | CF<sub>3</sub> | 3-pyridyl | 2-glycinoyl |
| 661 | CF<sub>3</sub> | 3-pyridyl | 2-(imidazol-1-ylacetyl) |
| 662 | CF<sub>3</sub> | 2-pyrimidyl | 2-(N-pyrrolidinyl-methyl)phenyl |
| 663 | CF<sub>3</sub> | 2-pyrimidyl | 2-(N-piperidinyl-methyl)phenyl |
| 664 | CF<sub>3</sub> | 2-pyrimidyl | 2-(N-morpholino-methyl)phenyl |
| 665 | CF<sub>3</sub> | 2-pyrimidyl | 2-(N,N'-methylmorpholinium-methyl)phenyl |
| 666 | CF<sub>3</sub> | 2-pyrimidyl | 2-(N-pyridinium-methyl)phenyl |
| 667 | CF<sub>3</sub> | 2-pyrimidyl | 2-(N-4-(N,N'-dimethylamino)-pyridinium-methyl)phenyl |
| 668 | CF<sub>3</sub> | 2-pyrimidyl | 2-(N-azatanyl-methyl)phenyl |
| 669 | CF<sub>3</sub> | 2-pyrimidyl | 2-(N-azetidinyl-methyl)phenyl |
| 670 | CF<sub>3</sub> | 2-pyrimidyl | 2-(N-piperazinyl-methyl)phenyl |
| 671 | CF<sub>3</sub> | 2-pyrimidyl | 2-(N,N'-BOC-piperazinyl-methyl)phenyl |
| 672 | CF<sub>3</sub> | 2-pyrimidyl | 2-(N-imidazolyl-methyl)phenyl |
| 673 | CF<sub>3</sub> | 2-pyrimidyl | 2-(N-methoxy-N-methylamino-methyl)phenyl |
| 674 | CF<sub>3</sub> | 2-pyrimidyl | 2-(N-pyridonyl-methyl)phenyl |
| 675 | CF<sub>3</sub> | 2-pyrimidyl | 2-(N-(N',N'-dimethylhydrazinyl-methyl)phenyl |
| 676 | CF<sub>3</sub> | 2-pyrimidyl | 2-(amidinyl)phenyl |
| 677 | CF<sub>3</sub> | 2-pyrimidyl | 2-(N-guanidinyl)phenyl |
| 678 | CF<sub>3</sub> | 2-pyrimidyl | 2-(imidazolyl)phenyl |
| 679 | CF<sub>3</sub> | 2-pyrimidyl | 2-(imidazolidinyl)phenyl |
| 680 | CF<sub>3</sub> | 2-pyrimidyl | 2-(2-imidazolidinyl-sulfonyl)phenyl |
| 681 | CF<sub>3</sub> | 2-pyrimidyl | 2-(2-pyrrolidinyl)phenyl |
| 682 | CF<sub>3</sub> | 2-pyrimidyl | 2-(2-piperidinyl)phenyl |
| 683 | CF<sub>3</sub> | 2-pyrimidyl | 2-(amidinyl-methyl)phenyl |
| 684 | CF<sub>3</sub> | 2-pyrimidyl | 2-(2-imidazolidinyl-methyl)phenyl |
| 685 | CF<sub>3</sub> | 2-pyrimidyl | 2-(N-(2-aminoimidazolyl)-methyl)phenyl |
| 686 | CF<sub>3</sub> | 2-pyrimidyl | 2-dimethylaminoimidazol-1-yl |
| 687 | CF<sub>3</sub> | 2-pyrimidyl | 2-(3-aminophenyl) |
| 688 | CF<sub>3</sub> | 2-pyrimidyl | 2-(3-pyrrolidinylcarbonyl) |
| 689 | CF<sub>3</sub> | 2-pyrimidyl | 2-glycinoyl |
| 690 | CF<sub>3</sub> | 2-pyrimidyl | 2-(imidazol-1-ylacetyl) |
| 691 | CF<sub>3</sub> | 2-Cl-phenyl | 2-(N-pyrrolidinyl-methyl)phenyl |
| 692 | CF<sub>3</sub> | 2-Cl-phenyl | 2-(N-piperidinyl-methyl)phenyl |
| 693 | CF<sub>3</sub> | 2-Cl-phenyl | 2-(N-morpholino-methyl)phenyl |
| 694 | CF<sub>3</sub> | 2-Cl-phenyl | 2-(N,N'-methylmorpholinium-methyl)phenyl |
| 695 | CF<sub>3</sub> | 2-Cl-phenyl | 2-(N-pyridinium-methyl)phenyl |
| 696 | CF<sub>3</sub> | 2-Cl-phenyl | 2-(N-4-(N,N'-dimethylamino)-pyridinium-methyl)phenyl |
| 697 | CF<sub>3</sub> | 2-Cl-phenyl | 2-(N-azatanyl-methyl)phenyl |
| 698 | CF<sub>3</sub> | 2-Cl-phenyl | 2-(N-azetidinyl-methyl)phenyl |
| 699 | CF<sub>3</sub> | 2-Cl-phenyl | 2-(N-piperazinyl-methyl)phenyl |
| 700 | CF<sub>3</sub> | 2-Cl-phenyl | 2-(N,N'-BOC-piperazinyl-methyl)phenyl |
| 701 | CF<sub>3</sub> | 2-Cl-phenyl | 2-(N-imidazolyl-methyl)phenyl |
| 702 | CF<sub>3</sub> | 2-Cl-phenyl | 2-(N-methoxy-N-methylamino-methyl)phenyl |
| 703 | CF<sub>3</sub> | 2-Cl-phenyl | 2-(N-pyridonyl-methyl)phenyl |
| 704 | CF<sub>3</sub> | 2-Cl-phenyl | 2-(N-(N',N'-dimethylhydrazinyl-methyl)phenyl |
| 705 | CF<sub>3</sub> | 2-Cl-phenyl | 2-(amidinyl)phenyl |
| 706 | CF<sub>3</sub> | 2-Cl-phenyl | 2-(N-guanidinyl)phenyl |
| 707 | CF<sub>3</sub> | 2-Cl-phenyl | 2-(imidazolyl)phenyl |
| 708 | CF<sub>3</sub> | 2-Cl-phenyl | 2-(imidazolidinyl)phenyl |
| 709 | CF<sub>3</sub> | 2-Cl-phenyl | 2-(2-imidazolidinyl-sultonyl)phenyl |
| 710 | CF<sub>3</sub> | 2-Cl-phenyl | 2-(2-pyrrolidinyl)phenyl |
| 711 | CF<sub>3</sub> | 2-Cl-phenyl | 2-(2-piperidinyl)phenyl |
| 712 | CF<sub>3</sub> | 2-Cl-phenyl | 2-(amidinyl-methyl)phenyl |
| 713 | CF<sub>3</sub> | 2-Cl-phenyl | 2-(2-imidazolidinyl-methyl)phenyl |
| 714 | CF<sub>3</sub> | 2-Cl-phenyl | 2-(N-(2-aminoimidazolyl)-methyl)phenyl |
| 715 | CF<sub>3</sub> | 2-Cl-phenyl | 2-dimethylaminoimidazol-1-yl |
| 716 | CF<sub>3</sub> | 2-Cl-phenyl | 2-(3-aminophenyl) |
| 717 | CF<sub>3</sub> | 2-Cl-phenyl | 2-(3-pyrrolidinylcarbonyl) |
| 718 | CF<sub>3</sub> | 2-Cl-phenyl | 2-glycinoyl |
| 719 | CF<sub>3</sub> | 2-Cl-phenyl | 2-(imidazol-1-ylacetyl) |
| 720 | CF<sub>3</sub> | 2-F-phenyl | 2-(N-pyrrolidinyl-methyl)phenyl |
| 721 | CF<sub>3</sub> | 2-F-phenyl | 2-(N-piperidinyl-methyl)phenyl |
| 722 | CF<sub>3</sub> | 2-F-phenyl | 2-(N-morpholino-methyl)phenyl |
| 723 | CF<sub>3</sub> | 2-F-phenyl | 2-(N,N'-methylmorpholinium-methyl)phenyl |
| 724 | CF<sub>3</sub> | 2-F-phenyl | 2-(N-pyridinium-methyl)phenyl |
| 725 | CF<sub>3</sub> | 2-F-phenyl | 2-(N-4-(N,N'-dimethylamino)-pyridinium-methyl)phenyl |
| 726 | CF<sub>3</sub> | 2-F-phenyl | 2-(N-azatanyl-methyl)phenyl |
| 727 | CF<sub>3</sub> | 2-F-phenyl | 2-(N-azetidinyl-methyl)phenyl |
| 728 | CF<sub>3</sub> | 2-F-phenyl | 2-(N-piperazinyl-methyl)phenyl |
| 729 | CF<sub>3</sub> | 2-F-phenyl | 2-(N,N'-BOC-piperazinyl-methyl)phenyl |
| 730 | CF<sub>3</sub> | 2-F-phenyl | 2-(N-imidazolyl-methyl)phenyl |
| 731 | CF<sub>3</sub> | 2-F-phenyl | 2-(N-methoxy-N-methylamino-methyl)phenyl |
| 732 | CF<sub>3</sub> | 2-F-phenyl | 2-(N-pyridonyl-methyl)phenyl |
| 733 | CF<sub>3</sub> | 2-F-phenyl | 2-(N-(N',N'-dimethylhydrazinyl-methyl)phenyl |
| 734 | CF<sub>3</sub> | 2-F-phenyl | 2-(amidinyl)phenyl |
| 735 | CF<sub>3</sub> | 2-F-phenyl | 2-(N-guanidinyl)phenyl |
| 736 | CF<sub>3</sub> | 2-F-phenyl | 2-(imidazolyl)phenyl |
| 737 | CF<sub>3</sub> | 2-F-phenyl | 2-(imidazolidinyl)phenyl |
| 738 | CF<sub>3</sub> | 2-F-phenyl | 2-(2-imidazolidinyl-sulfonyl)phenyl |
| 739 | CF<sub>3</sub> | 2-F-phenyl | 2-(2-pyrrolidinyl)phenyl |
| 740 | CF<sub>3</sub> | 2-F-phenyl | 2-(2-piperidinyl)phenyl |
| 741 | CF<sub>3</sub> | 2-F-phenyl | 2-(amidinyl-methyl)phenyl |
| 742 | CF<sub>3</sub> | 2-F-phenyl | 2-(2-imidazolidinyl-methyl)phenyl |
| 743 | CF<sub>3</sub> | 2-F-phenyl | 2-(N-(2-aminoimidazolyl)-methyl)phenyl |
| 744 | CF<sub>3</sub> | 2-F-phenyl | 2-dimethylaminoimidazol-1-yl |
| 745 | CF<sub>3</sub> | 2-F-phenyl | 2-(3-aminophenyl) |
| 746 | CF<sub>3</sub> | 2-F-phenyl | 2-(3-pyrrolidinylcarbonyl) |
| 747 | CF<sub>3</sub> | 2-F-phenyl | 2-glycinoyl |
| 748 | CF<sub>3</sub> | 2-F-phenyl | 2-(imidazol-1-ylacetyl) |
| 749 | CF<sub>3</sub> | 2,5-diF-phenyl | 2-(N-pyrrolidinyl-methyl)phenyl |
| 750 | CF<sub>3</sub> | 2,5-diF-phenyl | 2-(N-piperidinyl-methyl)phenyl |
| 751 | CF<sub>3</sub> | 2,5-diF-phenyl | 2-(N-morpholino-methyl)phenyl |
| 752 | CF<sub>3</sub> | 2,5-diF-phenyl | 2-(N,N'-methylmorpholinium-methyl)phenyl |
| 753 | CF<sub>3</sub> | 2,5-diF-phenyl | 2-(N-pyridinium-methyl)phenyl |
| 754 | CF<sub>3</sub> | 2,5-diF-phenyl | 2-(N-4-(N,N'-dimethylamino)-pyridinium-methyl)phenyl |
| 755 | CF<sub>3</sub> | 2,5-diF-phenyl | 2-(N-azatanyl-methyl)phenyl |
| 756 | CF<sub>3</sub> | 2,5-diF-phenyl | 2-(N-azetidinyl-methyl)phenyl |
| 757 | CF<sub>3</sub> | 2,5-diF-phenyl | 2-(N-piperazinyl-methyl)phenyl |
| 758 | CF<sub>3</sub> | 2,5-diF-phenyl | 2-(N,N'-BOC-piperazinyl-methyl)phenyl |
| 759 | CF<sub>3</sub> | 2,5-diF-phenyl | 2-(N-imidazolyl-methyl)phenyl |
| 760 | CF<sub>3</sub> | 2,5-diF-phenyl | 2-(N-methoxy-N-methylamino-methyl)phenyl |
| 761 | CF<sub>3</sub> | 2,5-diF-phenyl | 2-(N-pyridonyl-methyl)phenyl |
| 762 | CF<sub>3</sub> | 2,5-diF-phenyl | 2-(N-(N',N'-dimethylhydrazinyl-methyl)phenyl |
| 763 | CF<sub>3</sub> | 2,5-diF-phenyl | 2-(amidinyl)phenyl |
| 764 | CF<sub>3</sub> | 2,5-diF-phenyl | 2-(N-guanidinyl)phenyl |
| 765 | CF<sub>3</sub> | 2,5-diF-phenyl | 2-(imidazolyl)phenyl |
| 766 | CF<sub>3</sub> | 2,5-diF-phenyl | 2-(imidazolidinyl)phenyl |
| 767 | CF<sub>3</sub> | 2,5-diF-phenyl | 2-(2-imidazolidinyl- |

-continued

| Ex # | R¹ᵇ | A | B |
|---|---|---|---|
| 768 | CF₃ | 2,5-diF-phenyl | 2-(2-pyrrolidinyl)phenyl |
| 769 | CF₃ | 2,5-diF-phenyl | 2-(2-piperidinyl)phenyl |
| 770 | CF₃ | 2,5-diF-phenyl | 2-(amidinyl-methyl)phenyl |
| 771 | CF₃ | 2,5-diF-phenyl | 2-(2-imidazolidinyl-methyl)phenyl |
| 772 | CF₃ | 2,5-diF-phenyl | 2-(N-(2-aminoimidazolyl)-methyl)phenyl |
| 773 | CF₃ | 2,5-diF-phenyl | 2-dimethylaminoimidazol-1-yl |
| 774 | CF₃ | 2,5-diF-phenyl | 2-(3-aminophenyl) |
| 775 | CF₃ | 2,5-diF-phenyl | 2-(3-pyrrolidinylcarbonyl) |
| 776 | CF₃ | 2,5-diF-phenyl | 2-glycinoyl |
| 777 | CF₃ | 2,5-diF-phenyl | 2-(imidazol-1-ylacetyl) |
| 778 | CONH₂ | phenyl | 2-(aminosulfonyl)phenyl |
| 779 | CONH₂ | phenyl | 2-(methylaminosulfonyl)phenyl |
| 780 | CONH₂ | phenyl | 1-pyrrolidinocarbonyl |
| 781 | CONH₂ | phenyl | 2-(methylsulfonyl)phenyl |
| 782 | CONH₂ | phenyl | 4-morpholino |
| 783 | CONH₂ | phenyl | 2-(1'-CF₃-tetrazol-2-yl)phenyl |
| 784 | CONH₂ | phenyl | 4-morpholinocarbonyl |
| 785 | CONH₂ | 2-pyridyl | 2-(aminosulfonyl)phenyl |
| 786 | CONH₂ | 2-pyridyl | 2-(methylaminosulfonyl)phenyl |
| 787 | CONH₂ | 2-pyridyl | 1-pyrrolidinocarbonyl |
| 788 | CONH₂ | 2-pyridyl | 2-(methylsulfonyl)phenyl |
| 789 | CONH₂ | 2-pyridyl | 4-morpholino |
| 790 | CONH₂ | 2-pyridyl | 2-(1'-CF₃-tetrazol-2-yl)phenyl |
| 791 | CONH₂ | 2-pyridyl | 4-morpholinocarbonyl |
| 792 | CONH₂ | 3-pyridyl | 2-(aminosulfonyl)phenyl |
| 793 | CONH₂ | 3-pyridyl | 2-(methylaminosulfonyl)phenyl |
| 794 | CONH₂ | 3-pyridyl | 1-pyrrolidinocarbonyl |
| 795 | CONH₂ | 3-pyridyl | 2-(methylsulfonyl)phenyl |
| 796 | CONH₂ | 3-pyridyl | 4-morpholino |
| 797 | CONH₂ | 3-pyridyl | 2-(1'-CF₃-tetrazol-2-yl)phenyl |
| 798 | CONH₂ | 3-pyridyl | 4-morpholinocarbonyl |
| 799 | CONH₂ | 2-pyrimidyl | 2-(aminosulfonyl)phenyl |
| 800 | CONH₂ | 2-pyrimidyl | 2-(methylaminosulfonyl)phenyl |
| 801 | CONH₂ | 2-pyrimidyl | 1-pyrrolidinocarbonyl |
| 802 | CONH₂ | 2-pyrimidyl | 2-(methylsulfonyl)phenyl |
| 803 | CONH₂ | 2-pyrimidyl | 4-morpholino |
| 804 | CONH₂ | 2-pyrimidyl | 2-(1'-CF₃-tetrazol-2-yl)phenyl |
| 805 | CONH₂ | 2-pyrimidyl | 4-morpholinocarbonyl |
| 806 | CONH₂ | 5-pyrimidyl | 2-(aminosulfonyl)phenyl |
| 807 | CONH₂ | 5-pyrimidyl | 2-(methylaminosulfonyl)phenyl |
| 808 | CONH₂ | 5-pyrimidyl | 1-pyrrolidinocarbonyl |
| 809 | CONH₂ | 5-pyrimidyl | 2-(methylsulfonyl)phenyl |
| 810 | CONH₂ | 5-pyrimidyl | 4-morpholino |
| 811 | CONH₂ | 5-pyrimidyl | 2-(1'-CF₃-tetrazol-2-yl)phenyl |
| 812 | CONH₂ | 5-pyrimidyl | 4-morpholinocarbonyl |
| 813 | CONH₂ | 2-Cl-phenyl | 2-(aminosulfonyl)phenyl |
| 814 | CONH₂ | 2-Cl-phenyl | 2-(methylaminosulfonyl)phenyl |
| 815 | CONH₂ | 2-Cl-phenyl | 1-pyrrolidinocarbonyl |
| 816 | CONH₂ | 2-Cl-phenyl | 2-(methylsulfonyl)phenyl |
| 817 | CONH₂ | 2-Cl-phenyl | 4-morpholino |
| 818 | CONH₂ | 2-Cl-phenyl | 2-(1'-CF₃-tetrazol-2-yl)phenyl |
| 819 | CONH₂ | 2-Cl-phenyl | 4-morpholinocarbonyl |
| 820 | CONH₂ | 2-F-phenyl | 2-(aminosulfonyl)phenyl |
| 821 | CONH₂ | 2-F-phenyl | 2-(methylaminosulfonyl)phenyl |
| 822 | CONH₂ | 2-F-phenyl | 1-pyrrolidinocarbonyl |
| 823 | CONH₂ | 2-F-phenyl | 2-(methylsulfonyl)phenyl |
| 824 | CONH₂ | 2-F-phenyl | 4-morpholino |
| 825 | CONH₂ | 2-F-phenyl | 2-(1'-CF₃-tetrazol-2-yl)phenyl |
| 826 | CONH₂ | 2-F-phenyl | 4-morpholinocarbonyl |
| 827 | CONH₂ | 2,5-diF-phenyl | 2-(aminosulfonyl)phenyl |
| 828 | CONH₂ | 2,5-diF-phenyl | 2-(methylaminosulfonyl)phenyl |
| 829 | CONH₂ | 2,5-diF-phenyl | 1-pyrrolidinocarbonyl |
| 830 | CONH₂ | 2,5-diF-phenyl | 2-(methylsulfonyl)phenyl |
| 831 | CONH₂ | 2,5-diF-phenyl | 4-morpholino |
| 832 | CONH₂ | 2,5-diF-phenyl | 2-(1'-CF₃-tetrazol-2-yl)phenyl |
| 833 | CONH₂ | 2,5-diF-phenyl | 4-morpholinocarbonyl |
| 834 | CONH₂ | phenyl | 2-(N-pyrrolidinyl-methyl)phenyl |
| 835 | CONH₂ | phenyl | 2-(N-piperidinyl-methyl)phenyl |
| 836 | CONH₂ | phenyl | 2-(N-morpholino-methyl)phenyl |
| 837 | CONH₂ | phenyl | 2-(N,N'-methylmorpholinium-methyl)phenyl |
| 838 | CONH₂ | phenyl | 2-(N-pyridinium-methyl)phenyl |
| 839 | CONH₂ | phenyl | 2-(N-4-(N,N'-dimethylamino)-pyridinium-methyl)phenyl |
| 840 | CONH₂ | phenyl | 2-(N-azatanyl-methyl)phenyl |
| 841 | CONH₂ | phenyl | 2-(N-azetidinyl-methyl)phenyl |
| 842 | CONH₂ | phenyl | 2-(N-piperazinyl-methyl)phenyl |
| 843 | CONH₂ | phenyl | 2-(N,N'-BOC-piperazinyl-methyl)phenyl |
| 844 | CONH₂ | phenyl | 2-(N-imidazolyl-methyl)phenyl |
| 845 | CONH₂ | phenyl | 2-(N-methoxy-N-methylamino-methyl)phenyl |
| 846 | CONH₂ | phenyl | 2-(N-pyridonyl-methyl)phenyl |
| 847 | CONH₂ | phenyl | 2-(N-(N',N'-dimethylhydrazinyl-methyl)phenyl |
| 848 | CONH₂ | phenyl | 2-(amidinyl)phenyl |
| 849 | CONH₂ | phenyl | 2-(N-guanidinyl)phenyl |
| 850 | CONH₂ | phenyl | 2-(imidazolyl)phenyl |
| 851 | CONH₂ | phenyl | 2-(imidazolidinyl)phenyl |
| 852 | CONH₂ | phenyl | 2-(2-imidazolidinyl-sulfonyl)phenyl |
| 853 | CONH₂ | phenyl | 2-(2-pyrrolidinyl)phenyl |
| 854 | CONH₂ | phenyl | 2-(2-piperidinyl)phenyl |
| 855 | CONH₂ | phenyl | 2-(amidinyl-methyl)phenyl |
| 856 | CONH₂ | phenyl | 2-(2-imidazolidinyl-methyl)phenyl |
| 857 | CONH₂ | phenyl | 2-(N-(2-aminoimidazolyl)-methyl)phenyl |
| 858 | CONH₂ | phenyl | 2-dimethylaminoimidazol-1-yl |
| 859 | CONH₂ | phenyl | 2-(3-aminophenyl) |
| 860 | CONH₂ | phenyl | 2-(3-pyrrolidinylcarbonyl) |
| 861 | CONH₂ | phenyl | 2-glycinoyl |
| 862 | CONH₂ | phenyl | 2-(imidazol-1-ylacetyl) |
| 863 | CONH₂ | 2-pyridyl | 2-(N-pyrrolidinyl-methyl)phenyl |
| 864 | CONH₂ | 2-pyridyl | 2-(N-piperidinyl-methyl)phenyl |
| 865 | CONH₂ | 2-pyridyl | 2-(N-morpholino-methyl)phenyl |
| 866 | CONH₂ | 2-pyridyl | 2-(N,N'-methylmorpholinium-methyl)phenyl |
| 867 | CONH₂ | 2-pyridyl | 2-(N-pyridinium-methyl)phenyl |
| 868 | CONH₂ | 2-pyridyl | 2-(N-4-(N,N'-dimethylamino)-pyridinium-methyl)phenyl |
| 869 | CONH₂ | 2-pyridyl | 2-(N-azatanyl-methyl)phenyl |
| 870 | CONH₂ | 2-pyridyl | 2-(N-azetidinyl-methyl)phenyl |
| 871 | CONH₂ | 2-pyridyl | 2-(N-piperazinyl-methyl)phenyl |
| 872 | CONH₂ | 2-pyridyl | 2-(N,N'-BOC-piperazinyl-methyl)phenyl |
| 873 | CONH₂ | 2-pyridyl | 2-(N-imidazolyl-methyl)phenyl |
| 874 | CONH₂ | 2-pyridyl | 2-(N-methoxy-N-methylamino-methyl)phenyl |
| 875 | CONH₂ | 2-pyridyl | 2-(N-pyridonyl-methyl)phenyl |
| 876 | CONH₂ | 2-pyridyl | 2-(N-(N',N'-dimethylhydrazinyl-methyl)phenyl |
| 877 | CONH₂ | 2-pyridyl | 2-(amidinyl)phenyl |
| 878 | CONH₂ | 2-pyridyl | 2-(N-guanidinyl)phenyl |
| 879 | CONH₂ | 2-pyridyl | 2-(imidazolyl)phenyl |
| 880 | CONH₂ | 2-pyridyl | 2-(imidazolidinyl)phenyl |
| 881 | CONH₂ | 2-pyridyl | 2-(2-imidazolidinyl-sulfonyl)phenyl |
| 882 | CONH₂ | 2-pyridyl | 2-(2-pyrrolidinyl)phenyl |
| 883 | CONH₂ | 2-pyridyl | 2-(2-piperidinyl)phenyl |
| 884 | CONH₂ | 2-pyridyl | 2-(amidinyl-methyl)phenyl |
| 885 | CONH₂ | 2-pyridyl | 2-(2-imidazolidinyl-methyl)phenyl |
| 886 | CONH₂ | 2-pyridyl | 2-(N-(2-aminoimidazolyl)-methyl)phenyl |
| 887 | CONH₂ | 2-pyridyl | 2-dimethylaminoimidazol-1-yl |
| 888 | CONH₂ | 2-pyridyl | 2-(3-aminophenyl) |
| 889 | CONH₂ | 2-pyridyl | 2-(3-pyrrolidinylcarbonyl) |
| 890 | CONH₂ | 2-pyridyl | 2-glycinoyl |
| 891 | CONH₂ | 2-pyridyl | 2-(imidazol-1-ylacetyl) |
| 892 | CONH₂ | 3-pyridyl | 2-(N-pyrrolidinyl-methyl)phenyl |
| 893 | CONH₂ | 3-pyridyl | 2-(N-piperidinyl-methyl)phenyl |
| 894 | CONH₂ | 3-pyridyl | 2-(N-morpholino-methyl)phenyl |
| 895 | CONH₂ | 3-pyridyl | 2-(N,N'-methylmorpholinium-methyl)phenyl |
| 896 | CONH₂ | 3-pyridyl | 2-(N-pyridinium-methyl)phenyl |
| 897 | CONH₂ | 3-pyridyl | 2-(N-4-(N,N'-dimethylamino)-pyridinium-methyl)phenyl |
| 898 | CONH₂ | 3-pyridyl | 2-(N-azatanyl-methyl)phenyl |
| 899 | CONH₂ | 3-pyridyl | 2-(N-azetidinyl-methyl)phenyl |
| 900 | CONH₂ | 3-pyridyl | 2-(N-piperazinyl-methyl)phenyl |

-continued

| Ex # | R$^{1b}$ | A | B |
|---|---|---|---|
| 901 | CONH$_2$ | 3-pyridyl | 2-(N,N'-BOC-piperazinyl-methyl)phenyl |
| 902 | CONH$_2$ | 3-pyridyl | 2-(N-imidazolyl-methyl)phenyl |
| 903 | CONH$_2$ | 3-pyridyl | 2-(N-methoxy-N-methylamino-methyl)phenyl |
| 904 | CONH$_2$ | 3-pyridyl | 2-(N-pyridonyl-methyl)phenyl |
| 905 | CONH$_2$ | 3-pyridyl | 2-(N-(N',N'-dimethylhydrazinyl-methyl)phenyl |
| 906 | CONH$_2$ | 3-pyridyl | 2-(amidinyl)phenyl |
| 907 | CONH$_2$ | 3-pyridyl | 2-(N-guanidinyl)phenyl |
| 908 | CONH$_2$ | 3-pyridyl | 2-(imidazolyl)phenyl |
| 909 | CONH$_2$ | 3-pyridyl | 2-(imidazolidinyl)phenyl |
| 910 | CONH$_2$ | 3-pyridyl | 2-(2-imidazolidinyl-sulfonyl)phenyl |
| 911 | CONH$_2$ | 3-pyridyl | 2-(2-pyrrolidinyl)phenyl |
| 912 | CONH$_2$ | 3-pyridyl | 2-(2-piperidinyl)phenyl |
| 913 | CONH$_2$ | 3-pyridyl | 2-(amidinyl-methyl)phenyl |
| 914 | CONH$_2$ | 3-pyridyl | 2-(2-imidazolidinyl-methyl)phenyl |
| 915 | CONH$_2$ | 3-pyridyl | 2-(N-(2-aminoimidazolyl)-methyl)phenyl |
| 916 | CONH$_2$ | 3-pyridyl | 2-dimethylaminoimidazol-1-yl |
| 917 | CONH$_2$ | 3-pyridyl | 2-(3-aminophenyl) |
| 918 | CONH$_2$ | 3-pyridyl | 2-(3-pyrrolidinylcarbonyl) |
| 919 | CONH$_2$ | 3-pyridyl | 2-glycinoyl |
| 920 | CONH$_2$ | 3-pyridyl | 2-(imidazol-1-ylacetyl) |
| 921 | CONH$_2$ | 2-pyrimidyl | 2-(N-pyrrolidinyl-methyl)phenyl |
| 922 | CONH$_2$ | 2-pyrimidyl | 2-(N-piperidinyl-methyl)phenyl |
| 923 | CONH$_2$ | 2-pyrimidyl | 2-(N-morpholino-methyl)phenyl |
| 924 | CONH$_2$ | 2-pyrimidyl | 2-(N,N'-methylmorpholinium-methyl)phenyl |
| 925 | CONH$_2$ | 2-pyrimidyl | 2-(N-pyridinium-methyl)phenyl |
| 926 | CONH$_2$ | 2-pyrimidyl | 2-(N-4-(N,N'-dimethylamino)-pyridinium-methyl)phenyl |
| 927 | CONH$_2$ | 2-pyrimidyl | 2-(N-azatanyl-methyl)phenyl |
| 928 | CONH$_2$ | 2-pyrimidyl | 2-(N-azetidinyl-methyl)phenyl |
| 929 | CONH$_2$ | 2-pyrimidyl | 2-(N-piperazinyl-methyl)phenyl |
| 930 | CONH$_2$ | 2-pyrimidyl | 2-(N,N'-BOC-piperazinyl-methyl)phenyl |
| 931 | CONH$_2$ | 2-pyrimidyl | 2-(N-imidazolyl-methyl)phenyl |
| 932 | CONH$_2$ | 2-pyrimidyl | 2-(N-methoxy-N-methylamino-methyl)phenyl |
| 933 | CONH$_2$ | 2-pyrimidyl | 2-(N-pyridonyl-methyl)phenyl |
| 934 | CONH$_2$ | 2-pyrimidyl | 2-(N-(N',N'-dimethylhydrazinyl-methyl)phenyl |
| 935 | CONH$_2$ | 2-pyrimidyl | 2-(amidinyl)phenyl |
| 936 | CONH$_2$ | 2-pyrimidyl | 2-(N-guanidinyl)phenyl |
| 937 | CONH$_2$ | 2-pyrimidyl | 2-(imidazolyl)phenyl |
| 938 | CONH$_2$ | 2-pyrimidyl | 2-(imidazolidinyl)phenyl |
| 939 | CONH$_2$ | 2-pyrimidyl | 2-(2-imidazolidinyl-sulfonyl)phenyl |
| 940 | CONH$_2$ | 2-pyrimidyl | 2-(2-pyrrolidinyl)phenyl |
| 941 | CONH$_2$ | 2-pyrimidyl | 2-(2-piperidinyl)phenyl |
| 942 | CONH$_2$ | 2-pyrimidyl | 2-(amidinyl-methyl)phenyl |
| 943 | CONH$_2$ | 2-pyrimidyl | 2-(2-imidazolidinyl-methyl)phenyl |
| 944 | CONH$_2$ | 2-pyrimidyl | 2-(N-(2-aminoimidazolyl)-methyl)phenyl |
| 945 | CONH$_2$ | 2-pyrimidyl | 2-dimethylaminoimidazol-1-yl |
| 946 | CONH$_2$ | 2-pyrimidyl | 2-(3-aminophenyl) |
| 947 | CONH$_2$ | 2-pyrimidyl | 2-(3-pyrrolidinylcarbonyl) |
| 948 | CONH$_2$ | 2-pyrimidyl | 2-glycinoyl |
| 949 | CONH$_2$ | 2-pyrimidyl | 2-(imidazol-1-ylacetyl) |
| 950 | CONH$_2$ | 2-Cl-phenyl | 2-(N-pyrrolidinyl-methyl)phenyl |
| 951 | CONH$_2$ | 2-Cl-phenyl | 2-(N-piperidinyl-methyl)phenyl |
| 952 | CONH$_2$ | 2-Cl-phenyl | 2-(N-morpholino-methyl)phenyl |
| 953 | CONH$_2$ | 2-Cl-phenyl | 2-(N,N'-methylmorpholinium-methyl)phenyl |
| 954 | CONH$_2$ | 2-Cl-phenyl | 2-(N-pyridinium-methyl)phenyl |
| 955 | CONH$_2$ | 2-Cl-phenyl | 2-(N-4-(N,N'-dimethylamino)-pyridinium-methyl)phenyl |
| 956 | CONH$_2$ | 2-Cl-phenyl | 2-(N-azatanyl-methyl)phenyl |
| 957 | CONH$_2$ | 2-Cl-phenyl | 2-(N-azetidinyl-methyl)phenyl |
| 958 | CONH$_2$ | 2-Cl-phenyl | 2-(N-piperazinyl-methyl)phenyl |
| 959 | CONH$_2$ | 2-Cl-phenyl | 2-(N,N'-BOC-piperazinyl-methyl)phenyl |
| 960 | CONH$_2$ | 2-Cl-phenyl | 2-(N-imidazolyl-methyl)phenyl |
| 961 | CONH$_2$ | 2-Cl-phenyl | 2-(N-methoxy-N-methylamino-methyl)phenyl |
| 962 | CONH$_2$ | 2-Cl-phenyl | 2-(N-pyridonyl-methyl)phenyl |
| 963 | CONH$_2$ | 2-Cl-phenyl | 2-(N-(N',N'-dimethylhydrazinyl-methyl)phenyl |
| 964 | CONH$_2$ | 2-Cl-phenyl | 2-(amidinyl)phenyl |
| 965 | CONH$_2$ | 2-Cl-phenyl | 2-(N-guanidinyl)phenyl |
| 966 | CONH$_2$ | 2-Cl-phenyl | 2-(imidazolyl)phenyl |
| 967 | CONH$_2$ | 2-Cl-phenyl | 2-(imidazolidinyl)phenyl |
| 968 | CONH$_2$ | 2-Cl-phenyl | 2-(2-imidazolidinyl-sulfonyl)phenyl |
| 969 | CONH$_2$ | 2-Cl-phenyl | 2-(2-pyrrolidinyl)phenyl |
| 970 | CONH$_2$ | 2-Cl-phenyl | 2-(2-piperidinyl)phenyl |
| 971 | CONH$_2$ | 2-Cl-phenyl | 2-(amidinyl-methyl)phenyl |
| 972 | CONH$_2$ | 2-Cl-phenyl | 2-(2-imidazolidinyl-methyl)phenyl |
| 973 | CONH$_2$ | 2-Cl-phenyl | 2-(N-(2-aminoimidazolyl)-methyl)phenyl |
| 974 | CONH$_2$ | 2-Cl-phenyl | 2-dimethylaminoimidazol-1-yl |
| 975 | CONH$_2$ | 2-Cl-phenyl | 2-(3-aminophenyl) |
| 976 | CONH$_2$ | 2-Cl-phenyl | 2-(3-pyrrolidinylcarbonyl) |
| 977 | CONH$_2$ | 2-Cl-phenyl | 2-glycinoyl |
| 978 | CONH$_2$ | 2-Cl-phenyl | 2-(imidazol-1-ylacetyl) |
| 979 | CONH$_2$ | 2-F-phenyl | 2-(N-pyrrolidinyl-methyl)phenyl |
| 980 | CONH$_2$ | 2-F-phenyl | 2-(N-piperidinyl-methyl)phenyl |
| 981 | CONH$_2$ | 2-F-phenyl | 2-(N-morpholino-methyl)phenyl |
| 982 | CONH$_2$ | 2-F-phenyl | 2-(N,N'-methylmorpholinium-methyl)phenyl |
| 983 | CONH$_2$ | 2-F-phenyl | 2-(N-pyridinium-methyl)phenyl |
| 984 | CONH$_2$ | 2-F-phenyl | 2-(N-4-(N,N'-dimethylamino)-pyridinium-methyl)phenyl |
| 985 | CONH$_2$ | 2-F-phenyl | 2-(N-azatanyl-methyl)phenyl |
| 986 | CONH$_2$ | 2-F-phenyl | 2-(N-azetidinyl-methyl)phenyl |
| 987 | CONH$_2$ | 2-F-phenyl | 2-(N-piperazinyl-methyl)phenyl |
| 988 | CONH$_2$ | 2-F-phenyl | 2-(N,N'-BOC-piperazinyl-methyl)phenyl |
| 989 | CONH$_2$ | 2-F-phenyl | 2-(N-imidazolyl-methyl)phenyl |
| 990 | CONH$_2$ | 2-F-phenyl | 2-(N-methoxy-N-methylamino-methyl)phenyl |
| 991 | CONH$_2$ | 2-F-phenyl | 2-(N-pyridonyl-methyl)phenyl |
| 992 | CONH$_2$ | 2-F-phenyl | 2-(N-(N',N'-dimethylhydrazinyl-methyl)phenyl |
| 993 | CONH$_2$ | 2-F-phenyl | 2-(amidinyl)phenyl |
| 994 | CONH$_2$ | 2-F-phenyl | 2-(N-guanidinyl)phenyl |
| 995 | CONH$_2$ | 2-F-phenyl | 2-(imidazolyl)phenyl |
| 996 | CONH$_2$ | 2-F-phenyl | 2-(imidazolidinyl)phenyl |
| 997 | CONH$_2$ | 2-F-phenyl | 2-(2-imidazolidinyl-sulfonyl)phenyl |
| 998 | CONH$_2$ | 2-F-phenyl | 2-(2-pyrrolidinyl)phenyl |
| 999 | CONH$_2$ | 2-F-phenyl | 2-(2-piperidinyl)phenyl |
| 1000 | CONH$_2$ | 2-F-phenyl | 2-(amidinyl-methyl)phenyl |
| 1001 | CONH$_2$ | 2-F-phenyl | 2-(2-imidazolidinyl-methyl)phenyl |
| 1002 | CONH$_2$ | 2-F-phenyl | 2-(N-(2-aminoimidazolyl)-methyl)phenyl |
| 1003 | CONH$_2$ | 2-F-phenyl | 2-dimethylaminoimidazol-1-yl |
| 1004 | CONH$_2$ | 2-F-phenyl | 2-(3-aminophenyl) |
| 1005 | CONH$_2$ | 2-F-phenyl | 2-(3-pyrrolidinylcarbonyl) |
| 1006 | CONH$_2$ | 2-F-phenyl | 2-glycinoyl |
| 1007 | CONH$_2$ | 2-F-phenyl | 2-(imidazol-1-ylacetyl) |
| 1008 | CONH$_2$ | 2,5-diF-phenyl | 2-(N-pyrrolidinyl-methyl)phenyl |
| 1009 | CONH$_2$ | 2,5-diF-phenyl | 2-(N-piperidinyl-methyl)phenyl |
| 1010 | CONH$_2$ | 2,5-diF-phenyl | 2-(N-morpholino-methyl)phenyl |
| 1011 | CONH$_2$ | 2,5-diF-phenyl | 2-(N,N'-methylmorpholinium-methyl)phenyl |
| 1012 | CONH$_2$ | 2,5-diF-phenyl | 2-(N-pyridinium-methyl)phenyl |
| 1013 | CONH$_2$ | 2,5-diF-phenyl | 2-(N-4-(N,N'-dimethylamino)-pyridinium-methyl)phenyl |
| 1014 | CONH$_2$ | 2,5-diF-phenyl | 2-(N-azatanyl-methyl)phenyl |
| 1015 | CONH$_2$ | 2,5-diF-phenyl | 2-(N-azetidinyl-methyl)phenyl |
| 1016 | CONH$_2$ | 2,5-diF-phenyl | 2-(N-piperazinyl-methyl)phenyl |
| 1017 | CONH$_2$ | 2,5-diF-phenyl | 2-(N,N'-BOC-piperazinyl-methyl)phenyl |
| 1018 | CONH$_2$ | 2,5-diF-phenyl | 2-(N-imidazolyl-methyl)phenyl |
| 1019 | CONH$_2$ | 2,5-diF-phenyl | 2-(N-methoxy-N-methylamino-methyl)phenyl |
| 1020 | CONH$_2$ | 2,5-diF-phenyl | 2-(N-pyridonyl-methyl)phenyl |

-continued

| Ex # | R$^{1b}$ | A | B |
|---|---|---|---|
| 1021 | CONH$_2$ | 2,5-diF-phenyl | 2-(N-(N',N'-dimethylhydrazinyl-methyl)phenyl |
| 1022 | CONH$_2$ | 2,5-diF-phenyl | 2-(amidinyl)phenyl |
| 1023 | CONH$_2$ | 2,5-diF-phenyl | 2-(N-guanidinyl)phenyl |
| 1024 | CONH$_2$ | 2,5-diF-phenyl | 2-(imidazolyl)phenyl |
| 1025 | CONH$_2$ | 2,5-diF-phenyl | 2-(imidazolidinyl)phenyl |
| 1026 | CONH$_2$ | 2,5-diF-phenyl | 2-(2-imidazolidinyl-sulfonyl)phenyl |
| 1027 | CONH$_2$ | 2,5-diF-phenyl | 2-(2-pyrrolidinyl)phenyl |
| 1028 | CONH$_2$ | 2,5-diF-phenyl | 2-(2-piperidinyl)phenyl |
| 1029 | CONH$_2$ | 2,5-diF-phenyl | 2-(amidinyl-methyl)phenyl |
| 1030 | CONH$_2$ | 2,5-diF-phenyl | 2-(2-imidazolidinyl-methyl)phenyl |
| 1031 | CONH$_2$ | 2,5-diF-phenyl | 2-(N-(2-aminoimidazolyl)-methyl)phenyl |
| 1032 | CONH$_2$ | 2,5-diF-phenyl | 2-dimethylaminoimidazol-1-yl |
| 1033 | CONH$_2$ | 2,5-diF-phenyl | 2-(3-aminophenyl) |
| 1034 | CONH$_2$ | 2,5-diF-phenyl | 2-(3-pyrrolidinylcarbonyl) |
| 1035 | CONH$_2$ | 2,5-diF-phenyl | 2-glycinoyl |
| 1036 | CONH$_2$ | 2,5-diF-phenyl | 2-(imidazol-1-ylacetyl) |
| 1037 | SCH$_3$ | phenyl | 2-(aminosulfonyl)phenyl |
| 1038 | SCH$_3$ | phenyl | 2-(methylaminosulfonyl)phenyl |
| 1039 | SCH$_3$ | phenyl | 1-pyrrolidinocarbonyl |
| 1040 | SCH$_3$ | phenyl | 2-(methylsulfonyl)phenyl |
| 1041 | SCH$_3$ | phenyl | 4-morpholino |
| 1042 | SCH$_3$ | phenyl | 2-(1'-CF$_3$-tetrazol-2-yl)phenyl |
| 1043 | SCH$_3$ | phenyl | 4-morpholinocarbonyl |
| 1044 | SCH$_3$ | 2-pyridyl | 2-(aminosulfonyl)phenyl |
| 1045 | SCH$_3$ | 2-pyridyl | 2-(methylaminosulfonyl)phenyl |
| 1046 | SCH$_3$ | 2-pyridyl | 1-pyrrolidinocarbonyl |
| 1047 | SCH$_3$ | 2-pyridyl | 2-(methylsulfonyl)phenyl |
| 1048 | SCH$_3$ | 2-pyridyl | 4-morpholino |
| 1049 | SCH$_3$ | 2-pyridyl | 2-(1'-CF$_3$-tetrazol-2-yl)phenyl |
| 1050 | SCH$_3$ | 2-pyridyl | 4-morpholinocarbonyl |
| 1051 | SCH$_3$ | 3-pyridyl | 2-(aminosulfonyl)phenyl |
| 1052 | SCH$_3$ | 3-pyridyl | 2-(methylaminosulfonyl)phenyl |
| 1053 | SCH$_3$ | 3-pyridyl | 1-pyrrolidinocarbonyl |
| 1054 | SCH$_3$ | 3-pyridyl | 2-(methylsulfonyl)phenyl |
| 1055 | SCH$_3$ | 3-pyridyl | 4-morpholino |
| 1056 | SCH$_3$ | 3-pyridyl | 2-(1'-CF$_3$-tetrazol-2-yl)phenyl |
| 1057 | SCH$_3$ | 3-pyridyl | 4-morpholinocarbonyl |
| 1058 | SCH$_3$ | 2-pyrimidyl | 2-(aminosulfonyl)phenyl |
| 1059 | SCH$_3$ | 2-pyrimidyl | 2-(methylaminosulfonyl)phenyl |
| 1060 | SCH$_3$ | 2-pyrimidyl | 1-pyrrolidinocarbonyl |
| 1061 | SCH$_3$ | 2-pyrimidyl | 2-(methylsulfonyl)phenyl |
| 1062 | SCH$_3$ | 2-pyrimidyl | 4-morpholino |
| 1063 | SCH$_3$ | 2-pyrimidyl | 2-(1'-CF$_3$-tetrazol-2-yl)phenyl |
| 1064 | SCH$_3$ | 2-pyrimidyl | 4-morpholinocarbonyl |
| 1065 | SCH$_3$ | 5-pyrimidyl | 2-(aminosulfonyl)phenyl |
| 1066 | SCH$_3$ | 5-pyrimidyl | 2-(methylaminosulfonyl)phenyl |
| 1067 | SCH$_3$ | 5-pyrimidyl | 1-pyrrolidinocarbonyl |
| 1068 | SCH$_3$ | 5-pyrimidyl | 2-(methylsulfonyl)phenyl |
| 1069 | SCH$_3$ | 5-pyrimidyl | 4-morpholino |
| 1070 | SCH$_3$ | 5-pyrimidyl | 2-(1'-CF$_3$-tetrazol-2-yl)phenyl |
| 1071 | SCH$_3$ | 5-pyrimidyl | 4-morpholinocarbonyl |
| 1072 | SCH$_3$ | 2-Cl-phenyl | 2-(aminosulfonyl)phenyl |
| 1073 | SCH$_3$ | 2-Cl-phenyl | 2-(methylaminosulfonyl)phenyl |
| 1074 | SCH$_3$ | 2-Cl-phenyl | 1-pyrrolidinocarbonyl |
| 1075 | SCH$_3$ | 2-Cl-phenyl | 2-(methylsulfonyl)phenyl |
| 1076 | SCH$_3$ | 2-Cl-phenyl | 4-morpholino |
| 1077 | SCH$_3$ | 2-Cl-phenyl | 2-(1'-CF$_3$-tetrazol-2-yl)phenyl |
| 1078 | SCH$_3$ | 2-Cl-phenyl | 4-morpholinocarbonyl |
| 1079 | SCH$_3$ | 2-F-phenyl | 2-(aminosulfonyl)phenyl |
| 1080 | SCH$_3$ | 2-F-phenyl | 2-(methylaminosulfonyl)phenyl |
| 1081 | SCH$_3$ | 2-F-phenyl | 1-pyrrolidinocarbonyl |
| 1082 | SCH$_3$ | 2-F-phenyl | 2-(methylsulfonyl)phenyl |
| 1083 | SCH$_3$ | 2-F-phenyl | 4-morpholino |
| 1084 | SCH$_3$ | 2-F-phenyl | 2-(1'-CF$_3$-tetrazol-2-yl)phenyl |
| 1085 | SCH$_3$ | 2-F-phenyl | 4-morpholinocarbonyl |
| 1086 | SCH$_3$ | 2,5-diF-phenyl | 2-(aminosulfonyl)phenyl |
| 1087 | SCH$_3$ | 2,5-diF-phenyl | 2-(methylaminosulfonyl)phenyl |
| 1088 | SCH$_3$ | 2,5-diF-phenyl | 1-pyrrolidinocarbonyl |
| 1089 | SCH$_3$ | 2,5-diF-phenyl | 2-(methylsulfonyl)phenyl |
| 1090 | SCH$_3$ | 2,5-diF-phenyl | 4-morpholino |
| 1091 | SCH$_3$ | 2,5-diF-phenyl | 2-(1'-CF$_3$-tetrazol-2-yl)phenyl |
| 1092 | SCH$_3$ | 2,5-diF-phenyl | 4-morpholinocarbonyl |
| 1093 | SCH$_3$ | phenyl | 2-(N-pyrrolidinyl-methyl)phenyl |
| 1094 | SCH$_3$ | phenyl | 2-(N-piperidinyl-methyl)phenyl |
| 1095 | SCH$_3$ | phenyl | 2-(N-morpholino-methyl)phenyl |
| 1096 | SCH$_3$ | phenyl | 2-(N,N'-methylmorpholinium-methyl)phenyl |
| 1097 | SCH$_3$ | phenyl | 2-(N-pyridinium-methyl)phenyl |
| 1098 | SCH$_3$ | phenyl | 2-(N-4-(N,N'-dimethylamino)-pyridinium-methyl)phenyl |
| 1099 | SCH$_3$ | phenyl | 2-(N-azatanyl-methyl)phenyl |
| 1100 | SCH$_3$ | phenyl | 2-(N-azetidinyl-methyl)phenyl |
| 1101 | SCH$_3$ | phenyl | 2-(N-piperazinyl-methyl)phenyl |
| 1102 | SCH$_3$ | phenyl | 2-(N,N'-BOC-piperazinyl-methyl)phenyl |
| 1103 | SCH$_3$ | phenyl | 2-(N-imidazolyl-methyl)phenyl |
| 1104 | SCH$_3$ | phenyl | 2-(N-methoxy-N-methylamino-methyl)phenyl |
| 1105 | SCH$_3$ | phenyl | 2-(N-pyridonyl-methyl)phenyl |
| 1106 | SCH$_3$ | phenyl | 2-(N-(N',N'-dimethylhydrazinyl-methyl)phenyl |
| 1107 | SCH$_3$ | phenyl | 2-(amidinyl)phenyl |
| 1108 | SCH$_3$ | phenyl | 2-(N-guanidinyl)phenyl |
| 1109 | SCH$_3$ | phenyl | 2-(imidazolyl)phenyl |
| 1110 | SCH$_3$ | phenyl | 2-(imidazolidinyl)phenyl |
| 1111 | SCH$_3$ | phenyl | 2-(2-imidazolidinyl-sulfonyl)phenyl |
| 1112 | SCH$_3$ | phenyl | 2-(2-pyrrolidinyl)phenyl |
| 1113 | SCH$_3$ | phenyl | 2-(2-piperidinyl)phenyl |
| 1114 | SCH$_3$ | phenyl | 2-(amidinyl-methyl)phenyl |
| 1115 | SCH$_3$ | phenyl | 2-(2-imidazolidinyl-methyl)phenyl |
| 1116 | SCH$_3$ | phenyl | 2-(N-(2-aminoimidazolyl)-methyl)phenyl |
| 1117 | SCH$_3$ | phenyl | 2-dimethylaminoimidazol-1-yl |
| 1118 | SCH$_3$ | phenyl | 2-(3-aminophenyl) |
| 1119 | SCH$_3$ | phenyl | 2-(3-pyrrolidinylcarbonyl) |
| 1120 | SCH$_3$ | phenyl | 2-glycinoyl |
| 1121 | SCH$_3$ | phenyl | 2-(imidazol-1-ylacetyl) |
| 1122 | SCH$_3$ | 2-pyridyl | 2-(N-pyrrolidinyl-methyl)phenyl |
| 1123 | SCH$_3$ | 2-pyridyl | 2-(N-piperidinyl-methyl)phenyl |
| 1124 | SCH$_3$ | 2-pyridyl | 2 (N-morpholino-methyl)phenyl |
| 1125 | SCH$_3$ | 2-pyridyl | 2-(N,N'-methylmorpholinium-methyl)phenyl |
| 1126 | SCH$_3$ | 2-pyridyl | 2-(N-pyridinium-methyl)phenyl |
| 1127 | SCH$_3$ | 2-pyridyl | 2-(N-4-(N,N'-dimethylamino)-pyridinium-methyl)phenyl |
| 1128 | SCH$_3$ | 2-pyridyl | 2-(N-azatanyl-methyl)phenyl |
| 1129 | SCH$_3$ | 2-pyridyl | 2-(N-azetidinyl-methyl)phenyl |
| 1130 | SCH$_3$ | 2-pyridyl | 2-(N-piperazinyl-methyl)phenyl |
| 1131 | SCH$_3$ | 2-pyridyl | 2-(N,N'-BOC-piperazinyl-methyl)phenyl |
| 1132 | SCH$_3$ | 2-pyridyl | 2-(N-imidazolyl-methyl)phenyl |
| 1133 | SCH$_3$ | 2-pyridyl | 2-(N-methoxy-N-methylamino-methyl)phenyl |
| 1134 | SCH$_3$ | 2-pyridyl | 2-(N-pyridonyl-methyl)phenyl |
| 1135 | SCH$_3$ | 2-pyridyl | 2-(N-(N',N'-dimethylhydrazinyl-methyl)phenyl |
| 1136 | SCH$_3$ | 2-pyridyl | 2-(amidinyl)phenyl |
| 1137 | SCH$_3$ | 2-pyridyl | 2-(N-guanidinyl)phenyl |
| 1138 | SCH$_3$ | 2-pyridyl | 2-(imidazolyl)phenyl |
| 1139 | SCH$_3$ | 2-pyridyl | 2-(imidazolidinyl)phenyl |
| 1140 | SCH$_3$ | 2-pyridyl | 2-(2-imidazolidinyl-sulfonyl)phenyl |
| 1141 | SCH$_3$ | 2-pyridyl | 2-(2-pyrrolidinyl)phenyl |
| 1142 | SCH$_3$ | 2-pyridyl | 2-(2-piperidinyl)phenyl |
| 1143 | SCH$_3$ | 2-pyridyl | 2-(amidinyl-methyl)phenyl |
| 1144 | SCH$_3$ | 2-pyridyl | 2-(2-imidazolidinyl-methyl)phenyl |
| 1145 | SCH$_3$ | 2-pyridyl | 2-(N-(2-aminoimidazolyl)-methyl)phenyl |
| 1146 | SCH$_3$ | 2-pyridyl | 2-dimethylaminoimidazol-1-yl |
| 1147 | SCH$_3$ | 2-pyridyl | 2-(3-aminophenyl) |
| 1148 | SCH$_3$ | 2-pyridyl | 2-(3-pyrrolidinylcarbonyl) |
| 1149 | SCH$_3$ | 2-pyridyl | 2-glycinoyl |
| 1150 | SCH$_3$ | 2-pyridyl | 2-(imidazol-1-ylacetyl) |
| 1151 | SCH$_3$ | 3-pyridyl | 2-(N-pyrrolidinyl-methyl)phenyl |
| 1152 | SCH$_3$ | 3-pyridyl | 2-(N-piperidinyl-methyl)phenyl |
| 1153 | SCH$_3$ | 3-pyridyl | 2-(N-morpholino-methyl)phenyl |
| 1154 | SCH$_3$ | 3-pyridyl | 2-(N,N'-methylmorpholinium- |

| Ex # | R¹ᵇ | A | B |
|---|---|---|---|
| 1155 | SCH₃ | 3-pyridyl | 2-(N-pyridinium-methyl)phenyl |
| 1156 | SCH₃ | 3-pyridyl | 2-(N-4-(N,N'-dimethylamino)-pyridinium-methyl)phenyl |
| 1157 | SCH₃ | 3-pyridyl | 2-(N-azatanyl-methyl)phenyl |
| 1158 | SCH₃ | 3-pyridyl | 2-(N-azetidinyl-methyl)phenyl |
| 1159 | SCH₃ | 3-pyridyl | 2-(N-piperazinyl-methyl)phenyl |
| 1160 | SCH₃ | 3-pyridyl | 2-(N,N'-BOC-piperazinyl-methyl)phenyl |
| 1161 | SCH₃ | 3-pyridyl | 2-(N-imidazolyl-methyl)phenyl |
| 1162 | SCH₃ | 3-pyridyl | 2-(N-methoxy-N-methylamino-methyl)phenyl |
| 1163 | SCH₃ | 3-pyridyl | 2-(N-pyridonyl-methyl)phenyl |
| 1164 | SCH₃ | 3-pyridyl | 2-(N-(N',N'-dimethylhydrazinyl-methyl)phenyl |
| 1165 | SCH₃ | 3-pyridyl | 2-(amidinyl)phenyl |
| 1166 | SCH₃ | 3-pyridyl | 2-(N-guanidinyl)phenyl |
| 1167 | SCH₃ | 3-pyridyl | 2-(imidazolyl)phenyl |
| 1168 | SCH₃ | 3-pyridyl | 2-(imidazolidinyl)phenyl |
| 1169 | SCH₃ | 3-pyridyl | 2-(2-imidazolidinyl-sulfonyl)phenyl |
| 1170 | SCH₃ | 3-pyridyl | 2-(2-pyrrolidinyl)phenyl |
| 1171 | SCH₃ | 3-pyridyl | 2-(2-piperidinyl)phenyl |
| 1172 | SCH₃ | 3-pyridyl | 2-(amidinyl-methyl)phenyl |
| 1173 | SCH₃ | 3-pyridyl | 2-(2-imidazolidinyl-methyl)phenyl |
| 1174 | SCH₃ | 3-pyridyl | 2-(N-(2-aminoimidazolyl)-methyl)phenyl |
| 1175 | SCH₃ | 3-pyridyl | 2-dimethylaminoimidazol-1-yl |
| 1176 | SCH₃ | 3-pyridyl | 2-(3-aminophenyl) |
| 1177 | SCH₃ | 3-pyridyl | 2-(3-pyrrolidinylcarbonyl) |
| 1178 | SCH₃ | 3-pyridyl | 2-glycinoyl |
| 1179 | SCH₃ | 3-pyridyl | 2-(imidazol-1-ylacetyl) |
| 1180 | SCH₃ | 2-pyrimidyl | 2-(N-pyrrolidinyl-methyl)phenyl |
| 1181 | SCH₃ | 2-pyrimidyl | 2-(N-piperidinyl-methyl)phenyl |
| 1182 | SCH₃ | 2-pyrimidyl | 2-(N-morpholino-methyl)phenyl |
| 1183 | SCH₃ | 2-pyrimidyl | 2-(N,N'-methylmorpholinium-methyl)phenyl |
| 1184 | SCH₃ | 2-pyrimidyl | 2-(N-pyridinium-methyl)phenyl |
| 1185 | SCH₃ | 2-pyrimidyl | 2-(N-4-(N,N'-dimethylamino)-pyridinium-methyl)phenyl |
| 1186 | SCH₃ | 2-pyrimidyl | 2-(N-azatanyl-methyl)phenyl |
| 1187 | SCH₃ | 2-pyrimidyl | 2-(N-azetidinyl-methyl)phenyl |
| 1188 | SCH₃ | 2-pyrimidyl | 2-(N-piperazinyl-methyl)phenyl |
| 1189 | SCH₃ | 2-pyrimidyl | 2-(N,N'-BOC-piperazinyl-methyl)phenyl |
| 1190 | SCH₃ | 2-pyrimidyl | 2-(N-imidazolyl-methyl)phenyl |
| 1191 | SCH₃ | 2-pyrimidyl | 2-(N-methoxy-N-methylamino-methyl)phenyl |
| 1192 | SCH₃ | 2-pyrimidyl | 2-(N-pyridonyl-methyl)phenyl |
| 1193 | SCH₃ | 2-pyrimidyl | 2-(N-(N',N'-dimethylhydrazinyl-methyl)phenyl |
| 1194 | SCH₃ | 2-pyrimidyl | 2-(amidinyl)phenyl |
| 1195 | SCH₃ | 2-pyrimidyl | 2-(N-guanidinyl)phenyl |
| 1196 | SCH₃ | 2-pyrimidyl | 2-(imidazolyl)phenyl |
| 1197 | SCH₃ | 2-pyrimidyl | 2-(imidazolidinyl)phenyl |
| 1198 | SCH₃ | 2-pyrimidyl | 2-(2-imidazolidinyl-sulfonyl)phenyl |
| 1199 | SCH₃ | 2-pyrinidyl | 2-(2-pyrrolidinyl)phenyl |
| 1200 | SCH₃ | 2-pyrimidyl | 2-(2-piperidinyl)phenyl |
| 1201 | SCH₃ | 2-pyrimidyl | 2-(amidinyl-methyl)phenyl |
| 1202 | SCH₃ | 2-pyrimidyl | 2-(2-imidazolidinyl-methyl)phenyl |
| 1203 | SCH₃ | 2-pyrimidyl | 2-(N-(2-aminoimidazolyl)-methyl)phenyl |
| 1204 | SCH₃ | 2-pyrimidyl | 2-dimethylaminoimidazol-1-yl |
| 1205 | SCH₃ | 2-pyrimidyl | 2-(3-aminophenyl) |
| 1206 | SCH₃ | 2-pyrimidyl | 2-(3-pyrrolidinylcarbonyl) |
| 1207 | SCH₃ | 2-pyrimidyl | 2-glycinoyl |
| 1208 | SCH₃ | 2-pyrimidyl | 2-(imidazol-1-ylacetyl) |
| 1209 | SCH₃ | 2-Cl-phenyl | 2-(N-pyrrolidinyl-methyl)phenyl |
| 1210 | SCH₃ | 2-Cl-phenyl | 2-(N-piperidinyl-methyl)phenyl |
| 1211 | SCH₃ | 2-Cl-phenyl | 2-(N-morpholino-methyl)phenyl |
| 1212 | SCH₃ | 2-Cl-phenyl | 2-(N,N'-methylmorpholinium-methyl)phenyl |
| 1213 | SCH₃ | 2-Cl-phenyl | 2-(N-pyridinium-methyl)phenyl |
| 1214 | SCH₃ | 2-Cl-phenyl | 2-(N-4-(N,N'-dimethylamino)-pyridinium-methyl)phenyl |
| 1215 | SCH₃ | 2-Cl-phenyl | 2-(N-azatanyl-methyl)phenyl |
| 1216 | SCH₃ | 2-Cl-phenyl | 2-(N-azetidinyl-methyl)phenyl |
| 1217 | SCH₃ | 2-Cl-phenyl | 2-(N-piperazinyl-methyl)phenyl |
| 1218 | SCH₃ | 2-Cl-phenyl | 2-(N,N'-BOC-piperazinyl-methyl)phenyl |
| 1219 | SCH₃ | 2-Cl-phenyl | 2-(N-imidazolyl-methyl)phenyl |
| 1220 | SCH₃ | 2-Cl-phenyl | 2-(N-methoxy-N-methylamino-methyl)phenyl |
| 1221 | SCH₃ | 2-Cl-phenyl | 2-(N-pyridonyl-methyl)phenyl |
| 1222 | SCH₃ | 2-Cl-phenyl | 2-(N-(N',N'-dimethylhydrazinyl-methyl)phenyl |
| 1223 | SCH₃ | 2-Cl-phenyl | 2-(amidinyl)phenyl |
| 1224 | SCH₃ | 2-Cl-phenyl | 2-(N-guanidinyl)phenyl |
| 1225 | SCH₃ | 2-Cl-phenyl | 2-(imidazolyl)phenyl |
| 1226 | SCH₃ | 2-Cl-phenyl | 2-(imidazolidinyl)phenyl |
| 1227 | SCH₃ | 2-Cl-phenyl | 2-(2-imidazolidinyl-sulfonyl)phenyl |
| 1228 | SCH₃ | 2-Cl-phenyl | 2-(2-pyrrolidinyl)phenyl |
| 1229 | SCH₃ | 2-Cl-phenyl | 2-(2-piperidinyl)phenyl |
| 1230 | SCH₃ | 2-Cl-phenyl | 2-(amidinyl-methyl)phenyl |
| 1231 | SCH₃ | 2-Cl-phenyl | 2-(2-imidazolidinyl-methyl)phenyl |
| 1232 | SCH₃ | 2-Cl-phenyl | 2-(N-(2-aminoimidazolyl)-methyl)phenyl |
| 1233 | SCH₃ | 2-Cl-phenyl | 2-dimethylaminoimidazol-1-yl |
| 1234 | SCH₃ | 2-Cl-phenyl | 2-(3-aminophenyl) |
| 1235 | SCH₃ | 2-Cl-phenyl | 2-(3-pyrrolidinylcarbonyl) |
| 1236 | SCH₃ | 2-Cl-phenyl | 2-glycinoyl |
| 1237 | SCH₃ | 2-Cl-phenyl | 2-(imidazol-1-ylacetyl) |
| 1238 | SCH₃ | 2-F-phenyl | 2-(N-pyrrolidinyl-methyl)phenyl |
| 1239 | SCH₃ | 2-F-phenyl | 2-(N-piperidinyl-methyl)phenyl |
| 1240 | SCH₃ | 2-F-phenyl | 2-(N-morpholino-methyl)phenyl |
| 1241 | SCH₃ | 2-F-phenyl | 2-(N,N'-methylmorpholinium-methyl)phenyl |
| 1242 | SCH₃ | 2-F-phenyl | 2-(N-pyridinium-methyl)phenyl |
| 1243 | SCH₃ | 2-F-phenyl | 2-(N-4-(N,N'-dimethylamino)-pyridinium-methyl)phenyl |
| 1244 | SCH₃ | 2-F-phenyl | 2-(N-azatanyl-methyl)phenyl |
| 1245 | SCH₃ | 2-F-phenyl | 2-(N-azetidinyl-methyl)phenyl |
| 1246 | SCH₃ | 2-F-phenyl | 2-(N-piperazinyl-methyl)phenyl |
| 1247 | SCH₃ | 2-F-phenyl | 2-(N,N'-BOC-piperazinyl-methyl)phenyl |
| 1248 | SCH₃ | 2-F-phenyl | 2-(N-imidazolyl-methyl)phenyl |
| 1249 | SCH₃ | 2-F-phenyl | 2-(N-methoxy-N-methylamino-methyl)phenyl |
| 1250 | SCH₃ | 2-F-phenyl | 2-(N-pyridonyl-methyl)phenyl |
| 1251 | SCH₃ | 2-F-phenyl | 2-(N-(N',N'-dimethylhydrazinyl-methyl)phenyl |
| 1252 | SCH₃ | 2-F-phenyl | 2-(amidinyl)phenyl |
| 1253 | SCH₃ | 2-F-phenyl | 2-(N-guanidinyl)phenyl |
| 1254 | SCH₃ | 2-F-phenyl | 2-(imidazolyl)phenyl |
| 1255 | SCH₃ | 2-F-phenyl | 2-(imidazolidinyl)phenyl |
| 1256 | SCH₃ | 2-F-phenyl | 2-(2-imidazolidinyl-sulfonyl)phenyl |
| 1257 | SCH₃ | 2-F-phenyl | 2-(2-pyrrolidinyl)phenyl |
| 1258 | SCH₃ | 2-F-phenyl | 2-(2-piperidinyl)phenyl |
| 1259 | SCH₃ | 2-F-phenyl | 2-(amidinyl-methyl)phenyl |
| 1260 | SCH₃ | 2-F-phenyl | 2-(2-imidazolidinyl-methyl)phenyl |
| 1261 | SCH₃ | 2-F-phenyl | 2-(N-(2-aminoimidazolyl)-methyl)phenyl |
| 1262 | SCH₃ | 2-F-phenyl | 2-dimethylaminoimidazol-1-yl |
| 1263 | SCH₃ | 2-F-phenyl | 2-(3-aminophenyl) |
| 1264 | SCH₃ | 2-F-phenyl | 2-(3-pyrrolidinylcarbonyl) |
| 1265 | SCH₃ | 2-F-phenyl | 2-glycinoyl |
| 1266 | SCH₃ | 2-F-phenyl | 2-(imidazol-1-ylacetyl) |
| 1267 | SCH₃ | 2,5-diF-phenyl | 2-(N-pyrrolidinyl-methyl)phenyl |
| 1268 | SCH₃ | 2,5-diF-phenyl | 2-(N-piperidinyl-methyl)phenyl |
| 1269 | SCH₃ | 2,5-diF-phenyl | 2-(N-morpholino-methyl)phenyl |
| 1270 | SCH₃ | 2,5-diF-phenyl | 2-(N,N'-methylmorpholinium-methyl)phenyl |
| 1271 | SCH₃ | 2,5-diF-phenyl | 2-(N-pyridinium-methyl)phenyl |
| 1272 | SCH₃ | 2,5-diF-phenyl | 2-(N-4-(N,N'-dimethylamino)-pyridinium-methyl)phenyl |
| 1273 | SCH₃ | 2,5-diF-phenyl | 2-N-azatanyl-methyl)phenyl |
| 1274 | SCH₃ | 2,5-diF-phenyl | 2-(N-azetidinyl-methyl)phenyl |

| Ex # | R¹ᵇ | A | B |
|---|---|---|---|
| 1275 | SCH₃ | 2,5-diF-phenyl | 2-(N-piperazinyl-methyl)phenyl |
| 1276 | SCH₃ | 2,5-diF-phenyl | 2-(N,N'-BOC-piperazinyl-methyl)phenyl |
| 1277 | SCH₃ | 2,5-diF-phenyl | 2-(N-imidazolyl-methyl)phenyl |
| 1278 | SCH₃ | 2,5-diF-phenyl | 2-(N-methoxy-N-methylamino-methyl)phenyl |
| 1279 | SCH₃ | 2,5-diF-phenyl | 2-(N-pyridonyl-methyl)phenyl |
| 1280 | SCH₃ | 2,5-diF-phenyl | 2-(N-(N',N'-dimethylhydrazinyl-methyl)phenyl |
| 1281 | SCH₃ | 2,5-diF-phenyl | 2-(amidinyl)phenyl |
| 1282 | SCH₃ | 2,5-diF-phenyl | 2-(N-guanidinyl)phenyl |
| 1283 | SCH₃ | 2,5-diF-phenyl | 2-(imidazolyl)phenyl |
| 1284 | SCH₃ | 2,5-diF-phenyl | 2-(imidazolidinyl)phenyl |
| 1285 | SCH₃ | 2,5-diF-phenyl | 2-(2-imidazolidinyl-sulfonyl)phenyl |
| 1286 | SCH₃ | 2,5-diF-phenyl | 2-(2-pyrrolidinyl)phenyl |
| 1287 | SCH₃ | 2,5-diF-phenyl | 2-(2-piperidinyl)phenyl |
| 1288 | SCH₃ | 2,5-diF-phenyl | 2-(amidinyl-methyl)phenyl |
| 1289 | SCH₃ | 2,5-diF-phenyl | 2-(2-imidazolidinyl-methyl)phenyl |
| 1290 | SCH₃ | 2,5-diF-phenyl | 2-(N-(2-aminoimidazolyl)-methyl)phenyl |
| 1291 | SCH₃ | 2,5-diF-phenyl | 2-dimethylaminoimidazol-1-yl |
| 1292 | SCH₃ | 2,5-diF-phenyl | 2-(3-aminophenyl) |
| 1293 | SCH₃ | 2,5-diF-phenyl | 2-(3-pyrrolidinylcarbonyl) |
| 1294 | SCH₃ | 2,5-diF-phenyl | 2-glycinoyl |
| 1295 | SCH₃ | 2,5-diF-phenyl | 2-(imidazol-1-ylacetyl) |
| 1296 | SO₂CH₃ | phenyl | 2-(aminosulfonyl)phenyl |
| 1297 | SO₂CH₃ | phenyl | 2-(methylaminosulfonyl)phenyl |
| 1298 | SO₂CH₃ | phenyl | 1-pyrrolidinocarbonyl |
| 1299 | SO₂CH₃ | phenyl | 2-(methylsulfonyl)phenyl |
| 1300 | SO₂CH₃ | phenyl | 4-morpholino |
| 1301 | SO₂CH₃ | phenyl | 2-(1'-CF₃-tetrazol-2-yl)phenyl |
| 1302 | SO₂CH₃ | phenyl | 4-morpholinocarbonyl |
| 1303 | SO₂CH₃ | 2-pyridyl | 2-(aminosulfonyl)phenyl |
| 1304 | SO₂CH₃ | 2-pyridyl | 2-(methylaminosulfonyl)phenyl |
| 1305 | SO₂CH₃ | 2-pyridyl | 1-pyrrolidinocarbonyl |
| 1306 | SO₂CH₃ | 2-pyridyl | 2-(methylsulfonyl)phenyl |
| 1307 | SO₂CH₃ | 2-pyridyl | 4-morpholino |
| 1308 | SO₂CH₃ | 2-pyridyl | 2-(1'-CF₃-tetrazol-2-yl)phenyl |
| 1309 | SO₂CH₃ | 2-pyridyl | 4-morpholinocarbonyl |
| 1310 | SO₂CH₃ | 3-pyridyl | 2-(aminosulfonyl)phenyl |
| 1311 | SO₂CH₃ | 3-pyridyl | 2-(methylaminosulfonyl)phenyl |
| 1312 | SO₂CH₃ | 3-pyridyl | 1-pyrrolidinocarbonyl |
| 1313 | SO₂CH₃ | 3-pyridyl | 2-(methylsulfonyl)phenyl |
| 1314 | SO₂CH₃ | 3-pyridyl | 4-morpholino |
| 1315 | SO₂CH₃ | 3-pyridyl | 2-(1'-CF₃-tetrazol-2-yl)phenyl |
| 1316 | SO₂CH₃ | 3-pyridyl | 4-morpholinocarbonyl |
| 1317 | SO₂CH₃ | 2-pyrimidyl | 2-(aminosulfonyl)phenyl |
| 1318 | SO₂CH₃ | 2-pyrimidyl | 2-(methylaminosulfonyl)phenyl |
| 1319 | SO₂CH₃ | 2-pyrimidyl | 1-pyrrolidinocarbonyl |
| 1320 | SO₂CH₃ | 2-pyrimidyl | 2-(methylsulfonyl)phenyl |
| 1321 | SO₂CH₃ | 2-pyrimidyl | 4-morpholino |
| 1322 | SO₂CH₃ | 2-pyrimidyl | 2-(1'-CF₃-tetrazol-2-yl)phenyl |
| 1323 | SO₂CH₃ | 2-pyrimidyl | 4-morpholinocarbonyl |
| 1324 | SO₂CH₃ | 5-pyrimidyl | 2-(aminosulfonyl)phenyl |
| 1325 | SO₂CH₃ | 5-pyrimidyl | 2-(methylaminosulfonyl)phenyl |
| 1326 | SO₂CH₃ | 5-pyrimidyl | 1-pyrrolidinocarbonyl |
| 1327 | SO₂CH₃ | 5-pyrimidyl | 2-(methylsulfonyl)phenyl |
| 1328 | SO₂CH₃ | 5-pyrimidyl | 4-morpholino |
| 1329 | SO₂CH₃ | 5-pyrimidyl | 2-(1'-CF₃-tetrazol-2-yl)phenyl |
| 1330 | SO₂CH₃ | 5-pyrimidyl | 4-morpholinocarbonyl |
| 1331 | SO₂CH₃ | 2-Cl-phenyl | 2-(aminosulfonyl)phenyl |
| 1332 | SO₂CH₃ | 2-Cl-phenyl | 2-(methylaminosulfonyl)phenyl |
| 1333 | SO₂CH₃ | 2-Cl-phenyl | 1-pyrrolidinocarbonyl |
| 1334 | SO₂CH₃ | 2-Cl-phenyl | 2-(methylsulfonyl)phenyl |
| 1335 | SO₂CH₃ | 2-Cl-phenyl | 4-morpholino |
| 1336 | SO₂CH₃ | 2-Cl-phenyl | 2-(1'-CF₃-tetrazol-2-yl)phenyl |
| 1337 | SO₂CH₃ | 2-Cl-phenyl | 4-morpholinocarbonyl |
| 1338 | SO₂CH₃ | 2-F-phenyl | 2-(aminosulfonyl)phenyl |
| 1339 | SO₂CH₃ | 2-F-phenyl | 2-(methylaminosulfonyl)phenyl |
| 1340 | SO₂CH₃ | 2-F-phenyl | 1-pyrrolidinocarbonyl |
| 1341 | SO₂CH₃ | 2-F-phenyl | 2-(methylsulfonyl)phenyl |
| 1342 | SO₂CH₃ | 2-F-phenyl | 4-morpholino |
| 1343 | SO₂CH₃ | 2-F-phenyl | 2-(1'-CF₃-tetrazol-2-yl)phenyl |
| 1344 | SO₂CH₃ | 2-F-phenyl | 4-morpholinocarbonyl |
| 1345 | SO₂CH₃ | 2,5-diF-phenyl | 2-(aminosulfonyl)phenyl |
| 1346 | SO₂CH₃ | 2,5-diF-phenyl | 2-(methylaminosulfonyl)phenyl |
| 1347 | SO₂CH₃ | 2,5-diF-phenyl | 1-pyrrolidinocarbonyl |
| 1348 | SO₂CH₃ | 2,5-diF-phenyl | 2-(methylsulfonyl)phenyl |
| 1349 | SO₂CH₃ | 2,5-diF-phenyl | 4-morpholino |
| 1350 | SO₂CH₃ | 2,5-diF-phenyl | 2-(1'-CF₃-tetrazol-2-yl)phenyl |
| 1351 | SO₂CH₃ | 2,5-diF-phenyl | 4-morpholinocarbonyl |
| 1352 | SO₂CH₃ | phenyl | 2-(N-pyrrolidinyl-methyl)phenyl |
| 1353 | SO₂CH₃ | phenyl | 2-(N-piperidinyl-methyl)phenyl |
| 1354 | SO₂CH₃ | phenyl | 2-(N-morpholino-methyl)phenyl |
| 1355 | SO₂CH₃ | phenyl | 2-(N,N'-methylmorpholinium-methyl)phenyl |
| 1356 | SO₂CH₃ | phenyl | 2-(N-pyridinium-methyl)phenyl |
| 1357 | SO₂CH₃ | phenyl | 2-(N-4-(N,N'-dimethylamino)-pyridinium-methyl)phenyl |
| 1358 | SO₂CH₃ | phenyl | 2-(N-azatanyl-methyl)phenyl |
| 1359 | SO₂CH₃ | phenyl | 2-(N-azetidinyl-methyl)phenyl |
| 1360 | SO₂CH₃ | phenyl | 2-(N-piperazinyl-methyl)phenyl |
| 1361 | SO₂CH₃ | phenyl | 2-(N,N'-BOC-piperazinyl-methyl)phenyl |
| 1362 | SO₂CH₃ | phenyl | 2-(N-imidazolyl-methyl)phenyl |
| 1363 | SO₂CH₃ | phenyl | 2-(N-methoxy-N-methylamino-methyl)phenyl |
| 1364 | SO₂CH₃ | phenyl | 2-(N-pyridonyl-methyl)phenyl |
| 1365 | SO₂CH₃ | phenyl | 2-(N-(N',N'-dimethylhydrazinyl-methyl)phenyl |
| 1366 | SO₂CH₃ | phenyl | 2-(amidinyl)phenyl |
| 1367 | SO₂CH₃ | phenyl | 2-(N-guanidinyl)phenyl |
| 1368 | SO₂CH₃ | phenyl | 2-(imidazolyl)phenyl |
| 1369 | SO₂CH₃ | phenyl | 2-(imidazolidinyl)phenyl |
| 1370 | SO₂CH₃ | phenyl | 2-(2-imidazolidinyl-sulfonyl)phenyl |
| 1371 | SO₂CH₃ | phenyl | 2-(2-pyrrolidinyl)phenyl |
| 1372 | SO₂CH₃ | phenyl | 2-(2-piperidinyl)phenyl |
| 1373 | SO₂CH₃ | phenyl | 2-(amidinyl-methyl)phenyl |
| 1374 | SO₂CH₃ | phenyl | 2-(2-imidazolidinyl-methyl)phenyl |
| 1375 | SO₂CH₃ | phenyl | 2-(N-(2-aminoimidazolyl)-methyl)phenyl |
| 1376 | SO₂CH₃ | phenyl | 2-dimethylaminoimidazol-1-yl |
| 1377 | SO₂CH₃ | phenyl | 2-(3-aminophenyl) |
| 1378 | SO₂CH₃ | phenyl | 2-(3-pyrrolidinylcarbonyl) |
| 1379 | SO₂CH₃ | phenyl | 2-glycinoyl |
| 1380 | SO₂CH₃ | phenyl | 2-(imidazol-1-ylacetyl) |
| 1381 | SO₂CH₃ | 2-pyridyl | 2-(N-pyrrolidinyl-methyl)phenyl |
| 1382 | SO₂CH₃ | 2-pyridyl | 2-(N-piperidinyl-methyl)phenyl |
| 1383 | SO₂CH₃ | 2-pyridyl | 2-(N-morpholino-methyl)phenyl |
| 1384 | SO₂CH₃ | 2-pyridyl | 2-(N,N'-methylmorpholinium-methyl)phenyl |
| 1385 | SO₂CH₃ | 2-pyridyl | 2-(N-pyridinium-methyl)phenyl |
| 1386 | SO₂CH₃ | 2-pyridyl | 2-(N-4-(N,N'-dimethylamino)-pyridinium-methyl)phenyl |
| 1387 | SO₂CH₃ | 2-pyridyl | 2-(N-azatanyl-methyl)phenyl |
| 1388 | SO₂CH₃ | 2-pyridyl | 2-(N-azetidinyl-methyl)phenyl |
| 1389 | SO₂CH₃ | 2-pyridyl | 2-(N-piperazinyl-methyl)phenyl |
| 1390 | SO₂CH₃ | 2-pyridyl | 2-(N,N'-BOC-piperazinyl-methyl)phenyl |
| 1391 | SO₂CH₃ | 2-pyridyl | 2-(N-imidazolyl-methyl)phenyl |
| 1392 | SO₂CH₃ | 2-pyridyl | 2-(N-methoxy-N-methylamino-methyl)phenyl |
| 1393 | SO₂CH₃ | 2-pyridyl | 2-(N-pyridonyl-methyl)phenyl |
| 1394 | SO₂CH₃ | 2-pyridyl | 2-(N-(N',N'-dimethylhydrazinyl-methyl)phenyl |
| 1395 | SO₂CH₃ | 2-pyridyl | 2-(amidinyl)phenyl |
| 1396 | SO₂CH₃ | 2-pyridyl | 2-(N-guanidinyl)phenyl |
| 1397 | SO₂CH₃ | 2-pyridyl | 2-(imidazolyl)phenyl |
| 1398 | SO₂CH₃ | 2-pyridyl | 2-(imidazolidinyl)phenyl |
| 1399 | SO₂CH₃ | 2-pyridyl | 2-(2-imidazolidinyl-sulfonyl)phenyl |
| 1400 | SO₂CH₃ | 2-pyridyl | 2-(2-pyrrolidinyl)phenyl |
| 1401 | SO₂CH₃ | 2-pyridyl | 2-(2-piperidinyl)phenyl |
| 1402 | SO₂CH₃ | 2-pyridyl | 2-(amidinyl-methyl)phenyl |
| 1403 | SO₂CH₃ | 2-pyridyl | 2-(2-imidazolidinyl-methyl)phenyl |
| 1404 | SO₂CH₃ | 2-pyridyl | 2-(N-(2-aminoimidazolyl)-methyl)phenyl |
| 1405 | SO₂CH₃ | 2-pyridyl | 2-dimethylaminoimidazol-1-yl |
| 1406 | SO₂CH₃ | 2-pyridyl | 2-(3-aminophenyl) |

| Ex # | R¹ᵇ | A | B |
|---|---|---|---|
| 1407 | SO₂CH₃ | 2-pyridyl | 2-(3-pyrrolidinylcarbonyl) |
| 1408 | SO₂CH₃ | 2-pyridyl | 2-glycinoyl |
| 1409 | SO₂CH₃ | 2-pyridyl | 2-(imidazol-1-ylacetyl) |
| 1410 | SO₂CH₃ | 3-pyridyl | 2-(N-pyrrolidinyl-methyl)phenyl |
| 1411 | SO₂CH₃ | 3-pyridyl | 2-(N-piperidinyl-methyl)phenyl |
| 1412 | SO₂CH₃ | 3-pyridyl | 2-(N-morpholino-methyl)phenyl |
| 1413 | SO₂CH₃ | 3-pyridyl | 2-(N,N'-methylmorpholinium-methyl)phenyl |
| 1414 | SO₂CH₃ | 3-pyridyl | 2-(N-pyridinium-methyl)phenyl |
| 1415 | SO₂CH₃ | 3-pyridyl | 2-(N-4-(N,N'-dimethylamino)-pyridinium-methyl)phenyl |
| 1416 | SO₂CH₃ | 3-pyridyl | 2-(N-azatanyl-methyl)phenyl |
| 1417 | SO₂CH₃ | 3-pyridyl | 2-(N-azetidinyl-methyl)phenyl |
| 1418 | SO₂CH₃ | 3-pyridyl | 2-(N-piperazinyl-methyl)phenyl |
| 1419 | SO₂CH₃ | 3-pyridyl | 2-(N,N'-BOC-piperazinyl-methyl)phenyl |
| 1420 | SO₂CH₃ | 3-pyridyl | 2-(N-imidazolyl-methyl)phenyl |
| 1421 | SO₂CH₃ | 3-pyridyl | 2-(N-methoxy-N-methylamino-methyl)phenyl |
| 1422 | SO₂CH₃ | 3-pyridyl | 2-(N-pyridonyl-methyl)phenyl |
| 1423 | SO₂CH₃ | 3-pyridyl | 2-(N-(N',N'-dimethylhydrazinyl-methyl)phenyl |
| 1424 | SO₂CH₃ | 3-pyridyl | 2-(amidinyl)phenyl |
| 1425 | SO₂CH₃ | 3-pyridyl | 2-(N-guanidinyl)phenyl |
| 1426 | SO₂CH₃ | 3-pyridyl | 2-(imidazolyl)phenyl |
| 1427 | SO₂CH₃ | 3-pyridyl | 2-(imidazolidinyl)phenyl |
| 1428 | SO₂CH₃ | 3-pyridyl | 2-(2-imidazolidinyl-sulfonyl)phenyl |
| 1429 | SO₂CH₃ | 3-pyridyl | 2-(2-pyrrolidinyl)phenyl |
| 1430 | SO₂CH₃ | 3-pyridyl | 2-(2-piperidinyl)phenyl |
| 1431 | SO₂CH₃ | 3-pyridyl | 2-(amidinyl-methyl)phenyl |
| 1432 | SO₂CH₃ | 3-pyridyl | 2-(2-imidazolidinyl-methyl)phenyl |
| 1433 | SO₂CH₃ | 3-pyridyl | 2-(N-(2-aminoimidazolyl)-methyl)phenyl |
| 1434 | SO₂CH₃ | 3-pyridyl | 2-dimethylaminoimidazol-1-yl |
| 1435 | SO₂CH₃ | 3-pyridyl | 2-(3-aminophenyl) |
| 1436 | SO₂CH₃ | 3-pyridyl | 2-(3-pyrrolidinylcarbonyl) |
| 1437 | SO₂CH₃ | 3-pyridyl | 2-glycinoyl |
| 1438 | SO₂CH₃ | 3-pyridyl | 2-(imidazol-1-ylacetyl) |
| 1439 | SO₂CH₃ | 2-pyrimidyl | 2-(N-pyrrolidinyl-methyl)phenyl |
| 1440 | SO₂CH₃ | 2-pyrimidyl | 2-(N-piperidinyl-methyl)phenyl |
| 1441 | SO₂CH₃ | 2-pyrimidyl | 2-(N-morpholino-methyl)phenyl |
| 1442 | SO₂CH₃ | 2-pyrimidyl | 2-(N,N'-methylmorpholinium-methyl)phenyl |
| 1443 | SO₂CH₃ | 2-pyrimidyl | 2-(N-pyridinium-methyl)phenyl |
| 1444 | SO₂CH₃ | 2-pyrimidyl | 2-(N-4-(N,N'-dimethylamino)-pyridinium-methyl)phenyl |
| 1445 | SO₂CH₃ | 2-pyrimidyl | 2-(N-azatanyl-methyl)phenyl |
| 1446 | SO₂CH₃ | 2-pyrimidyl | 2-(N-azetidinyl-methyl)phenyl |
| 1447 | SO₂CH₃ | 2-pyrimidyl | 2-(N-piperazinyl-methyl)phenyl |
| 1448 | SO₂CH₃ | 2-pyrimidyl | 2-(N,N'-BOC-piperazinyl-methyl)phenyl |
| 1449 | SO₂CH₃ | 2-pyrimidyl | 2-(N-imidazolyl-methyl)phenyl |
| 1450 | SO₂CH₃ | 2-pyrimidyl | 2-(N-methoxy-N-methylamino-methyl)phenyl |
| 1451 | SO₂CH₃ | 2-pyrimidyl | 2-(N-pyridonyl-methyl)phenyl |
| 1452 | SO₂CH₃ | 2-pyrimidyl | 2-(N-(N',N'-dimethylhydrazinyl-methyl)phenyl |
| 1453 | SO₂CH₃ | 2-pyrimidyl | 2-(amidinyl)phenyl |
| 1454 | SO₂CH₃ | 2-pyrimidyl | 2-(N-guanidinyl)phenyl |
| 1455 | SO₂CH₃ | 2-pyrimidyl | 2-(imidazolyl)phenyl |
| 1456 | SO₂CH₃ | 2-pyrimidyl | 2-(imidazolidinyl)phenyl |
| 1457 | SO₂CH₃ | 2-pyrimidyl | 2-(2-imidazolidinyl-sulfonyl)phenyl |
| 1458 | SO₂CH₃ | 2-pyrimidyl | 2-(2-pyrrolidinyl)phenyl |
| 1459 | SO₂CH₃ | 2-pyrimidyl | 2-(2-piperidinyl)phenyl |
| 1460 | SO₂CH₃ | 2-pyrimidyl | 2-(amidinyl-methyl)phenyl |
| 1461 | SO₂CH₃ | 2-pyrimidyl | 2-(2-imidazolidinyl-methyl)phenyl |
| 1462 | SO₂CH₃ | 2-pyrimidyl | 2-(N-(2-aminoimidazolyl)-methyl)phenyl |
| 1463 | SO₂CH₃ | 2-pyrimidyl | 2-dimethylaminoimidazol-1-yl |
| 1464 | SO₂CH₃ | 2-pyrimidyl | 2-(3-aminophenyl) |
| 1465 | SO₂CH₃ | 2-pyrimidyl | 2-(3-pyrrolidinylcarbonyl) |
| 1466 | SO₂CH₃ | 2-pyrimidyl | 2-glycinoyl |
| 1467 | SO₂CH₃ | 2-pyrimidyl | 2-(imidazol-1-ylacetyl) |
| 1468 | SO₂CH₃ | 2-Cl-phenyl | 2-(N-pyrrolidinyl-methyl)phenyl |
| 1469 | SO₂CH₃ | 2-Cl-phenyl | 2-(N-piperidinyl-methyl)phenyl |
| 1470 | SO₂CH₃ | 2-Cl-phenyl | 2-(N-morpholino-methyl)phenyl |
| 1471 | SO₂CH₃ | 2-Cl-phenyl | 2-(N,N'-methylmorpholinium-methyl)phenyl |
| 1472 | SO₂CH₃ | 2-Cl-phenyl | 2-(N-pyridinium-methyl)phenyl |
| 1473 | SO₂CH₃ | 2-Cl-phenyl | 2-(N-4-(N,N'-dimethylamino)-pyridinium-methyl)phenyl |
| 1474 | SO₂CH₃ | 2-Cl-phenyl | 2-(N-azatanyl-methyl)phenyl |
| 1475 | SO₂CH₃ | 2-Cl-phenyl | 2-(N-azetidinyl-methyl)phenyl |
| 1476 | SO₂CH₃ | 2-Cl-phenyl | 2-(N-piperazinyl-methyl)phenyl |
| 1477 | SO₂CH₃ | 2-Cl-phenyl | 2-(N,N'-BOC-piperazinyl-methyl)phenyl |
| 1478 | SO₂CH₃ | 2-Cl-phenyl | 2-(N-imidazolyl-methyl)phenyl |
| 1479 | SO₂CH₃ | 2-Cl-phenyl | 2-(N-methoxy-N-methylamino-methyl)phenyl |
| 1480 | SO₂CH₃ | 2-Cl-phenyl | 2-(N-pyridonyl-methyl)phenyl |
| 1481 | SO₂CH₃ | 2-Cl-phenyl | 2-(N-(N',N'-dimethylhydrazinyl-methyl)phenyl |
| 1482 | SO₂CH₃ | 2-Cl-phenyl | 2-(amidinyl)phenyl |
| 1483 | SO₂CH₃ | 2-Cl-phenyl | 2-(N-guanidinyl)phenyl |
| 1484 | SO₂CH₃ | 2-Cl-phenyl | 2-(imidazolyl)phenyl |
| 1485 | SO₂CH₃ | 2-Cl-phenyl | 2-(imidazolidinyl)phenyl |
| 1486 | SO₂CH₃ | 2-Cl-phenyl | 2-(2-imidazolidinyl-sulfonyl)phenyl |
| 1487 | SO₂CH₃ | 2-Cl-phenyl | 2-(2-pyrrolidinyl)phenyl |
| 1488 | SO₂CH₃ | 2-Cl-phenyl | 2-(2-piperidinyl)phenyl |
| 1489 | SO₂CH₃ | 2-Cl-phenyl | 2-(amidinyl-methyl)phenyl |
| 1490 | SO₂CH₃ | 2-Cl-phenyl | 2-(2-imidazolidinyl-methyl)phenyl |
| 1491 | SO₂CH₃ | 2-Cl-phenyl | 2-(N-(2-aminoimidazolyl)-methyl)phenyl |
| 1492 | SO₂CH₃ | 2-Cl-phenyl | 2-dimethylaminoimidazol-1-yl |
| 1493 | SO₂CH₃ | 2-Cl-phenyl | 2-(3-aminophenyl) |
| 1494 | SO₂CH₃ | 2-Cl-phenyl | 2-(3-pyrrolidinylcarbonyl) |
| 1495 | SO₂CH₃ | 2-Cl-phenyl | 2-glycinoyl |
| 1496 | SO₂CH₃ | 2-Cl-phenyl | 2-(imidazol-1-ylacetyl) |
| 1497 | SO₂CH₃ | 2-F-phenyl | 2-(N-pyrrolidinyl-methyl)phenyl |
| 1498 | SO₂CH₃ | 2-F-phenyl | 2-(N-piperidinyl-methyl)phenyl |
| 1499 | SO₂CH₃ | 2-F-phenyl | 2-(N-morpholino-methyl)phenyl |
| 1500 | SO₂CH₃ | 2-F-phenyl | 2-(N,N'-methylmorpholinium-methyl)phenyl |
| 1501 | SO₂CH₃ | 2-F-phenyl | 2-(N-pyridinium-methyl)phenyl |
| 1502 | SO₂CH₃ | 2-F-phenyl | 2-(N-4-(N,N'-dimethylamino)-pyridinium-methyl)phenyl |
| 1503 | SO₂CH₃ | 2-F-phenyl | 2-(N-azatanyl-methyl)phenyl |
| 1504 | SO₂CH₃ | 2-F-phenyl | 2-(N-azetidinyl-methyl)phenyl |
| 1505 | SO₂CH₃ | 2-F-phenyl | 2-(N-piperazinyl-methyl)phenyl |
| 1506 | SO₂CH₃ | 2-F-phenyl | 2-(N,N'-BOC-piperazinyl-methyl)phenyl |
| 1507 | SO₂CH₃ | 2-F-phenyl | 2-(N-imidazolyl-methyl)phenyl |
| 1508 | SO₂CH₃ | 2-F-phenyl | 2-(N-methoxy-N-methylamino-methyl)phenyl |
| 1509 | SO₂CH₃ | 2-F-phenyl | 2-(N-pyridonyl-methyl)phenyl |
| 1510 | SO₂CH₃ | 2-F-phenyl | 2-(N-(N',N'-dimethylhydrazinyl-methyl)phenyl |
| 1511 | SO₂CH₃ | 2-F-phenyl | 2-(amidinyl)phenyl |
| 1512 | SO₂CH₃ | 2-F-phenyl | 2-(N-guanidinyl)phenyl |
| 1513 | SO₂CH₃ | 2-F-phenyl | 2-(imidazolyl)phenyl |
| 1514 | SO₂CH₃ | 2-F-phenyl | 2-(imidazolidinyl)phenyl |
| 1515 | SO₂CH₃ | 2-F-phenyl | 2-(2-imidazolidinyl-sulfonyl)phenyl |
| 1516 | SO₂CH₃ | 2-F-phenyl | 2-(2-pyrrolidinyl)phenyl |
| 1517 | SO₂CH₃ | 2-F-phenyl | 2-(2-piperidinyl)phenyl |
| 1518 | SO₂CH₃ | 2-F-phenyl | 2-(amidinyl-methyl)phenyl |
| 1519 | SO₂CH₃ | 2-F-phenyl | 2-(2-imidazolidinyl-methyl)phenyl |
| 1520 | SO₂CH₃ | 2-F-phenyl | 2-(N-(2-aminoimidazolyl)-methyl)phenyl |
| 1521 | SO₂CH₃ | 2-F-phenyl | 2-dimethylaminoimidazol-1-yl |
| 1522 | SO₂CH₃ | 2-F-phenyl | 2-(3-aminophenyl) |
| 1523 | SO₂CH₃ | 2-F-phenyl | 2-(3-pyrrolidinylcarbonyl) |
| 1524 | SO₂CH₃ | 2-F-phenyl | 2-glycinoyl |
| 1525 | SO₂CH₃ | 2-F-phenyl | 2-(imidazol-1-ylacetyl) |
| 1526 | SO₂CH₃ | 2,5-diF-phenyl | 2-(N-pyrrolidinyl-methyl)phenyl |
| 1527 | SO₂CH₃ | 2,5-diF-phenyl | 2-(N-piperidinyl-methyl)phenyl |
| 1528 | SO₂CH₃ | 2,5-diF-phenyl | 2-(N-morpholino-methyl)phenyl |

-continued

| Ex # | R¹ᵇ | A | B |
|---|---|---|---|
| 1529 | SO₂CH₃ | 2,5-diF-phenyl | 2-(N,N'-methylmorpholinium-methyl)phenyl |
| 1530 | SO₂CH₃ | 2,5-diF-phenyl | 2-(N-pyridinium-methyl)phenyl |
| 1531 | SO₂CH₃ | 2,5-diF-phenyl | 2-(N-4-(N,N'-dimethylamino)-pyridinium-methyl)phenyl |
| 1532 | SO₂CH₃ | 2,5-diF-phenyl | 2-(N-azatanyl-methyl)phenyl |
| 1533 | SO₂CH₃ | 2,5-diF-phenyl | 2-(N-azetidinyl-methyl)phenyl |
| 1534 | SO₂CH₃ | 2,5-diF-phenyl | 2-(N-piperazinyl-methyl)phenyl |
| 1535 | SO₂CH₃ | 2,5-diF-phenyl | 2-(N,N'-BOC-piperazinyl-methyl)phenyl |
| 1536 | SO₂CH₃ | 2,5-diF-phenyl | 2-(N-imidazolyl-methyl)phenyl |
| 1537 | SO₂CH₃ | 2,5-diF-phenyl | 2-(N-methoxy-N-methylamino-methyl)phenyl |
| 1538 | SO₂CH₃ | 2,5-diF-phenyl | 2-(N-pyridonyl-methyl)phenyl |
| 1539 | SO₂CH₃ | 2,5-diF-phenyl | 2-(N-(N',N'-dimethylhydrazinyl-methyl)phenyl |
| 1540 | SO₂CH₃ | 2,5-diF-phenyl | 2-(amidinyl)phenyl |
| 1541 | SO₂CH₃ | 2,5-diF-phenyl | 2-(N-guanidinyl)phenyl |
| 1542 | SO₂CH₃ | 2,5-diF-phenyl | 2-(imidazolyl)phenyl |
| 1543 | SO₂CH₃ | 2,5-diF-phenyl | 2-(imidazolidinyl)phenyl |
| 1544 | SO₂CH₃ | 2,5-diF-phenyl | 2-(2-imidazolidinyl-sulfonyl)phenyl |
| 1545 | SO₂CH₃ | 2,5-diF-phenyl | 2-(2-pyrrolidinyl)phenyl |
| 1546 | SO₂CH₃ | 2,5-diF-phenyl | 2-(2-piperidinyl)phenyl |
| 1547 | SO₂CH₃ | 2,5-diF-phenyl | 2-(amidinyl-methyl)phenyl |
| 1548 | SO₂CH₃ | 2,5-diF-phenyl | 2-(2-imidazolidinyl-methyl)phenyl |
| 1549 | SO₂CH₃ | 2,5-diF-phenyl | 2-(N-(2-aminoimidazolyl)-methyl)phenyl |
| 1550 | SO₂CH₃ | 2,5-diF-phenyl | 2-dimethylaminoimidazol-1-yl |
| 1551 | SO₂CH₃ | 2,5-diF-phenyl | 2-(3-aminophenyl) |
| 1552 | SO₂CH₃ | 2,5-diF-phenyl | 2-(3-pyrrolidinylcarbonyl) |
| 1553 | SO₂CH₃ | 2,5-diF-phenyl | 2-glycinoyl |
| 1554 | SO₂CH₃ | 2,5-diF-phenyl | 2-(imidazol-1-ylacetyl) |
| 1555 | NHSO₂CH₃ | phenyl | 2-(aminosulfonyl)phenyl |
| 1556 | NHSO₂CH₃ | phenyl | 2-(methylaminosulfonyl)phenyl |
| 1557 | NHSO₂CH₃ | phenyl | 1-pyrrolidinocarbonyl |
| 1558 | NHSO₂CH₃ | phenyl | 2-(methylsulfonyl)phenyl |
| 1559 | NHSO₂CH₃ | phenyl | 4-morpholino |
| 1560 | NHSO₂CH₃ | phenyl | 2-(1'-CF₃-tetrazol-2-yl)phenyl |
| 1561 | NHSO₂CH₃ | phenyl | 4-morpholinocarbonyl |
| 1562 | NHSO₂CH₃ | 2-pyridyl | 2-(aminosulfonyl)phenyl |
| 1563 | NHSO₂CH₃ | 2-pyridyl | 2-(methylaminosulfonyl)phenyl |
| 1564 | NHSO₂CH₃ | 2-pyridyl | 1-pyrrolidinocarbonyl |
| 1565 | NHSO₂CH₃ | 2-pyridyl | 2-(methylsulfonyl)phenyl |
| 1566 | NHSO₂CH₃ | 2-pyridyl | 4-morpholino |
| 1567 | NHSO₂CH₃ | 2-pyridyl | 2-(1'-CF₃-tetrazol-2-yl)phenyl |
| 1568 | NHSO₂CH₃ | 2-pyridyl | 4-morpholinocarbonyl |
| 1569 | NHSO₂CH₃ | 3-pyridyl | 2-(aminosulfonyl)phenyl |
| 1570 | NHSO₂CH₃ | 3-pyridyl | 2-(methylaminosulfonyl)phenyl |
| 1571 | NHSO₂CH₃ | 3-pyridyl | 1-pyrrolidinocarbonyl |
| 1572 | NHSO₂CH₃ | 3-pyridyl | 2-(methylsulfonyl)phenyl |
| 1573 | NHSO₂CH₃ | 3-pyridyl | 4-morpholino |
| 1574 | NHSO₂CH₃ | 3-pyridyl | 2-(1'-CF₃-tetrazol-2-yl)phenyl |
| 1575 | NHSO₂CH₃ | 3-pyridyl | 4-morpholinocarbonyl |
| 1576 | NHSO₂CH₃ | 2-pyrimidyl | 2-(aminosulfonyl)phenyl |
| 1577 | NHSO₂CH₃ | 2-pyrimidyl | 2-(methylaminosulfonyl)phenyl |
| 1578 | NHSO₂CH₃ | 2-pyrimidyl | 1-pyrrolidinocarbonyl |
| 1579 | NHSO₂CH₃ | 2-pyrimidyl | 2-(methylsulfonyl)phenyl |
| 1580 | NHSO₂CH₃ | 2-pyrimidyl | 4-morpholino |
| 1581 | NHSO₂CH₃ | 2-pyrimidyl | 2-(1'-CF₃-tetrazol-2-yl)phenyl |
| 1582 | NHSO₂CH₃ | 2-pyrimidyl | 4-morpholinocarbonyl |
| 1583 | NHSO₂CH₃ | 5-pyrimidyl | 2-(aminosulfonyl)phenyl |
| 1584 | NHSO₂CH₃ | 5-pyrimidyl | 2-(methylaminosulfonyl)phenyl |
| 1585 | NHSO₂CH₃ | 5-pyrimidyl | 1-pyrrolidinocarbonyl |
| 1586 | NHSO₂CH₃ | 5-pyrimidyl | 2-(methylsulfonyl)phenyl |
| 1587 | NHSO₂CH₃ | 5-pyrimidyl | 4-morpholino |
| 1588 | NHSO₂CH₃ | 5-pyrimidyl | 2-(1'-CF₃-tetrazol-2-yl)phenyl |
| 1589 | NHSO₂CH₃ | 5-pyrimidyl | 4-morpholinocarbonyl |
| 1590 | NHSO₂CH₃ | 2-Cl-phenyl | 2-(aminosulfonyl)phenyl |
| 1591 | NHSO₂CH₃ | 2-Cl-phenyl | 2-(methylaminosulfonyl)phenyl |
| 1592 | NHSO₂CH₃ | 2-Cl-phenyl | 1-pyrrolidinocarbonyl |
| 1593 | NHSO₂CH₃ | 2-Cl-phenyl | 2-(methylsulfonyl)phenyl |
| 1594 | NHSO₂CH₃ | 2-Cl-phenyl | 4-morpholino |
| 1595 | NHSO₂CH₃ | 2-Cl-phenyl | 2-(1'-CF₃-tetrazol-2-yl)phenyl |
| 1596 | NHSO₂CH₃ | 2-Cl-phenyl | 4-morpholinocarbonyl |
| 1597 | NHSO₂CH₃ | 2-F-phenyl | 2-(aminosulfonyl)phenyl |
| 1598 | NHSO₂CH₃ | 2-F-phenyl | 2-(methylaminosulfonyl)phenyl |
| 1599 | NHSO₂CH₃ | 2-F-phenyl | 1-pyrrolidinocarbonyl |
| 1600 | NHSO₂CH₃ | 2-F-phenyl | 2-(methylsulfonyl)phenyl |
| 1601 | NHSO₂CH₃ | 2-F-phenyl | 4-morpholino |
| 1602 | NHSO₂CH₃ | 2-F-phenyl | 2-(1'-CF₃-tetrazol-2-yl)phenyl |
| 1603 | NHSO₂CH₃ | 2-F-phenyl | 4-morpholinocarbonyl |
| 1604 | NHSO₂CH₃ | 2,5-diF-phenyl | 2-(aminosulfonyl)phenyl |
| 1605 | NHSO₂CH₃ | 2,5-diF-phenyl | 2-(methylaminosulfonyl)phenyl |
| 1606 | NHSO₂CH₃ | 2,5-diF-phenyl | 1-pyrrolidinocarbonyl |
| 1607 | NHSO₂CH₃ | 2,5-diF-phenyl | 2-(methylsulfonyl)phenyl |
| 1608 | NHSO₂CH₃ | 2,5-diF-phenyl | 4-morpholino |
| 1609 | NHSO₂CH₃ | 2,5-diF-phenyl | 2-(1'-CF₃-tetrazol-2-yl)phenyl |
| 1610 | NHSO₂CH₃ | 2,5-diF-phenyl | 4-morpholinocarbonyl |
| 1611 | NHSO₂CH₃ | phenyl | 2-(N-pyrrolidinyl-methyl)phenyl |
| 1612 | NHSO₂CH₃ | phenyl | 2-(N-piperidinyl-methyl)phenyl |
| 1613 | NHSO₂CH₃ | phenyl | 2-(N-morpholino-methyl)phenyl |
| 1614 | NHSO₂CH₃ | phenyl | 2-(N,N'-methylmorpholinium-methyl)phenyl |
| 1615 | NHSO₂CH₃ | phenyl | 2-(N-pyridinium-methyl)phenyl |
| 1616 | NHSO₂CH₃ | phenyl | 2-(N-4-(N,N'-dimethylamino)-pyridinium-methyl)phenyl |
| 1617 | NHSO₂CH₃ | phenyl | 2-(N-azatanyl-methyl)phenyl |
| 1618 | NHSO₂CH₃ | phenyl | 2-(N-azetidinyl-methyl)phenyl |
| 1619 | NHSO₂CH₃ | phenyl | 2-(N-piperazinyl-methyl)phenyl |
| 1620 | NHSO₂CH₃ | phenyl | 2-(N,N'-BOC-piperazinyl-methyl)phenyl |
| 1621 | NHSO₂CH₃ | phenyl | 2-(N-imidazolyl-methyl)phenyl |
| 1622 | NHSO₂CH₃ | phenyl | 2-(N-methoxy-N-methylamino-methyl)phenyl |
| 1623 | NHSO₂CH₃ | phenyl | 2-(N-pyridonyl-methyl)phenyl |
| 1624 | NHSO₂CH₃ | phenyl | 2-(N-(N',N'-dimethylhydrazinyl-methyl)phenyl |
| 1625 | NHSO₂CH₃ | phenyl | 2-(amidinyl)phenyl |
| 1626 | NHSO₂CH₃ | phenyl | 2-(N-guanidinyl)phenyl |
| 1627 | NHSO₂CH₃ | phenyl | 2-(imidazolyl)phenyl |
| 1628 | NHSO₂CH₃ | phenyl | 2-(imidazolidinyl)phenyl |
| 1629 | NHSO₂CH₃ | phenyl | 2-(2-imidazolidinyl-sulfonyl)phenyl |
| 1630 | NHSO₂CH₃ | phenyl | 2-(2-pyrrolidinyl)phenyl |
| 1631 | NHSO₂CH₃ | phenyl | 2-(2-piperidinyl)phenyl |
| 1632 | NHSO₂CH₃ | phenyl | 2-(amidinyl-methyl)phenyl |
| 1633 | NHSO₂CH₃ | phenyl | 2-(2-imidazolidinyl-methyl)phenyl |
| 1634 | NHSO₂CH₃ | phenyl | 2-(N-(2-aminoimidazolyl)-methyl)phenyl |
| 1635 | NHSO₂CH₃ | phenyl | 2-dimethylaminoimidazol-1-yl |
| 1636 | NHSO₂CH₃ | phenyl | 2-(3-aminophenyl) |
| 1637 | NHSO₂CH₃ | phenyl | 2-(3-pyrrolidinylcarbonyl) |
| 1638 | NHSO₂CH₃ | phenyl | 2-glycinoyl |
| 1639 | NHSO₂CH₃ | phenyl | 2-(imidazol-1-ylacetyl) |
| 1640 | NHSO₂CH₃ | 2-pyridyl | 2-(N-pyrrolidinyl-methyl)phenyl |
| 1641 | NHSO₂CH₃ | 2-pyridyl | 2-(N-piperidinyl-methyl)phenyl |
| 1642 | NHSO₂CH₃ | 2-pyridyl | 2-(N-morpholino-methyl)phenyl |
| 1643 | NHSO₂CH₃ | 2-pyridyl | 2-(N,N'-methylmorpholinium-methyl)phenyl |
| 1644 | NHSO₂CH₃ | 2-pyridyl | 2-(N-pyridinium-methyl)phenyl |
| 1645 | NHSO₂CH₃ | 2-pyridyl | 2-(N-4-(N,N'-dimethylamino)-pyridinium-methyl)phenyl |
| 1646 | NHSO₂CH₃ | 2-pyridyl | 2-(N-azatanyl-methyl)phenyl |
| 1647 | NHSO₂CH₃ | 2-pyridyl | 2-(N-azetidinyl-methyl)phenyl |
| 1648 | NHSO₂CH₃ | 2-pyridyl | 2-(N-piperazinyl-methyl)phenyl |
| 1649 | NHSO₂CH₃ | 2-pyridyl | 2-(N,N'-BOC-piperazinyl-methyl)phenyl |
| 1650 | NHSO₂CH₃ | 2-pyridyl | 2-(N-imidazolyl-methyl)phenyl |
| 1651 | NHSO₂CH₃ | 2-pyridyl | 2-(N-methoxy-N-methylamino-methyl)phenyl |
| 1652 | NHSO₂CH₃ | 2-pyridyl | 2-(N-pyridonyl-methyl)phenyl |
| 1653 | NHSO₂CH₃ | 2-pyridyl | 2-(N-(N',N'-dimethylhydrazinyl-methyl)phenyl |
| 1654 | NHSO₂CH₃ | 2-pyridyl | 2-(amidinyl)phenyl |
| 1655 | NHSO₂CH₃ | 2-pyridyl | 2-(N-guanidinyl)phenyl |
| 1656 | NHSO₂CH₃ | 2-pyridyl | 2-(imidazolyl)phenyl |
| 1657 | NHSO₂CH₃ | 2-pyridyl | 2-(imidazolidinyl)phenyl |
| 1658 | NHSO₂CH₃ | 2-pyridyl | 2-(2-imidazolidinyl-sulfonyl)phenyl |
| 1659 | NHSO₂CH₃ | 2-pyridyl | 2-(2-pyrrolidinyl)phenyl |
| 1660 | NHSO₂CH₃ | 2-pyridyl | 2-(2-piperidinyl)phenyl |

| Ex # | R$^{1b}$ | A | B |
|---|---|---|---|
| 1661 | NHSO$_2$CH$_3$ | 2-pyridyl | 2-(amidinyl-methyl)phenyl |
| 1662 | NHSO$_2$CH$_3$ | 2-pyridyl | 2-(2-imidazolidinyl-methyl)phenyl |
| 1663 | NHSO$_2$CH$_3$ | 2-pyridyl | 2-(N-(2-aminoimidazolyl)-methyl)phenyl |
| 1664 | NHSO$_2$CH$_3$ | 2-pyridyl | 2-dimethylaminoimidazol-1-yl |
| 1665 | NHSO$_2$CH$_3$ | 2-pyridyl | 2-(3-aminophenyl) |
| 1666 | NHSO$_2$CH$_3$ | 2-pyridyl | 2-(3-pyrrolidinylcarbonyl) |
| 1667 | NHSO$_2$CH$_3$ | 2-pyridyl | 2-glycinoyl |
| 1668 | NHSO$_2$CH$_3$ | 2-pyridyl | 2-(imidazol-1-ylacetyl) |
| 1669 | NHSO$_2$CH$_3$ | 3-pyridyl | 2-(N-pyrrolidinyl-methyl)phenyl |
| 1670 | NHSO$_2$CH$_3$ | 3-pyridyl | 2-(N-piperidinyl-methyl)phenyl |
| 1671 | NHSO$_2$CH$_3$ | 3-pyridyl | 2-(N-morpholino-methyl)phenyl |
| 1672 | NHSO$_2$CH$_3$ | 3-pyridyl | 2-(N,N'-methylmorpholinium-methyl)phenyl |
| 1673 | NHSO$_2$CH$_3$ | 3-pyridyl | 2-(N-pyridiniuin-methyl)phenyl |
| 1674 | NHSO$_2$CH$_3$ | 3-pyridyl | 2-(N-4-(N,N'-dimethylamino)-pyridinium-methyl)phenyl |
| 1675 | NHSO$_2$CH$_3$ | 3-pyridyl | 2-(N-azatanyl-methyl)phenyl |
| 1676 | NHSO$_2$CH$_3$ | 3-pyridyl | 2-(N-azetidinyl-methyl)phenyl |
| 1677 | NHSO$_2$CH$_3$ | 3-pyridyl | 2-(N-piperazinyl-methyl)phenyl |
| 1678 | NHSO$_2$CH$_3$ | 3-pyridyl | 2-(N,N'-BOC-piperazinyl-methyl)phenyl |
| 1679 | NHSO$_2$CH$_3$ | 3-pyridyl | 2-(N-imidazolyl-methyl)phenyl |
| 1680 | NHSO$_2$CH$_3$ | 3-pyridyl | 2-(N-methoxy-N-methylamino-methyl)phenyl |
| 1681 | NHSO$_2$CH$_3$ | 3-pyridyl | 2-(N-pyridonyl-methyl)phenyl |
| 1682 | NHSO$_2$CH$_3$ | 3-pyridyl | 2-(N-(N',N'-dimethylhydrazinyl-methyl)phenyl |
| 1683 | NHSO$_2$CH$_3$ | 3-pyridyl | 2-(amidinyl)phenyl |
| 1684 | NHSO$_2$CH$_3$ | 3-pyridyl | 2-(N-guanidinyl)phenyl |
| 1685 | NHSO$_2$CH$_3$ | 3-pyridyl | 2-(imidazolyl)phenyl |
| 1686 | NHSO$_2$CH$_3$ | 3-pyridyl | 2-(imidazolidinyl)phenyl |
| 1687 | NHSO$_2$CH$_3$ | 3-pyridyl | 2-(2-imidazolidinyl-sulfonyl)phenyl |
| 1688 | NHSO$_2$CH$_3$ | 3-pyridyl | 2-(2-pyrrolidinyl)phenyl |
| 1689 | NHSO$_2$CH$_3$ | 3-pyridyl | 2-(2-piperidinyl)phenyl |
| 1690 | NHSO$_2$CH$_3$ | 3-pyridyl | 2-(amidinyl-methyl)phenyl |
| 1691 | NHSO$_2$CH$_3$ | 3-pyridyl | 2-(2-imidazolidinyl-methyl)phenyl |
| 1692 | NHSO$_2$CH$_3$ | 3-pyridyl | 2-(N-(2-aminoimidazolyl)-methyl)phenyl |
| 1693 | NHSO$_2$CH$_3$ | 3-pyridyl | 2-dimethylaminoimidazol-1-yl |
| 1694 | NHSO$_2$CH$_3$ | 3-pyridyl | 2-(3-aminophenyl) |
| 1695 | NHSO$_2$CH$_3$ | 3-pyridyl | 2-(3-pyrrolidinylcarbonyl) |
| 1696 | NHSO$_2$CH$_3$ | 3-pyridyl | 2-glycinoyl |
| 1697 | NHSO$_2$CH$_3$ | 3-pyridyl | 2-(imidazol-1-ylacetyl) |
| 1698 | NHSO$_2$CH$_3$ | 2-pyrimidyl | 2-(N-pyrrolidinyl-methyl)phenyl |
| 1699 | NHSO$_2$CH$_3$ | 2-pyrimidyl | 2-(N-piperidinyl-methyl)phenyl |
| 1700 | NHSO$_2$CH$_3$ | 2-pyrimidyl | 2-(N-morpholino-methyl)phenyl |
| 1701 | NHSO$_2$CH$_3$ | 2-pyrimidyl | 2-(N,N'-methylmorpholinium-methyl)phenyl |
| 1702 | NHSO$_2$CH$_3$ | 2-pyrimidyl | 2-(N-pyridinium-methyl)phenyl |
| 1703 | NHSO$_2$CH$_3$ | 2-pyrimidyl | 2-(N-4-(N,N'-dimethylamino)-pyridinium-methyl)phenyl |
| 1704 | NHSO$_2$CH$_3$ | 2-pyrimidyl | 2-(N-azatanyl-methyl)phenyl |
| 1705 | NHSO$_2$CH$_3$ | 2-pyrimidyl | 2-(N-azetidinyl-methyl)phenyl |
| 1706 | NHSO$_2$CH$_3$ | 2-pyrimidyl | 2-(N-piperazinyl-methyl)phenyl |
| 1707 | NHSO$_2$CH$_3$ | 2-pyrimidyl | 2-(N,N'-BOC-piperazinyl-methyl)phenyl |
| 1708 | NHSO$_2$CH$_3$ | 2-pyrimidyl | 2-(N-imidazolyl-methyl)phenyl |
| 1709 | NHSO$_2$CH$_3$ | 2-pyrimidyl | 2-(N-methoxy-N-methylamino-methyl)phenyl |
| 1710 | NHSO$_2$CH$_3$ | 2-pyrimidyl | 2-(N-pyridonyl-methyl)phenyl |
| 1711 | NHSO$_2$CH$_3$ | 2-pyrimidyl | 2-(N-(N',N'-dimethylhydrazinyl-methyl)phenyl |
| 1712 | NHSO$_2$CH$_3$ | 2-pyrimidyl | 2-(amidinyl)phenyl |
| 1713 | NHSO$_2$CH$_3$ | 2-pyrimidyl | 2-(N-guanidinyl)phenyl |
| 1714 | NHSO$_2$CH$_3$ | 2-pyrimidyl | 2-(imidazolyl)phenyl |
| 1715 | NHSO$_2$CH$_3$ | 2-pyrimidyl | 2-(imidazolidinyl)phenyl |
| 1716 | NHSO$_2$CH$_3$ | 2-pyrimidyl | 2-(2-imidazolidinyl-sulfonyl)phenyl |
| 1717 | NHSO$_2$CH$_3$ | 2-pyrimidyl | 2-(2-pyrrolidinyl)phenyl |
| 1718 | NHSO$_2$CH$_3$ | 2-pyrimidyl | 2-(2-piperidinyl)phenyl |
| 1719 | NHSO$_2$CH$_3$ | 2-pyrimidyl | 2-(amidinyl-methyl)phenyl |
| 1720 | NHSO$_2$CH$_3$ | 2-pyrimidyl | 2-(2-imidazolidinyl-methyl)phenyl |
| 1721 | NHSO$_2$CH$_3$ | 2-pyrimidyl | 2-(N-(2-aminoimidazolyl)-methyl)phenyl |
| 1722 | NHSO$_2$CH$_3$ | 2-pyrimidyl | 2-dimethylaminoimidazol-1-yl |
| 1723 | NHSO$_2$CH$_3$ | 2-pyrimidyl | 2-(3-aminophenyl) |
| 1724 | NHSO$_2$CH$_3$ | 2-pyrimidyl | 2-(3-pyrrolidinylcarbonyl) |
| 1725 | NHSO$_2$CH$_3$ | 2-pyrimidyl | 2-glycinoyl |
| 1726 | NHSO$_2$CH$_3$ | 2-pyrimidyl | 2-(imidazol-1-ylacetyl) |
| 1727 | NHSO$_2$CH$_3$ | 2-Cl-phenyl | 2-(N-pyrrolidinyl-methyl)phenyl |
| 1728 | NHSO$_2$CH$_3$ | 2-Cl-phenyl | 2-(N-piperidinyl-methyl)phenyl |
| 1729 | NHSO$_2$CH$_3$ | 2-Cl-phenyl | 2-(N-morpholino-methyl)phenyl |
| 1730 | NHSO$_2$CH$_3$ | 2-Cl-phenyl | 2-(N,N'-methylmorpholinium-methyl)phenyl |
| 1731 | NHSO$_2$CH$_3$ | 2-Cl-phenyl | 2-(N-pyridinium-methyl)phenyl |
| 1732 | NHSO$_2$CH$_3$ | 2-Cl-phenyl | 2-(N-4-(N,N'-dimethylamino)-pyridinium-methyl)phenyl |
| 1733 | NHSO$_2$CH$_3$ | 2-Cl-phenyl | 2-(N-azatanyl-methyl)phenyl |
| 1734 | NHSO$_2$CH$_3$ | 2-Cl-phenyl | 2-(N-azetidinyl-methyl)phenyl |
| 1735 | NHSO$_2$CH$_3$ | 2-Cl-phenyl | 2-(N-piperazinyl-methyl)phenyl |
| 1736 | NHSO$_2$CH$_3$ | 2-Cl-phenyl | 2-(N,N'-BOC-piperazinyl-methyl)phenyl |
| 1737 | NHSO$_2$CH$_3$ | 2-Cl-phenyl | 2-(N-imidazolyl-methyl)phenyl |
| 1738 | NHSO$_2$CH$_3$ | 2-Cl-phenyl | 2-(N-methoxy-N-methylamino-methyl)phenyl |
| 1739 | NHSO$_2$CH$_3$ | 2-Cl-phenyl | 2-(N-pyridonyl-methyl)phenyl |
| 1740 | NHSO$_2$CH$_3$ | 2-Cl-phenyl | 2-(N-(N',N'-dimethylhydrazinyl-methyl)phenyl |
| 1741 | NHSO$_2$CH$_3$ | 2-Cl-phenyl | 2-(amidinyl)phenyl |
| 1742 | NHSO$_2$CH$_3$ | 2-Cl-phenyl | 2-(N-guanidinyl)phenyl |
| 1743 | NHSO$_2$CH$_3$ | 2-Cl-phenyl | 2-(imidazolyl)phenyl |
| 1744 | NHSO$_2$CH$_3$ | 2-Cl-phenyl | 2-(imidazolidinyl)phenyl |
| 1745 | NHSO$_2$CH$_3$ | 2-Cl-phenyl | 2-(2-imidazolidinyl-sulfonyl)phenyl |
| 1746 | NHSO$_2$CH$_3$ | 2-Cl-phenyl | 2-(2-pyrrolidinyl)phenyl |
| 1747 | NHSO$_2$CH$_3$ | 2-Cl-phenyl | 2-(2-piperidinyl)phenyl |
| 1748 | NHSO$_2$CH$_3$ | 2-Cl-phenyl | 2-(amidinyl-methyl)phenyl |
| 1749 | NHSO$_2$CH$_3$ | 2-Cl-phenyl | 2-(2-imidazolidinyl-methyl)phenyl |
| 1750 | NHSO$_2$CH$_3$ | 2-Cl-phenyl | 2-(N-(2-aminoimidazolyl)-methyl)phenyl |
| 1751 | NHSO$_2$CH$_3$ | 2-Cl-phenyl | 2-dimethylaminoimidazol-1-yl |
| 1752 | NHSO$_2$CH$_3$ | 2-Cl-phenyl | 2-(3-aminophenyl) |
| 1753 | NHSO$_2$CH$_3$ | 2-Cl-phenyl | 2-(3-pyrrolidinylcarbonyl) |
| 1754 | NHSO$_2$CH$_3$ | 2-Cl-phenyl | 2-glycinoyl |
| 1755 | NHSO$_2$CH$_3$ | 2-Cl-phenyl | 2-(imidazol-1-ylacetyl) |
| 1756 | NHSO$_2$CH$_3$ | 2-F-phenyl | 2-(N-pyrrolidinyl-methyl)phenyl |
| 1757 | NHSO$_2$CH$_3$ | 2-F-phenyl | 2-(N-piperidinyl-methyl)phenyl |
| 1758 | NHSO$_2$CH$_3$ | 2-F-phenyl | 2-(N-morpholino-methyl)phenyl |
| 1759 | NHSO$_2$CH$_3$ | 2-F-phenyl | 2-(N,N'-methylmorpholinium-methyl)phenyl |
| 1760 | NHSO$_2$CH$_3$ | 2-F-phenyl | 2-(N-pyridinium-methyl)phenyl |
| 1761 | NHSO$_2$CH$_3$ | 2-F-phenyl | 2-(N-4-(N,N'-dimethylamino)-pyridinium-methyl)phenyl |
| 1762 | NHSO$_2$CH$_3$ | 2-F-phenyl | 2-(N-azatanyl-methyl)phenyl |
| 1763 | NHSO$_2$CH$_3$ | 2-F-phenyl | 2-(N-azetidinyl-methyl)phenyl |
| 1764 | NHSO$_2$CH$_3$ | 2-F-phenyl | 2-(N-piperazinyl-methyl)phenyl |
| 1765 | NHSO$_2$CH$_3$ | 2-F-phenyl | 2-(N,N'-BOC-piperazinyl-methyl)phenyl |
| 1766 | NHSO$_2$CH$_3$ | 2-F-phenyl | 2-(N-imidazolyl-methyl)phenyl |
| 1767 | NHSO$_2$CH$_3$ | 2-F-phenyl | 2-(N-methoxy-N-methylamino-methyl)phenyl |
| 1768 | NHSO$_2$CH$_3$ | 2-F-phenyl | 2-(N-pyridonyl-methyl)phenyl |
| 1769 | NHSO$_2$CH$_3$ | 2-F-phenyl | 2-(N-(N',N'-dimethylhydrazinyl-methyl)phenyl |
| 1770 | NHSO$_2$CH$_3$ | 2-F-phenyl | 2-(amidinyl)phenyl |
| 1771 | NHSO$_2$CH$_3$ | 2-F-phenyl | 2-(N-guanidinyl)phenyl |
| 1772 | NHSO$_2$CH$_3$ | 2-F-phenyl | 2-(imidazolyl)phenyl |
| 1773 | NHSO$_2$CH$_3$ | 2-F-phenyl | 2-(imidazolidinyl)phenyl |
| 1774 | NHSO$_2$CH$_3$ | 2-F-phenyl | 2-(2-imidazolidinyl-sulfonyl)phenyl |
| 1775 | NHSO$_2$CH$_3$ | 2-F-phenyl | 2-(2-pyrrolidinyl)phenyl |
| 1776 | NHSO$_2$CH$_3$ | 2-F-phenyl | 2-(2-piperidinyl)phenyl |
| 1777 | NHSO$_2$CH$_3$ | 2-F-phenyl | 2-(amidinyl-methyl)phenyl |
| 1778 | NHSO$_2$CH$_3$ | 2-F-phenyl | 2-(2-imidazolidinyl-methyl)phenyl |
| 1779 | NHSO$_2$CH$_3$ | 2-F-phenyl | 2-(N-(2-aminoimidazolyl)-methyl)phenyl |
| 1780 | NHSO$_2$CH$_3$ | 2-F-phenyl | 2-dimethylaminoimidazol-1-yl |

-continued

| Ex # | $R^{1b}$ | A | B |
|---|---|---|---|
| 1781 | $NHSO_2CH_3$ | 2-F-phenyl | 2-(3-aminophenyl) |
| 1782 | $NHSO_2CH_3$ | 2-F-phenyl | 2-(3-pyrrolidinylcarbonyl) |
| 1783 | $NHSO_2CH_3$ | 2-F-phenyl | 2-glycinoyl |
| 1784 | $NHSO_2CH_3$ | 2-F-phenyl | 2-(imidazol-1-ylacetyl) |
| 1785 | $NHSO_2CH_3$ | 2,5-diF-phenyl | 2-(N-pyrrolidinyl-methyl)phenyl |
| 1786 | $NHSO_2CH_3$ | 2,5-diF-phenyl | 2-(N-piperidinyl-methyl)phenyl |
| 1787 | $NHSO_2CH_3$ | 2,5-diF-phenyl | 2-(N-morpholino-methyl)phenyl |
| 1788 | $NHSO_2CH_3$ | 2,5-diF-phenyl | 2-(N,N'-methylmorpholinium-methyl)phenyl |
| 1789 | $NHSO_2CH_3$ | 2,5-diF-phenyl | 2-(N-pyridinium-methyl)phenyl |
| 1790 | $NHSO_2CH_3$ | 2,5-diF-phenyl | 2-(N-4-(N,N'-dimethylamino)-pyridinium-methyl)phenyl |
| 1791 | $NHSO_2CH_3$ | 2,5-diF-phenyl | 2-(N-azatanyl-methyl)phenyl |
| 1792 | $NHSO_2CH_3$ | 2,5-diF-phenyl | 2-(N-azetidinyl-methyl)phenyl |
| 1793 | $NHSO_2CH_3$ | 2,5-diF-phenyl | 2-(N-piperazinyl-methyl)phenyl |
| 1794 | $NHSO_2CH_3$ | 2,5-diF-phenyl | 2-(N,N'-BOC-piperazinyl-methyl)phenyl |
| 1795 | $NHSO_2CH_3$ | 2,5-diF-phenyl | 2-(N-imidazolyl-methyl)phenyl |
| 1796 | $NHSO_2CH_3$ | 2,5-diF-phenyl | 2-(N-methoxy-N-methylamino-methyl)phenyl |
| 1797 | $NHSO_2CH_3$ | 2,5-diF-phenyl | 2-(N-pyridonyl-methyl)phenyl |
| 1798 | $NHSO_2CH_3$ | 2,5-diF-phenyl | 2-(N-(N',N'-dimethylhydrazinyl-methyl)phenyl |
| 1799 | $NHSO_2CH_3$ | 2,5-diF-phenyl | 2-(amidinyl)phenyl |
| 1800 | $NHSO_2CH_3$ | 2,5-diF-phenyl | 2-(N-guanidinyl)phenyl |
| 1801 | $NHSO_2CH_3$ | 2,5-diF-phenyl | 2-(imidazolyl)phenyl |
| 1802 | $NHSO_2CH_3$ | 2,5-diF-phenyl | 2-(imidazolidinyl)phenyl |
| 1803 | $NHSO_2CH_3$ | 2,5-diF-phenyl | 2-(2-imidazolidinyl-sulfonyl)phenyl |
| 1804 | $NHSO_2CH_3$ | 2,5-diF-phenyl | 2-(2-pyrrolidinyl)phenyl |
| 1805 | $NHSO_2CH_3$ | 2,5-diF-phenyl | 2-(2-piperidinyl)phenyl |
| 1806 | $NHSO_2CH_3$ | 2,5-diF-phenyl | 2-(amidinyl-methyl)phenyl |
| 1807 | $NHSO_2CH_3$ | 2,5-diF-phenyl | 2-(2-imidazolidinyl-methyl)phenyl |
| 1808 | $NHSO_2CH_3$ | 2,5-diF-phenyl | 2-(N-(2-aminoimidazolyl)-methyl)phenyl |
| 1809 | $NHSO_2CH_3$ | 2,5-diF-phenyl | 2-dimethylaminoimidazol-1-yl |
| 1810 | $NHSO_2CH_3$ | 2,5-diF-phenyl | 2-(3-aminophenyl) |
| 1811 | $NHSO_2CH_3$ | 2,5-diF-phenyl | 2-(3-pyrrolidinylcarbonyl) |
| 1812 | $NHSO_2CH_3$ | 2,5-diF-phenyl | 2-glycinoyl |
| 1813 | $NHSO_2CH_3$ | 2,5-diF-phenyl | 2-(imidazol-1-ylacetyl) |

TABLE 3

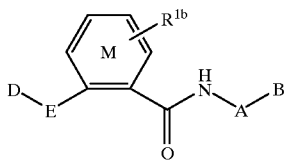

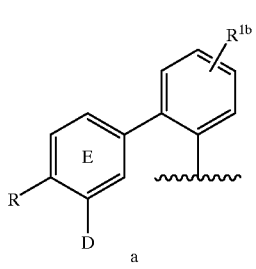 a

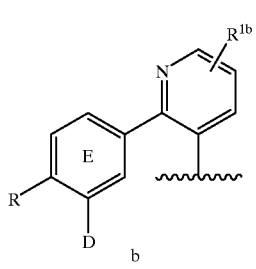 b

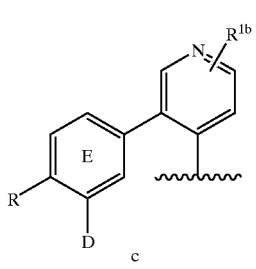 c

| | | | | | |
|---|---|---|---|---|---|
| $a_1$ | R = F, D = $NH_2$ | $b_1$ | R = F, D = $NH_2$ | $c_1$ | R = F, D = $NH_2$ |
| $a_2$ | R = H, D = $NH_2$ | $b_2$ | R = H, D = $NH_2$ | $c_2$ | R = H, D = $NH_2$ |
| $a_3$ | R = F, D = $CH_2NH_2$ | $b_3$ | R = F, D = $CH_2NH_2$ | $c_3$ | R = F, D = $CH_2NH_2$ |
| $a_4$ | R = H, D = $CH_2NH_2$ | $b_4$ | R = H, D = $CH_2NH_2$ | $c_4$ | R = H, D = $CH_2NH_2$ |
| $a_5$ | R = F, D = C(=NH)$NH_2$ | $b_5$ | R = F, D = C(=NH)$NH_2$ | $c_5$ | R = F, D = C(=NH)$NH_2$ |
| $a_6$ | R = H, D = C(=NH)$NH_2$ | $b_6$ | R = H, D = C(=NH)$NH_2$ | $c_6$ | R = H, D = C(=NH)$NH_2$ |
| $a_7$ | R = F, D = C(O)$NH_2$ | $b_7$ | R = F, D = C(O)$NH_2$ | $c_7$ | R = F, D = C(O)$NH_2$ |
| $a_8$ | R = H, D = C(O)$NH_2$ | $b_8$ | R = H, D = C(O)$NH_2$ | $c_8$ | R = H, D = C(O)$NH_2$ |

TABLE 3-continued

[Structure: M ring with R¹ᵇ substituent, connected via C(=O)NH-A-B group, with D-E substituents]

| d | e | f |
|---|---|---|
| d₁ R = F, D = NH₂ | e₁ R = F, D = NH₂ | f₁ R = F, D = NH₂ |
| d₂ R = H, D = NH₂ | e₂ R = H, D = NH₂ | f₂ R = H, D = NH₂ |
| d₃ R = F, D = CH₂NH₂ | e₃ R = F, D = CH₂NH₂ | f₃ R = F, D = CH₂NH₂ |
| d₄ R = H, D = CH₂NH₂ | e₄ R = H, D = CH₂NH₂ | f₄ R = H, D = CH₂NH₂ |
| d₅ R = F, D = C(=NH)NH₂ | e₅ R = F, D = C(=NH)NH₂ | f₅ R = F, D = C(=NH)NH₂ |
| d₆ R = H, D = C(=NH)NH₂ | e₆ R = H, D = C(=NH)NH₂ | f₆ R = H, D = C(=NH)NH₂ |
| d₇ R = F, D = C(O)NH₂ | e₇ R = F, D = C(O)NH₂ | f₇ R = F, D = C(O)NH₂ |
| d₈ R = H, D = C(O)NH₂ | e₈ R = H, D = C(O)NH₂ | f₈ R = H, D = C(O)NH₂ |

| g | h | i |
|---|---|---|
| g₁ R = F, D = NH₂ | h₁ R = F, D = NH₂ | i₁ R = F, D = NH₂ |
| g₂ R = H, D = NH₂ | h₂ R = H, D = NH₂ | i₂ R = H, D = NH₂ |
| g₃ R = F, D = CH₂NH₂ | h₃ R = F, D = CH₂NH₂ | i₃ R = F, D = CH₂NH₂ |
| g₄ R = H, D = CH₂NH₂ | h₄ R = H, D = CH₂NH₂ | i₄ R = H, D = CH₂NH₂ |
| g₅ R = F, D = C(=NH)NH₂ | h₅ R = F, D = C(=NH)NH₂ | i₅ R = F, D = C(=NH)NH₂ |
| g₆ R = H, D = C(=NH)NH₂ | h₆ R = H, D = C(=NH)NH₂ | i₆ R = H, D = C(=NH)NH₂ |
| g₇ R = F, D = C(O)NH₂ | h₇ R = F, D = C(O)NH₂ | i₇ R = F, D = C(O)NH₂ |
| g₈ R = H, D = C(O)NH₂ | h₈ R = H, D = C(O)NH₂ | i₈ R = H, D = C(O)NH₂ |

| j | k | l |
|---|---|---|
| j₁ R = F, D = NH₂ | k₁ R = F, D = NH₂ | l₁ R = F, D = NH₂ |
| j₂ R = H, D = NH₂ | k₂ R = H, D = NH₂ | l₂ R = H, D = NH₂ |
| j₃ R = F, D = CH₂NH₂ | k₃ R = F, D = CH₂NH₂ | l₃ R = F, D = CH₂NH₂ |
| j₄ R = H, D = CH₂NH₂ | k₄ R = H, D = CH₂NH₂ | l₄ R = H, D = CH₂NH₂ |
| j₅ R = F, D = C(=NH)NH₂ | k₅ R = F, D = C(=NH)NH₂ | l₅ R = F, D = C(=NH)NH₂ |
| j₆ R = H, D = C(=NH)NH₂ | k₆ R = H, D = C(=NH)NH₂ | l₆ R = H, D = C(=NH)NH₂ |
| j₇ R = F, D = C(O)NH₂ | k₇ R = F, D = C(O)NH₂ | l₇ R = F, D = C(O)NH₂ |
| j₈ R = H, D = C(O)NH₂ | k₈ R = H, D = C(O)NH₂ | l₈ R = H, D = C(O)NH₂ |

TABLE 3-continued

|     |                        |     |                        |     |                        |
|-----|------------------------|-----|------------------------|-----|------------------------|
| m₁  | R = F, D = NH₂         | n₁  | R = F, D = NH₂         | o₁  | R = F, D = NH₂         |
| m₂  | R = H, D = NH₂         | n₂  | R = H, D = NH₂         | o₂  | R = H, D = NH₂         |
| m₃  | R = F, D = CH₂NH₂      | n₃  | R = F, D = CH₂NH₂      | o₃  | R = F, D = CH₂NH₂      |
| m₄  | R = H, D = CH₂NH₂      | n₄  | R = H, D = CH₂NH₂      | o₄  | R = H, D = CH₂NH₂      |
| m₅  | R = F, D = C(=NH)NH₂   | n₅  | R = F, D = C(=NH)NH₂   | o₅  | R = F, D = C(=NH)NH₂   |
| m₆  | R = H, D = C(=NH)NH₂   | n₆  | R = H, D = C(=NH)NH₂   | o₆  | R = H, D = C(=NH)NH₂   |
| m₇  | R = F, D = C(O)NH₂     | n₇  | R = F, D = C(O)NH₂     | o₇  | R = F, D = C(O)NH₂     |
| m₈  | R = H, D = C(O)NH₂     | n₈  | R = H, D = C(O)NH₂     | o₈  | R = H, D = C(O)NH₂     |

|      |                          |      |                          |      |                          |
|------|--------------------------|------|--------------------------|------|--------------------------|
| p₁   | R = F, D = NH₂           | q₁   | R = F, D = NH₂           | r₁   | R = F, D = NH₂           |
| p₂   | R = Cl, D = NH₂          | q₂   | R = Cl, D = NH₂          | r₂   | R = Cl, D = NH₂          |
| p₃   | R = OMe, D = NH₂         | q₃   | R = OMe, D = NH₂         | r₃   | R = OMe, D = NH₂         |
| p₄   | R = F, D = CH₂NH₂        | q₄   | R = F, D = CH₂NH₂        | r₄   | R = F, D = CH₂NH₂        |
| p₅   | R = Cl, D = CH₂NH₂       | q₅   | R = Cl, D = CH₂NH₂       | r₅   | R = Cl, D = CH₂NH₂       |
| p₆   | R = OMe, D = CH₂NH₂      | q₆   | R = OMe, D = CH₂NH₂      | r₆   | R = OMe, D = CH₂NH₂      |
| p₇   | R = F, D = C(=NH)NH₂     | q₇   | R = F, D = C(=NH)NH₂     | r₇   | R = F, D = C(=NH)NH₂     |
| p₈   | R = Cl, D = C(=NH)NH₂    | q₈   | R = Cl, D = C(=NH)NH₂    | r₈   | R = Cl, D = C(=NH)NH₂    |
| p₉   | R = OMe, D = C(=NH)NH₂   | q₉   | R = OMe, D = C(=NH)NH₂   | r₉   | R = OMe, D = C(=NH)NH₂   |
| p₁₀  | R = F, D = C(O)NH₂       | q₁₀  | R = F, D = C(O)NH₂       | r₁₀  | R = F, D = C(O)NH₂       |
| p₁₁  | R = Cl, D = C(O)NH₂      | q₁₁  | R = Cl, D = C(O)NH₂      | r₁₁  | R = Cl, D = C(O)NH₂      |
| p₁₂  | R = OMe, D = C(O)NH₂     | q₁₂  | R = OMe, D = C(O)NH₂     | r₁₂  | R = OMe, D = C(O)NH₂     |

|     |                        |     |                        |     |                        |
|-----|------------------------|-----|------------------------|-----|------------------------|
| s₁  | R = F, D = NH₂         | t₁  | R = F, D = NH₂         | u₁  | R = F, D = NH₂         |
| s₂  | R = Cl, D = NH₂        | t₂  | R = Cl, D = NH₂        | u₂  | R = Cl, D = NH₂        |
| s₃  | R = OMe, D = NH₂       | t₃  | R = OMe, D = NH₂       | u₃  | R = OMe, D = NH₂       |
| s₄  | R = F, D = CH₂NH₂      | t₄  | R = F, D = CH₂NH₂      | u₄  | R = F, D = CH₂NH₂      |
| s₅  | R = Cl, D = CH₂NH₂     | t₅  | R = Cl, D = CH₂NH₂     | u₅  | R = Cl, D = CH₂NH₂     |
| s₆  | R = OMe, D = CH₂NH₂    | t₆  | R = OMe, D = CH₂NH₂    | u₆  | R = OMe, D = CH₂NH₂    |
| s₇  | R = F, D = C(=NH)NH₂   | t₇  | R = F, D = C(=NH)NH₂   | u₇  | R = F, D = C(=NH)NH₂   |

TABLE 3-continued

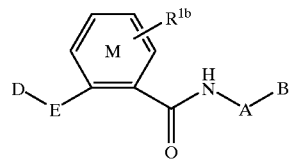

| | | | | | |
|---|---|---|---|---|---|
| s$_8$ | R = Cl, D = C(=NH)NH$_2$ | t$_8$ | R = Cl, D = C(=NH)NH$_2$ | u$_8$ | R = Cl, D = C(=NH)NH$_2$ |
| s$_9$ | R = OMe, D = C(=NH)NH$_2$ | t$_9$ | R = OMe, D = C(=NH)NH$_2$ | u$_9$ | R = OMe, D = C(=NH)NH$_2$ |
| s$_{10}$ | R = F, D = C(O)NH$_2$ | t$_{10}$ | R = F, D = C(O)NH$_2$ | u$_{10}$ | R = F, D = C(O)NH$_2$ |
| s$_{11}$ | R = Cl, D = C(O)NH$_2$ | t$_{11}$ | R = Cl, D = C(O)NH$_2$ | u$_{11}$ | R = Cl, D = C(O)NH$_2$ |
| s$_{12}$ | R = OMe, D = C(O)NH$_2$ | t$_{12}$ | R = OMe, D = C(O)NH$_2$ | u$_{12}$ | R = OMe, D = C(O)NH$_2$ |

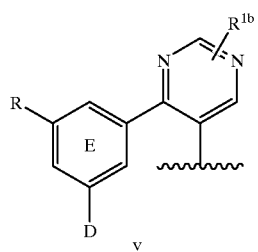
v

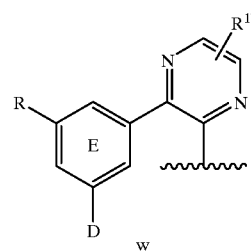
w

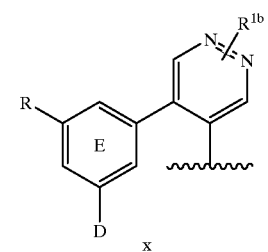
x

| | | | | | |
|---|---|---|---|---|---|
| v$_1$ | R = F, D = NH$_2$ | w$_1$ | R = F, D = NH$_2$ | x$_1$ | R = F, D = NH$_2$ |
| v$_2$ | R = Cl, D = NH$_2$ | w$_2$ | R = Cl, D = NH$_2$ | x$_2$ | R = Cl, D = NH$_2$ |
| v$_3$ | R = OMe, D = NH$_2$ | w$_3$ | R = OMe, D = NH$_2$ | x$_3$ | R = OMe, D = NH$_2$ |
| v$_4$ | R = F, D = CH$_2$NH$_2$ | w$_4$ | R = F, D = CH$_2$NH$_2$ | x$_4$ | R = F, D = CH$_2$NH$_2$ |
| v$_5$ | R = Cl, D = CH$_2$NH$_2$ | w$_5$ | R = Cl, D = CH$_2$NH$_2$ | x$_5$ | R = Cl, D = CH$_2$NH$_2$ |
| v$_6$ | R = OMe, D = CH$_2$NH$_2$ | w$_6$ | R = OMe, D = CH$_2$NH$_2$ | x$_6$ | R = OMe, D = CH$_2$NH$_2$ |
| v$_7$ | R = F, D = C(=NH)NH$_2$ | w$_7$ | R = F, D = C(=NH)NH$_2$ | x$_7$ | R = F, D = C(=NH)NH$_2$ |
| v$_8$ | R = Cl, D = C(=NH)NH$_2$ | w$_8$ | R = Cl, D = C(=NH)NH$_2$ | x$_8$ | R = Cl, D = C(=NH)NH$_2$ |
| v$_9$ | R = OMe, D = C(=NH)NH$_2$ | w$_9$ | R = OMe, D = C(=NH)NH$_2$ | x$_9$ | R = OMe, D = C(=NH)NH$_2$ |
| v$_{10}$ | R = F, D = C(O)NH$_2$ | w$_{10}$ | R = F, D = C(O)NH$_2$ | x$_{10}$ | R = F, D = C(O)NH$_2$ |
| v$_{11}$ | R = Cl, D = C(O)NH$_2$ | w$_{11}$ | R = Cl, D = C(O)NH$_2$ | x$_{11}$ | R = Cl, D = C(O)NH$_2$ |
| v$_{12}$ | R = OMe, D = C(O)NH$_2$ | w$_{12}$ | R = OMe, D = C(O)NH$_2$ | x$_{12}$ | R = OMe, D = C(O)NH$_2$ |

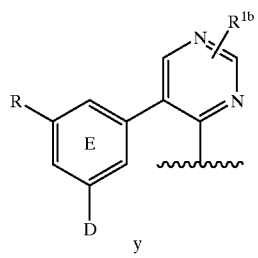
y

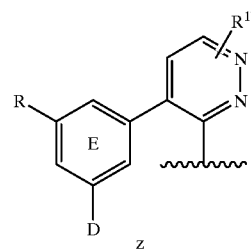
z

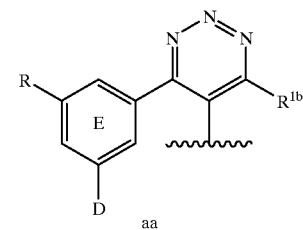
aa

| | | | | | |
|---|---|---|---|---|---|
| y$_1$ | R = F, D = NH$_2$ | z$_1$ | R = F, D = NH$_2$ | aa$_1$ | R = F, D = NH$_2$ |
| y$_2$ | R = Cl, D = NH$_2$ | z$_2$ | R = Cl, D = NH$_2$ | aa$_2$ | R = Cl, D = NH$_2$ |
| y$_3$ | R = OMe, D = NH$_2$ | z$_3$ | R = OMe, D = NH$_2$ | aa$_3$ | R = OMe, D = NH$_2$ |
| y$_4$ | R = F, D = CH$_2$NH$_2$ | z$_4$ | R = F, D = CH$_2$NH$_2$ | aa$_4$ | R = F, D = CH$_2$NH$_2$ |
| y$_5$ | R = Cl, D = CH$_2$NH$_2$ | z$_5$ | R = Cl, D = CH$_2$NH$_2$ | aa$_5$ | R = Cl, D = CH$_2$NH$_2$ |
| y$_6$ | R = OMe, D = CH$_2$NH$_2$ | z$_6$ | R = OMe, D = CH$_2$NH$_2$ | aa$_6$ | R = OMe, D = CH$_2$NH$_2$ |
| y$_7$ | R = F, D = C(=NH)NH$_2$ | z$_7$ | R = F, D = C(=NH)NH$_2$ | aa$_7$ | R = F, D = C(=NH)NH$_2$ |
| y$_8$ | R = Cl, D = C(=NH)NH$_2$ | z$_8$ | R = Cl, D = C(=NH)NH$_2$ | aa$_8$ | R = Cl, D = C(=NH)NH$_2$ |
| y$_9$ | R = OMe, D = C(=NH)NH$_2$ | z$_9$ | R = OMe, D = C(=NH)NH$_2$ | aa$_9$ | R = OMe, D = C(=NH)NH$_2$ |
| y$_{10}$ | R = F, D = C(O)NH$_2$ | z$_{10}$ | R = F, D = C(O)NH$_2$ | aa$_{10}$ | R = F, D = C(O)NH$_2$ |
| y$_{11}$ | R = Cl, D = C(O)NH$_2$ | z$_{11}$ | R = Cl, D = C(O)NH$_2$ | aa$_{11}$ | R = Cl, D = C(O)NH$_2$ |
| y$_{12}$ | R = OMe, D = C(O)NH$_2$ | z$_{12}$ | R = OMe, D = C(O)NH$_2$ | aa$_{12}$ | R = OMe, D = C(O)NH$_2$ |

TABLE 3-continued

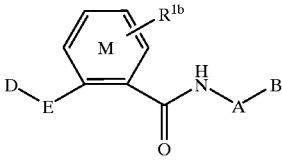

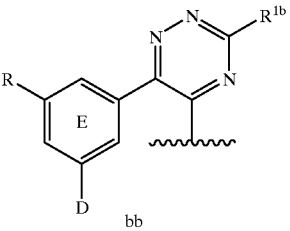

| | | | | | |
|---|---|---|---|---|---|
| bb₁ | R = F, D = NH₂ | cc₁ | R = F, D = NH₂ | dd₁ | R = F, D = NH₂ |
| bb₂ | R = Cl, D = NH₂ | cc₂ | R = Cl, D = NH₂ | dd₂ | R = Cl, D = NH₂ |
| bb₃ | R = OMe, D = NH₂ | cc₃ | R = OMe, D = NH₂ | dd₃ | R = OMe, D = NH₂ |
| bb₄ | R = F, D = CH₂NH₂ | cc₄ | R = F, D = CH₂NH₂ | dd₄ | R = F, D = CH₂NH₂ |
| bb₅ | R = Cl, D = CH₂NH₂ | cc₅ | R = Cl, D = CH₂NH₂ | dd₅ | R = Cl, D = CH₂NH₂ |
| bb₆ | R = OMe, D = CH₂NH₂ | cc₆ | R = OMe, D = CH₂NH₂ | dd₆ | R = OMe, D = CH₂NH₂ |
| bb₇ | R = F, D = C(=NH)NH₂ | cc₇ | R = F, D = C(=NH)NH₂ | dd₇ | R = F, D = C(=NH)NH₂ |
| bb₈ | R = Cl, D = C(=NH)NH₂ | cc₈ | R = Cl, D = C(=NH)NH₂ | dd₈ | R = Cl, D = C(=NH)NH₂ |
| bb₉ | R = OMe, D = C(=NH)NH₂ | cc₉ | R = OMe, D = C(=NH)NH₂ | dd₉ | R = OMe, D = C(=NH)NH₂ |
| bb₁₀ | R = F, D = C(O)NH₂ | cc₁₀ | R = F, D = C(O)NH₂ | dd₁₀ | R = F, D = C(O)NH₂ |
| bb₁₁ | R = Cl, D = C(O)NH₂ | cc₁₁ | R = Cl, D = C(O)NH₂ | dd₁₁ | R = Cl, D = C(O)NH₂ |
| bb₁₂ | R = OMe, D = C(O)NH₂ | cc₁₂ | R = OMe, D = C(O)NH₂ | dd₁₂ | R = OMe, D = C(O)NH₂ |

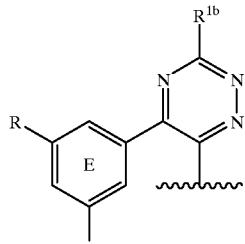

| | | | | | |
|---|---|---|---|---|---|
| ee₁ | R = F, D = CH₂NH₂ | ff₁ | R = F, D = CH₂NH₂ | gg₁ | R = F, D = CH₂NH₂ |
| ee₂ | R = Cl, D = CH₂NH₂ | ff₂ | R = Cl, D = CH₂NH₂ | gg₂ | R = Cl, D = CH₂NH₂ |
| ee₃ | R = OMe, D = CH₂NH₂ | ff₃ | R = OMe, D = CH₂NH₂ | gg₃ | R = OMe, D = CH₂NH₂ |
| ee₄ | R = CH₂NH₂, D = CH₂NH₂ | ff₄ | R = CH₂NH₂, D = CH₂NH₂ | gg₄ | R = CH₂NH₂, D = CH₂NH₂ |

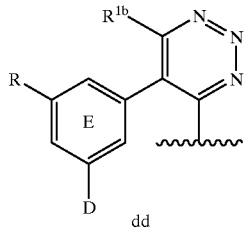

| | | | | | |
|---|---|---|---|---|---|
| hh₁ | R = F, D = CH₂NH₂ | ii₁ | R = F, D = CH₂NH₂ | jj₁ | R = F, D = CH₂NH₂ |
| hh₂ | R = Cl, D = CH₂NH₂ | ii₂ | R = Cl, D = CH₂NH₂ | jj₂ | R = Cl, D = CH₂NH₂ |
| hh₃ | R = OMe, D = CH₂NH₂ | ii₃ | R = OMe, D = CH₂NH₂ | jj₃ | R = OMe, D = CH₂NH₂ |
| hh₄ | R = CH₂NH₂, D = CH₂NH₂ | ii₄ | R = CH₂NH₂, D = CH₂NH₂ | jj₄ | R = CH₂NH₂, D = CH₂NH₂ |

TABLE 3-continued

| | | |
|---|---|---|
| kk | ll | mm |
| kk₁ R = F, D = CH₂NH₂<br>kk₂ R = Cl, D = CH₂NH₂<br>kk₃ R = OMe, D = CH₂NH₂<br>kk₄ R = CH₂NH₂, D = CH₂NH₂ | ll₁ R = F, D = CH₂NH₂<br>ll₂ R = Cl, D = CH₂NH₂<br>ll₃ R = OMe, D = CH₂NH₂<br>ll₄ R = CH₂NH₂, D = CH₂NH₂ | mm₁ R = F, D = CH₂NH₂<br>mm₂ R = Cl, D = CH₂NH₂<br>mm₃ R = OMe, D = CH₂NH₂<br>mm₄ R = CH₂NH₂, D = CH₂NH₂ |
| nn | oo | pp |
| nn₁ R = F, D = CH₂NH₂<br>nn₂ R = Cl, D = CH₂NH₂<br>nn₃ R = OMe, D = CH₂NH₂<br>nn₄ R = CH₂NH₂, D = CH₂NH₂ | oo₁ R = F, D = CH₂NH₂<br>oo₂ R = Cl, D = CH₂NH₂<br>oo₃ R = OMe, D = CH₂NH₂<br>oo₄ R = CH₂NH₂, D = CH₂NH₂ | pp₁ R = F, D = CH₂NH₂<br>pp₂ R = Cl, D = CH₂NH₂<br>pp₃ R = OMe, D = CH₂NH₂<br>pp₄ R = CH₂NH₂, D = CH₂NH₂ |
| qq | rr | ss |
| qq₁ R = F, D = CH₂NH₂<br>qq₂ R = Cl, D = CH₂NH₂<br>qq₃ R = OMe, D = CH₂NH₂<br>qq₄ R = CH₂NH₂, D = CH₂NH₂ | rr₁ R = F, D = CH₂NH₂<br>rr₂ R = Cl, D = CH₂NH₂<br>rr₃ R = OMe, D = CH₂NH₂<br>rr₄ R = CH₂NH₂, D = CH₂NH₂ | ss₁ R = F, D = CH₂NH₂<br>ss₂ R = Cl, D = CH₂NH₂<br>ss₃ R = OMe, D = CH₂NH₂<br>ss₄ R = CH₂NH₂, D = CH₂NH₂ |

| Ex# | $R^{1b}$ | A | B |
|---|---|---|---|
| 1 | H | phenyl | 2-((Me)₂N-methyl)phenyl |
| 2 | H | phenyl | 2-((Me)NH-methyl)phenyl |
| 3 | H | phenyl | 2-(H₂N-methyl)phenyl |
| 4 | H | phenyl | 2-HOCH₂-phenyl |
| 5 | H | 2-F-phenyl | 2-((Me)₂N-methyl)phenyl |
| 6 | H | 2-F-phenyl | 2-((Me)NH-methyl)phenyl |
| 7 | H | 2-F-phenyl | 2-(H₂N-methyl)phenyl |
| 8 | H | 2-F-phenyl | 2-HOCH₂-phenyl |

-continued

| Ex# | R¹ᵇ | A | B |
|---|---|---|---|
| 9 | H | phenyl | 2-methylimidazol-1-yl |
| 10 | H | phenyl | 2-ethylimidazol-1-yl |
| 11 | H | phenyl | 2-((Me)₂N-methyl)imidazol-1-yl |
| 12 | H | phenyl | 2-CH₃SO₂-imidazol-1-yl |
| 13 | H | phenyl | 2-CH₃OCH₂-imidazol-1-yl |
| 14 | H | 2-F-phenyl | 2-methylimidazol-1-yl |
| 15 | H | 2-F-phenyl | 2-ethylimidazol-1-yl |
| 16 | H | 2-F-phenyl | 2-((Me)₂N-methyl)imidazol-1-yl |
| 17 | H | 2-F-phenyl | 2-CH₃SO₂-imidazol-1-yl |
| 18 | H | 2-F-phenyl | 2-CH₃OCH₂-imidazol-1-yl |
| 19 | H | 2-Cl-phenyl | 2-methylimidazol-1-yl |
| 20 | H | 2-Cl-phenyl | 2-ethylimidazol-1-yl |
| 21 | H | 2-Cl-phenyl | 2-((Me)₂N-methyl)imidazol-1-yl |
| 22 | H | 2-Cl-phenyl | 2-CH₃SO₂-imidazol-1-yl |
| 23 | H | 2-Cl-phenyl | 2-CH₃OCH₂-imidazo1-1-y1 |
| 24 | H | 2-(Me)₂N-phenyl | 2-methylimidazol-1-yl |
| 25 | H | 2-(Me)₂N-phenyl | 2-ethylimidazol-1-yl |
| 26 | H | 2-(Me)₂N-phenyl | 2-((Me)₂N-methyl)imidazol-1-yl |
| 27 | H | 2-(Me)₂N-phenyl | 2-CH₃SO₂-imidazol-1-yl |
| 28 | H | 2-(Me)₂N-phenyl | 2-CH₃OCH₂-imidazol-1-yl |
| 29 | H | phenyl | N-methylimidazol-2-yl |
| 30 | H | phenyl | 4-methylimidazol-5-yl |
| 31 | H | phenyl | 5-CF₃-pyrazol-1-yl |
| 32 | H | 2-F-phenyl | N-methylimidazol-2-yl |
| 33 | H | 2-F-phenyl | 4-methylimidazol-5-yl |
| 34 | H | 2-F-phenyl | 5-CF₃-pyrazol-1-yl |
| 35 | H | phenyl | guanidino |
| 36 | H | phenyl | 2-thiazolin-2-ylamine |
| 37 | H | phenyl | N-methyl-2-imidazolin-2-yl |
| 38 | H | phenyl | N-methyl-1,4,5,6-tetrahydropyrimid-2-yl |
| 39 | H | phenyl | N-methylimidazol-2-ylthiol |
| 40 | H | phenyl | t-butoxycarbonylamine |
| 41 | H | phenyl | (N-pyrrolidino)formylimino |
| 42 | H | phenyl | (N-pyrrolidino)formyl-N-(methanesulfamoyl)imino |
| 43 | H | 2-F-phenyl | guanidino |
| 44 | H | 2-F-phenyl | 2-thiazolin-2-ylamine |
| 45 | H | 2-F-phenyl | N-methyl-2-imidazolin-2-yl |
| 46 | H | 2-F-phenyl | N-methyl-1,4,5,6-tetrahydropyrimid-2-yl |
| 47 | H | 2-F-phenyl | N-methylimidazol-2-ylthio |
| 48 | H | 2-F-phenyl | t-butoxycarbonylamine |
| 49 | H | 2-F-phenyl | (N-pyrrolidino)formylimino |
| 50 | H | 2-F-phenyl | (N-pyrrolidino)formyl-N-(methanesulfamoyl)imino |
| 51 | H | 2-CH₃O-phenyl | (N-pyrrolidino)formylimino |
| 52 | H | 2-CH₃O-phenyl | (N-pyrrolidino)formyl-N-(methanesulfamoyl)imino |
| 53 | —CN | phenyl | 2-((Me)₂N-methyl)phenyl |
| 54 | —CN | phenyl | 2-((Me)NH-methyl)phenyl |
| 55 | —CN | phenyl | 2-(H₂N-methyl)phenyl |
| 56 | —CN | phenyl | 2-HOCH₂-phenyl |
| 57 | —CN | 2-F-phenyl | 2-((Me)₂N-methyl)phenyl |
| 58 | —CN | 2-F-phenyl | 2-((Me)NH-methyl)phenyl |
| 59 | —CN | 2-F-phenyl | 2-(H₂N-methyl)phenyl |
| 60 | —CN | 2-F-phenyl | 2-HOCH₂-phenyl |
| 61 | —CN | phenyl | 2-methylimidazol-1-yl |
| 62 | —CN | phenyl | 2-ethylimidazol-1-yl |
| 63 | —CN | phenyl | 2-((Me)₂N-methyl)imidazol-1-yl |
| 64 | —CN | phenyl | 2-CH₃SO₂-imidazol-1-yl |
| 65 | —CN | phenyl | 2-CH₃OCH₂-imidazol-1-yl |
| 66 | —CN | 2-F-phenyl | 2-methylimidazol-1-yl |
| 67 | —CN | 2-F-phenyl | 2-ethylimidazol-1-yl |
| 68 | —CN | 2-F-phenyl | 2-((Me)₂N-methyl)imidazol-1-yl |
| 69 | —CN | 2-F-phenyl | 2-CH₃SO₂-imidazol-1-yl |
| 70 | —CN | 2-F-phenyl | 2-CH₃OCH₂-imidazol-1-yl |
| 71 | —CN | 2-Cl-phenyl | 2-methylimidazol-1-yl |
| 72 | —CN | 2-Cl-phenyl | 2-ethylimidazol-1-yl |
| 73 | —CN | 2-Cl-phenyl | 2-((Me)₂N-methyl)imidazol-1-yl |
| 74 | —CN | 2-Cl-phenyl | 2-CH₃SO₂-imidazol-1-yl |
| 75 | —CN | 2-Cl-phenyl | 2-CH₃OCH₂-imidazol-1-yl |
| 76 | —CN | 2-(Me)₂N-phenyl | 2-methylimidazol-1-yl |
| 77 | —CN | 2-(Me)₂N-phenyl | 2-ethylimidazol-1-yl |
| 78 | —CN | 2-(Me)₂N-phenyl | 2-((Me)₂N-methyl)imidazol-1-yl |
| 79 | —CN | 2-(Me)₂N-phenyl | 2-CH₃SO₂-imidazol-1-yl |
| 80 | —CN | 2-(Me)₂N-phenyl | 2-CH₃OCH₂-imidazol-1-yl |
| 81 | —CN | phenyl | N-methylimidazol-2-yl |
| 82 | —CN | phenyl | 4-methylimidazol-5-yl |
| 83 | —CN | phenyl | 5-CF₃-pyrazol-1-yl |
| 84 | —CN | 2-F-phenyl | N-methylimidazol-2-yl |
| 85 | —CN | 2-F-phenyl | 4-methylimidazol-5-yl |
| 86 | —CN | 2-F-phenyl | 5-CF₃-pyrazol-1-yl |
| 87 | —CN | phenyl | guanidino |
| 88 | —CN | phenyl | 2-thiazolin-2-ylamine |
| 89 | —CN | phenyl | N-methyl-2-imidazolin-2-yl |
| 90 | —CN | phenyl | N-methyl-1,4,5,6-tetrahydropyrimid-2-yl |
| 91 | —CN | phenyl | N-methylimidazol-2-ylthiol |
| 92 | —CN | phenyl | t-butoxycarbonylamine |
| 93 | —CN | phenyl | (N-pyrrolidino)formylimino |
| 94 | —CN | phenyl | (N-pyrrolidino)formyl-N-(methanesulfamoyl)imino |
| 95 | —CN | 2-F-phenyl | guanidino |
| 96 | —CN | 2-F-phenyl | 2-thiazolin-2-ylamine |
| 97 | —CN | 2-F-phenyl | N-methyl-2-imidazolin-2-yl |
| 98 | —CN | 2-F-phenyl | N-methyl-1,4,5,6-tetrahydropyrimid-2-yl |
| 99 | —CN | 2-F-phenyl | N-methylimidazol-2-ylthio |
| 100 | —CN | 2-F-phenyl | t-butoxycarbonylamine |
| 101 | —CN | 2-F-phenyl | (N-pyrrolidino)formylimino |
| 102 | —CN | 2-F-phenyl | (N-pyrrolidino)formyl-N-(methanesulfamoyl)imino |
| 103 | —CN | 2-CH₃O-phenyl | (N-pyrrolidino)formylimino |
| 104 | —CN | 2-CH₃O-phenyl | (N-pyrrolidino)formyl-N-(methanesulfamoyl)imino |
| 105 | CF₃ | phenyl | 2-((Me)₂N-methyl)phenyl |
| 106 | CF₃ | phenyl | 2-((Me)NH-methyl)phenyl |
| 107 | CF₃ | phenyl | 2-(H₂N-methyl)phenyl |
| 108 | CF₃ | phenyl | 2-HOCH₂-phenyl |
| 109 | CF₃ | 2-F-phenyl | 2-((Me)₂N-methyl)phenyl |
| 110 | CF₃ | 2-F-phenyl | 2-((Me)NH-methyl)phenyl |
| 111 | CF₃ | 2-F-phenyl | 2-(H₂N-methyl)phenyl |
| 112 | CF₃ | 2-F-phenyl | 2-HOCH₂-phenyl |
| 113 | CF₃ | phenyl | 2-methylimidazol-1-yl |
| 114 | CF₃ | phenyl | 2-ethylimidazol-1-yl |
| 115 | CF₃ | phenyl | 2-((Me)₂N-methyl)imidazol-1-yl |
| 116 | CF₃ | phenyl | 2-CH₃SO₂-imidazol-1-yl |
| 117 | CF₃ | phenyl | 2-CH₃OCH₂-imidazol-1-yl |
| 118 | CF₃ | 2-F-phenyl | 2-methylimidazol-1-yl |
| 119 | CF₃ | 2-F-phenyl | 2-ethylimidazol-1-yl |
| 120 | CF₃ | 2-F-phenyl | 2-((Me)₂N-methyl)imidazol-1-yl |
| 121 | CF₃ | 2-F-phenyl | 2-CH₃SO₂-imidazol-1-yl |
| 122 | CF₃ | 2-F-phenyl | 2-CH₃OCH₂-imidazol-1-yl |
| 123 | CF₃ | 2-Cl-phenyl | 2-methylimidazol-1-yl |
| 124 | CF₃ | 2-Cl-phenyl | 2-ethylimidazol-1-yl |
| 125 | CF₃ | 2-Cl-phenyl | 2-((Me)₂N-methyl)imidazol-1-yl |
| 126 | CF₃ | 2-Cl-phenyl | 2-CH₃SO₂-imidazol-1-yl |
| 127 | CF₃ | 2-Cl-phenyl | 2-CH₃OCH₂-imidazol-1-yl |
| 128 | CF₃ | 2-(Me)₂N-phenyl | 2-methylimidazol-1-yl |
| 129 | CF₃ | 2-(Me)₂N-phenyl | 2-ethylimidazol-1-yl |
| 130 | CF₃ | 2-(Me)₂N-phenyl | 2-((Me)₂N-methyl)imidazol-1-yl |
| 131 | CF₃ | 2-(Me)₂N-phenyl | 2-CH₃SO₂-imidazol-1-yl |
| 132 | CF₃ | 2-(Me)₂N-phenyl | 2-CH₃OCH₂-imidazol-1-yl |
| 133 | CF₃ | phenyl | N-methylimidazol-2-yl |
| 134 | CF₃ | phenyl | 4-methylimidazol-5-yl |
| 135 | CF₃ | phenyl | 5-CF₃-pyrazol-1-yl |
| 136 | CF₃ | 2-F-phenyl | N-methylimidazol-2-yl |
| 137 | CF₃ | 2-F-phenyl | 4-methylimidazol-5-yl |
| 138 | CF₃ | 2-F-phenyl | 5-CF₃-pyrazol-1-yl |
| 139 | CF₃ | phenyl | guanidino |
| 140 | CF₃ | phenyl | 2-thiazolin-2-ylamine |
| 141 | CF₃ | phenyl | N-methyl-2-imidazolin-2-yl |
| 142 | CF₃ | phenyl | N-methyl-1,4,5,6-tetrahydropyrimid-2-yl |
| 143 | CF₃ | phenyl | N-methylimidazol-2-ylthiol |
| 144 | CF₃ | phenyl | t-butoxycarbonylamine |
| 145 | CF₃ | phenyl | (N-pyrrolidino)formylimino |
| 146 | CF₃ | phenyl | (N-pyrrolidino)formyl-N-(methanesulfamoyl)imino |
| 147 | CF₃ | 2-F-phenyl | guanidino |
| 148 | CF₃ | 2-F-phenyl | 2-thiazolin-2-ylamine |
| 149 | CF₃ | 2-F-phenyl | N-methyl-2-imidazolin-2-yl |
| 150 | CF₃ | 2-F-phenyl | N-methyl-1,4,5,6- |

-continued

| Ex# | R$^{1b}$ | A | B |
|---|---|---|---|
| 151 | CF$_3$ | 2-F-phenyl | N-methylimidazol-2-ylthio |
| 152 | CF$_3$ | 2-F-phenyl | t-butoxycarbonylamine |
| 153 | CF$_3$ | 2-F-phenyl | (N-pyrrolidino)formylimino |
| 154 | CF$_3$ | 2-F-phenyl | (N-pyrrolidino)formyl-N-(methanesulfamoyl)imino |
| 155 | CF$_3$ | 2-CH$_3$O-phenyl | (N-pyrrolidino)formylimino |
| 156 | CF$_3$ | 2-CH$_3$O-phenyl | (N-pyrrolidino)formyl-N-(methanesulfamoyl)imino |
| 157 | CONH$_2$ | phenyl | 2-((Me)$_2$N-methyl)phenyl |
| 158 | CONH$_2$ | phenyl | 2-((Me)NH-methyl)phenyl |
| 159 | CONH$_2$ | phenyl | 2-(H$_2$N-methyl)phenyl |
| 160 | CONH$_2$ | phenyl | 2-HOCH$_2$-phenyl |
| 161 | CONH$_2$ | 2-F-phenyl | 2-((Me)$_2$N-methyl)phenyl |
| 162 | CONH$_2$ | 2-F-phenyl | 2-((Me)NH-methyl)phenyl |
| 163 | CONH$_2$ | 2-F-phenyl | 2-(H$_2$N-methyl)phenyl |
| 164 | CONH$_2$ | 2-F-phenyl | 2-HOCH$_2$-phenyl |
| 165 | CONH$_2$ | phenyl | 2-methylimidazol-1-yl |
| 166 | CONH$_2$ | phenyl | 2-ethylimidazol-1-yl |
| 167 | CONH$_2$ | phenyl | 2-((Me)$_2$N-methyl)imidazol-1-yl |
| 168 | CONH$_2$ | phenyl | 2-CH$_3$SO$_2$-imidazol-1-yl |
| 169 | CONH$_2$ | phenyl | 2-CH$_3$OCH$_2$-imidazol-1-yl |
| 170 | CONH$_2$ | 2-F-phenyl | 2-methylimidazol-1-yl |
| 171 | CONH$_2$ | 2-F-phenyl | 2-ethylimidazol-1-yl |
| 172 | CONH$_2$ | 2-F-phenyl | 2-((Me)$_2$N-methyl)imidazol-1-yl |
| 173 | CONH$_2$ | 2-F-phenyl | 2-CH$_3$SO$_2$-imidazol-1-yl |
| 174 | CONH$_2$ | 2-F-phenyl | 2-CH$_3$OCH$_2$-imidazol-1-yl |
| 175 | CONH$_2$ | 2-Cl-phenyl | 2-methylimidazol-1-yl |
| 176 | CONH$_2$ | 2-Cl-phenyl | 2-ethylimidazol-1-yl |
| 177 | CONH$_2$ | 2-Cl-phenyl | 2-((Me)$_2$N-methyl)imidazol-1-yl |
| 178 | CONH$_2$ | 2-Cl-phenyl | 2-CH$_3$SO$_2$-imidazol-1-yl |
| 179 | CONH$_2$ | 2-Cl-phenyl | 2-CH$_3$OCH$_2$-imidazol-1-yl |
| 180 | CONH$_2$ | 2-(Me)$_2$N-phenyl | 2-methylimidazol-1-yl |
| 181 | CONH$_2$ | 2-(Me)$_2$N-phenyl | 2-ethylimidazol-1-yl |
| 182 | CONH$_2$ | 2-(Me)$_2$N-phenyl | 2-((Me)$_2$N-methyl)imidazol-1-yl |
| 183 | CONH$_2$ | 2-(Me)$_2$N-phenyl | 2-CH$_3$SO$_2$-imidazol-1-yl |
| 184 | CONH$_2$ | 2-(Me)$_2$N-phenyl | 2-CH$_3$OCH$_2$-imidazol-1-yl |
| 185 | CONH$_2$ | phenyl | N-methylimidazol-2-yl |
| 186 | CONH$_2$ | phenyl | 4-methylimidazol-5-yl |
| 187 | CONH$_2$ | phenyl | 5-CF$_3$-pyrazol-1-yl |
| 188 | CONH$_2$ | 2-F-phenyl | N-methylimidazol-2-yl |
| 189 | CONH$_2$ | 2-F-phenyl | 4-methylimidazol-5-yl |
| 190 | CONH$_2$ | 2-F-phenyl | 5-CF$_3$-pyrazol-1-yl |
| 191 | CONH$_2$ | phenyl | guanidino |
| 192 | CONH$_2$ | phenyl | 2-thiazolin-2-ylamine |
| 193 | CONH$_2$ | phenyl | N-methyl-2-imidazolin-2-yl |
| 194 | CONH$_2$ | phenyl | N-methyl-1,4,5,6-tetrahydropyrimid-2-yl |
| 195 | CONH$_2$ | phenyl | N-methylimidazol-2-ylthiol |
| 196 | CONH$_2$ | phenyl | t-butoxycarbonylamine |
| 197 | CONH$_2$ | phenyl | (N-pyrrolidino)formylimino |
| 198 | CONH$_2$ | phenyl | (N-pyrrolidino)formyl-N-(methanesulfamoyl)imino |
| 199 | CONH$_2$ | 2-F-phenyl | guanidino |
| 200 | CONH$_2$ | 2-F-phenyl | 2-thiazolin-2-ylamine |
| 201 | CONH$_2$ | 2-F-phenyl | N-methyl-2-imidazolin-2-yl |
| 202 | CONH$_2$ | 2-F-phenyl | N-methyl-1,4,5,6-tetrahydropyrimid-2-yl |
| 203 | CONH$_2$ | 2-F-phenyl | N-methylimidazol-2-ylthio |
| 204 | CONH$_2$ | 2-F-phenyl | t-butoxycarbonylamine |
| 205 | CONH$_2$ | 2-F-phenyl | (N-pyrrolidino)formylimino |
| 206 | CONH$_2$ | 2-F-phenyl | (N-pyrrolidino)formyl-N-(methanesulfamoyl)imino |
| 207 | CONH$_2$ | 2-CH$_3$O-phenyl | (N-pyrrolidino)formylimino |
| 208 | CONH$_2$ | 2-CH$_3$O-phenyl | (N-pyrrolidino)formyl-N-(methanesulfamoyl)imino |
| 209 | SCH$_3$ | phenyl | 2-((Me)$_2$N-methyl)phenyl |
| 210 | SCH$_3$ | phenyl | 2-((Me)NH-methyl)phenyl |
| 211 | SCH$_3$ | phenyl | 2-(H$_2$N-methyl)phenyl |
| 212 | SCH$_3$ | phenyl | 2-HOCH$_2$-phenyl |
| 213 | SCH$_3$ | 2-F-phenyl | 2-((Me)$_2$N-methyl)phenyl |
| 214 | SCH$_3$ | 2-F-phenyl | 2-((Me)NH-methyl)phenyl |
| 215 | SCH$_3$ | 2-F-phenyl | 2-(H$_2$N-methyl)phenyl |
| 216 | SCH$_3$ | 2-F-phenyl | 2-HOCH$_2$-phenyl |
| 217 | SCH$_3$ | phenyl | 2-methylimidazol-1-yl |
| 218 | SCH$_3$ | phenyl | 2-ethylimidazol-1-yl |
| 219 | SCH$_3$ | phenyl | 2-((Me)$_2$N-methyl)imidazol-1-yl |
| 220 | SCH$_3$ | phenyl | 2-CH$_3$SO$_2$-imidazol-1-yl |
| 221 | SCH$_3$ | phenyl | 2-CH$_3$OCH$_2$-imidazol-1-yl |
| 222 | SCH$_3$ | 2-F-phenyl | 2-methylimidazol-1-yl |
| 223 | SCH$_3$ | 2-F-phenyl | 2-ethylimidazol-1-yl |
| 224 | SCH$_3$ | 2-F-phenyl | 2-((Me)$_2$N-methyl)imidazol-1-yl |
| 225 | SCH$_3$ | 2-F-phenyl | 2-CH$_3$SO$_2$-imidazol-1-yl |
| 226 | SCH$_3$ | 2-F-phenyl | 2-CH$_3$OCH$_2$-imidazol-1-yl |
| 227 | SCH$_3$ | 2-Cl-phenyl | 2-methylimidazol-1-yl |
| 228 | SCH$_3$ | 2-Cl-phenyl | 2-ethylimidazol-1-yl |
| 229 | SCH$_3$ | 2-Cl-phenyl | 2-((Me)$_2$N-methyl)imidazol-1-yl |
| 230 | SCH$_3$ | 2-Cl-phenyl | 2-CH$_3$SO$_2$-imidazol-1-yl |
| 231 | SCH$_3$ | 2-Cl-phenyl | 2-CH$_3$OCH$_2$-imidazol-1-yl |
| 232 | SCH$_3$ | 2-(Me)$_2$N-phenyl | 2-methylimidazol-1-yl |
| 233 | SCH$_3$ | 2-(Me)$_2$N-phenyl | 2-ethylimidazol-1-yl |
| 234 | SCH$_3$ | 2-(Me)$_2$N-phenyl | 2-((Me)$_2$N-methyl)imidazol-1-yl |
| 235 | SCH$_3$ | 2-(Me)$_2$N-phenyl | 2-CH$_3$SO$_2$-imidazol-1-yl |
| 236 | SCH$_3$ | 2-(Me)$_2$N-phenyl | 2-CH$_3$OCH$_2$-imidazol-1-yl |
| 237 | SCH$_3$ | phenyl | N-methylimidazol-2-yl |
| 238 | SCH$_3$ | phenyl | 4-methylimidazol-5-yl |
| 239 | SCH$_3$ | phenyl | 5-CF$_3$-pyrazol-1-yl |
| 240 | SCH$_3$ | 2-F-phenyl | N-methylimidazol-2-yl |
| 241 | SCH$_3$ | 2-F-phenyl | 4-methylimidazol-5-yl |
| 242 | SCH$_3$ | 2-F-phenyl | 5-CF$_3$-pyrazol-1-yl |
| 243 | SCH$_3$ | phenyl | guanidino |
| 244 | SCH$_3$ | phenyl | 2-thiazolin-2-ylamine |
| 245 | SCH$_3$ | phenyl | N-methyl-2-imidazolin-2-yl |
| 246 | SCH$_3$ | phenyl | N-methyl-1,4,5,6-tetrahydropyrimid-2-yl |
| 247 | SCH$_3$ | phenyl | N-methylimidazol-2-ylthiol |
| 248 | SCH$_3$ | phenyl | t-butoxycarbonylamine |
| 249 | SCH$_3$ | phenyl | (N-pyrrolidino)formylimino |
| 250 | SCH$_3$ | phenyl | (N-pyrrolidino)formyl-N-(methanesulfamoyl)imino |
| 251 | SCH$_3$ | 2-F-phenyl | guanidino |
| 252 | SCH$_3$ | 2-F-phenyl | 2-thiazolin-2-ylamine |
| 253 | SCH$_3$ | 2-F-phenyl | N-methyl-2-imidazolin-2-yl |
| 254 | SCH$_3$ | 2-F-phenyl | N-methyl-1,4,5,6-tetrahydropyrimid-2-yl |
| 255 | SCH$_3$ | 2-F-phenyl | N-methylimidazol-2-ylthio |
| 256 | SCH$_3$ | 2-F-phenyl | t-butoxycarbonylamine |
| 257 | SCH$_3$ | 2-F-phenyl | (N-pyrrolidino)formylimino |
| 258 | SCH$_3$ | 2-F-phenyl | (N-pyrrolidino)formyl-N-(methanesulfamoyl)imino |
| 259 | SCH$_3$ | 2-CH$_3$O-phenyl | (N-pyrrolidino)formylimino |
| 260 | SCH$_3$ | 2-CH$_3$O-phenyl | (N-pyrrolidino)formyl-N-(methanesulfamoyl)imino |
| 261 | SO$_2$CH$_3$ | phenyl | 2-((Me)$_2$N-methyl)phenyl |
| 262 | SO$_2$CH$_3$ | phenyl | 2-((Me)NH-methyl)phenyl |
| 263 | SO$_2$CH$_3$ | phenyl | 2-(H$_2$N-methyl)phenyl |
| 264 | SO$_2$CH$_3$ | phenyl | 2-HOCH$_2$-phenyl |
| 265 | SO$_2$CH$_3$ | 2-F-phenyl | 2-((Me)$_2$N-methyl)phenyl |
| 266 | SO$_2$CH$_3$ | 2-F-phenyl | 2-((Me)NH-methyl)phenyl |
| 267 | SO$_2$CH$_3$ | 2-F-phenyl | 2-(H$_2$N-methyl)phenyl |
| 268 | SO$_2$CH$_3$ | 2-F-phenyl | 2-HOCH$_2$-phenyl |
| 269 | SO$_2$CH$_3$ | phenyl | 2-methylimidazol-1-yl |
| 270 | SO$_2$CH$_3$ | phenyl | 2-ethylimidazol-1-yl |
| 271 | SO$_2$CH$_3$ | phenyl | 2-((Me)$_2$N-methyl)imidazol-1-yl |
| 272 | SO$_2$CH$_3$ | phenyl | 2-CH$_3$SO$_2$-imidazol-1-yl |
| 273 | SO$_2$CH$_3$ | phenyl | 2-CH$_3$OCH$_2$-imidazol-1-yl |
| 274 | SO$_2$CH$_3$ | 2-F-phenyl | 2-methylimidazol-1-yl |
| 275 | SO$_2$CH$_3$ | 2-F-phenyl | 2-ethylimidazol-1-yl |
| 276 | SO$_2$CH$_3$ | 2-F-phenyl | 2-((Me)$_2$N-methyl)imidazol-1-yl |
| 277 | SO$_2$CH$_3$ | 2-F-phenyl | 2-CH$_3$SO$_2$-imidazol-1-yl |
| 278 | SO$_2$CH$_3$ | 2-F-phenyl | 2-CH$_3$OCH$_2$-imidazol-1-yl |
| 279 | SO$_2$CH$_3$ | 2-Cl-phenyl | 2-methylimidazol-1-yl |
| 280 | SO$_2$CH$_3$ | 2-Cl-phenyl | 2-ethylimidazol-1-yl |
| 281 | SO$_2$CH$_3$ | 2-Cl-phenyl | 2-((Me)$_2$N-methyl)imidazol-1-yl |
| 282 | SO$_2$CH$_3$ | 2-Cl-phenyl | 2-CH$_3$SO$_2$-imidazol-1-yl |
| 283 | SO$_2$CH$_3$ | 2-Cl-phenyl | 2-CH$_3$OCH$_2$-imidazol-1-yl |
| 284 | SO$_2$CH$_3$ | 2-(Me)$_2$N-phenyl | 2-methylimidazol-1-yl |
| 285 | SO$_2$CH$_3$ | 2-(Me)$_2$N-phenyl | 2-ethylimidazol-1-yl |
| 286 | SO$_2$CH$_3$ | 2-(Me)$_2$N-phenyl | 2-((Me)$_2$N-methyl)imidazol-1-yl |
| 287 | SO$_2$CH$_3$ | 2-(Me)$_2$N-phenyl | 2-CH$_3$SO$_2$-imidazol-1-yl |
| 288 | SO$_2$CH$_3$ | 2-(Me)$_2$N-phenyl | 2-CH$_3$OCH$_2$-imidazol-1-yl |
| 289 | SO$_2$CH$_3$ | phenyl | N-methylimidazol-2-yl |
| 290 | SO$_2$CH$_3$ | phenyl | 4-methylimidazol-5-yl |
| 291 | SO$_2$CH$_3$ | phenyl | 5-CF$_3$-pyrazol-1-yl |

-continued

| Ex# | R¹ᵇ | A | B |
|---|---|---|---|
| 292 | SO₂CH₃ | 2-F-phenyl | N-methylimidazol-2-yl |
| 293 | SO₂CH₃ | 2-F-phenyl | 4-methylimidazol-5-yl |
| 294 | SO₂CH₃ | 2-F-phenyl | 5-CF₃-pyrazol-1-yl |
| 295 | SO₂CH₃ | phenyl | guanidino |
| 296 | SO₂CH₃ | phenyl | 2-thiazolin-2-ylamine |
| 297 | SO₂CH₃ | phenyl | N-methyl-2-imidazolin-2-yl |
| 298 | SO₂CH₃ | phenyl | N-methyl-1,4,5,6-tetrahydropyrimid-2-yl |
| 299 | SO₂CH₃ | phenyl | N-methylimidazol-2-ylthiol |
| 300 | SO₂CH₃ | phenyl | t-butoxycarbonylamine |
| 301 | SO₂CH₃ | phenyl | (N-pyrrolidino)formylimino |
| 302 | SO₂CH₃ | phenyl | (N-pyrrolidino)formyl-N-(methanesulfamoyl)imino |
| 303 | SO₂CH₃ | 2-F-phenyl | guanidino |
| 304 | SO₂CH₃ | 2-F-phenyl | 2-thiazolin-2-ylamine |
| 305 | SO₂CH₃ | 2-F-phenyl | N-methyl-2-imidazolin-2-yl |
| 306 | SO₂CH₃ | 2-F-phenyl | N-methyl-1,4,5,6-tetrahydropyrimid-2-yl |
| 307 | SO₂CH₃ | 2-F-phenyl | N-methylimidazol-2-ylthio |
| 308 | SO₂CH₃ | 2-F-phenyl | t-butoxycarbonylamine |
| 309 | SO₂CH₃ | 2-F-phenyl | (N-pyrrolidino)formylimino |
| 310 | SO₂CH₃ | 2-F-phenyl | (N-pyrrolidino)formyl-N-(methanesulfamoyl)imino |
| 311 | SO₂CH₃ | 2-CH₃O-phenyl | (N-pyrrolidino)formylimino |
| 312 | SO₂CH₃ | 2-CH₃O-phenyl | (N-pyrrolidino)formyl-N-(methanesulfamoyl)imino |
| 313 | NHSO₂CH₃ | phenyl | 2-((Me)₂N-methyl)phenyl |
| 314 | NHSO₂CH₃ | phenyl | 2-((Me)NH-methyl)phenyl |
| 315 | NHSO₂CH₃ | phenyl | 2-(H₂N-methyl)phenyl |
| 316 | NHSO₂CH₃ | phenyl | 2-HOCH₂-phenyl |
| 317 | NHSO₂CH₃ | 2-F-phenyl | 2-((Me)₂N-methyl)phenyl |
| 318 | NHSO₂CH₃ | 2-F-phenyl | 2-((Me)NH-methyl)phenyl |
| 319 | NHSO₂CH₃ | 2-F-phenyl | 2-(H₂N-methyl)phenyl |
| 320 | NHSO₂CH₃ | 2-F-phenyl | 2-HOCH₂-phenyl |
| 321 | NHSO₂CH₃ | phenyl | 2-methylimidazol-1-yl |
| 322 | NHSO₂CH₃ | phenyl | 2-ethylimidazol-1-yl |
| 323 | NHSO₂CH₃ | phenyl | 2-((Me)₂N-methyl)imidazol-1-yl |
| 324 | NHSO₂CH₃ | phenyl | 2-CH₃SO₂-imidazol-1-yl |
| 325 | NHSO₂CH₃ | phenyl | 2-CH₃OCH₂-imidazol-1-yl |
| 326 | NHSO₂CH₃ | 2-F-phenyl | 2-methylimidazol-1-yl |
| 327 | NHSO₂CH₃ | 2-F-phenyl | 2-ethylimidazol-1-yl |
| 328 | NHSO₂CH₃ | 2-F-phenyl | 2-((Me)₂N-methyl)imidazol-1-yl |
| 329 | NHSO₂CH₃ | 2-F-phenyl | 2-CH₃SO₂-imidazol-1-yl |
| 330 | NHSO₂CH₃ | 2-F-phenyl | 2-CH₃OCH₂-imidazol-1-yl |
| 331 | NHSO₂CH₃ | 2-Cl-phenyl | 2-methylimidazol-1-yl |
| 332 | NHSO₂CH₃ | 2-Cl-phenyl | 2-ethylimidazol-1-yl |
| 333 | NHSO₂CH₃ | 2-Cl-phenyl | 2-((Me)₂N-methyl)imidazol-1-yl |
| 334 | NHSO₂CH₃ | 2-Cl-phenyl | 2-CH₃SO₂-imidazol-1-yl |
| 335 | NHSO₂CH₃ | 2-Cl-phenyl | 2-CH₃OCH₂-imidazol-1-yl |
| 336 | NHSO₂CH₃ | 2-(Me)₂N-phenyl | 2-methylimidazol-1-yl |
| 337 | NHSO₂CH₃ | 2-(Me)₂N-phenyl | 2-ethylimidazol-1-yl |
| 338 | NHSO₂CH₃ | 2-(Me)₂N-phenyl | 2-((Me)₂N-methyl)imidazol-1-yl |
| 339 | NHSO₂CH₃ | 2-(Me)₂N-phenyl | 2-CH₃SO₂-imidazol-1-yl |
| 340 | NHSO₂CH₃ | 2-(Me)₂N-phenyl | 2-CH₃OCH₂-imidazol-1-yl |
| 341 | NHSO₂CH₃ | phenyl | N-methylimidazol-2-yl |
| 342 | NHSO₂CH₃ | phenyl | 4-methylimidazol-5-yl |
| 343 | NHSO₂CH₃ | phenyl | 5-CF₃-pyrazol-1-yl |
| 344 | NHSO₂CH₃ | 2-F-phenyl | N-methylimidazol-2-yl |
| 345 | NHSO₂CH₃ | 2-F-phenyl | 4-methylimidazol-5-yl |
| 346 | NHSO₂CH₃ | 2-F-phenyl | 5-CF₃-pyrazol-1-yl |
| 347 | NHSO₂CH₃ | phenyl | guanidino |
| 348 | NHSO₂CH₃ | phenyl | 2-thiazolin-2-ylamine |
| 349 | NHSO₂CH₃ | phenyl | N-methyl-2-imidazolin-2-yl |
| 350 | NHSO₂CH₃ | phenyl | N-methyl-1,4,5,6-tetrahydropyrimid-2-yl |
| 351 | NHSO₂CH₃ | phenyl | N-methylimidazol-2-ylthiol |
| 352 | NHSO₂CH₃ | phenyl | t-butoxycarbonylamine |
| 353 | NHSO₂CH₃ | phenyl | (N-pyrrolidino)formylimino |
| 354 | NHSO₂CH₃ | phenyl | (N-pyrrolidino)formyl-N-(methanesulfamoyl)imino |
| 355 | NHSO₂CH₃ | 2-F-phenyl | guanidino |
| 356 | NHSO₂CH₃ | 2-F-phenyl | 2-thiazolin-2-ylamine |
| 357 | NHSO₂CH₃ | 2-F-phenyl | N-methyl-2-imidazolin-2-yl |
| 358 | NHSO₂CH₃ | 2-F-phenyl | N-methyl-1,4,5,6-tetrahydropyrimid-2-yl |
| 359 | NHSO₂CH₃ | 2-F-phenyl | N-methylimidazol-2-ylthio |
| 360 | NHSO₂CH₃ | 2-F-phenyl | t-butoxycarbonylamine |
| 361 | NHSO₂CH₃ | 2-F-phenyl | (N-pyrrolidino)formylimino |
| 362 | NHSO₂CH₃ | 2-F-phenyl | (N-pyrrolidino)formyl-N-(methanesulfamoyl)imino |
| 363 | NHSO₂CH₃ | 2-CH₃O-phenyl | (N-pyrrolidino)formylimino |
| 364 | NHSO₂CH₃ | 2-CH₃O-phenyl | (N-pyrrolidino)formyl-N-(methanesulfamoyl)imino |

TABLE 4

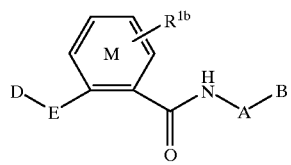

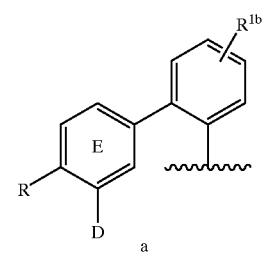

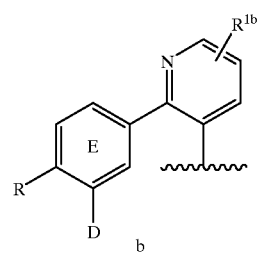

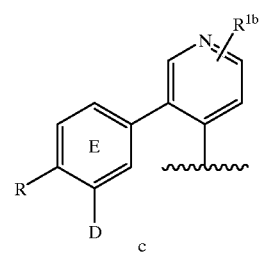

a₁  R = F, D = NH₂  
a₂  R = H, D = NH₂ b₁  R = F, D = NH₂  
b₂  R = H, D = NH₂ c₁  R = F, D = NH₂  
c₂  R = H, D = NH₂

TABLE 4-continued

| | | | | | |
|---|---|---|---|---|---|
| a$_3$ | R = F, D = CH$_2$NH$_2$ | b$_3$ | R = F, D = CH$_2$NH$_2$ | c$_3$ | R = F, D = CH$_2$NH$_2$ |
| a$_4$ | R = H, D = CH$_2$NH$_2$ | b$_4$ | R = H, D = CH$_2$NH$_2$ | c$_4$ | R = H, D = CH$_2$NH$_2$ |
| a$_5$ | R = F, D = C(=NH)NH$_2$ | b$_5$ | R = F, D = C(=NH)NH$_2$ | c$_5$ | R = F, D = C(=NH)NH$_2$ |
| a$_6$ | R = H, D = C(=NH)NH$_2$ | b$_6$ | R = H, D = C(=NH)NH$_2$ | c$_6$ | R = H, D = C(=NH)NH$_2$ |
| a$_7$ | R = F, D = C(O)NH$_2$ | b$_7$ | R = F, D = C(O)NH$_2$ | c$_7$ | R = F, D = C(O)NH$_2$ |
| a$_8$ | R = H, D = C(O)NH$_2$ | b$_8$ | R = H, D = C(O)NH$_2$ | c$_8$ | R = H, D = C(O)NH$_2$ |

| | | | | | |
|---|---|---|---|---|---|
| d$_1$ | R = F, D = NH$_2$ | e$_1$ | R = F, D = NH$_2$ | f$_1$ | R = F, D = NH$_2$ |
| d$_2$ | R = H, D = NH$_2$ | e$_2$ | R = H, D = NH$_2$ | f$_2$ | R = H, D = NH$_2$ |
| d$_3$ | R = F, D = CH$_2$NH$_2$ | e$_3$ | R = F, D = CH$_2$NH$_2$ | f$_3$ | R = F, D = CH$_2$NH$_2$ |
| d$_4$ | R = H, D = CH$_2$NH$_2$ | e$_4$ | R = H, D = CH$_2$NH$_2$ | f$_4$ | R = H, D = CH$_2$NH$_2$ |
| d$_5$ | R = F, D = C(=NH)NH$_2$ | e$_5$ | R = F, D = C(=NH)NH$_2$ | f$_5$ | R = F, D = C(=NH)NH$_2$ |
| d$_6$ | R = H, D = C(=NH)NH$_2$ | e$_6$ | R = H, D = C(=NH)NH$_2$ | f$_6$ | R = H, D = C(=NH)NH$_2$ |
| d$_7$ | R = F, D = C(O)NH$_2$ | e$_7$ | R = F, D = C(O)NH$_2$ | f$_7$ | R = F, D = C(O)NH$_2$ |
| d$_8$ | R = H, D = C(O)NH$_2$ | e$_8$ | R = H, D = C(O)NH$_2$ | f$_8$ | R = H, D = C(O)NH$_2$ |

| | | | | | |
|---|---|---|---|---|---|
| g$_1$ | R = F, D = NH$_2$ | h$_1$ | R = F, D = NH$_2$ | i$_1$ | R = F, D = NH$_2$ |
| g$_2$ | R = H, D = NH$_2$ | h$_2$ | R = H, D = NH$_2$ | i$_2$ | R = H, D = NH$_2$ |
| g$_3$ | R = F, D = CH$_2$NH$_2$ | h$_3$ | R = F, D = CH$_2$NH$_2$ | i$_3$ | R = F, D = CH$_2$NH$_2$ |
| g$_4$ | R = H, D = CH$_2$NH$_2$ | h$_4$ | R = H, D = CH$_2$NH$_2$ | i$_4$ | R = H, D = CH$_2$NH$_2$ |
| g$_5$ | R = F, D = C(=NH)NH$_2$ | h$_5$ | R = F, D = C(=NH)NH$_2$ | i$_5$ | R = F, D = C(=NH)NH$_2$ |
| g$_6$ | R = H, D = C(=NH)NH$_2$ | h$_6$ | R = H, D = C(=NH)NH$_2$ | i$_6$ | R = H, D = C(=NH)NH$_2$ |
| g$_7$ | R = F, D = C(O)NH$_2$ | h$_7$ | R = F, D = C(O)NH$_2$ | i$_7$ | R = F, D = C(O)NH$_2$ |
| g$_8$ | R = H, D = C(O)NH$_2$ | h$_8$ | R = H, D = C(O)NH$_2$ | i$_8$ | R = H, D = C(O)NH$_2$ |

| | | | | | |
|---|---|---|---|---|---|
| j$_1$ | R = F, D = NH$_2$ | k$_1$ | R = F, D = NH$_2$ | l$_1$ | R = F, D = NH$_2$ |
| j$_2$ | R = H, D = NH$_2$ | k$_2$ | R = H, D = NH$_2$ | l$_2$ | R = H, D = NH$_2$ |
| j$_3$ | R = F, D = CH$_2$NH$_2$ | k$_3$ | R = F, D = CH$_2$NH$_2$ | l$_3$ | R = F, D = CH$_2$NH$_2$ |
| j$_4$ | R = H, D = CH$_2$NH$_2$ | k$_4$ | R = H, D = CH$_2$NH$_2$ | l$_4$ | R = H, D = CH$_2$NH$_2$ |

TABLE 4-continued

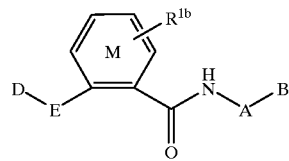

| | | | | | |
|---|---|---|---|---|---|
| $j_5$ | R = F, D = C(=NH)NH$_2$ | $k_5$ | R = F, D = C(=NH)NH$_2$ | $l_5$ | R = F, D = C(=NH)NH$_2$ |
| $j_6$ | R = H, D = C(=NH)NH$_2$ | $k_6$ | R = H, D = C(=NH)NH$_2$ | $l_6$ | R = H, D = C(=NH)NH$_2$ |
| $j_7$ | R = F, D = C(O)NH$_2$ | $k_7$ | R = F, D = C(O)NH$_2$ | $l_7$ | R = F, D = C(O)NH$_2$ |
| $j_8$ | R = H, D = C(O)NH$_2$ | $k_8$ | R = H, D = C(O)NH$_2$ | $l_8$ | R = H, D = C(O)NH$_2$ |

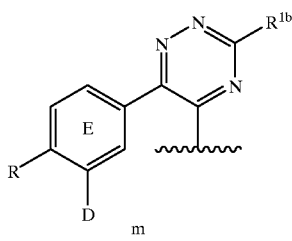
m

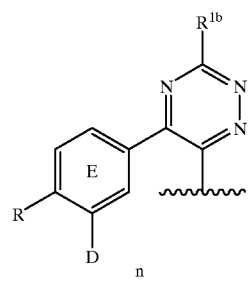
n

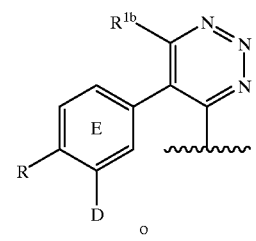
o

| | | | | | |
|---|---|---|---|---|---|
| $m_1$ | R = F, D = NH$_2$ | $n_1$ | R = F, D = NH$_2$ | $o_1$ | R = F, D = NH$_2$ |
| $m_2$ | R = H, D = NH$_2$ | $n_2$ | R = H, D = NH$_2$ | $o_2$ | R = H, D = NH$_2$ |
| $m_3$ | R = F, D = CH$_2$NH$_2$ | $n_3$ | R = F, D = CH$_2$NH$_2$ | $o_3$ | R = F, D = CH$_2$NH$_2$ |
| $m_4$ | R = H, D = CH$_2$NH$_2$ | $n_4$ | R = H, D = CH$_2$NH$_2$ | $o_4$ | R = H, D = CH$_2$NH$_2$ |
| $m_5$ | R = F, D = C(=NH)NH$_2$ | $n_5$ | R = F, D = C(=NH)NH$_2$ | $o_5$ | R = F, D = C(=NH)NH$_2$ |
| $m_6$ | R = H, D = C(=NH)NH$_2$ | $n_6$ | R = H, D = C(=NH)NH$_2$ | $o_6$ | R = H, D = C(=NH)NH$_2$ |
| $m_7$ | R = F, D = C(O)NH$_2$ | $n_7$ | R = F, D = C(O)NH$_2$ | $o_7$ | R = F, D = C(O)NH$_2$ |
| $m_8$ | R = H, D = C(O)NH$_2$ | $n_8$ | R = H, D = C(O)NH$_2$ | $o_8$ | R = H, D = C(O)NH$_2$ |

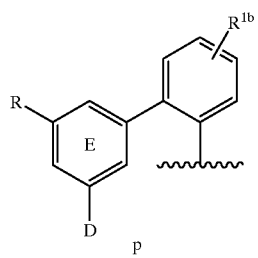
p

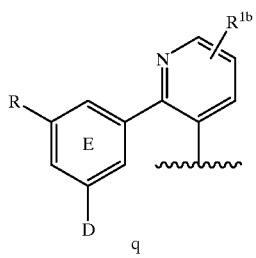
q

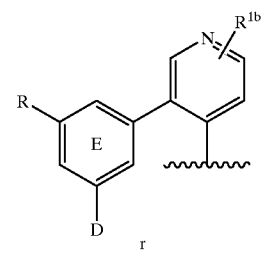
r

| | | | | | |
|---|---|---|---|---|---|
| $p_1$ | R = F, D = NH$_2$ | $q_1$ | R = F, D = NH$_2$ | $r_1$ | R = F, D = NH$_2$ |
| $p_2$ | R = Cl, D = NH$_2$ | $q_2$ | R = Cl, D = NH$_2$ | $r_2$ | R = Cl, D = NH$_2$ |
| $p_3$ | R = OMe, D = NH$_2$ | $q_3$ | R = OMe, D = NH$_2$ | $r_3$ | R = OMe, D = NH$_2$ |
| $p_4$ | R = F, D = CH$_2$NH$_2$ | $q_4$ | R = F, D = CH$_2$NH$_2$ | $r_4$ | R = F, D = CH$_2$NH$_2$ |
| $p_5$ | R = Cl, D = CH$_2$NH$_2$ | $q_5$ | R = Cl, D = CH$_2$NH$_2$ | $r_5$ | R = Cl, D = CH$_2$NH$_2$ |
| $p_6$ | R = OMe, D = CH$_2$NH$_2$ | $q_6$ | R = OMe, D = CH$_2$NH$_2$ | $r_6$ | R = OMe, D = CH$_2$NH$_2$ |
| $p_7$ | R = F, D = C(=NH)NH$_2$ | $q_7$ | R = F, D = C(=NH)NH$_2$ | $r_7$ | R = F, D = C(=NH)NH$_2$ |
| $p_8$ | R = Cl, D = C(=NH)NH$_2$ | $q_8$ | R = Cl, D = C(=NH)NH$_2$ | $r_8$ | R = Cl, D = C(=NH)NH$_2$ |
| $p_9$ | R = OMe, D = C(=NH)NH$_2$ | $q_9$ | R = OMe, D = C(=NH)NH$_2$ | $r_9$ | R = OMe, D = C(=NH)NH$_2$ |
| $p_{10}$ | R = F, D = C(O)NH$_2$ | $q_{10}$ | R = F, D = C(O)NH$_2$ | $r_{10}$ | R = F, D = C(O)NH$_2$ |
| $p_{11}$ | R = Cl, D = C(O)NH$_2$ | $q_{11}$ | R = Cl, D = C(O)NH$_2$ | $r_{11}$ | R = Cl, D = C(O)NH$_2$ |
| $p_{12}$ | R = OMe, D = C(O)NH$_2$ | $q_{12}$ | R = OMe, D = C(O)NH$_2$ | $r_{12}$ | R = OMe, D = C(O)NH$_2$ |

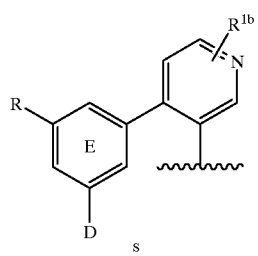
s

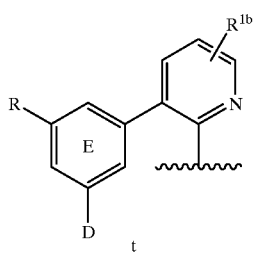
t

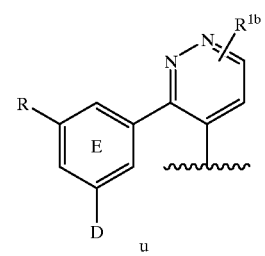
u

| | | | | | |
|---|---|---|---|---|---|
| $s_1$ | R = F, D = NH$_2$ | $t_1$ | R = F, D = NH$_2$ | $u_1$ | R = F, D = NH$_2$ |

TABLE 4-continued

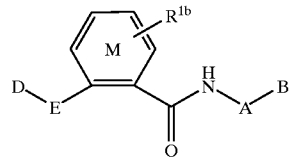

| | | | | | |
|---|---|---|---|---|---|
| s₂ | R = Cl, D = NH₂ | t₂ | R = Cl, D = NH₂ | u₂ | R = Cl, D = NH₂ |
| s₃ | R = OMe, D = NH₂ | t₃ | R = OMe, D = NH₂ | u₃ | R = OMe, D = NH₂ |
| s₄ | R = F, D = CH₂NH₂ | t₄ | R = F, D = CH₂NH₂ | u₄ | R = F, D = CH₂NH₂ |
| s₅ | R = Cl, D = CH₂NH₂ | t₅ | R = Cl, D = CH₂NH₂ | u₅ | R = Cl, D = CH₂NH₂ |
| s₆ | R = OMe, D = CH₂NH₂ | t₆ | R = OMe, D = CH₂NH₂ | u₆ | R = OMe, D = CH₂NH₂ |
| s₇ | R = F, D = C(=NH)NH₂ | t₇ | R = F, D = C(=NH)NH₂ | u₇ | R = F, D = C(=NH)NH₂ |
| s₈ | R = Cl, D = C(=NH)NH₂ | t₈ | R = Cl, D = C(=NH)NH₂ | u₈ | R = Cl, D = C(=NH)NH₂ |
| s₉ | R = OMe, D = C(=NH)NH₂ | t₉ | R = OMe, D = C(=NH)NH₂ | u₉ | R = OMe, D = C(=NH)NH₂ |
| s₁₀ | R = F, D = C(O)NH₂ | t₁₀ | R = F, D = C(O)NH₂ | u₁₀ | R = F, D = C(O)NH₂ |
| s₁₁ | R = Cl, D = C(O)NH₂ | t₁₁ | R = Cl, D = C(O)NH₂ | u₁₁ | R = Cl, D = C(O)NH₂ |
| s₁₂ | R = OMe, D = C(O)NH₂ | t₁₂ | R = OMe, D = C(O)NH₂ | u₁₂ | R = OMe, D = C(O)NH₂ |

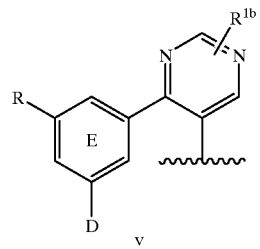
v

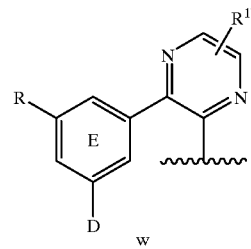
w

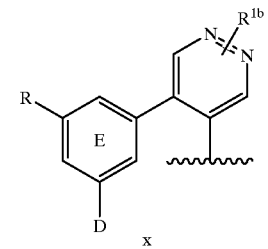
x

| | | | | | |
|---|---|---|---|---|---|
| v₁ | R = F, D = NH₂ | w₁ | R = F, D = NH₂ | x₁ | R = F, D = NH₂ |
| v₂ | R = Cl, D = NH₂ | w₂ | R = Cl, D = NH₂ | x₂ | R = Cl, D = NH₂ |
| v₃ | R = OMe, D = NH₂ | w₃ | R = OMe, D = NH₂ | x₃ | R = OMe, D = NH₂ |
| v₄ | R = F, D = CH₂NH₂ | w₄ | R = F, D = CH₂NH₂ | x₄ | R = F, D = CH₂NH₂ |
| v₅ | R = Cl, D = CH₂NH₂ | w₅ | R = Cl, D = CH₂NH₂ | x₅ | R = Cl, D = CH₂NH₂ |
| v₆ | R = OMe, D = CH₂NH₂ | w₆ | R = OMe, D = CH₂NH₂ | x₆ | R = OMe, D = CH₂NH₂ |
| v₇ | R = F, D = C(=NH)NH₂ | w₇ | R = F, D = C(=NH)NH₂ | x₇ | R = F, D = C(=NH)NH₂ |
| v₈ | R = Cl, D = C(=NH)NH₂ | w₈ | R = Cl, D = C(=NH)NH₂ | x₈ | R = Cl, D = C(=NH)NH₂ |
| v₉ | R = OMe, D = C(=NH)NH₂ | w₉ | R = OMe, D = C(=NH)NH₂ | x₉ | R = OMe, D = C(=NH)NH₂ |
| v₁₀ | R = F, D = C(O)NH₂ | w₁₀ | R = F, D = C(O)NH₂ | x₁₀ | R = F, D = C(O)NH₂ |
| v₁₁ | R = Cl, D = C(O)NH₂ | w₁₁ | R = Cl, D = C(O)NH₂ | x₁₁ | R = Cl, D = C(O)NH₂ |
| v₁₂ | R = OMe, D = C(O)NH₂ | w₁₂ | R = OMe, D = C(O)NH₂ | x₁₂ | R = OMe, D = C(O)NH₂ |

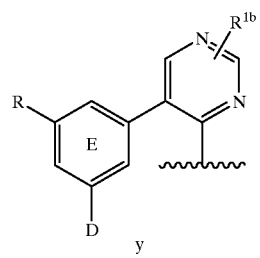
y

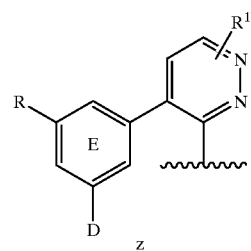
z

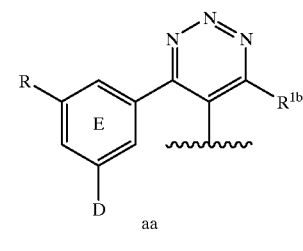
aa

| | | | | | |
|---|---|---|---|---|---|
| y₁ | R = F, D = NH₂ | z₁ | R = F, D = NH₂ | aa₁ | R = F, D = NH₂ |
| y₂ | R = Cl, D = NH₂ | z₂ | R = Cl, D = NH₂ | aa₂ | R = Cl, D = NH₂ |
| y₃ | R = OMe, D = NH₂ | z₃ | R = OMe, D = NH₂ | aa₃ | R = OMe, D = NH₂ |
| y₄ | R = F, D = CH₂NH₂ | z₄ | R = F, D = CH₂NH₂ | aa₄ | R = F, D = CH₂NH₂ |
| y₅ | R = Cl, D = CH₂NH₂ | z₅ | R = Cl, D = CH₂NH₂ | aa₅ | R = Cl, D = CH₂NH₂ |
| y₆ | R = OMe, D = CH₂NH₂ | z₆ | R = OMe, D = CH₂NH₂ | aa₆ | R = OMe, D = CH₂NH₂ |
| y₇ | R = F, D = C(=NH)NH₂ | z₇ | R = F, D = C(=NH)NH₂ | aa₇ | R = F, D = C(=NH)NH₂ |
| y₈ | R = Cl, D = C(=NH)NH₂ | z₈ | R = Cl, D = C(=NH)NH₂ | aa₈ | R = Cl, D = C(=NH)NH₂ |
| y₉ | R = OMe, D = C(=NH)NH₂ | z₉ | R = OMe, D = C(=NH)NH₂ | aa₉ | R = OMe, D = C(=NH)NH₂ |
| y₁₀ | R = F, D = C(O)NH₂ | z₁₀ | R = F, D = C(O)NH₂ | aa₁₀ | R = F, D = C(O)NH₂ |
| y₁₁ | R = Cl, D = C(O)NH₂ | z₁₁ | R = Cl, D = C(O)NH₂ | aa₁₁ | R = Cl, D = C(O)NH₂ |
| y₁₂ | R = OMe, D = C(O)NH₂ | z₁₂ | R = OMe, D = C(O)NH₂ | aa₁₂ | R = OMe, D = C(O)NH₂ |

TABLE 4-continued

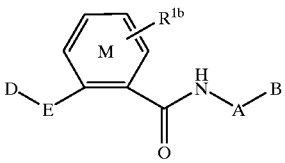

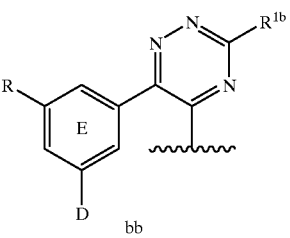
bb

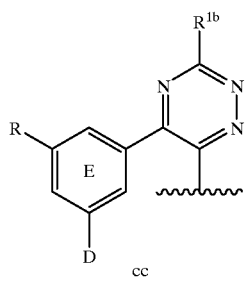
cc

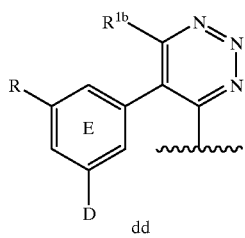
dd

| | | |
|---|---|---|
| bb$_1$  R = F, D = NH$_2$ | cc$_1$  R = F, D = NH$_2$ | dd$_1$  R = F, D = NH$_2$ |
| bb$_2$  R = Cl, D = NH$_2$ | cc$_2$  R = Cl, D = NH$_2$ | dd$_2$  R = Cl, D = NH$_2$ |
| bb$_3$  R = OMe, D = NH$_2$ | cc$_3$  R = OMe, D = NH$_2$ | dd$_3$  R = OMe, D = NH$_2$ |
| bb$_4$  R = F, D = CH$_2$NH$_2$ | cc$_4$  R = F, D = CH$_2$NH$_2$ | dd$_4$  R = F, D = CH$_2$NH$_2$ |
| bb$_5$  R = Cl, D = CH$_2$NH$_2$ | cc$_5$  R = Cl, D = CH$_2$NH$_2$ | dd$_5$  R = Cl, D = CH$_2$NH$_2$ |
| bb$_6$  R = OMe, D = CH$_2$NH$_2$ | cc$_6$  R = OMe, D = CH$_2$NH$_2$ | dd$_6$  R = OMe, D = CH$_2$NH$_2$ |
| bb$_7$  R = F, D = C(=NH)NH$_2$ | cc$_7$  R = F, D = C(=NH)NH$_2$ | dd$_7$  R = F, D = C(=NH)NH$_2$ |
| bb$_8$  R = Cl, D = C(=NH)NH$_2$ | cc$_8$  R = Cl, D = C(=NH)NH$_2$ | dd$_8$  R = Cl, D = C(=NH)NH$_2$ |
| bb$_9$  R = OMe, D = C(=NH)NH$_2$ | cc$_9$  R = OMe, D = C(=NH)NH$_2$ | dd$_9$  R = OMe, D = C(=NH)NH$_2$ |
| bb$_{10}$  R = F, D = C(O)NH$_2$ | cc$_{10}$  R = F, D = C(O)NH$_2$ | dd$_{10}$  R = F, D = C(O)NH$_2$ |
| bb$_{11}$  R = Cl, D = C(O)NH$_2$ | cc$_{11}$  R = Cl, D = C(O)NH$_2$ | dd$_{11}$  R = Cl, D = C(O)NH$_2$ |
| bb$_{12}$  R = OMe, D = C(O)NH$_2$ | cc$_{12}$  R = OMe, D = C(O)NH$_2$ | dd$_{12}$  R = OMe, D = C(O)NH$_2$ |

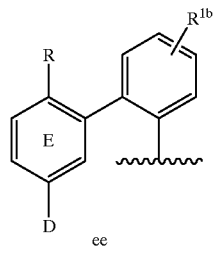
ee

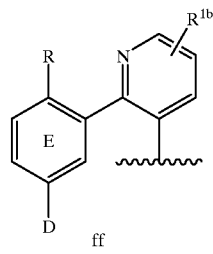
ff

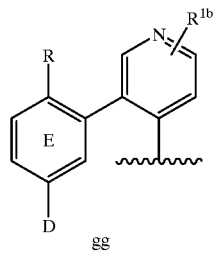
gg

| | | |
|---|---|---|
| ee$_1$  R = F, D = CH$_2$NH$_2$ | ff$_1$  R = F, D = CH$_2$NH$_2$ | gg$_1$  R = F, D = CH$_2$NH$_2$ |
| ee$_2$  R = Cl, D = CH$_2$NH$_2$ | ff$_2$  R = Cl, D = CH$_2$NH$_2$ | gg$_2$  R = Cl, D = CH$_2$NH$_2$ |
| ee$_3$  R = OMe, D = CH$_2$NH$_2$ | ff$_3$  R = OMe, D = CH$_2$NH$_2$ | gg$_3$  R = OMe, D = CH$_2$NH$_2$ |
| ee$_4$  R = CH$_2$NH$_2$, D = CH$_2$NH$_2$ | ff$_4$  R = CH$_2$NH$_2$, D = CH$_2$NH$_2$ | gg$_4$  R = CH$_2$NH$_2$, D = CH$_2$NH$_2$ |

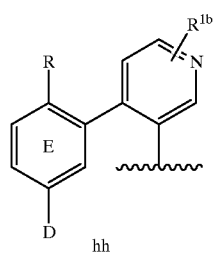
hh

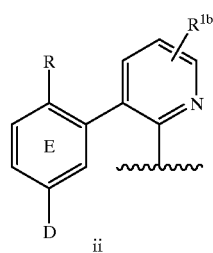
ii jj

| | | |
|---|---|---|
| hh$_1$  R = F, D = CH$_2$NH$_2$ | ii$_1$  R = F, D = CH$_2$NH$_2$ | jj$_1$  R = F, D = CH$_2$NH$_2$ |
| hh$_2$  R = Cl, D = CH$_2$NH$_2$ | ii$_2$  R = Cl, D = CH$_2$NH$_2$ | jj$_2$  R = Cl, D = CH$_2$NH$_2$ |
| hh$_3$  R = OMe, D = CH$_2$NH$_2$ | ii$_3$  R = OMe, D = CH$_2$NH$_2$ | jj$_3$  R = OMe, D = CH$_2$NH$_2$ |
| hh$_4$  R = CH$_2$NH$_2$, D = CH$_2$NH$_2$ | ii$_4$  R = CH$_2$NH$_2$, D = CH$_2$NH$_2$ | jj$_4$  R = CH$_2$NH$_2$, D = CH$_2$NH$_2$ |

TABLE 4-continued

| | kk | | ll | | mm |
|---|---|---|---|---|---|
| kk$_1$ | R = F, D = CH$_2$NH$_2$ | ll$_1$ | R = F, D = CH$_2$NH$_2$ | mm$_1$ | R = F, D = CH$_2$NH$_2$ |
| kk$_2$ | R = Cl, D = CH$_2$NH$_2$ | ll$_2$ | R = Cl, D = CH$_2$NH$_2$ | mm$_2$ | R = Cl, D = CH$_2$NH$_2$ |
| kk$_3$ | R = OMe, D = CH$_2$NH$_2$ | ll$_3$ | R = OMe, D = CH$_2$NH$_2$ | mm$_3$ | R = OMe, D = CH$_2$NH$_2$ |
| kk$_4$ | R = CH$_2$NH$_2$, D = CH$_2$NH$_2$ | ll$_4$ | R = CH$_2$NH$_2$, D = CH$_2$NH$_2$ | mm$_4$ | R = CH$_2$NH$_2$, D = CH$_2$NH$_2$ |

| | nn | | oo | | pp |
|---|---|---|---|---|---|
| nn$_1$ | R = F, D = CH$_2$NH$_2$ | oo$_1$ | R = F, D = CH$_2$NH$_2$ | pp$_1$ | R = F, D = CH$_2$NH$_2$ |
| nn$_2$ | R = Cl, D = CH$_2$NH$_2$ | oo$_2$ | R = Cl, D = CH$_2$NH$_2$ | pp$_2$ | R = Cl, D = CH$_2$NH$_2$ |
| nn$_3$ | R = OMe, D = CH$_2$NH$_2$ | oo$_3$ | R = OMe, D = CH$_2$NH$_2$ | pp$_3$ | R = OMe, D = CH$_2$NH$_2$ |
| nn$_4$ | R = CH$_2$NH$_2$, D = CH$_2$NH$_2$ | oo$_4$ | R = CH$_2$NH$_2$, D = CH$_2$NH$_2$ | pp$_4$ | R = CH$_2$NH$_2$, D = CH$_2$NH$_2$ |

| | qq | | rr | | ss |
|---|---|---|---|---|---|
| qq$_1$ | R = F, D = CH$_2$NH$_2$ | rr$_1$ | R = F, D = CH$_2$NH$_2$ | ss$_1$ | R = F, D = CH$_2$NH$_2$ |
| qq$_2$ | R = Cl, D = CH$_2$NH$_2$ | rr$_2$ | R = Cl, D = CH$_2$NH$_2$ | ss$_2$ | R = Cl, D = CH$_2$NH$_2$ |
| qq$_3$ | R = OMe, D = CH$_2$NH$_2$ | rr$_3$ | R = OMe, D = CH$_2$NH$_2$ | ss$_3$ | R = OMe, D = CH$_2$NH$_2$ |
| qq$_4$ | R = CH$_2$NH$_2$, D = CH$_2$NH$_2$ | rr$_4$ | R = CH$_2$NH$_2$, D = CH$_2$NH$_2$ | ss$_4$ | R = CH$_2$NH$_2$, D = CH$_2$NH$_2$ |

| Ex# | R$^{1b}$ | A | B |
|---|---|---|---|
| 1 | H | phenyl | 2-(aminosulfonyl)phenyl |
| 2 | H | phenyl | 2-(methylaminosulfonyl)phenyl |
| 3 | H | phenyl | 1-pyrrolidinocarbonyl |
| 4 | H | phenyl | 2-(methylsulfonyl)phenyl |
| 5 | H | phenyl | 4-morpholino |
| 6 | H | phenyl | 2-(1'-CF$_3$-tetrazol-2-yl)phenyl |

-continued

| Ex# | R¹ᵇ | A | B |
|---|---|---|---|
| 7 | H | phenyl | 4-morpholinocarbonyl |
| 8 | H | 2-pyridyl | 2-(aminosulfonyl)phenyl |
| 9 | H | 2-pyridyl | 2-(methylaminosulfonyl)phenyl |
| 10 | H | 2-pyridyl | 1-pyrrolidinocarbonyl |
| 11 | H | 2-pyridyl | 2-(methylsulfonyl)phenyl |
| 12 | H | 2-pyridyl | 4-morpholino |
| 13 | H | 2-pyridyl | 2-(1'-CF$_3$-tetrazol-2-yl)phenyl |
| 14 | H | 2-pyridyl | 4-morpholinocarbonyl |
| 15 | H | 3-pyridyl | 2-(aminosulfonyl)phenyl |
| 16 | H | 3-pyridyl | 2-(methylaminosulfonyl)phenyl |
| 17 | H | 3-pyridyl | 1-pyrrolidinocarbonyl |
| 18 | H | 3-pyridyl | 2-(methylsulfonyl)phenyl |
| 19 | H | 3-pyridyl | 4-morpholino |
| 20 | H | 3-pyridyl | 2-(1'-CF$_3$-tetrazol-2-yl)phenyl |
| 21 | H | 3-pyridyl | 4-morpholinocarbonyl |
| 22 | H | 2-pyrimidyl | 2-(aminosulfonyl)phenyl |
| 23 | H | 2-pyrimidyl | 2-(methylaminosulfonyl)phenyl |
| 24 | H | 2-pyrimidyl | 1-pyrrolidinocarbonyl |
| 25 | H | 2-pyrimidyl | 2-(methylsulfonyl)phenyl |
| 26 | H | 2-pyrimidyl | 4-morpholino |
| 27 | H | 2-pyrimidyl | 2-(1'-CF$_3$-tetrazol-2-yl)phenyl |
| 28 | H | 2-pyrimidyl | 4-morpholinocarbonyl |
| 29 | H | 5-pyrimidyl | 2-(aminosulfonyl)phenyl |
| 30 | H | 5-pyrimidyl | 2-(methylaminosulfonyl)phenyl |
| 31 | H | 5-pyrimidyl | 1-pyrrolidinocarbonyl |
| 32 | H | 5-pyrimidyl | 2-(methylsulfonyl)phenyl |
| 33 | H | 5-pyrimidyl | 4-morpholino |
| 34 | H | 5-pyrimidyl | 2-(1'-CF$_3$-tetrazol-2-yl)phenyl |
| 35 | H | 5-pyrimidyl | 4-morpholinocarbonyl |
| 36 | H | 2-Cl-phenyl | 2-(aminosulfonyl)phenyl |
| 37 | H | 2-Cl-phenyl | 2-(methylaminosulfonyl)phenyl |
| 38 | H | 2-Cl-phenyl | 1-pyrrolidinocarbonyl |
| 39 | H | 2-Cl-phenyl | 2-(methylsulfonyl)phenyl |
| 40 | H | 2-Cl-phenyl | 4-morpholino |
| 41 | H | 2-Cl-phenyl | 2-(1'-CF$_3$-tetrazol-2-yl)phenyl |
| 42 | H | 2-Cl-phenyl | 4-morpholinocarbonyl |
| 43 | H | 2-F-phenyl | 2-(aminosulfonyl)phenyl |
| 44 | H | 2-F-phenyl | 2-(methylaminosulfonyl)phenyl |
| 45 | H | 2-F-phenyl | 1-pyrrolidinocarbonyl |
| 46 | H | 2-F-phenyl | 2-(methylsulfonyl)phenyl |
| 47 | H | 2-F-phenyl | 4-morpholino |
| 48 | H | 2-F-phenyl | 2-(1'-CF$_3$-tetrazol-2-yl)phenyl |
| 49 | H | 2-F-phenyl | 4-morpholinocarbonyl |
| 50 | H | 2,5-diF-phenyl | 2-(aminosulfonyl)phenyl |
| 51 | H | 2,5-diF-phenyl | 2-(methylaminosulfonyl)phenyl |
| 52 | H | 2,5-diF-phenyl | 1-pyrrolidinocarbonyl |
| 53 | H | 2,5-diF-phenyl | 2-(methylsulfonyl)phenyl |
| 54 | H | 2,5-diF-phenyl | 4-morpholino |
| 55 | H | 2,5-diF-phenyl | 2-(1'-CF$_3$-tetrazol-2-yl)phenyl |
| 56 | H | 2,5-diF-phenyl | 4-morpholinocarbonyl |
| 57 | —CN | phenyl | 2-(aminosulfonyl)phenyl |
| 58 | —CN | phenyl | 2-(methylaminosulfonyl)phenyl |
| 59 | —CN | phenyl | 1-pyrrolidinocarbonyl |
| 60 | —CN | phenyl | 2-(methylsulfonyl)phenyl |
| 61 | —CN | phenyl | 4-morpholino |
| 62 | —CN | phenyl | 2-(1'-CF$_3$-tetrazol-2-yl)phenyl |
| 63 | —CN | phenyl | 4-morpholinocarbonyl |
| 64 | —CN | 2-pyridyl | 2-(aminosulfonyl)phenyl |
| 65 | —CN | 2-pyridyl | 2-(methylaminosulfonyl)phenyl |
| 66 | —CN | 2-pyridyl | 1-pyrrolidinocarbonyl |
| 67 | —CN | 2-pyridyl | 2-(methylsulfonyl)phenyl |
| 68 | —CN | 2-pyridyl | 4-morpholino |
| 69 | —CN | 2-pyridyl | 2-(1'-CF$_3$-tetrazol-2-yl)phenyl |
| 70 | —CN | 2-pyridyl | 4-morpholinocarbonyl |
| 71 | —CN | 3-pyridyl | 2-(aminosulfonyl)phenyl |
| 72 | —CN | 3-pyridyl | 2-(methylaminosulfonyl)phenyl |
| 73 | —CN | 3-pyridyl | 1-pyrrolidinocarbonyl |
| 74 | —CN | 3-pyridyl | 2-(methylsulfonyl)phenyl |
| 75 | —CN | 3-pyridyl | 4-morpholino |
| 76 | —CN | 3-pyridyl | 2-(1'-CF$_3$-tetrazol-2-yl)phenyl |
| 77 | —CN | 3-pyridyl | 4-morpholinocarbonyl |
| 78 | —CN | 2-pyrimidyl | 2-(aminosulfonyl)phenyl |
| 79 | —CN | 2-pyrimidyl | 2-(methylaminosulfonyl)phenyl |
| 80 | —CN | 2-pyrimidyl | 1-pyrrolidinocarbonyl |
| 81 | —CN | 2-pyrimidyl | 2-(methylsulfonyl)phenyl |
| 82 | —CN | 2-pyrimidyl | 4-morpholino |
| 83 | —CN | 2-pyrimidyl | 2-(1'-CF$_3$-tetrazol-2-yl)phenyl |
| 84 | —CN | 2-pyrimidyl | 4-morpholinocarbonyl |
| 85 | —CN | 5-pyrimidyl | 2-(aminosulfonyl)phenyl |
| 86 | —CN | 5-pyrimidyl | 2-(methylaminosulfonyl)phenyl |
| 87 | —CN | 5-pyrimidyl | 1-pyrrolidinocarbonyl |
| 88 | —CN | 5-pyrimidyl | 2-(methylsulfonyl)phenyl |
| 89 | —CN | 5-pyrimidyl | 4-morpholino |
| 90 | —CN | 5-pyrimidyl | 2-(1'-CF$_3$-tetrazol-2-yl)phenyl |
| 91 | —CN | 5-pyrimidyl | 4-morpholinocarbonyl |
| 92 | —CN | 2-Cl-phenyl | 2-(aminosulfonyl)phenyl |
| 93 | —CN | 2-Cl-phenyl | 2-(methylaminosulfonyl)phenyl |
| 94 | —CN | 2-Cl-phenyl | 1-pyrrolidinocarbonyl |
| 95 | —CN | 2-Cl-phenyl | 2-(methylsulfonyl)phenyl |
| 96 | —CN | 2-Cl-phenyl | 4-morpholino |
| 97 | —CN | 2-Cl-phenyl | 2-(1'-CF$_3$-tetrazol-2-yl)phenyl |
| 98 | —CN | 2-Cl-phenyl | 4-morpholinocarbonyl |
| 99 | —CN | 2-F-phenyl | 2-(aminosulfonyl)phenyl |
| 100 | —CN | 2-F-phenyl | 2-(methylaminosulfonyl)phenyl |
| 101 | —CN | 2-F-phenyl | 1-pyrrolidinocarbonyl |
| 102 | —CN | 2-F-phenyl | 2-(methylsulfonyl)phenyl |
| 103 | —CN | 2-F-phenyl | 4-morpholino |
| 104 | —CN | 2-F-phenyl | 2-(1'-CF$_3$-tetrazol-2-yl)phenyl |
| 105 | —CN | 2-F-phenyl | 4-morpholinocarbonyl |
| 106 | —CN | 2,5-diF-phenyl | 2-(aminosulfonyl)phenyl |
| 107 | —CN | 2,5-diF-phenyl | 2-(methylaminosulfonyl)phenyl |
| 108 | —CN | 2,5-diF-phenyl | 1-pyrrolidinocarbonyl |
| 109 | —CN | 2,5-diF-phenyl | 2-(methylsulfonyl)phenyl |
| 110 | —CN | 2,5-diF-phenyl | 4-morpholino |
| 111 | —CN | 2,5-diF-phenyl | 2-(1'-CF$_3$-tetrazol-2-yl)phenyl |
| 112 | —CN | 2,5-diF-phenyl | 4-morpholinocarbonyl |
| 113 | CF$_3$ | phenyl | 2-(aminosulfonyl)phenyl |
| 114 | CF$_3$ | phenyl | 2-(methylaminosulfonyl)phenyl |
| 115 | CF$_3$ | phenyl | 1-pyrrolidinocarbonyl |
| 116 | CF$_3$ | phenyl | 2-(methylsulfonyl)phenyl |
| 117 | CF$_3$ | phenyl | 4-morpholino |
| 118 | CF$_3$ | phenyl | 2-(1'-CF$_3$-tetrazol-2-yl)phenyl |
| 119 | CF$_3$ | phenyl | 4-morpholinocarbonyl |
| 120 | CF$_3$ | 2-pyridyl | 2-(aminosulfonyl)phenyl |
| 121 | CF$_3$ | 2-pyridyl | 2-(methylaminosulfonyl)phenyl |
| 122 | CF$_3$ | 2-pyridyl | 1-pyrrolidinocarbonyl |
| 123 | CF$_3$ | 2-pyridyl | 2-(methylsulfonyl)phenyl |
| 124 | CF$_3$ | 2-pyridyl | 4-morpholino |
| 125 | CF$_3$ | 2-pyridyl | 2-(1'-CF$_3$-tetrazol-2-yl)phenyl |
| 126 | CF$_3$ | 2-pyridyl | 4-morpholinocarbonyl |
| 127 | CF$_3$ | 3-pyridyl | 2-(aminosulfonyl)phenyl |
| 128 | CF$_3$ | 3-pyridyl | 2-(methylaminosulfonyl)phenyl |
| 129 | CF$_3$ | 3-pyridyl | 1-pyrrolidinocarbonyl |
| 130 | CF$_3$ | 3-pyridyl | 2-(methylsulfonyl)phenyl |
| 131 | CF$_3$ | 3-pyridyl | 4-morpholino |
| 132 | CF$_3$ | 3-pyridyl | 2-(1'-CF$_3$-tetrazol-2-yl)phenyl |
| 133 | CF$_3$ | 3-pyridyl | 4-morpholinocarbonyl |
| 134 | CF$_3$ | 2-pyrimidyl | 2-(aminosulfonyl)phenyl |
| 135 | CF$_3$ | 2-pyrimidyl | 2-(methylaminosulfonyl)phenyl |
| 136 | CF$_3$ | 2-pyrimidyl | 1-pyrrolidinocarbonyl |
| 137 | CF$_3$ | 2-pyrimidyl | 2-(methylsulfonyl)phenyl |
| 138 | CF$_3$ | 2-pyrimidyl | 4-morpholino |
| 139 | CF$_3$ | 2-pyrimidyl | 2-(1'-CF$_3$-tetrazol-2-yl)phenyl |
| 140 | CF$_3$ | 2-pyrimidyl | 4-morpholinocarbonyl |
| 141 | CF$_3$ | 5-pyrimidyl | 2-(aminosulfonyl)phenyl |
| 142 | CF$_3$ | 5-pyrimidyl | 2-(methylaminosulfonyl)phenyl |
| 143 | CF$_3$ | 5-pyrimidyl | 1-pyrrolidinocarbonyl |
| 144 | CF$_3$ | 5-pyrimidyl | 2-(methylsulfonyl)phenyl |
| 145 | CF$_3$ | 5-pyrimidyl | 4-morpholino |
| 146 | CF$_3$ | 5-pyrimidyl | 2-(1'-CF$_3$-tetrazol-2-yl)phenyl |
| 147 | CF$_3$ | 5-pyrimidyl | 4-morpholinocarbonyl |
| 148 | CF$_3$ | 2-Cl-phenyl | 2-(aminosulfonyl)phenyl |
| 149 | CF$_3$ | 2-Cl-phenyl | 2-(methylaminosulfonyl)phenyl |
| 150 | CF$_3$ | 2-Cl-phenyl | 1-pyrrolidinocarbonyl |
| 151 | CF$_3$ | 2-Cl-phenyl | 2-(methylsulfonyl)phenyl |
| 152 | CF$_3$ | 2-Cl-phenyl | 4-morpholino |
| 153 | CF$_3$ | 2-Cl-phenyl | 2-(1'-CF$_3$-tetrazol-2-yl)phenyl |
| 154 | CF$_3$ | 2-Cl-phenyl | 4-morpholinocarbonyl |
| 155 | CF$_3$ | 2-F-phenyl | 2-(aminosulfonyl)phenyl |
| 156 | CF$_3$ | 2-F-phenyl | 2-(methylaminosulfonyl)phenyl |
| 157 | CF$_3$ | 2-F-phenyl | 1-pyrrolidinocarbonyl |
| 158 | CF$_3$ | 2-F-phenyl | 2-(methylsulfonyl)phenyl |
| 159 | CF$_3$ | 2-F-phenyl | 4-morpholino |
| 160 | CF$_3$ | 2-F-phenyl | 2-(1'-CF$_3$-tetrazol-2-yl)phenyl |

-continued

| Ex# | R$^{1b}$ | A | B |
|---|---|---|---|
| 161 | CF$_3$ | 2-F-phenyl | 4-morpholinocarbonyl |
| 162 | CF$_3$ | 2,5-diF-phenyl | 2-(aminosulfonyl)phenyl |
| 163 | CF$_3$ | 2,5-diF-phenyl | 2-(methylaminosulfonyl)phenyl |
| 164 | CF$_3$ | 2,5-diF-phenyl | 1-pyrrolidinocarbonyl |
| 165 | CF$_3$ | 2,5-diF-phenyl | 2-(methylsulfonyl)phenyl |
| 166 | CF$_3$ | 2,5-diF-phenyl | 4-morpholino |
| 167 | CF$_3$ | 2,5-diF-phenyl | 2-(1'-CF$_3$-tetrazol-2-yl)phenyl |
| 168 | CF$_3$ | 2,5-diF-phenyl | 4-morpholinocarbonyl |
| 169 | CONH$_2$ | phenyl | 2-(aminosulfonyl)phenyl |
| 170 | CONH$_2$ | phenyl | 2-(methylaminosulfonyl)phenyl |
| 171 | CONH$_2$ | phenyl | 1-pyrrolidinocarbonyl |
| 172 | CONH$_2$ | phenyl | 2-(methylsulfonyl)phenyl |
| 173 | CONH$_2$ | phenyl | 4-morpholino |
| 174 | CONH$_2$ | phenyl | 2-(1'-CF$_3$-tetrazol-2-yl)phenyl |
| 175 | CONH$_2$ | phenyl | 4-morpholinocarbonyl |
| 176 | CONH$_2$ | 2-pyridyl | 2-(aminosulfonyl)phenyl |
| 177 | CONH$_2$ | 2-pyridyl | 2-(methylaminosulfonyl)phenyl |
| 178 | CONH$_2$ | 2-pyridyl | 1-pyrrolidinocarbonyl |
| 179 | CONH$_2$ | 2-pyridyl | 2-(methylsulfonyl)phenyl |
| 180 | CONH$_2$ | 2-pyridyl | 4-morpholino |
| 181 | CONH$_2$ | 2-pyridyl | 2-(1'-CF$_3$-tetrazol-2-yl)phenyl |
| 182 | CONH$_2$ | 2-pyridyl | 4-morpholinocarbonyl |
| 183 | CONH$_2$ | 3-pyridyl | 2-(aminosulfonyl)phenyl |
| 184 | CONH$_2$ | 3-pyridyl | 2-(methylaminosulfonyl)phenyl |
| 185 | CONH$_2$ | 3-pyridyl | 1-pyrrolidinocarbonyl |
| 186 | CONH$_2$ | 3-pyridyl | 2-(methylsulfonyl)phenyl |
| 187 | CONH$_2$ | 3-pyridyl | 4-morpholino |
| 188 | CONH$_2$ | 3-pyridyl | 2-(1'-CF$_3$-tetrazol-2-yl)phenyl |
| 189 | CONH$_2$ | 3-pyridyl | 4-morpholinocarbonyl |
| 190 | CONH$_2$ | 2-pyrimidyl | 2-(aminosulfonyl)phenyl |
| 191 | CONH$_2$ | 2-pyrimidyl | 2-(methylaminosulfonyl)phenyl |
| 192 | CONH$_2$ | 2-pyrimidyl | 1-pyrrolidinocarbonyl |
| 193 | CONH$_2$ | 2-pyrimidyl | 2-(methylsulfonyl)phenyl |
| 194 | CONH$_2$ | 2-pyrimidyl | 4-morpholino |
| 195 | CONH$_2$ | 2-pyrimidyl | 2-(1'-CF$_3$-tetrazol-2-yl)phenyl |
| 196 | CONH$_2$ | 2-pyrimidyl | 4-morpholinocarbonyl |
| 197 | CONH$_2$ | 5-pyrimidyl | 2-(aminosulfonyl)phenyl |
| 198 | CONH$_2$ | 5-pyrimidyl | 2-(methylaminosulfonyl)phenyl |
| 199 | CONH$_2$ | 5-pyrimidyl | 1-pyrrolidinocarbonyl |
| 200 | CONH$_2$ | 5-pyrimidyl | 2-(methylsulfonyl)phenyl |
| 201 | CONH$_2$ | 5-pyrimidyl | 4-morpholino |
| 202 | CONH$_2$ | 5-pyrimidyl | 2-(1'-CF$_3$-tetrazol-2-yl)phenyl |
| 203 | CONH$_2$ | 5-pyrimidyl | 4-morpholinocarbonyl |
| 204 | CONH$_2$ | 2-Cl-phenyl | 2-(aminosulfonyl)phenyl |
| 205 | CONH$_2$ | 2-Cl-phenyl | 2-(methylaminosulfonyl)phenyl |
| 206 | CONH$_2$ | 2-Cl-phenyl | 1-pyrrolidinocarbonyl |
| 207 | CONH$_2$ | 2-Cl-phenyl | 2-(methylsulfonyl)phenyl |
| 208 | CONH$_2$ | 2-Cl-phenyl | 4-morpholino |
| 209 | CONH$_2$ | 2-Cl-phenyl | 2-(1'-CF$_3$-tetrazol-2-yl)phenyl |
| 210 | CONH$_2$ | 2-Cl-phenyl | 4-morpholinocarbonyl |
| 211 | CONH$_2$ | 2-F-phenyl | 2-(aminosulfonyl)phenyl |
| 212 | CONH$_2$ | 2-F-phenyl | 2-(methylaminosulfonyl)phenyl |
| 213 | CONH$_2$ | 2-F-phenyl | 1-pyrrolidinocarbonyl |
| 214 | CONH$_2$ | 2-F-phenyl | 2-(methylsulfonyl)phenyl |
| 215 | CONH$_2$ | 2-F-phenyl | 4-morpholino |
| 216 | CONH$_2$ | 2-F-phenyl | 2-(1'-CF$_3$-tetrazol-2-yl)phenyl |
| 217 | CONH$_2$ | 2-F-phenyl | 4-morpholinocarbonyl |
| 218 | CONH$_2$ | 2,5-diF-phenyl | 2-(aminosulfonyl)phenyl |
| 219 | CONH$_2$ | 2,5-diF-phenyl | 2-(methylaminosulfonyl)phenyl |
| 220 | CONH$_2$ | 2,5-diF-phenyl | 1-pyrrolidinocarbonyl |
| 221 | CONH$_2$ | 2,5-diF-phenyl | 2-(methylsulfonyl)phenyl |
| 222 | CONH$_2$ | 2,5-diF-phenyl | 4-morpholino |
| 223 | CONH$_2$ | 2,5-diF-phenyl | 2-(1'-CF$_3$-tetrazol-2-yl)phenyl |
| 224 | CONH$_2$ | 2,5-diF-phenyl | 4-morpholinocarbonyl |
| 225 | SCH$_3$ | phenyl | 2-(aminosulfonyl)phenyl |
| 226 | SCH$_3$ | phenyl | 2-(methylaminosulfonyl)phenyl |
| 227 | SCH$_3$ | phenyl | 1-pyrrolidinocarbonyl |
| 228 | SCH$_3$ | phenyl | 2-(methylsulfonyl)phenyl |
| 229 | SCH$_3$ | phenyl | 4-morpholino |
| 230 | SCH$_3$ | phenyl | 2-(1'-CF$_3$-tetrazol-2-yl)phenyl |
| 231 | SCH$_3$ | phenyl | 4-morpholinocarbonyl |
| 232 | SCH$_3$ | 2-pyridyl | 2-(aminosulfonyl)phenyl |
| 233 | SCH$_3$ | 2-pyridyl | 2-(methylaminosulfonyl)phenyl |
| 234 | SCH$_3$ | 2-pyridyl | 1-pyrrolidinocarbonyl |
| 235 | SCH$_3$ | 2-pyridyl | 2-(methylsulfonyl)phenyl |
| 236 | SCH$_3$ | 2-pyridyl | 4-morpholino |
| 237 | SCH$_3$ | 2-pyridyl | 2-(1'-CF$_3$-tetrazol-2-yl)phenyl |
| 238 | SCH$_3$ | 2-pyridyl | 4-morpholinocarbonyl |
| 239 | SCH$_3$ | 3-pyridyl | 2-(aminosulfonyl)phenyl |
| 240 | SCH$_3$ | 3-pyridyl | 2-(methylaminosulfonyl)phenyl |
| 241 | SCH$_3$ | 3-pyridyl | 1-pyrrolidinocarbonyl |
| 242 | SCH$_3$ | 3-pyridyl | 2-(methylsulfonyl)phenyl |
| 243 | SCH$_3$ | 3-pyridyl | 4-morpholino |
| 244 | SCH$_3$ | 3-pyridyl | 2-(1'-CF$_3$-tetrazol-2-yl)phenyl |
| 245 | SCH$_3$ | 3-pyridyl | 4-morpholinocarbonyl |
| 246 | SCH$_3$ | 2-pyrimidyl | 2-(aminosulfonyl)phenyl |
| 247 | SCH$_3$ | 2-pyrimidyl | 2-(methylaminosulfonyl)phenyl |
| 248 | SCH$_3$ | 2-pyrimidyl | 1-pyrrolidinocarbonyl |
| 249 | SCH$_3$ | 2-pyrimidyl | 2-(methylsulfonyl)phenyl |
| 250 | SCH$_3$ | 2-pyrimidyl | 4-morpholino |
| 251 | SCH$_3$ | 2-pyrimidyl | 2-(1'-CF$_3$-tetrazol-2-yl)phenyl |
| 252 | SCH$_3$ | 2-pyrimidyl | 4-morpholinocarbonyl |
| 253 | SCH$_3$ | 5-pyrimidyl | 2-(aminosulfonyl)phenyl |
| 254 | SCH$_3$ | 5-pyrimidyl | 2-(methylaminosulfonyl)phenyl |
| 255 | SCH$_3$ | 5-pyrimidyl | 1-pyrrolidinocarbonyl |
| 256 | SCH$_3$ | 5-pyrimidyl | 2-(methylsulfonyl)phenyl |
| 257 | SCH$_3$ | 5-pyrimidyl | 4-morpholino |
| 258 | SCH$_3$ | 5-pyrimidyl | 2-(1'-CF$_3$-tetrazol-2-yl)phenyl |
| 259 | SCH$_3$ | 5-pyrimidyl | 4-morpholinocarbonyl |
| 260 | SCH$_3$ | 2-Cl-phenyl | 2-(aminosulfonyl)phenyl |
| 261 | SCH$_3$ | 2-Cl-phenyl | 2-(methylaminosulfonyl)phenyl |
| 262 | SCH$_3$ | 2-Cl-phenyl | 1-pyrrolidinocarbonyl |
| 263 | SCH$_3$ | 2-Cl-phenyl | 2-(methylsulfonyl)phenyl |
| 264 | SCH$_3$ | 2-Cl-phenyl | 4-morpholino |
| 265 | SCH$_3$ | 2-Cl-phenyl | 2-(1'-CF$_3$-tetrazol-2-yl)phenyl |
| 266 | SCH$_3$ | 2-Cl-phenyl | 4-morpholinocarbonyl |
| 267 | SCH$_3$ | 2-F-phenyl | 2-(aminosulfonyl)phenyl |
| 268 | SCH$_3$ | 2-F-phenyl | 2-(methylaminosulfonyl)phenyl |
| 269 | SCH$_3$ | 2-F-phenyl | 1-pyrrolidinocarbonyl |
| 270 | SCH$_3$ | 2-F-phenyl | 2-(methylsulfonyl)phenyl |
| 271 | SCH$_3$ | 2-F-phenyl | 4-morpholino |
| 272 | SCH$_3$ | 2-F-phenyl | 2-(1'-CF$_3$-tetrazol-2-yl)phenyl |
| 273 | SCH$_3$ | 2-F-phenyl | 4-morpholinocarbonyl |
| 274 | SCH$_3$ | 2,5-diF-phenyl | 2-(aminosulfonyl)phenyl |
| 275 | SCH$_3$ | 2,5-diF-phenyl | 2-(methylaminosulfonyl)phenyl |
| 276 | SCH$_3$ | 2,5-diF-phenyl | 1-pyrrolidinocarbonyl |
| 277 | SCH$_3$ | 2,5-diF-phenyl | 2-(methylsulfonyl)phenyl |
| 278 | SCH$_3$ | 2,5-diF-phenyl | 4-morpholino |
| 279 | SCH$_3$ | 2,5-diF-phenyl | 2-(1'-CF$_3$-tetrazol-2-yl)phenyl |
| 280 | SCH$_3$ | 2,5-diF-phenyl | 4-morpholinocarbonyl |
| 281 | SO$_2$CH$_3$ | phenyl | 2-(aminosulfonyl)phenyl |
| 282 | SO$_2$CH$_3$ | phenyl | 2-(methylaminosulfonyl)phenyl |
| 283 | SO$_2$CH$_3$ | phenyl | 1-pyrrolidinocarbonyl |
| 284 | SO$_2$CH$_3$ | phenyl | 2-(methylsulfonyl)phenyl |
| 285 | SO$_2$CH$_3$ | phenyl | 4-morpholino |
| 286 | SO$_2$CH$_3$ | phenyl | 2-(1'-CF$_3$-tetrazol-2-yl)phenyl |
| 287 | SO$_2$CH$_3$ | phenyl | 4-morpholinocarbonyl |
| 288 | SO$_2$CH$_3$ | 2-pyridyl | 2-(aminosulfonyl)phenyl |
| 289 | SO$_2$CH$_3$ | 2-pyridyl | 2-(methylaminosulfonyl)phenyl |
| 290 | SO$_2$CH$_3$ | 2-pyridyl | 1-pyrrolidinocarbonyl |
| 291 | SO$_2$CH$_3$ | 2-pyridyl | 2-(methylsulfonyl)phenyl |
| 292 | SO$_2$CH$_3$ | 2-pyridyl | 4-morpholino |
| 293 | SO$_2$CH$_3$ | 2-pyridyl | 2-(1'-CF$_3$-tetrazol-2-yl)phenyl |
| 294 | SO$_2$CH$_3$ | 2-pyridyl | 4-morpholinocarbonyl |
| 295 | SO$_2$CH$_3$ | 3-pyridyl | 2-(aminosulfonyl)phenyl |
| 296 | SO$_2$CH$_3$ | 3-pyridyl | 2-(methylaminosulfonyl)phenyl |
| 297 | SO$_2$CH$_3$ | 3-pyridyl | 1-pyrrolidinocarbonyl |
| 298 | SO$_2$CH$_3$ | 3-pyridyl | 2-(methylsulfonyl)phenyl |
| 299 | SO$_2$CH$_3$ | 3-pyridyl | 4-morpholino |
| 300 | SO$_2$CH$_3$ | 3-pyridyl | 2-(1'-CF$_3$-tetrazol-2-yl)phenyl |
| 301 | SO$_2$CH$_3$ | 3-pyridyl | 4-morpholinocarbonyl |
| 302 | SO$_2$CH$_3$ | 2-pyrimidyl | 2-(aminosulfonyl)phenyl |
| 303 | SO$_2$CH$_3$ | 2-pyrimidyl | 2-(methylaminosulfonyl)phenyl |
| 304 | SO$_2$CH$_3$ | 2-pyrimidyl | 1-pyrrolidinocarbonyl |
| 305 | SO$_2$CH$_3$ | 2-pyrimidyl | 2-(methylsulfonyl)phenyl |
| 306 | SO$_2$CH$_3$ | 2-pyrimidyl | 4-morpholino |
| 307 | SO$_2$CH$_3$ | 2-pyrimidyl | 2-(1'-CF$_3$-tetrazol-2-yl)phenyl |
| 308 | SO$_2$CH$_3$ | 2-pyrimidyl | 4-morpholinocarbonyl |
| 309 | SO$_2$CH$_3$ | 5-pyrimidyl | 2-(aminosulfonyl)phenyl |
| 310 | SO$_2$CH$_3$ | 5-pyrimidyl | 2-(methylaminosulfonyl)phenyl |
| 311 | SO$_2$CH$_3$ | 5-pyrimidyl | 1-pyrrolidinocarbonyl |
| 312 | SO$_2$CH$_3$ | 5-pyrimidyl | 2-(methylsulfonyl)phenyl |
| 313 | SO$_2$CH$_3$ | 5-pyrimidyl | 4-morpholino |
| 314 | SO$_2$CH$_3$ | 5-pyrimidyl | 2-(1'-CF$_3$-tetrazol-2-yl)phenyl |

-continued

| Ex# | $R^{1b}$ | A | B |
|---|---|---|---|
| 315 | $SO_2CH_3$ | 5-pyrimidyl | 4-morpholinocarbonyl |
| 316 | $SO_2CH_3$ | 2-Cl-phenyl | 2-(aminosulfonyl)phenyl |
| 317 | $SO_2CH_3$ | 2-Cl-phenyl | 2-(methylaminosulfonyl)phenyl |
| 318 | $SO_2CH_3$ | 2-Cl-phenyl | 1-pyrrolidinocarbonyl |
| 319 | $SO_2CH_3$ | 2-Cl-phenyl | 2-(methylsulfonyl)phenyl |
| 320 | $SO_2CH_3$ | 2-Cl-phenyl | 4-morpholino |
| 321 | $SO_2CH_3$ | 2-Cl-phenyl | 2-(1'-$CF_3$-tetrazol-2-yl)phenyl |
| 322 | $SO_2CH_3$ | 2-Cl-phenyl | 4-morpholinocarbonyl |
| 323 | $SO_2CH_3$ | 2-F-phenyl | 2-(aminosulfonyl)phenyl |
| 324 | $SO_2CH_3$ | 2-F-phenyl | 2-(methylaminosulfonyl)phenyl |
| 325 | $SO_2CH_3$ | 2-F-phenyl | 1-pyrrolidinocarbonyl |
| 326 | $SO_2CH_3$ | 2-F-phenyl | 2-(methylsulfonyl)phenyl |
| 327 | $SO_2CH_3$ | 2-F-phenyl | 4-morpholino |
| 328 | $SO_2CH_3$ | 2-F-phenyl | 2-(1'-$CF_3$-tetrazol-2-yl)phenyl |
| 329 | $SO_2CH_3$ | 2-F-phenyl | 4-morpholinocarbonyl |
| 330 | $SO_2CH_3$ | 2,5-diF-phenyl | 2-(aminosulfonyl)phenyl |
| 331 | $SO_2CH_3$ | 2,5-diF-phenyl | 2-(methylaminosulfonyl)phenyl |
| 332 | $SO_2CH_3$ | 2,5-diF-phenyl | 1-pyrrolidinocarbonyl |
| 333 | $SO_2CH_3$ | 2,5-diF-phenyl | 2-(methylsulfonyl)phenyl |
| 334 | $SO_2CH_3$ | 2,5-diF-phenyl | 4-morpholino |
| 335 | $SO_2CH_3$ | 2,5-diF-phenyl | 2-(1'-$CF_3$-tetrazol-2-yl)phenyl |
| 336 | $SO_2CH_3$ | 2,5-diF-phenyl | 4-morpholinocarbonyl |
| 337 | $NHSO_2CH_3$ | phenyl | 2-(aminosulfonyl)phenyl |
| 338 | $NHSO_2CH_3$ | phenyl | 2-(methylaminosulfonyl)phenyl |
| 339 | $NHSO_2CH_3$ | phenyl | 1-pyrrolidinocarbonyl |
| 340 | $NHSO_2CH_3$ | phenyl | 2-(methylsulfonyl)phenyl |
| 341 | $NHSO_2CH_3$ | phenyl | 4-morpholino |
| 342 | $NHSO_2CH_3$ | phenyl | 2-(1'-$CF_3$-tetrazol-2-yl)phenyl |
| 343 | $NHSO_2CH_3$ | phenyl | 4-morpholinocarbonyl |
| 344 | $NHSO_2CH_3$ | 2-pyridyl | 2-(aminosulfonyl)phenyl |
| 345 | $NHSO_2CH_3$ | 2-pyridyl | 2-(methylaminosulfonyl)phenyl |
| 346 | $NHSO_2CH_3$ | 2-pyridyl | 1-pyrrolidinocarbonyl |
| 347 | $NHSO_2CH_3$ | 2-pyridyl | 2-(methylsulfonyl)phenyl |
| 348 | $NHSO_2CH_3$ | 2-pyridyl | 4-morpholino |
| 349 | $NHSO_2CH_3$ | 2-pyridyl | 2-(1'-$CF_3$-tetrazol-2-yl)phenyl |
| 350 | $NHSO_2CH_3$ | 2-pyridyl | 4-morpholinocarbonyl |
| 351 | $NHSO_2CH_3$ | 3-pyridyl | 2-(aminosulfonyl)phenyl |
| 352 | $NHSO_2CH_3$ | 3-pyridyl | 2-(methylaminosulfonyl)phenyl |
| 353 | $NHSO_2CH_3$ | 3-pyridyl | 1-pyrrolidinocarbonyl |
| 354 | $NHSO_2CH_3$ | 3-pyridyl | 2-(methylsulfonyl)phenyl |
| 355 | $NHSO_2CH_3$ | 3-pyridyl | 4-morpholino |
| 356 | $NHSO_2CH_3$ | 3-pyridyl | 2-(1'-$CF_3$-tetrazol-2-yl)phenyl |
| 357 | $NHSO_2CH_3$ | 3-pyridyl | 4-morpholinocarbonyl |
| 358 | $NHSO_2CH_3$ | 2-pyrimidyl | 2-(aminosulfonyl)phenyl |
| 359 | $NHSO_2CH_3$ | 2-pyrimidyl | 2-(methylaminosulfonyl)phenyl |
| 360 | $NHSO_2CH_3$ | 2-pyrimidyl | 1-pyrrolidinocarbonyl |
| 361 | $NHSO_2CH_3$ | 2-pyrimidyl | 2-(methylsulfonyl)phenyl |
| 362 | $NHSO_2CH_3$ | 2-pyrimidyl | 4-morpholino |
| 363 | $NHSO_2CH_3$ | 2-pyrimidyl | 2-(1'-$CF_3$-tetrazol-2-yl)phenyl |
| 364 | $NHSO_2CH_3$ | 2-pyrimidyl | 4-morpholinocarbonyl |
| 365 | $NHSO_2CH_3$ | 5-pyrimidyl | 2-(aminosulfonyl)phenyl |
| 366 | $NHSO_2CH_3$ | 5-pyrimidyl | 2-(methylaminosulfonyl)phenyl |
| 367 | $NHSO_2CH_3$ | 5-pyrimidyl | 1-pyrrolidinocarbonyl |
| 368 | $NHSO_2CH_3$ | 5-pyrimidyl | 2-(methylsulfonyl)phenyl |
| 369 | $NHSO_2CH_3$ | 5-pyrimidyl | 4-morpholino |
| 370 | $NHSO_2CH_3$ | 5-pyrimidyl | 2-(1'-$CF_3$-tetrazol-2-yl)phenyl |
| 371 | $NHSO_2CH_3$ | 5-pyrimidyl | 4-morpholinocarbonyl |
| 372 | $NHSO_2CH_3$ | 2-Cl-phenyl | 2-(aminosulfonyl)phenyl |
| 373 | $NHSO_2CH_3$ | 2-Cl-phenyl | 2-(methylaminosulfonyl)phenyl |
| 374 | $NHSO_2CH_3$ | 2-Cl-phenyl | 1-pyrrolidinocarbonyl |
| 375 | $NHSO_2CH_3$ | 2-Cl-phenyl | 2-(methylsulfonyl)phenyl |
| 376 | $NHSO_2CH_3$ | 2-Cl-phenyl | 4-morpholino |
| 377 | $NHSO_2CH_3$ | 2-Cl-phenyl | 2-(1'-$CF_3$-tetrazol-2-yl)phenyl |
| 378 | $NHSO_2CH_3$ | 2-Cl-phenyl | 4-morpholinocarbonyl |
| 379 | $NHSO_2CH_3$ | 2-F-phenyl | 2-(aminosulfonyl)phenyl |
| 380 | $NHSO_2CH_3$ | 2-F-phenyl | 2-(methylaminosulfonyl)phenyl |
| 381 | $NHSO_2CH_3$ | 2-F-phenyl | 1-pyrrolidinocarbonyl |
| 382 | $NHSO_2CH_3$ | 2-F-phenyl | 2-(methylsulfonyl)phenyl |
| 383 | $NHSO_2CH_3$ | 2-F-phenyl | 4-morpholino |
| 384 | $NHSO_2CH_3$ | 2-F-phenyl | 2-(1'-$CF_3$-tetrazol-2-yl)phenyl |
| 385 | $NHSO_2CH_3$ | 2-F-phenyl | 4-morpholinocarbonyl |
| 386 | $NHSO_2CH_3$ | 2,5-diF-phenyl | 2-(aminosulfonyl)phenyl |
| 387 | $NHSO_2CH_3$ | 2,5-diF-phenyl | 2-(methylaminosulfonyl)phenyl |
| 388 | $NHSO_2CH_3$ | 2,5-diF-phenyl | 1-pyrrolidinocarbonyl |
| 389 | $NHSO_2CH_3$ | 2,5-diF-phenyl | 2-(methylsulfonyl)phenyl |
| 390 | $NHSO_2CH_3$ | 2,5-diF-phenyl | 4-morpholino |
| 391 | $NHSO_2CH_3$ | 2,5-diF-phenyl | 2-(1'-$CF_3$-tetrazol-2-yl)phenyl |
| 392 | $NHSO_2CH_3$ | 2,5-diF-phenyl | 4-morpholinocarbonyl |

TABLE 5

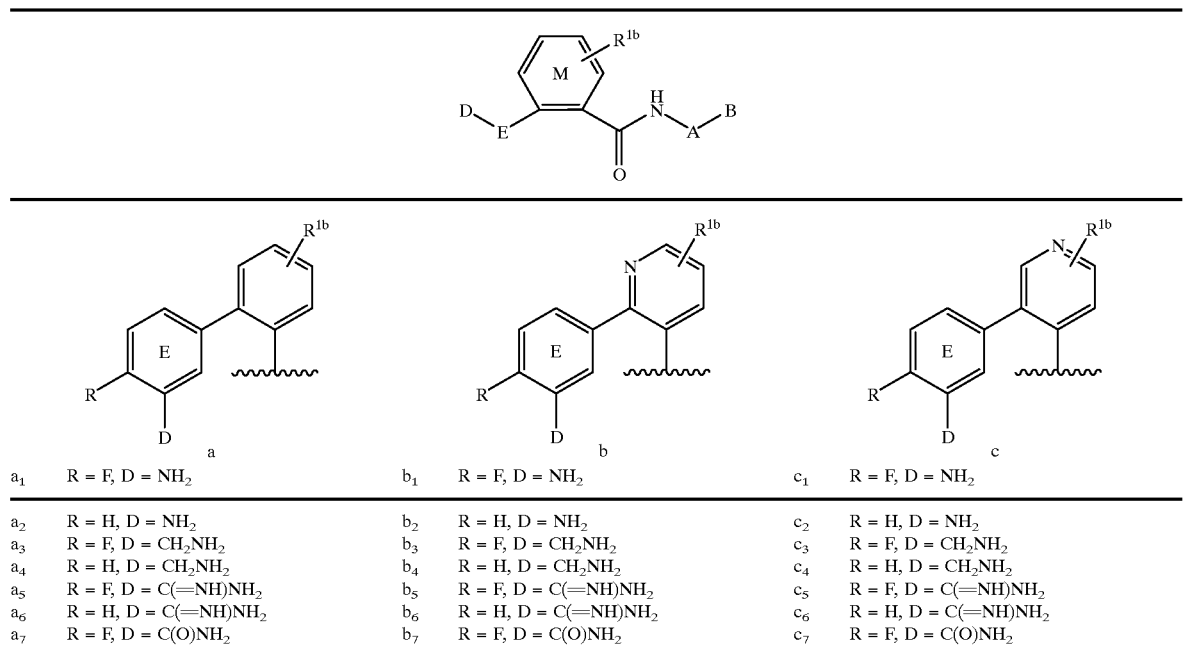

|  | a |  | b |  | c |
|---|---|---|---|---|---|
| $a_1$ | R = F, D = $NH_2$ | $b_1$ | R = F, D = $NH_2$ | $c_1$ | R = F, D = $NH_2$ |
| $a_2$ | R = H, D = $NH_2$ | $b_2$ | R = H, D = $NH_2$ | $c_2$ | R = H, D = $NH_2$ |
| $a_3$ | R = F, D = $CH_2NH_2$ | $b_3$ | R = F, D = $CH_2NH_2$ | $c_3$ | R = F, D = $CH_2NH_2$ |
| $a_4$ | R = H, D = $CH_2NH_2$ | $b_4$ | R = H, D = $CH_2NH_2$ | $c_4$ | R = H, D = $CH_2NH_2$ |
| $a_5$ | R = F, D = C(=NH)$NH_2$ | $b_5$ | R = F, D = C(=NH)$NH_2$ | $c_5$ | R = F, D = C(=NH)$NH_2$ |
| $a_6$ | R = H, D = C(=NH)$NH_2$ | $b_6$ | R = H, D = C(=NH)$NH_2$ | $c_6$ | R = H, D = C(=NH)$NH_2$ |
| $a_7$ | R = F, D = C(O)$NH_2$ | $b_7$ | R = F, D = C(O)$NH_2$ | $c_7$ | R = F, D = C(O)$NH_2$ |

TABLE 5-continued

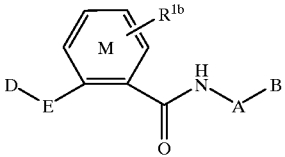

| | | | | | |
|---|---|---|---|---|---|
| a₈ | R = H, D = C(O)NH₂ | b₈ | R = H, D = C(O)NH₂ | c₈ | R = H, D = C(O)NH₂ |

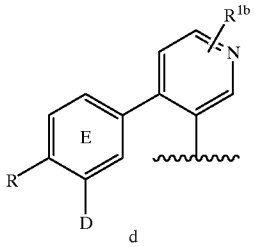

| | | | | | |
|---|---|---|---|---|---|
| d₁ | R = F, D = NH₂ | e₁ | R = F, D = NH₂ | f₁ | R = F, D = NH₂ |
| d₂ | R = H, D = NH₂ | e₂ | R = H, D = NH₂ | f₂ | R = H, D = NH₂ |
| d₃ | R = F, D = CH₂NH₂ | e₃ | R = F, D = CH₂NH₂ | f₃ | R = F, D = CH₂NH₂ |
| d₄ | R = H, D = CH₂NH₂ | e₄ | R = H, D = CH₂NH₂ | f₄ | R = H, D = CH₂NH₂ |
| d₅ | R = F, D = C(=NH)NH₂ | e₅ | R = F, D = C(=NH)NH₂ | f₅ | R = F, D = C(=NH)NH₂ |
| d₆ | R = H, D = C(=NH)NH₂ | e₆ | R = H, D = C(=NH)NH₂ | f₆ | R = H, D = C(=NH)NH₂ |
| d₇ | R = F, D = C(O)NH₂ | e₇ | R = F, D = C(O)NH₂ | f₇ | R = F, D = C(O)NH₂ |
| d₈ | R = H, D = C(O)NH₂ | e₈ | R = H, D = C(O)NH₂ | f₈ | R = H, D = C(O)NH₂ |

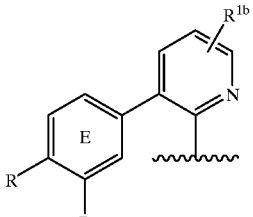

| | | | | | |
|---|---|---|---|---|---|
| g₁ | R = F, D = NH₂ | h₁ | R = F, D = NH₂ | i₁ | R = F, D = NH₂ |
| g₂ | R = H, D = NH₂ | h₂ | R = H, D = NH₂ | i₂ | R = H, D = NH₂ |
| g₃ | R = F, D = CH₂NH₂ | h₃ | R = F, D = CH₂NH₂ | i₃ | R = F, D = CH₂NH₂ |
| g₄ | R = H, D = CH₂NH₂ | h₄ | R = H, D = CH₂NH₂ | i₄ | R = H, D = CH₂NH₂ |
| g₅ | R = F, D = C(=NH)NH₂ | h₅ | R = F, D = C(=NH)NH₂ | i₅ | R = F, D = C(=NH)NH₂ |
| g₆ | R = H, D = C(=NH)NH₂ | h₆ | R = H, D = C(=NH)NH₂ | i₆ | R = H, D = C(=NH)NH₂ |
| g₇ | R = F, D = C(O)NH₂ | h₇ | R = F, D = C(O)NH₂ | i₇ | R = F, D = C(O)NH₂ |
| g₈ | R = H, D = C(O)NH₂ | h₈ | R = H, D = C(O)NH₂ | i₈ | R = H, D = C(O)NH₂ |

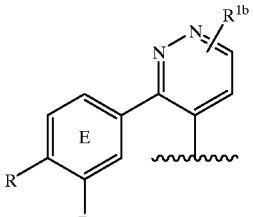

| | | | | | |
|---|---|---|---|---|---|
| j₁ | R = F, D = NH₂ | k₁ | R = F, D = NH₂ | l₁ | R = F, D = NH₂ |
| j₂ | R = H, D = NH₂ | k₂ | R = H, D = NH₂ | l₂ | R = H, D = NH₂ |
| j₃ | R = F, D = CH₂NH₂ | k₃ | R = F, D = CH₂NH₂ | l₃ | R = F, D = CH₂NH₂ |
| j₄ | R = H, D = CH₂NH₂ | k₄ | R = H, D = CH₂NH₂ | l₄ | R = H, D = CH₂NH₂ |
| j₅ | R = F, D = C(=NH)NH₂ | k₅ | R = F, D = C(=NH)NH₂ | l₅ | R = F, D = C(=NH)NH₂ |
| j₆ | R = H, D = C(=NH)NH₂ | k₆ | R = H, D = C(=NH)NH₂ | l₆ | R = H, D = C(=NH)NH₂ |
| j₇ | R = F, D = C(O)NH₂ | k₇ | R = F, D = C(O)NH₂ | l₇ | R = F, D = C(O)NH₂ |
| j₈ | R = H, D = C(O)NH₂ | k₈ | R = H, D = C(O)NH₂ | l₈ | R = H, D = C(O)NH₂ |

TABLE 5-continued

|   | m | | n | | o |
|---|---|---|---|---|---|
| m₁ | R = F, D = NH₂ | n₁ | R = F, D = NH₂ | o₁ | R = F, D = NH₂ |
| m₂ | R = H, D = NH₂ | n₂ | R = H, D = NH₂ | o₂ | R = H, D = NH₂ |
| m₃ | R = F, D = CH₂NH₂ | n₃ | R = F, D = CH₂NH₂ | o₃ | R = F, D = CH₂NH₂ |
| m₄ | R = H, D = CH₂NH₂ | n₄ | R = H, D = CH₂NH₂ | o₄ | R = H, D = CH₂NH₂ |
| m₅ | R = F, D = C(=NH)NH₂ | n₅ | R = F, D = C(=NH)NH₂ | o₅ | R = F, D = C(=NH)NH₂ |
| m₆ | R = H, D = C(=NH)NH₂ | n₆ | R = H, D = C(=NH)NH₂ | o₆ | R = H, D = C(=NH)NH₂ |
| m₇ | R = F, D = C(O)NH₂ | n₇ | R = F, D = C(O)NH₂ | o₇ | R = F, D = C(O)NH₂ |
| m₈ | R = H, D = C(O)NH₂ | n₈ | R = H, D = C(O)NH₂ | o₈ | R = H, D = C(O)NH₂ |

|   | p | | q | | r |
|---|---|---|---|---|---|
| p₁ | R = F, D = NH₂ | q₁ | R = F, D = NH₂ | r₁ | R = F, D = NH₂ |
| p₂ | R = Cl, D = NH₂ | q₂ | R = Cl, D = NH₂ | r₂ | R = Cl, D = NH₂ |
| p₃ | R = OMe, D = NH₂ | q₃ | R = OMe, D = NH₂ | r₃ | R = OMe, D = NH₂ |
| p₄ | R = F, D = CH₂NH₂ | q₄ | R = F, D = CH₂NH₂ | r₄ | R = F, D = CH₂NH₂ |
| p₅ | R = Cl, D = CH₂NH₂ | q₅ | R = Cl, D = CH₂NH₂ | r₅ | R = Cl, D = CH₂NH₂ |
| p₆ | R = OMe, D = CH₂NH₂ | q₆ | R = OMe, D = CH₂NH₂ | r₆ | R = OMe, D = CH₂NH₂ |
| p₇ | R = F, D = C(=NH)NH₂ | q₇ | R = F, D = C(=NH)NH₂ | r₇ | R = F, D = C(=NH)NH₂ |
| p₈ | R = Cl, D = C(=NH)NH₂ | q₈ | R = Cl, D = C(=NH)NH₂ | r₈ | R = Cl, D = C(=NH)NH₂ |
| p₉ | R = OMe, D = C(=NH)NH₂ | q₉ | R = OMe, D = C(=NH)NH₂ | r₉ | R = OMe, D = C(=NH)NH₂ |
| p₁₀ | R = F, D = C(O)NH₂ | q₁₀ | R = F, D = C(O)NH₂ | r₁₀ | R = F, D = C(O)NH₂ |
| p₁₁ | R = Cl, D = C(O)NH₂ | q₁₁ | R = Cl, D = C(O)NH₂ | r₁₁ | R = Cl, D = C(O)NH₂ |
| p₁₂ | R = OMe, D = C(O)NH₂ | q₁₂ | R = OMe, D = C(O)NH₂ | r₁₂ | R = OMe, D = C(O)NH₂ |

|   | s | | t | | u |
|---|---|---|---|---|---|
| s₁ | R = F, D = NH₂ | t₁ | R = F, D = NH₂ | u₁ | R = F, D = NH₂ |
| s₂ | R = Cl, D = NH₂ | t₂ | R = Cl, D = NH₂ | u₂ | R = Cl, D = NH₂ |
| s₃ | R = OMe, D = NH₂ | t₃ | R = OMe, D = NH₂ | u₃ | R = OMe, D = NH₂ |
| s₄ | R = F, D = CH₂NH₂ | t₄ | R = F, D = CH₂NH₂ | u₄ | R = F, D = CH₂NH₂ |
| s₅ | R = Cl, D = CH₂NH₂ | t₅ | R = Cl, D = CH₂NH₂ | u₅ | R = Cl, D = CH₂NH₂ |
| s₆ | R = OMe, D = CH₂NH₂ | t₆ | R = OMe, D = CH₂NH₂ | u₆ | R = OMe, D = CH₂NH₂ |
| s₇ | R = F, D = C(=NH)NH₂ | t₇ | R = F, D = C(=NH)NH₂ | u₇ | R = F, D = C(=NH)NH₂ |

TABLE 5-continued

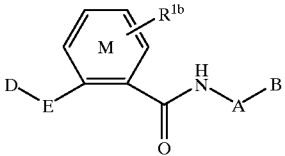

| | | | | | |
|---|---|---|---|---|---|
| s$_8$ | R = Cl, D = C(=NH)NH$_2$ | t$_8$ | R = Cl, D = C(=NH)NH$_2$ | u$_8$ | R = Cl, D = C(=NH)NH$_2$ |
| s$_9$ | R = OMe, D = C(=NH)NH$_2$ | t$_9$ | R = OMe, D = C(=NH)NH$_2$ | u$_9$ | R = OMe, D = C(=NH)NH$_2$ |
| s$_{10}$ | R = F, D = C(O)NH$_2$ | t$_{10}$ | R = F, D = C(O)NH$_2$ | u$_{10}$ | R = F, D = C(O)NH$_2$ |
| s$_{11}$ | R = Cl, D = C(O)NH$_2$ | t$_{11}$ | R = Cl, D = C(O)NH$_2$ | u$_{11}$ | R = Cl, D = C(O)NH$_2$ |
| s$_{12}$ | R = OMe, D = C(O)NH$_2$ | t$_{12}$ | R = OMe, D = C(O)NH$_2$ | u$_{12}$ | R = OMe, D = C(O)NH$_2$ |

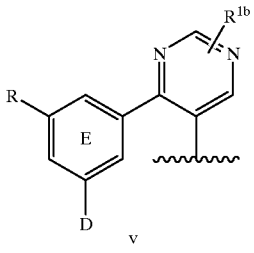
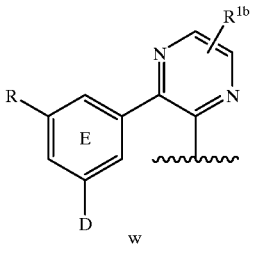
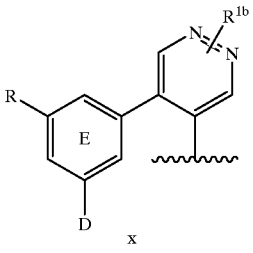

v    w    x

| | | | | | |
|---|---|---|---|---|---|
| v$_1$ | R = F, D = NH$_2$ | w$_1$ | R = F, D = NH$_2$ | x$_1$ | R = F, D = NH$_2$ |
| v$_2$ | R = Cl, D = NH$_2$ | w$_2$ | R = Cl, D = NH$_2$ | x$_2$ | R = Cl, D = NH$_2$ |
| v$_3$ | R = OMe, D = NH$_2$ | w$_3$ | R = OMe, D = NH$_2$ | x$_3$ | R = OMe, D = NH$_2$ |
| v$_4$ | R = F, D = CH$_2$NH$_2$ | w$_4$ | R = F, D = CH$_2$NH$_2$ | x$_4$ | R = F, D = CH$_2$NH$_2$ |
| v$_5$ | R = Cl, D = CH$_2$NH$_2$ | w$_5$ | R = Cl, D = CH$_2$NH$_2$ | x$_5$ | R = Cl, D = CH$_2$NH$_2$ |
| v$_6$ | R = OMe, D = CH$_2$NH$_2$ | w$_6$ | R = OMe, D = CH$_2$NH$_2$ | x$_6$ | R = OMe, D = CH$_2$NH$_2$ |
| v$_7$ | R = F, D = C(=NH)NH$_2$ | w$_7$ | R = F, D = C(=NH)NH$_2$ | x$_7$ | R = F, D = C(=NH)NH$_2$ |
| v$_8$ | R = Cl, D = C(=NH)NH$_2$ | w$_8$ | R = Cl, D = C(=NH)NH$_2$ | x$_8$ | R = Cl, D = C(=NH)NH$_2$ |
| v$_9$ | R = OMe, D = C(=NH)NH$_2$ | w$_9$ | R = OMe, D = C(=NH)NH$_2$ | x$_9$ | R = OMe, D = C(=NH)NH$_2$ |
| v$_{10}$ | R = F, D = C(O)NH$_2$ | w$_{10}$ | R = F, D = C(O)NH$_2$ | x$_{10}$ | R = F, D = C(O)NH$_2$ |
| v$_{11}$ | R = Cl, D = C(O)NH$_2$ | w$_{11}$ | R = Cl, D = C(O)NH$_2$ | x$_{11}$ | R = Cl, D = C(O)NH$_2$ |
| v$_{12}$ | R = OMe, D = C(O)NH$_2$ | w$_{12}$ | R = OMe, D = C(O)NH$_2$ | x$_{12}$ | R = OMe, D = C(O)NH$_2$ |

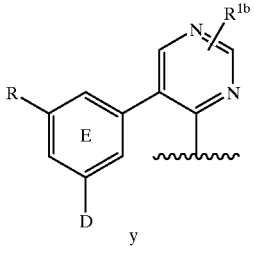
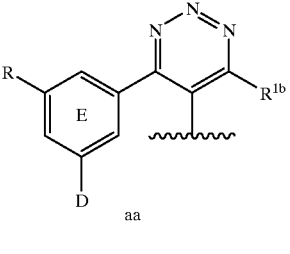

y    z    aa

| | | | | | |
|---|---|---|---|---|---|
| y$_1$ | R = F, D = NH$_2$ | z$_1$ | R = F, D = NH$_2$ | aa$_1$ | R = F, D = NH$_2$ |
| y$_2$ | R = Cl, D = NH$_2$ | z$_2$ | R = Cl, D = NH$_2$ | aa$_2$ | R = Cl, D = NH$_2$ |
| y$_3$ | R = OMe, D = NH$_2$ | z$_3$ | R = OMe, D = NH$_2$ | aa$_3$ | R = OMe, D = NH$_2$ |
| y$_4$ | R = F, D = CH$_2$NH$_2$ | z$_4$ | R = F, D = CH$_2$NH$_2$ | aa$_4$ | R = F, D = CH$_2$NH$_2$ |
| y$_5$ | R = Cl, D = CH$_2$NH$_2$ | z$_5$ | R = Cl, D = CH$_2$NH$_2$ | aa$_5$ | R = Cl, D = CH$_2$NH$_2$ |
| y$_6$ | R = OMe, D = CH$_2$NH$_2$ | z$_6$ | R = OMe, D = CH$_2$NH$_2$ | aa$_6$ | R = OMe, D = CH$_2$NH$_2$ |
| y$_7$ | R = F, D = C(=NH)NH$_2$ | z$_7$ | R = F, D = C(=NH)NH$_2$ | aa$_7$ | R = F, D = C(=NH)NH$_2$ |
| y$_8$ | R = Cl, D = C(=NH)NH$_2$ | z$_8$ | R = Cl, D = C(=NH)NH$_2$ | aa$_8$ | R = Cl, D = C(=NH)NH$_2$ |
| y$_9$ | R = OMe, D = C(=NH)NH$_2$ | z$_9$ | R = OMe, D = C(=NH)NH$_2$ | aa$_9$ | R = OMe, D = C(=NH)NH$_2$ |
| y$_{10}$ | R = F, D = C(O)NH$_2$ | z$_{10}$ | R = F, D = C(O)NH$_2$ | aa$_{10}$ | R = F, D = C(O)NH$_2$ |
| y$_{11}$ | R = Cl, D = C(O)NH$_2$ | z$_{11}$ | R = Cl, D = C(O)NH$_2$ | aa$_{11}$ | R = Cl, D = C(O)NH$_2$ |
| y$_{12}$ | R = OMe, D = C(O)NH$_2$ | z$_{12}$ | R = OMe, D = C(O)NH$_2$ | aa$_{12}$ | R = OMe, D = C(O)NH$_2$ |

TABLE 5-continued

| | | |
|---|---|---|
| bb₁ R = F, D = NH₂ | cc₁ R = F, D = NH₂ | dd₁ R = F, D = NH₂ |
| bb₂ R = Cl, D = NH₂ | cc₂ R = Cl, D = NH₂ | dd₂ R = Cl, D = NH₂ |
| bb₃ R = OMe, D = NH₂ | cc₃ R = OMe, D = NH₂ | dd₃ R = OMe, D = NH₂ |
| bb₄ R = F, D = CH₂NH₂ | cc₄ R = F, D = CH₂NH₂ | dd₄ R = F, D = CH₂NH₂ |
| bb₅ R = Cl, D = CH₂NH₂ | cc₅ R = Cl, D = CH₂NH₂ | dd₅ R = Cl, D = CH₂NH₂ |
| bb₆ R = OMe, D = CH₂NH₂ | cc₆ R = OMe, D = CH₂NH₂ | dd₆ R = OMe, D = CH₂NH₂ |
| bb₇ R = F, D = C(=NH)NH₂ | cc₇ R = F, D = C(=NH)NH₂ | dd₇ R = F, D = C(=NH)NH₂ |
| bb₈ R = Cl, D = C(=NH)NH₂ | cc₈ R = Cl, D = C(=NH)NH₂ | dd₈ R = Cl, D = C(=NH)NH₂ |
| bb₉ R = OMe, D = C(=NH)NH₂ | cc₉ R = OMe, D = C(=NH)NH₂ | dd₉ R = OMe, D = C(=NH)NH₂ |
| bb₁₀ R = F, D = C(O)NH₂ | cc₁₀ R = F, D = C(O)NH₂ | dd₁₀ R = F, D = C(O)NH₂ |
| bb₁₁ R = Cl, D = C(O)NH₂ | cc₁₁ R = Cl, D = C(O)NH₂ | dd₁₁ R = Cl, D = C(O)NH₂ |
| bb₁₂ R = OMe, D = C(O)NH₂ | cc₁₂ R = OMe, D = C(O)NH₂ | dd₁₂ R = OMe, D = C(O)NH₂ |

| | | |
|---|---|---|
| ee₁ R = F, D = CH₂NH₂ | ff₁ R = F, D = CH₂NH₂ | gg₁ R = F, D = CH₂NH₂ |
| ee₂ R = Cl, D = CH₂NH₂ | ff₂ R = Cl, D = CH₂NH₂ | gg₂ R = Cl, D = CH₂NH₂ |
| ee₃ R = OMe, D = CH₂NH₂ | ff₃ R = OMe, D = CH₂NH₂ | gg₃ R = OMe, D = CH₂NH₂ |
| ee₄ R = CH₂NH₂, D = CH₂NH₂ | ff₄ R = CH₂NH₂, D = CH₂NH₂ | gg₄ R = CH₂NH₂, D = CH₂NH₂ |

| | | |
|---|---|---|
| hh₁ R = F, D = CH₂NH₂ | ii₁ R = F, D = CH₂NH₂ | jj₁ R = F, D = CH₂NH₂ |
| hh₂ R = Cl, D = CH₂NH₂ | ii₂ R = Cl, D = CH₂NH₂ | jj₂ R = Cl, D = CH₂NH₂ |
| hh₃ R = OMe, D = CH₂NH₂ | ii₃ R = OMe, D = CH₂NH₂ | jj₃ R = OMe, D = CH₂NH₂ |
| hh₄ R = CH₂NH₂, D = CH₂NH₂ | ii₄ R = CH₂NH₂, D = CH₂NH₂ | jj₄ R = CH₂NH₂, D = CH₂NH₂ |

TABLE 5-continued

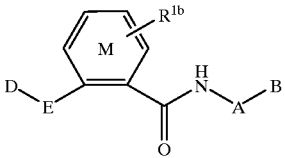

| | kk | | ll | | mm |
|---|---|---|---|---|---|
| kk₁ | R = F, D = CH₂NH₂ | ll₁ | R = F, D = CH₂NH₂ | mm₁ | R = F, D = CH₂NH₂ |
| kk₂ | R = Cl, D = CH₂NH₂ | ll₂ | R = Cl, D = CH₂NH₂ | mm₂ | R = Cl, D = CH₂NH₂ |
| kk₃ | R = OMe, D = CH₂NH₂ | ll₃ | R = OMe, D = CH₂NH₂ | mm₃ | R = OMe, D = CH₂NH₂ |
| kk₄ | R = CH₂NH₂, D = CH₂NH₂ | ll₄ | R = CH₂NH₂, D = CH₂NH₂ | mm₄ | R = CH₂NH₂, D = CH₂NH₂ |

| | nn | | oo | | pp |
|---|---|---|---|---|---|
| nn₁ | R = F, D = CH₂NH₂ | oo₁ | R = F, D = CH₂NH₂ | pp₁ | R = F, D = CH₂NH₂ |
| nn₂ | R = Cl, D = CH₂NH₂ | oo₂ | R = Cl, D = CH₂NH₂ | pp₂ | R = Cl, D = CH₂NH₂ |
| nn₃ | R = OMe, D = CH₂NH₂ | oo₃ | R = OMe, D = CH₂NH₂ | pp₃ | R = OMe, D = CH₂NH₂ |
| nn₄ | R = CH₂NH₂, D = CH₂NH₂ | oo₄ | R = CH₂NH₂, D = CH₂NH₂ | pp₄ | R = CH₂NH₂, D = CH₂NH₂ |

| | qq | | rr | | ss |
|---|---|---|---|---|---|
| qq₁ | R = F, D = CH₂NH₂ | rr₁ | R = F, D = CH₂NH₂ | ss₁ | R = F, D = CH₂NH₂ |
| qq₂ | R = Cl, D = CH₂NH₂ | rr₂ | R = Cl, D = CH₂NH₂ | ss₂ | R = Cl, D = CH₂NH₂ |
| qq₃ | R = OMe, D = CH₂NH₂ | rr₃ | R = OMe, D = CH₂NH₂ | ss₃ | R = OMe, D = CH₂NH₂ |
| qq₄ | R = CH₂NH₂, D = CH₂NH₂ | rr₄ | R = CH₂NH₂, D = CH₂NH₂ | ss₄ | R = CH₂NH₂, D = CH₂NH₂ |

| Ex# | $R^{1b}$ | A | B | Ex# | $R^{1b}$ | A | B |
|---|---|---|---|---|---|---|---|
| 1 | H | phenyl | 2-((Me)₂N-methyl)phenyl | 5 | H | 2-F-phenyl | 2-((Me)₂N-methyl)phenyl |
| 2 | H | phenyl | 2-((Me)NH-methyl)phenyl | 6 | H | 2-F-phenyl | 2-((Me)NH-methyl)phenyl |
| 3 | H | phenyl | 2-(H₂N-methyl)phenyl | 7 | H | 2-F-phenyl | 2-(H₂N-methyl)phenyl |
| 4 | H | phenyl | 2-HOCH₂-phenyl | 8 | H | 2-F-phenyl | 2-HOCH₂-phenyl |

-continued

| Ex# | R¹ᵇ | A | B |
|---|---|---|---|
| 9 | H | phenyl | 2-methylimidazol-1-yl |
| 10 | H | phenyl | 2-ethylimidazol-1-yl |
| 11 | H | phenyl | 2-((Me)₂N-methyl)imidazol-1-yl |
| 12 | H | phenyl | 2-CH₃NHSO₂-imidazol-1-yl |
| 13 | H | phenyl | 2-CH₃OCH₂-imidazol-1-yl |
| 14 | H | 2-F-phenyl | 2-methylimidazol-1-yl |
| 15 | H | 2-F-phenyl | 2-ethylimidazol-1-yl |
| 16 | H | 2-F-phenyl | 2-((Me)₂N-methyl)imidazol-1-yl |
| 17 | H | 2-F-phenyl | 2-CH₃SO₂-imidazol-1-yl |
| 18 | H | 2-F-phenyl | 2-CH₃OCH₂-imidazol-1-yl |
| 19 | H | 2-Cl-phenyl | 2-methylimidazol-1-yl |
| 20 | H | 2-Cl-phenyl | 2-ethylimidazol-1-yl |
| 21 | H | 2-Cl-phenyl | 2-((Me)₂N-methyl)imidazol-1-yl |
| 22 | H | 2-Cl-phenyl | 2-CH₃SO₂-imidazol-1-yl |
| 23 | H | 2-Cl-phenyl | 2-CH₃OCH₂-imidazol-1-yl |
| 24 | H | 2-(Me)₂N-phenyl | 2-methylimidazol-1-yl |
| 25 | H | 2-(Me)₂N-phenyl | 2-ethylimidazol-1-yl |
| 26 | H | 2-(Me)₂N-phenyl | 2-((Me)₂N-methyl)imidazol-1-yl |
| 27 | H | 2-(Me)₂N-phenyl | 2-CH₃SO₂-imidazol-1-yl |
| 28 | H | 2-(Me)₂N-phenyl | 2-CH₃OCH₂-imidazol-1-yl |
| 29 | H | phenyl | N-methylimidazol-2-yl |
| 30 | H | phenyl | 4-methylimidazol-5-yl |
| 31 | H | phenyl | 5-CF₃-pyrazol-1-yl |
| 32 | H | 2-F-phenyl | N-methylimidazol-2-yl |
| 33 | H | 2-F-phenyl | 4-methylimidazol-5-yl |
| 34 | H | 2-F-phenyl | 5-CF₃-pyrazol-1-yl |
| 35 | H | phenyl | guanidino |
| 36 | H | phenyl | 2-thiazolin-2-ylamine |
| 37 | H | phenyl | N-methyl-2-imidazolin-2-yl |
| 38 | H | phenyl | N-methyl-1,4,5,6-tetrahydropyrimid-2-yl |
| 39 | H | phenyl | N-methylimidazol-2-ylthiol |
| 40 | H | phenyl | t-butoxycarbonylamine |
| 41 | H | phenyl | (N-pyrrolidino)formylimino |
| 42 | H | phenyl | (N-pyrrolidino)formyl-N-(methanesulfamoyl)imino |
| 43 | H | 2-F-phenyl | guanidino |
| 44 | H | 2-F-phenyl | 2-thiazolin-2-ylamine |
| 45 | H | 2-F-phenyl | N-methyl-2-imidazolin-2-yl |
| 46 | H | 2-F-phenyl | N-methyl-1,4,5,6-tetrahydropyrimid-2-yl |
| 47 | H | 2-F-phenyl | N-methylimidazol-2-ylthio |
| 48 | H | 2-F-phenyl | t-butoxycarbonylamine |
| 49 | H | 2-F-phenyl | (N-pyrrolidino)formylimino |
| 50 | H | 2-F-phenyl | (N-pyrrolidino)formyl-N-(methanesulfamoyl)imino |
| 51 | H | 2-CH₃O-phenyl | (N-pyrrolidino)formylimino |
| 52 | H | 2-CH₃O-phenyl | (N-pyrrolidino)formyl-N-(methanesulfamoyl)imino |
| 53 | —CN | phenyl | 2-((Me)₂N-methyl)phenyl |
| 54 | —CN | phenyl | 2-((Me)NH-methyl)phenyl |
| 55 | —CN | phenyl | 2-(H₂N-methyl)phenyl |
| 56 | —CN | phenyl | 2-HOCH₂-phenyl |
| 57 | —CN | 2-F-phenyl | 2-((Me)₂N-methyl)phenyl |
| 58 | —CN | 2-F-phenyl | 2-((Me)NH-methyl)phenyl |
| 59 | —CN | 2-F-phenyl | 2-(H₂N-methyl)phenyl |
| 60 | —CN | 2-F-phenyl | 2-HOCH₂-phenyl |
| 61 | —CN | phenyl | 2-methylimidazol-1-yl |
| 62 | —CN | phenyl | 2-ethylimidazol-1-yl |
| 63 | —CN | phenyl | 2-((Me)₂N-methyl)imidazol-1-yl |
| 64 | —CN | phenyl | 2-CH₃SO₂-imidazol-1-yl |
| 65 | —CN | phenyl | 2-CH₃OCH₂-imidazol-1-yl |
| 66 | —CN | 2-F-phenyl | 2-methylimidazol-1-yl |
| 67 | —CN | 2-F-phenyl | 2-ethylimidazol-1-yl |
| 68 | —CN | 2-F-phenyl | 2-((Me)₂N-methyl)imidazol-1-yl |
| 69 | —CN | 2-F-phenyl | 2-CH₃SO₂-imidazol-1-yl |
| 70 | —CN | 2-F-phenyl | 2-CH₃OCH₂-imidazol-1-yl |
| 71 | —CN | 2-Cl-phenyl | 2-methylimidazol-1-yl |
| 72 | —CN | 2-Cl-phenyl | 2-ethylimidazol-1-yl |
| 73 | —CN | 2-Cl-phenyl | 2-((Me)₂N-methyl)imidazol-1-yl |
| 74 | —CN | 2-Cl-phenyl | 2-CH₃SO₂-imidazol-1-yl |
| 75 | —CN | 2-Cl-phenyl | 2-CH₃OCH₂-imidazol-1-yl |
| 76 | —CN | 2-(Me)₂N-phenyl | 2-methylimidazol-1-yl |
| 77 | —CN | 2-(Me)₂N-phenyl | 2-ethylimidazol-1-yl |
| 78 | —CN | 2-(Me)₂N-phenyl | 2-((Me)₂N-methyl)imidazol-1-yl |
| 79 | —CN | 2-(Me)₂N-phenyl | 2-CH₃SO₂-imidazol-1-yl |
| 80 | —CN | 2-(Me)₂N-phenyl | 2-CH₃OCH₂-imidazol-1-yl |
| 81 | —CN | phenyl | N-methylimidazol-2-yl |
| 82 | —CN | phenyl | 4-methylimidazol-5-yl |
| 83 | —CN | phenyl | 5-CF₃-pyrazol-1-yl |
| 84 | —CN | 2-F-phenyl | N-methylimidazol-2-yl |
| 85 | —CN | 2-F-phenyl | 4-methylimidazol-5-yl |
| 86 | —CN | 2-F-phenyl | 5-CF₃-pyrazol-1-yl |
| 87 | —CN | phenyl | guanidino |
| 88 | —CN | phenyl | 2-thiazolin-2-ylamine |
| 89 | —CN | phenyl | N-methyl-2-imidazolin-2-yl |
| 90 | —CN | phenyl | N-methyl-1,4,5,6-tetrahydropyrimid-2-yl |
| 91 | —CN | phenyl | N-methylimidazol-2-ylthiol |
| 92 | —CN | phenyl | t-butoxycarbonylamine |
| 93 | —CN | phenyl | (N-pyrrolidino)formylimino |
| 94 | —CN | phenyl | (N-pyrrolidino)formyl-N-(methanesulfamoyl)imino |
| 95 | —CN | 2-F-phenyl | guanidino |
| 96 | —CN | 2-F-phenyl | 2-thiazolin-2-ylamine |
| 97 | —CN | 2-F-phenyl | N-methyl-2-imidazolin-2-yl |
| 98 | —CN | 2-F-phenyl | N-methyl-1,4,5,6-tetrahydropyrimid-2-yl |
| 99 | —CN | 2-F-phenyl | N-methylimidazol-2-ylthio |
| 100 | —CN | 2-F-phenyl | t-butoxycarbonylamine |
| 101 | —CN | 2-F-phenyl | (N-pyrrolidino)formylimino |
| 102 | —CN | 2-F-phenyl | (N-pyrrolidino)formyl-N-(methanesulfamoyl)imino |
| 103 | —CN | 2-CH₃O-phenyl | (N-pyrrolidino)formylimino |
| 104 | —CN | 2-CH₃O-phenyl | (N-pyrrolidino)formyl-N-(methanesulfamoyl)imino |
| 105 | CF₃ | phenyl | 2-((Me)₂N-methyl)phenyl |
| 106 | CF₃ | phenyl | 2-((Me)NH-methyl)phenyl |
| 107 | CF₃ | phenyl | 2-(H₂N-methyl)phenyl |
| 108 | CF₃ | phenyl | 2-HOCH₂-phenyl |
| 109 | CF₃ | 2-F-phenyl | 2-((Me)₂N-methyl)phenyl |
| 110 | CF₃ | 2-F-phenyl | 2-((Me)NH-methyl)phenyl |
| 111 | CF₃ | 2-F-phenyl | 2-(H₂N-methyl)phenyl |
| 112 | CF₃ | 2-F-phenyl | 2-HOCH₂-phenyl |
| 113 | CF₃ | phenyl | 2-methylimidazol-1-yl |
| 114 | CF₃ | phenyl | 2-ethylimidazol-1-yl |
| 115 | CF₃ | phenyl | 2-((Me)₂N-methyl)imidazol-1-yl |
| 116 | CF₃ | phenyl | 2-CH₃SO₂-imidazol-1-yl |
| 117 | CF₃ | phenyl | 2-CH₃OCH₂-imidazol-1-yl |
| 118 | CF₃ | 2-F-phenyl | 2-methylimidazol-1-yl |
| 119 | CF₃ | 2-F-phenyl | 2-ethylimidazol-1-yl |
| 120 | CF₃ | 2-F-phenyl | 2-((Me)₂N-methyl)imidazol-1-yl |
| 121 | CF₃ | 2-F-phenyl | 2-CH₃SO₂-imidazol-1-yl |
| 122 | CF₃ | 2-F-phenyl | 2-CH₃OCH₂-imidazol-1-yl |
| 123 | CF₃ | 2-Cl-phenyl | 2-methylimidazol-1-yl |
| 124 | CF₃ | 2-Cl-phenyl | 2-ethylimidazol-1-yl |
| 125 | CF₃ | 2-Cl-phenyl | 2-((Me)₂N-methyl)imidazol-1-yl |
| 126 | CF₃ | 2-Cl-phenyl | 2-CH₃SO₂-imidazol-1-yl |
| 127 | CF₃ | 2-Cl-phenyl | 2-CH₃OCH₂-imidazol-1-yl |
| 128 | CF₃ | 2-(Me)₂N-phenyl | 2-methylimidazol-1-yl |
| 129 | CF₃ | 2-(Me)₂N-phenyl | 2-ethylimidazol-1-yl |
| 130 | CF₃ | 2-(Me)₂N-phenyl | 2-((Me)₂N-methyl)imidazol-1-yl |
| 131 | CF₃ | 2-(Me)₂N-phenyl | 2-CH₃SO₂-imidazol-1-yl |
| 132 | CF₃ | 2-(Me)₂N-phenyl | 2-CH₃OCH₂-imidazol-1-yl |
| 133 | CF₃ | phenyl | N-methylimidazol-2-yl |
| 134 | CF₃ | phenyl | 4-methylimidazol-5-yl |
| 135 | CF₃ | phenyl | 5-CF₃-pyrazol-1-yl |
| 136 | CF₃ | 2-F-phenyl | N-methylimidazol-2-yl |
| 137 | CF₃ | 2-F-phenyl | 4-methylimidazol-5-yl |
| 138 | CF₃ | 2-F-phenyl | 5-CF₃-pyrazol-1-yl |
| 139 | CF₃ | phenyl | guanidino |
| 140 | CF₃ | phenyl | 2-thiazolin-2-ylamine |
| 141 | CF₃ | phenyl | N-methyl-2-imidazolin-2-yl |
| 142 | CF₃ | phenyl | N-methyl-1,4,5,6-tetrahydropyrimid-2-yl |
| 143 | CF₃ | phenyl | N-methylimidazol-2-ylthiol |
| 144 | CF₃ | phenyl | t-butoxycarbonylamine |
| 145 | CF₃ | phenyl | (N-pyrrolidino)formylimino |
| 146 | CF₃ | phenyl | (N-pyrrolidino)formyl-N-(methanesulfamoyl)imino |
| 147 | CF₃ | 2-F-phenyl | guanidino |
| 148 | CF₃ | 2-F-phenyl | 2-thiazolin-2-ylamine |
| 149 | CF₃ | 2-F-phenyl | N-methyl-2-imidazolin-2-yl |
| 150 | CF₃ | 2-F-phenyl | N-methyl-1,4,5,6- |

| Ex# | R¹ᵇ | A | B |
|---|---|---|---|
| 151 | CF₃ | 2-F-phenyl | N-methylimidazol-2-ylthio |
| 152 | CF₃ | 2-F-phenyl | t-butoxycarbonylamine |
| 153 | CF₃ | 2-F-phenyl | (N-pyrrolidino)formylimino |
| 154 | CF₃ | 2-F-phenyl | (N-pyrrolidino)formyl-N-(methanesulfamoyl)imino |
| 155 | CF₃ | 2-CH₃O-phenyl | (N-pyrrolidino)formylimino |
| 156 | CF₃ | 2-CH₃O-phenyl | (N-pyrrolidino)formyl-N-(methanesulfamoyl)imino |
| 157 | CONH₂ | phenyl | 2-((Me)₂N-methyl)phenyl |
| 158 | CONH₂ | phenyl | 2-((Me)NH-methyl)phenyl |
| 159 | CONH₂ | phenyl | 2-(H₂N-methyl)phenyl |
| 160 | CONH₂ | phenyl | 2-HOCH₂-phenyl |
| 161 | CONH₂ | 2-F-phenyl | 2-((Me)₂N-methyl)phenyl |
| 162 | CONH₂ | 2-F-phenyl | 2-((Me)NH-methyl)phenyl |
| 163 | CONH₂ | 2-F-phenyl | 2-(H₂N-methyl)phenyl |
| 164 | CONH₂ | 2-F-phenyl | 2-HOCH₂-phenyl |
| 165 | CONH₂ | phenyl | 2-methylimidazol-1-yl |
| 166 | CONH₂ | phenyl | 2-ethylimidazol-1-yl |
| 167 | CONH₂ | phenyl | 2-((Me)₂N-methyl)imidazol-1-yl |
| 168 | CONH₂ | phenyl | 2-CH₃SO₂-imidazol-1-yl |
| 169 | CONH₂ | phenyl | 2-CH₃OCH₂-imidazol-1-yl |
| 170 | CONH₂ | 2-F-phenyl | 2-methylimidazol-1-yl |
| 171 | CONH₂ | 2-F-phenyl | 2-ethylimidazol-1-yl |
| 172 | CONH₂ | 2-F-phenyl | 2-((Me)₂N-methyl)imidazol-1-yl |
| 173 | CONH₂ | 2-F-phenyl | 2-CH₃SO₂-imidazol-1-yl |
| 174 | CONH₂ | 2-F-phenyl | 2-CH₃OCH₂-imidazol-1-y1 |
| 175 | CONH₂ | 2-Cl-phenyl | 2-methylimidazol-1-yl |
| 176 | CONH₂ | 2-Cl-phenyl | 2-ethylimidazol-1-yl |
| 177 | CONH₂ | 2-Cl-phenyl | 2-((Me)₂N-methyl)imidazol-1-yl |
| 178 | CONH₂ | 2-Cl-phenyl | 2-CH₃SO₂-imidazol-1-yl |
| 179 | CONH₂ | 2-Cl-phenyl | 2-CH₃OCH₂-imidazol-1-yl |
| 180 | CONH₂ | 2-(Me)₂N-phenyl | 2-methylimidazol-1-yl |
| 181 | CONH₂ | 2-(Me)₂N-phenyl | 2-ethylimidazol-1-yl |
| 182 | CONH₂ | 2-(Me)₂N-phenyl | 2-((Me)₂N-methyl)imidazol-1-yl |
| 183 | CONH₂ | 2-(Me)₂N-phenyl | 2-CH₃SO₂-imidazol-1-yl |
| 184 | CONH₂ | 2-(Me)₂N-phenyl | 2-CH₃OCH₂-imidazol-1-yl |
| 185 | CONH₂ | phenyl | N-methylimidazol-2-yl |
| 186 | CONH₂ | phenyl | 4-methylimidazol-5-yl |
| 187 | CONH₂ | phenyl | 5-CF₃-pyrazol-1-yl |
| 188 | CONH₂ | 2-F-phenyl | N-methylimidazol-2-yl |
| 189 | CONH₂ | 2-F-phenyl | 4-methylimidazol-5-yl |
| 190 | CONH₂ | 2-F-phenyl | 5-CF₃-pyrazol-1-yl |
| 191 | CONH₂ | phenyl | guanidino |
| 192 | CONH₂ | phenyl | 2-thiazolin-2-ylamine |
| 193 | CONH₂ | phenyl | N-methyl-2-imidazolin-2-yl |
| 194 | CONH₂ | phenyl | N-methyl-1,4,5,6-tetrahydropyrimid-2-yl |
| 195 | CONH₂ | phenyl | N-methylimidazol-2-ylthiol |
| 196 | CONH₂ | phenyl | t-butoxycarbonylamine |
| 197 | CONH₂ | phenyl | (N-pyrrolidino)formylimino |
| 198 | CONH₂ | phenyl | (N-pyrrolidino)formyl-N-(methanesulfamoyl)imino |
| 199 | CONH₂ | 2-F-phenyl | guanidino |
| 200 | CONH₂ | 2-F-phenyl | 2-thiazolin-2-ylamine |
| 201 | CONH₂ | 2-F-phenyl | N-methyl-2-imidazolin-2-yl |
| 202 | CONH₂ | 2-F-phenyl | N-methyl-1,4,5,6-tetrahydropyrimid-2-yl |
| 203 | CONH₂ | 2-F-phenyl | N-methylimidazol-2-ylthio |
| 204 | CONH₂ | 2-F-phenyl | t-butoxycarbonylamine |
| 205 | CONH₂ | 2-F-phenyl | (N-pyrrolidino)formylimino |
| 206 | CONH₂ | 2-F-phenyl | (N-pyrrolidino)formyl-N-(methanesulfamoyl)imino |
| 207 | CONH₂ | 2-CH₃O-phenyl | (N-pyrrolidino)formylimino |
| 208 | CONH₂ | 2-CH₃O-phenyl | (N-pyrrolidino)formyl-N-(methanesulfamoyl)imino |
| 209 | SCH₃ | phenyl | 2-((Me)₂N-methyl)phenyl |
| 210 | SCH₃ | phenyl | 2-((Me)NH-methyl)phenyl |
| 211 | SCH₃ | phenyl | 2-(H₂N-methyl)phenyl |
| 212 | SCH₃ | phenyl | 2-HOCH₂-phenyl |
| 213 | SCH₃ | 2-F-phenyl | 2-((Me)₂N-methyl)phenyl |
| 214 | SCH₃ | 2-F-phenyl | 2-((Me)NH-methyl)phenyl |
| 215 | SCH₃ | 2-F-phenyl | 2-(H₂N-methyl)phenyl |
| 216 | SCH₃ | 2-F-phenyl | 2-HOCH₂-phenyl |
| 217 | SCH₃ | phenyl | 2-methylimidazol-1-yl |
| 218 | SCH₃ | phenyl | 2-ethylimidazol-1-yl |
| 219 | SCH₃ | phenyl | 2-((Me)₂N-methyl)imidazol-1-yl |
| 220 | SCH₃ | phenyl | 2-CH₃SO₂-imidazol-1-yl |
| 221 | SCH₃ | phenyl | 2-CH₃OCH₂-imidazol-1-yl |
| 222 | SCH₃ | 2-F-phenyl | 2-methylimidazol-1-yl |
| 223 | SCH₃ | 2-F-phenyl | 2-ethylimidazol-1-yl |
| 224 | SCH₃ | 2-F-phenyl | 2-((Me)₂N-methyl)imidazol-1-yl |
| 225 | SCH₃ | 2-F-phenyl | 2-CH₃SO₂-imidazol-1-yl |
| 226 | SCH₃ | 2-F-phenyl | 2-CH₃OCH₂-imidazol-1-yl |
| 227 | SCH₃ | 2-Cl-phenyl | 2-methylimidazol-1-yl |
| 228 | SCH₃ | 2-Cl-phenyl | 2-ethylimidazol-1-yl |
| 229 | SCH₃ | 2-Cl-phenyl | 2-((Me)₂N-methyl)imidazol-1-yl |
| 230 | SCH₃ | 2-Cl-phenyl | 2-CH₃SO₂-imidazol-1-yl |
| 231 | SCH₃ | 2-Cl-phenyl | 2-CH₃OCH₂-imidazol-1-yl |
| 232 | SCH₃ | 2-(Me)₂N-phenyl | 2-methylimidazol-1-yl |
| 233 | SCH₃ | 2-(Me)₂N-phenyl | 2-ethylimidazol-1-yl |
| 234 | SCH₃ | 2-(Me)₂N-phenyl | 2-((Me)₂N-methyl)imidazol-1-yl |
| 235 | SCH₃ | 2-(Me)₂N-phenyl | 2-CH₃SO₂-imidazol-1-yl |
| 236 | SCH₃ | 2-(Me)₂N-phenyl | 2-CH₃OCH₂-imidazol-1-yl |
| 237 | SCH₃ | phenyl | N-methylimidazol-2-yl |
| 238 | SCH₃ | phenyl | 4-methylimidazol-5-yl |
| 239 | SCH₃ | phenyl | 5-CF₃-pyrazol-1-yl |
| 240 | SCH₃ | 2-F-phenyl | N-methylimidazol-2-yl |
| 241 | SCH₃ | 2-F-phenyl | 4-methylimidazol-5-yl |
| 242 | SCH₃ | 2-F-phenyl | 5-CF₃-pyrazol-1-yl |
| 243 | SCH₃ | phenyl | guanidino |
| 244 | SCH₃ | phenyl | 2-thiazolin-2-ylamine |
| 245 | SCH₃ | phenyl | N-methyl-2-imidazolin-2-yl |
| 246 | SCH₃ | phenyl | N-methyl-1,4,5,6-tetrahydropyrimid-2-yl |
| 247 | SCH₃ | phenyl | N-methylimidazol-2-ylthiol |
| 248 | SCH₃ | phenyl | t-butoxycarbonylamine |
| 249 | SCH₃ | phenyl | (N-pyrrolidino)formylimino |
| 250 | SCH₃ | phenyl | (N-pyrrolidino)formyl-N-(methanesulfamoyl)imino |
| 251 | SCH₃ | 2-F-phenyl | guanidino |
| 252 | SCH₃ | 2-F-phenyl | 2-thiazolin-2-ylamine |
| 253 | SCH₃ | 2-F-phenyl | N-methyl-2-imidazolin-2-yl |
| 254 | SCH₃ | 2-F-phenyl | N-methyl-1,4,5,6-tetrahydropyrimid-2-yl |
| 255 | SCH₃ | 2-F-phenyl | N-methylimidazol-2-ylthio |
| 256 | SCH₃ | 2-F-phenyl | t-butoxycarbonylamine |
| 257 | SCH₃ | 2-F-phenyl | (N-pyrrolidino)formylimino |
| 258 | SCH₃ | 2-F-phenyl | (N-pyrrolidino)formyl-N-(methanesulfamoyl)imino |
| 259 | SCH₃ | 2-CH₃O-phenyl | (N-pyrrolidino)formylimino |
| 260 | SCH₃ | 2-CH₃O-phenyl | (N-pyrrolidino)formyl-N-(methanesulfamoyl)imino |
| 261 | SO₂CH₃ | phenyl | 2-((Me)₂N-methyl)phenyl |
| 262 | SO₂CH₃ | phenyl | 2-((Me)NH-methyl)phenyl |
| 263 | SO₂CH₃ | phenyl | 2-(H₂N-methyl)phenyl |
| 264 | SO₂CH₃ | phenyl | 2-HOCH₂-phenyl |
| 265 | SO₂CH₃ | 2-F-phenyl | 2-((Me)₂N-methyl)phenyl |
| 266 | SO₂CH₃ | 2-F-phenyl | 2-((Me)NH-methyl)phenyl |
| 267 | SO₂CH₃ | 2-F-phenyl | 2-(H₂N-methyl)phenyl |
| 268 | SO₂CH₃ | 2-F-phenyl | 2-HOCH₂-phenyl |
| 269 | SO₂CH₃ | phenyl | 2-methylimidazol-1-yl |
| 270 | SO₂CH₃ | phenyl | 2-ethylimidazol-1-yl |
| 271 | SO₂CH₃ | phenyl | 2-((Me)₂N-methyl)imidazol-1-yl |
| 272 | SO₂CH₃ | phenyl | 2-CH₃SO₂-imidazol-1-yl |
| 273 | SO₂CH₃ | phenyl | 2-CH₃OCH₂-imidazol-1-yl |
| 274 | SO₂CH₃ | 2-F-phenyl | 2-methylimidazol-1-yl |
| 275 | SO₂CH₃ | 2-F-phenyl | 2-ethylimidazol-1-yl |
| 276 | SO₂CH₃ | 2-F-phenyl | 2-((Me)₂N-methyl)imidazol-1-yl |
| 277 | SO₂CH₃ | 2-F-phenyl | 2-CH₃SO₂-imidazol-1-yl |
| 278 | SO₂CH₃ | 2-F-phenyl | 2-CH₃OCH₂-imidazol-1-yl |
| 279 | SO₂CH₃ | 2-Cl-phenyl | 2-methylimidazol-1-yl |
| 280 | SO₂CH₃ | 2-Cl-phenyl | 2-ethylimidazol-1-yl |
| 281 | SO₂CH₃ | 2-Cl-phenyl | 2-((Me)₂N-methyl)imidazol-1-yl |
| 282 | SO₂CH₃ | 2-Cl-phenyl | 2-CH₃SO₂-imidazol-1-yl |
| 283 | SO₂CH₃ | 2-Cl-phenyl | 2-CH₃OCH₂-imidazol-1-yl |
| 284 | SO₂CH₃ | 2-(Me)₂N-phenyl | 2-methylimidazol-1-yl |
| 285 | SO₂CH₃ | 2-(Me)₂N-phenyl | 2-ethylimidazol-1-yl |
| 286 | SO₂CH₃ | 2-(Me)₂N-phenyl | 2-((Me)₂N-methyl)imidazol-1-yl |
| 287 | SO₂CH₃ | 2-(Me)₂N-phenyl | 2-CH₃SO₂-imidazol-1-yl |
| 288 | SO₂CH₃ | 2-(Me)₂N-phenyl | 2-CH₃OCH₂-imidazol-1-yl |
| 289 | SO₂CH₃ | phenyl | N-methylimidazol-2-yl |
| 290 | SO₂CH₃ | phenyl | 4-methylimidazol-5-yl |
| 291 | SO₂CH₃ | phenyl | 5-CF₃-pyrazol-1-yl |

-continued

| Ex# | R$^{1b}$ | A | B |
|---|---|---|---|
| 292 | SO$_2$CH$_3$ | 2-F-phenyl | N-methylimidazol-2-yl |
| 293 | SO$_2$CH$_3$ | 2-F-phenyl | 4-methylimidazol-5-yl |
| 294 | SO$_2$CH$_3$ | 2-F-phenyl | 5-CF$_3$-pyrazol-1-yl |
| 295 | SO$_2$CH$_3$ | phenyl | guanidino |
| 296 | SO$_2$CH$_3$ | phenyl | 2-thiazolin-2-ylamine |
| 297 | SO$_2$CH$_3$ | phenyl | N-methyl-2-imidazolin-2-yl |
| 298 | SO$_2$CH$_3$ | phenyl | N-methyl-1,4,5,6-tetrahydropyrimid-2-yl |
| 299 | SO$_2$CH$_3$ | phenyl | N-methylimidazol-2-ylthiol |
| 300 | SO$_2$CH$_3$ | phenyl | t-butoxycarbonylamine |
| 301 | SO$_2$CH$_3$ | phenyl | (N-pyrrolidino)formylimino |
| 302 | SO$_2$CH$_3$ | phenyl | (N-pyrrolidino)formyl-N-(methanesulfamoyl)imino |
| 303 | SO$_2$CH$_3$ | 2-F-phenyl | guanidino |
| 304 | SO$_2$CH$_3$ | 2-F-phenyl | 2-thiazolin-2-ylamine |
| 305 | SO$_2$CH$_3$ | 2-F-phenyl | N-methyl-2-imidazolin-2-yl |
| 306 | SO$_2$CH$_3$ | 2-F-phenyl | N-methyl-1,4,5,6-tetrahydropyrimid-2-yl |
| 307 | SO$_2$CH$_3$ | 2-F-phenyl | N-methylimidazol-2-ylthio |
| 308 | SO$_2$CH$_3$ | 2-F-phenyl | t-butoxycarbonylamine |
| 309 | SO$_2$CH$_3$ | 2-F-phenyl | (N-pyrrolidino)formylimino |
| 310 | SO$_2$CH$_3$ | 2-F-phenyl | (N-pyrrolidino)formyl-N-(methanesulfamoyl)imino |
| 311 | SO$_2$CH$_3$ | 2-CH$_3$O-phenyl | (N-pyrrolidino)formylimino |
| 312 | SO$_2$CH$_3$ | 2-CH$_3$O-phenyl | (N-pyrrolidino)formyl-N-(methanesulfamoyl)imino |
| 313 | NHSO$_2$CH$_3$ | phenyl | 2-((Me)$_2$N-methyl)phenyl |
| 314 | NHSO$_2$CH$_3$ | phenyl | 2-((Me)NH-methyl)phenyl |
| 315 | NHSO$_2$CH$_3$ | phenyl | 2-(H$_2$N-methyl)phenyl |
| 316 | NHSO$_2$CH$_3$ | phenyl | 2-HOCH$_2$-phenyl |
| 317 | NHSO$_2$CH$_3$ | 2-F-phenyl | 2-((Me)$_2$N-methyl)phenyl |
| 318 | NHSO$_2$CH$_3$ | 2-F-phenyl | 2-((Me)NH-methyl)phenyl |
| 319 | NHSO$_2$CH$_3$ | 2-F-phenyl | 2-(H$_2$N-methyl)phenyl |
| 320 | NHSO$_2$CH$_3$ | 2-F-phenyl | 2-HOCH$_2$-phenyl |
| 321 | NHSO$_2$CH$_3$ | phenyl | 2-methylimidazol-1-yl |
| 322 | NHSO$_2$CH$_3$ | phenyl | 2-ethylimidazol-1-yl |
| 323 | NHSO$_2$CH$_3$ | phenyl | 2-((Me)$_2$N-methyl)imidazol-1-yl |
| 324 | NHSO$_2$CH$_3$ | phenyl | 2-CH$_3$SO$_2$-imidazol-1-yl |
| 325 | NHSO$_2$CH$_3$ | phenyl | 2-CH$_3$OCH$_2$-imidazol-1-yl |
| 326 | NHSO$_2$CH$_3$ | 2-F-phenyl | 2-methylimidazol-1-yl |
| 327 | NHSO$_2$CH$_3$ | 2-F-phenyl | 2-ethylimidazol-1-yl |
| 328 | NHSO$_2$CH$_3$ | 2-F-phenyl | 2-((Me)$_2$N-methyl)imidazol-1-yl |
| 329 | NHSO$_2$CH$_3$ | 2-F-phenyl | 2-CH$_3$SO$_2$-imidazol-1-yl |
| 330 | NHSO$_2$CH$_3$ | 2-F-phenyl | 2-CH$_3$OCH$_2$-imidazol-1-yl |
| 331 | NHSO$_2$CH$_3$ | 2-Cl-phenyl | 2-methylimidazol-1-yl |
| 332 | NHSO$_2$CH$_3$ | 2-Cl-phenyl | 2-ethylimidazol-1-yl |
| 333 | NHSO$_2$CH$_3$ | 2-Cl-phenyl | 2-((Me)$_2$N-methyl)imidazol-1-yl |
| 334 | NHSO$_2$CH$_3$ | 2-Cl-phenyl | 2-CH$_3$SO$_2$-imidazol-1-yl |
| 335 | NHSO$_2$CH$_3$ | 2-Cl-phenyl | 2-CH$_3$OCH$_2$-imidazol-1-yl |
| 336 | NHSO$_2$CH$_3$ | 2-(Me)$_2$N-phenyl | 2-methylimidazol-1-yl |
| 337 | NHSO$_2$CH$_3$ | 2-(Me)$_2$N-phenyl | 2-ethylimidazol-1-yl |
| 338 | NHSO$_2$CH$_3$ | 2-(Me)$_2$N-phenyl | 2-((Me)$_2$N-methyl)imidazol-1-yl |
| 339 | NHSO$_2$CH$_3$ | 2-(Me)$_2$N-phenyl | 2-CH$_3$SO$_2$-imidazol-1-yl |
| 340 | NHSO$_2$CH$_3$ | 2-(Me)$_2$N-phenyl | 2-CH$_3$OCH$_2$-imidazol-1-yl |
| 341 | NHSO$_2$CH$_3$ | phenyl | N-methylimidazol-2-yl |
| 342 | NHSO$_2$CH$_3$ | phenyl | 4-methylimidazol-5-yl |
| 343 | NHSO$_2$CH$_3$ | phenyl | 5-CF$_3$-pyrazol-1-yl |
| 344 | NHSO$_2$CH$_3$ | 2-F-phenyl | N-methylimidazol-2-yl |
| 345 | NHSO$_2$CH$_3$ | 2-F-phenyl | 4-methylimidazol-5-yl |
| 346 | NHSO$_2$CH$_3$ | 2-F-phenyl | 5-CF$_3$-pyrazol-1-yl |
| 347 | NHSO$_2$CH$_3$ | phenyl | guanidino |
| 348 | NHSO$_2$CH$_3$ | phenyl | 2-thiazolin-2-ylamine |
| 349 | NHSO$_2$CH$_3$ | phenyl | N-methyl-2-imidazolin-2-yl |
| 350 | NHSO$_2$CH$_3$ | phenyl | N-methyl-1,4,5,6-tetrahydropyrimid-2-yl |
| 351 | NHSO$_2$CH$_3$ | phenyl | N-methylimidazol-2-ylthiol |
| 352 | NHSO$_2$CH$_3$ | phenyl | t-butoxycarbonylamine |
| 353 | NHSO$_2$CH$_3$ | phenyl | (N-pyrrolidino)formylimino |
| 354 | NHSO$_2$CH$_3$ | phenyl | (N-pyrrolidino)formyl-N-(methanesulfamoyl)imino |
| 355 | NHSO$_2$CH$_3$ | 2-F-phenyl | guanidino |
| 356 | NHSO$_2$CH$_3$ | 2-F-phenyl | 2-thiazolin-2-ylamine |
| 357 | NHSO$_2$CH$_3$ | 2-F-phenyl | N-methyl-2-imidazolin-2-yl |
| 358 | NHSO$_2$CH$_3$ | 2-F-phenyl | N-methyl-1,4,5,6-tetrahydropyrimid-2-yl |
| 359 | NHSO$_2$CH$_3$ | 2-F-phenyl | N-methylimidazol-2-ylthio |
| 360 | NHSO$_2$CH$_3$ | 2-F-phenyl | t-butoxycarbonylamine |
| 361 | NHSO$_2$CH$_3$ | 2-F-phenyl | (N-pyrrolidino)formylimino |
| 362 | NHSO$_2$CH$_3$ | 2-F-phenyl | (N-pyrrolidino)formyl-N-(methanesulfamoyl)imino |
| 363 | NHSO$_2$CH$_3$ | 2-CH$_3$O-phenyl | (N-pyrrolidino)formylimino |
| 364 | NHSO$_2$CH$_3$ | 2-CH$_3$O-phenyl | (N-pyrrolidino)formyl-N-(methanesulfamoyl)imino |

Utility

The compounds of this invention are useful as anticoagulants for the treatment or prevention of thromboembolic disorders in mammals. The term "thromboembolic disorders" as used herein includes arterial or venous cardiovascular or cerebrovascular thromboembolic disorders, including, for example, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, cerebral embolism, kidney embolisms, and pulmonary embolisms. The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Kabi Pharmacia, Franklin, Ohio) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis was determined at 25° C. using the method of Lineweaver and Burk. Values of $K_i$ were determined by allowing 0.2–0.5 nM human factor Xa (Enzyme Research Laboratories, South Bend, IN) to react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values:

$$(v_o - v_s)/v_s = I/(K_i(1+S/K_m))$$

where:

$v_o$ is the velocity of the control in the absence of inhibitor;

$v_s$ is the velocity in the presence of inhibitor;

I is the concentration of inhibitor;

$K_i$ is the dissociation constant of the enzyme:inhibitor complex;

S is the concentration of substrate;

$K_m$ is the Michaelis constant.

Using the methodology described above, a number of compounds of the present invention were found to exhibit a $K_i$ of ≦15 µM, thereby confirming the utility of the compounds of the present invention as effective Xa inhibitors.

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing which contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The ID50 values (dose which produces 50% inhibition of thrombus formation) are estimated by linear regression.

The compounds of formula (I) may also be useful as inhibitors of serine proteases, notably human thrombin, plasma kallikrein and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 265, 18289–18297 (1990), herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20 M NaCl, and 0.5% PEG 6000, was incubated with various substrate concentrations ranging from 0.20 to 0.02 mM. After 25 to 30 minutes of incubation, thrombin activity was assayed by monitoring the rate of increase in absorbance at 405 nm which arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than 15 μm, thereby confirming the utility of the compounds of the present invention as effective Xa inhibitors.

The compounds of the present invention can be administered alone or in combination with one or more additional therapeutic agents. These include other anti-coagulant or coagulation inhibitory agents, anti-platelet or platelet inhibitory agents, thrombin inhibitors, or thrombolytic or fibrinolytic agents.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the,disease.

By "administered in combination" or "combination therapy" it is meant that the compound of Formula I and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Other anticoagulant agents (or coagulation inhibitory agents) that may be used in combination with the compounds of this invention include warfarin and heparin, as well as other factor Xa inhibitors such as those described in the publications identified above under Background of the Invention.

The term anti-platelet agents (or platelet inhibitory agents), as used herein, denotes agents that inhibit platelet function such as by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam are preferred. Other suitable anti-platelet agents include ticlopidine, including pharmaceutically acceptable salts or prodrugs thereof. Ticlopidine is also a preferred compound since it is known to be gentle on the gastro-intestinal tract in use. Still other suitable platelet inhibitory agents include IIb/IIIa antagonists, thromboxane-A2-receptor antagonists and thromboxane-A2-synthetase inhibitors, as well as pharmaceutically acceptable salts or prodrugs thereof.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and European Patent Application Publication Number 293 881 A2, the disclosures of which are hereby incorporated herein by reference. Other suitable boroarginine derivatives and boropeptide thrombin inhibitors include those disclosed in PCT Application Publication Number 92/07869 and European Patent Application Publication Number 471,651 A2, the disclosures of which are hereby incorporated herein by reference.

The term thrombolytics (or fibrinolytic) agents (or thrombolytics or fibrinolytics), as used herein, denotes agents that lyse blood clots (thrombi). Such agents include tissue plasminogen activator, anistreplase, urokinase or streptokinase, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Administration of the compounds of Formula I of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but no compound of the present invention, then one would conclude factor Xa was present.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient,and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of Formula I are administered in combination with an anti-platelet agent, by way of general guidance, typically a daily dosage may be about 0.01 to 25 milligrams of the compound of Formula I and about 50 to 150 milligrams of the anti-platelet agent, preferably about 0.1 to 1 milligrams of the compound of Formula I and about 1 to 3 milligrams of antiplatelet agents, per kilogram of patient body weight.

Where the compounds of Formula I are adminstered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Obviously, numerous modifications and variations of the present invention are possible in light of the above teachings. It is therefore to be understood that within the scope of the appended claims, the invention may be practiced otherwise than as specifically described herein.

What is claimed is:

1. A compound of formula I:

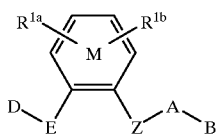

or a stereoisomer or pharmaceutically acceptable salt form thereof, wherein;

ring M contains from 0–1 N atoms;

D is selected from CN, C(=NR$^7$)NR$^8$R$^9$, NHC(=NR$^7$)NR$^8$R$^9$, NR$^8$CH(=NR$^7$), C(O)NR$^8$R$^9$, and (CR$^8$R$^9$)$_t$NR$^8$R$^9$;

E is selected from phenyl, 2-pyridyl, 4-pyridyl, pyrimidyl, and piperidinyl substituted with 1 R;

R is selected from H, F, Cl, Br, I, OR$^3$, SR$^3$, CO$_2$R$^3$, NO$_2$, and CH$_2$OR$^3$, and (CR$^8$R$^9$)$_t$NR$^8$R$^9$;

with the proviso that if t is equal to 0 and E is selected from phenyl, then R is selected from F, Cl, Br, and I;

alternatively, E and R combine to form methylenedioxy or ethylenedioxy;

Z is selected from a bond, C$_{1-4}$ alkylene, (CH$_2$)$_r$O(CH$_2$)$_r$, (CH$_2$)$_r$NR$^3$(CH$_2$)$_r$, (CH$_2$)$_r$C(O) (CH$_2$)$_r$, (CH$_2$)$_r$C(O)O(CH$_2$)$_r$, (CH$_2$)$_r$OC(O)(CH$_2$)$_r$, (CH$_2$)$_r$C(O)NR$^3$(CH$_2$)$_r$, (CH$_2$)$_r$NR$^3$C(O)(CH$_2$)$_r$, (CH$_2$)$_r$OC(O)O(CH$_2$)$_r$, (CH$_2$)$_r$OC(O)NR$^3$(CH$_2$)$_r$, (CH$_2$)$_r$NR$^3$C(O)O(CH$_2$)$_r$, (CH$_2$)$_r$NR$^3$C(O)NR$^3$(CH$_2$)$_r$, (CH$_2$)$_r$S(O)$_p$(CH$_2$)$_r$, (CH$_2$)$_r$SO$_2$NR$^3$(CH$_2$)$_r$, (CH$_2$)$_r$NR$^3$SO2(CH$_2$)$_r$, and (CH$_2$)$_r$NR$^3$SO$_2$NR$^3$(CH$_2$)$_r$, provided that Z does not form a N—N, N—O, N—S, NCH$_2$N, NCH$_2$O, or NCH$_2$S bond with ring M or group A;

R$^{1a}$ and R$^{1b}$ are independently absent or selected from —(CH$_2$)$_r$—R$^{1'}$, —CH=CH—R$^{1'}$, NCH$_2$R$^{1'}$, OCH$_2$R$^{1'}$, SCH$_2$R$^{1'}$, NH(CH$_2$)$_2$(CH$_2$)$_r$R$^{1'}$, O(CH$_2$)$_2$(CH$_2$)$_r$R$^{1'}$, and S(CH$_2$)$_2$(CH$_2$)$_r$R$^{1'}$;

alternatively, R$^{1a}$ and R$^{1b}$, when attached to adjacent carbon atoms, together with the atoms to which they are attached form a 5–8 membered saturated, partially saturated or unsaturated ring substituted with 0–2 R$^4$ and which contains from 0–2 heteroatoms selected from the group consisting of N, O, and S;

alternatively, when Z is C(O)NH and R$^{1a}$ is attached to a ring carbon adjacent to Z, then R$^{1a}$ is a C(O) which replaces the amide hydrogen of Z to form a cyclic imide;

R$^{1'}$ is selected from H, C$_{1-3}$ alkyl, F, Cl, Br, I, —CN, —CHO, (CF$_2$)$_r$CF$_3$, (CH$_2$)$_r$OR$^2$, NR$^2$R$^{2a}$, C(O) R$^{2c}$, OC(O)R$^2$, (CF$_2$)$_r$CO$_2$R$^{2c}$, S(O)$_p$R$^{2b}$, NR$^2$(CH$_2$)$_r$OR$^2$, CH(=NR$^{2c}$)NR$^2$R$^{2a}$, NR$^2$C(O)R$^{2b}$, NR$^2$C(O)NHR$^{2b}$, NR$^2$C(O)$_2$R$^{2a}$, OC(O)NR$^{2a}$R$^{2b}$, C(O)NR$^2$R$^{2a}$, C(O)NR$^2$(CH$_2$)$_r$OR$^2$, SO$_2$NR$^2$R$^{2a}$, NR$^2$SO$_2$R$^{2b}$, C$_{3-6}$ carbocyclic residue substituted with 0–2 R$^4$, and 5–10 membered heterocyclic system containing from 1–4 heteroatoms selected from the group consisting of N, O, and S substituted with 0–2 R$^4$;

R$^{1''}$ is selected from H, CH(CH$_2$OR$^2$)$_2$, C(O)R$^{2c}$, C(O)NR$^2$R$^{2a}$, S(O)R$^{2b}$, S(O)$_2$R$^{2b}$, and SO$_2$NR$^2$R$^{2a}$;

R$^2$, at each occurrence, is selected from H, CF$_3$, C$_{1-6}$ alkyl, benzyl, C$_{3-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

R$^{2a}$, at each occurrence, is selected from H, CF$_3$, C$_{1-6}$ alkyl, benzyl, phenethyl, C$_{3-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

R$^{2b}$, at each occurrence, is selected from CF$_3$, C$_{1-4}$ alkoxy, C$_{1-6}$ alkyl, benzyl, C$_{3-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

R$^{2c}$, at each occurrence, is selected from CF$_3$, OH, C$_{1-4}$ alkoxy, C$_{1-6}$ alkyl, benzyl, C$_{3-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

alternatively, R$^2$ and R$^{2a}$, together with the atom to which they are attached, combine to form a 5 or 6 membered saturated, partially saturated or unsaturated ring substituted with 0–2 R$^{4b}$ and containing from 0–1 additional heteroatoms selected from the group consisting of N, O, and S;

R$^3$, at each occurrence, is selected from H, C$_{1-4}$ alkyl, and phenyl;

R$^{3a}$, at each occurrence, is selected from H, C$_{1-4}$ alkyl, and phenyl;

R$^{3b}$, at each occurrence, is selected from H, C$_{1-4}$ alkyl, and phenyl;

R$^{3c}$, at each occurrence, is selected from C$_{1-4}$ alkyl, and phenyl;

A is selected from:

C$_{3-10}$ carbocyclic residue substituted with 0–2 R$^{4f}$, and 5–10 membered heterocyclic system containing from 1–4 heteroatoms selected from the group consisting of N, O, and S substituted with 0–2 R$^4$];

B is selected from: H, Y, and X—Y;

X is selected from C$_{1-4}$ alkylene, —CR$^2$(CR$^2$R$^{2b}$)(CH$_2$)$_r$—, —C(O)—, —C(=NR$^{1''}$)—, —CR$^2$(NR$^{1''}$R$^2$)—, —CR$^2$(OR$^2$)—, —CR$^2$(SR$^2$)—, —C(O)CR$^2$R$^{2a}$—, —CR$^2$R$^{2a}$C(O), —S(O)$_p$—, —S(O)$_p$CR$^2$R$^{2a}$—, —CR$^2$R$^{2a}$S(O)$_p$—, —S(O)$_2$NR$^2$—, —NR$^2$S(O)$_2$—, —NR$^2$S(O)$_2$CR$^2$R$^{2a}$—, —CR$^2$R$^{2a}$S(O)$_2$NR$^2$—, —NR$^2$S(O)$_2$NR$^2$—, —C(O)NR$^2$—, —NR$^2$C(O)—, —C(O)NR$^{2c}$R$^2$R$^{2a}$—, —NR$^2$C(O)CR$^2$R$^{2a}$—, —CR$^2$R$^{2a}$C(O)NR$^2$—, —CR$^2$R$^{2a}$NR$^2$C(O)—, —NR$^2$C(O)O—, —OC(O)NR$^2$—, —NR$^2$C(O)NR$^2$—, —NR$^2$—, —NR$^{2c}$R$^2$R$^{2a}$—, —CR$^2$R$^{2a}$NR$^2$—, O, —CR$^2$R$^{2a}$O—, and —OCR$^2$R$^{2a}$—;

Y is selected from:

(CH$_2$)$_r$NR$^2$R$^{2a}$, provided that X—Y do not form a N—N, O—N, or S—N bond, C$_{3-10}$ carbocyclic residue substituted with 0–2 R$^{4a}$, and 5–10 membered heterocyclic system containing from 1–4 heteroatoms selected from the group consisting of N, O, and S substituted with 0–2 R$^{4a}$;

R$^4$, at each occurrence, is selected from H, =O, (CH$_2$)$_r$R$^2$, F, Cl, Br, I, C$_{1-4}$ alkyl, —CN, NO$_2$, (CH$_2$)

$_r$ NR$^2$R$^{2a}$, (CH$_2$)$_r$C(O)R$^{2c}$, NR$^2$C(O)R$^{2b}$, C(O)
NR$^2$R$^{2a}$, NR$^2$C(O)NR$^2$R$^{2a}$, CH(=NR$^2$)NR$^2$R$^{2a}$,
CH(=NS(O)$_2$ R$^5$)NR$^2$R$^{2a}$, NHC(=NR$^2$)NR$^2$R$^{2a}$,
C(O)NHC(=NR$^2$)NR$^2$R$^{2a}$, SO$_2$NR$^2$R$^{2a}$,
NR$^2$SO$_2$NR$^2$R$^{2a}$, NR$^2$SO$_2$-C$_{1-4}$ alkyl, NR$^2$SO$_2$R$^5$,
S(O)$_p$R$^5$, (CF$_2$)$_r$CF$_3$, NCH$_2$R$^{1''}$, OCH$_2$R$^{1''}$, SCH$_2$R$^{1''}$,
N(CH$_2$)$_2$(CH$_2$)$_r$R$^{1'}$, O(CH$_2$)$_2$(CH$_2$)$_r$R$^{1'}$, and S(CH$_2$)$_2$
(CH$_2$)$_r$R$^{1'}$;

alternatively, one R$^4$ is a 5–6 membered aromatic heterocycle containing from 1–4 heteroatoms selected from the group consisting of N, O, and S;

R$^{4a}$, at each occurrence, is selected from H, =O, (CH$_2$)$_r$ OR$^2$, (CH$_2$)$_r$—F, (CH$_2$)$_r$—Br, (CH$_2$)$_r$—Cl, I, C$_{1-4}$ alkyl, —CN, NO$_2$, (CH$_2$) rNR$^2$R$^{2a}$, (CH$_2$)$_r$NR$^2$R$^{2b}$, (CH$_2$)$_r$C(O)R$^{2c}$, NR$^2$C(O)R$^{2b}$, C(O)NR$^2$R$^{2a}$, C(O)NH (CH$_2$)$_2$NR$^2$R$^{2a}$, NR$^2$C(O)NR$^2$R$^{2a}$, CH(=NR$^2$) NR$^2$R$^{2a}$, NHC(=NR$^2$)NR$^2$R$^{2a}$, SO$_2$NR$^2$R$^{2a}$, NR$^2$SO$_2$NR$^2$SO$_2$R$^5$, NR$^2$SO$_2$—C$_{1-4}$ alkyl, C(O) NHSO$_2$—C$_{1-4}$ alkyl, NR$^2$SO$_2$R$^5$, S(O)$_p$R$^5$, and (CF$_2$)$_r$ CF$_3$;

alternatively, one R$^{4a}$ is a 5–6 membered aromatic heterocycle containing from 1–4 heteroatoms selected from the group consisting of N, O, and S and substituted with 0–1 R$^5$;

R$^{4b}$, at each occurrence, is selected from H, =O, (CH$_2$)$_r$ OR$^3$, F, Cl, Br, I, C$_{1-4}$ alkyl, —CN, NO$_2$, (CH$_2$)$_r$ NR$^3$R$^{3a}$, (CH$_2$)$_r$C(O)R$^3$, (CH$_2$)$_r$C(O)OR$^{3c}$, NR$^3$C(O) R$^{3a}$, C(O)NR$^3$R$^{3a}$, NR$^3$C(O)NR$^3$R$^{3a}$, CH(=NR$^3$) NR$^3$R$^{3a}$, NH$^3$C(=NR$^3$)NR$^3$R$^{3a}$, SO$_2$NR$^3$R$^{3a}$, NR$^3$SO$_2$NR$^3$R$^{3a}$, NR$^3$SO$_2$-C$_{1-4}$ alkyl, NR$^3$SO$_2$CF$_3$, NR$^3$SO$_2$-phenyl, S(O)$_p$CF$_3$, S(O)$_p$-C$_{1-4}$ alkyl, S(O)$_p$-phenyl, and (CF$_2$)$_r$CF$_3$;

R$^5$, at each occurrence, is selected from CF$_3$, C$_{1-6}$ alkyl, phenyl substituted with 0–2 R$^6$, and benzyl substituted with 0–2 R$^6$;

R$^6$, at each occurrence, is selected from H, OH, (CH$_2$)$_r$ OR$^2$, F, Cl, Br, I, C$_{1-4}$ alkyl, CN, NO$_2$, (CH$_2$)$_r$NR$^2$R$^{2a}$, (CH$_2$)$_r$C(O)R$^{2b}$, NR$^2$C(O)R$^{2b}$, NR$^2$C(O)NR$^2$R$^{2a}$, CH(=NH)NH$_2$, NHC(=NH)NH$_2$, SO$_2$NR$^2$R$^{2a}$, NR$^2$SO$_2$NR$^2$R$^{2a}$, and NR$^2$SO$_2$C$_{1-4}$ alkyl;

R$^7$, at each occurrence, is selected from H, OH, C$_{1-6}$ alkyl, C$_{1-6}$ alkylcarbonyl, C$_{1-6}$ alkoxy, C$_{1-4}$ alkoxycarbonyl, (CH$_2$)$_n$-phenyl, C$_{6-10}$ aryloxy, C$_{6-10}$ aryloxycarbonyl, C$_{6-10}$ arylmethylcarbonyl, C$_{1-4}$ alkylcarbonyloxy C$_{1-4}$ alkoxycarbonyl, C$_{6-10}$ arylcarbonyloxy C$_{1-4}$ alkoxycarbonyl, C$_{1-6}$ alkylaminocarbonyl, phenylaminocarbonyl, and phenyl-C$_{1-4}$ alkoxycarbonyl;

R$^8$, at each occurrence, is selected from H, C$_{1-6}$ alkyl and (CH$_2$)$_n$-phenyl;

alternatively, R$^7$ and R$^8$ combine to form a 5 or 6 membered saturated, ring which contains from 0–1 additional heteroatoms selected from the group consisting of N, O, and S;

R$^9$, at each occurrence, is selected from H, C$_{1-6}$ alkyl and (CH$_2$)$_n$-phenyl;

n is selected from 0, 1, 2, and 3;

m is selected from 0, 1, and 2;

p is selected from 0, 1, and 2;

r is selected from 0, 1, 2, and 3;

s is selected from 0, 1, and 2; and, t is selected from 0 and 1.

2. A compound according to claim 1, wherein is of formulae Ia–Ie:

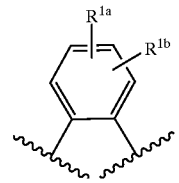

a

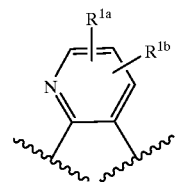

b

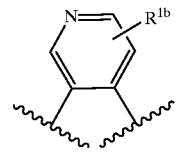

c

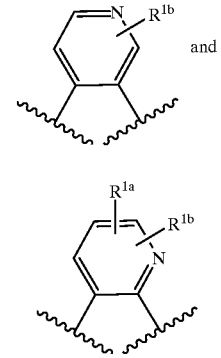

d and e wherein:

Z is selected from a bond, CH$_2$O, OCH$_2$, CH$_2$NH, NHCH$_2$, CH$_2$C(O), C(O)CH$_2$, C(O)NH, C(O)NH, CH$_2$S(O)$_2$, S(O)$_2$(CH$_2$), SO$_2$NH, and SO$_2$NH;

B is selected from: Y, X—Y, and NR$^2$R$^{2a}$;

Y is selected from one of the following carbocyclic and heterocyclic systems which are substituted with 0–2 R$^{4a}$;

phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, 1,3,4-triazole, benzofuran, benzothiofuran, indole, benzimidazole, benzoxazole, benzthiazole, indazole, benzisoxazole, benzisothiazole, and isoindazole;

Y may also be selected from the following bicyclic heteroaryl ring systems:

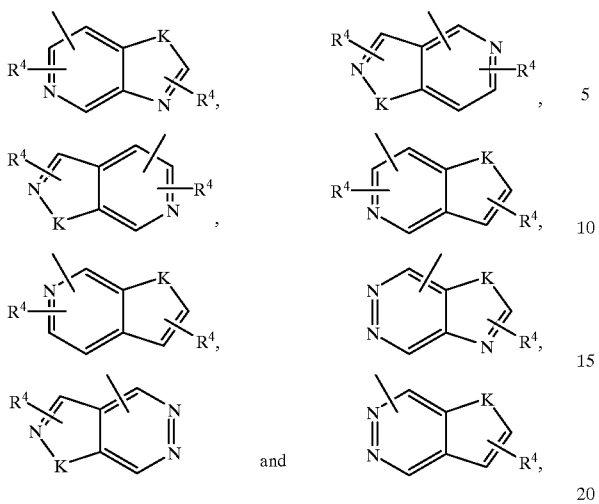

K is selected from O, S, NH, and N.

3. A compound according to claim 2, wherein is of formulae:

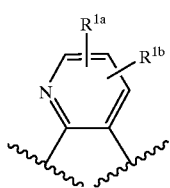

b wherein:

D is selected from C(=NR$^7$)NR$^8$R$^9$ and (CR$^8$R$^9$)$_r$NR$^8$R$^9$;

R is selected from H, F, Cl, OR$^3$, CH$_2$OR$^3$, CH$_2$NH$_2$;

A is selected from:

C$_{5-6}$ carbocyclic residue substituted with 0–2 R$^4$;

Y is selected from one of the following carbocyclic and heterocyclic systems which are substituted with 0–2 R$^{4a}$;

phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, benzimidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, and 1,3,4-triazole.

4. A compound according to claim 3, wherein:

E is phenyl;

D is selected from C(=NH)NH$_2$ and CH$_2$NH$_2$;

R is selected from H, F, Cl, and Br;

A is selected from:

C$_{5-6}$ carbocyclic residue substituted with 0–2 R$^4$;

Y is selected from one of the following carbocyclic and heterocyclic systems which are substituted with 0–2 R$^{4a}$;

phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, benzimidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, and 1,3,4-triazole;

R$^2$, at each occurrence, is selected from H, CF$_3$, C$_{1-6}$ alkyl, benzyl, C$_{5-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

R$^{2a}$, at each occurrence, is selected from H, CF$_3$, C$_{1-6}$ alkyl, benzyl, phenethyl, C$_{5-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

R$^{2b}$, at each occurrence, is selected from CF$_3$, C$_{1-4}$ alkoxy, C$_{1-6}$ alkyl, benzyl, C$_{5-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

R$^{2c}$, at each occurrence, is selected from CF$_3$, OH, C$_{1-4}$ alkoxy, C$_{1-6}$ alkyl, benzyl, C$_{5-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

alternatively, R$^2$ and R$^{2a}$, together with the atom to which they are attached, combine to form a ring selected from imidazolyl, morpholino, piperazinyl, pyridyl, and pyrrolidinyl, substituted with 0–2 R$^{4b}$;

R$^4$, at each occurrence, is selected from H, =O, OR$^2$, CH$_2$OR$^2$, F, Cl, C$_{1-4}$ alkyl, NR$^2$R$^{2a}$, CH$_2$NR$^2$R$^{2a}$, C(O)R$^{2c}$, CH$_2$C(O)R$^{2c}$, C(O)NR$^2$R$^{2a}$, CH(=NR$^2$)NR$^2$R$^{2a}$, CH(=NS(O)$_2$R$^5$)NR$^2$R$^{2a}$, SO$_2$NR$^2$R$^{2a}$, NR$^2$SO$_2$-C$_{1-4}$ alkyl, S(O)$_2$R$^5$, and CF$_3$ provided that if B is H, then R$^4$ is other than tetrazole, C(O)-alkoxy, and C(O)NR$^2$R$^{2a}$;

R$^{4a}$, at each occurrence, is selected from H, =O, (CH$_2$)$_r$OR$^2$, F, Cl, C$_{1-4}$ alkyl, NR$^2$R$^{2a}$, CH$_2$NR$^2$R$^{2a}$, NR$^2$R$^{2b}$, CH$_2$NR$^2$R$^{2b}$, (CH$_2$)$_r$C(O)R$^{2c}$, NR$^2$C(O) R$^{2b}$, C(O) NR$^2$R$^{2a}$, C(O)NH(CH$_2$)$_2$NR$^2$R$^{2a}$, NR$^2$C(O)NR$^2$R$^{2a}$, SO$_2$NR$^2$R$^{2a}$, S(O)$_2$R$^5$, and CF$_3$; and, R$^{4b}$, at each occurrence, is selected from H, =O, (CH$_2$)$_r$OR$^3$, F, Cl, C$_{1-4}$ alkyl, NR$^3$R$^{3a}$, CH$_2$NR$^3$R$^{3a}$, C(O)R$^3$, CH$_2$C(O)R$^3$, C(O)OR$^{3c}$, C(O)NR$^3$R$^{3a}$, CH(=NR$^3$) NR$^3$R$^{3a}$, SO$_2$NR$^3$R$^{3a}$, NR$^3$SO$_2$-C$_{1-4}$ alkyl, NR$^3$SO$_2$CF$_3$, NR$^3$SO$_2$-phenyl, S(O)$_2$CF$_3$, S(O)$_2$-C$_{1-4}$ alkyl, S(O)$_2$-phenyl, and CF$_3$.

5. A compound according to claim 1, wherein the compound is selected from:

N-(2'-Aminosulfonyl-[1,1']biphen-4-yl)-2-(3'-amidinophenyl)nicotinamide;

N-[5-(2-aminosulfonyl)phenylpyrid-2-yl]-2-(3'-amidinophenyl)nicotinamide;

N-[5-(2-t-butylaminosulfonyl)phenylpyrid-2-yl]-2-(3'-amidinophenyl)nicotinamide; and, N-[5-(2-aminosulfonyl)phenylpyrid-2-yl]-2-(3'-carboxamidophenyl)nicotinamide;

or a pharmaceutically acceptable salt thereof.

6. A pharmaceutical composition, comprising: a pharmaceutically acceptable carrier and a therapeutically effective amount of a compound according to claim 1 or a pharmaceutically acceptable salt thereof.

7. A pharmaceutical composition, comprising: a pharmaceutically acceptable carrier and a therapeutically effective amount of a compound according to claim 2 or a pharmaceutically acceptable salt thereof.

8. A pharmaceutical composition, comprising: a pharmaceutically acceptable carrier and a therapeutically effective amount of a compound according to claim 3 or a pharmaceutically acceptable salt thereof.

9. A pharmaceutical composition, comprising: a pharmaceutically acceptable carrier and a therapeutically effective amount of a compound according to claim 4 or a pharmaceutically acceptable salt thereof.

10. A pharmaceutical composition, comprising: a pharmaceutically acceptable carrier and a therapeutically effective amount of a compound according to claim 5 or a pharmaceutically acceptable salt thereof.

11. A method for treating or preventing a thromboembolic disorder, comprising: administering to a patient in need thereof a therapeutically effective amount of a compound according to claim 1 or a pharmaceutically acceptable salt thereof.

12. A method for treating or preventing a thromboembolic disorder, comprising: administering to a patient in need thereof a therapeutically effective amount of a compound according to claim 2 or a pharmaceutically acceptable salt thereof.

13. A method for treating or preventing a thromboembolic disorder, comprising: administering to a patient in need thereof a therapeutically effective amount of a compound according to claim 3 or a pharmaceutically acceptable salt thereof.

14. A method for treating or preventing a thromboembolic disorder, comprising: administering to a patient in need thereof a therapeutically effective amount of a compound according to claim 4 or a pharmaceutically acceptable salt thereof.

15. A method for treating or preventing a thromboembolic disorder, comprising: administering to a patient in need thereof a therapeutically effective amount of a compound according to claim 5 or a pharmaceutically acceptable salt thereof.

* * * * *